(12) United States Patent
Chamberlin

(10) Patent No.: US 12,285,428 B2
(45) Date of Patent: Apr. 29, 2025

(54) METHODS OF TREATING KIDNEY CONDITIONS USING MODIFIED FORMS OF TRIMETAZIDINE

(71) Applicant: IMBRIA PHARMACEUTICALS, INC., Boston, MA (US)

(72) Inventor: Paul Chamberlin, Brookline, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 18/519,782

(22) Filed: Nov. 27, 2023

(65) Prior Publication Data

US 2024/0091222 A1   Mar. 21, 2024

Related U.S. Application Data

(63) Continuation of application No. 17/735,594, filed on May 3, 2022, now Pat. No. 11,883,396.

(60) Provisional application No. 63/183,303, filed on May 3, 2021.

(51) Int. Cl.
*A61K 31/496* (2006.01)
*A61P 13/12* (2006.01)

(52) U.S. Cl.
CPC ............ *A61K 31/496* (2013.01); *A61P 13/12* (2018.01)

(58) Field of Classification Search
CPC .............................. A61K 31/496; A61P 13/12
See application file for complete search history.

(56) References Cited

U.S. PATENT DOCUMENTS

| | | | |
|---|---|---|---|
| 4,100,285 A | 7/1978 | Murai et al. |
| 4,166,452 A | 9/1979 | Generales, Jr. |
| 4,256,108 A | 3/1981 | Theeuwes |
| 4,265,874 A | 5/1981 | Bonsen et al. |
| 4,574,156 A | 3/1986 | Morita et al. |
| 4,845,099 A | 7/1989 | Ruger et al. |
| 4,876,257 A | 10/1989 | Hajos et al. |
| 4,885,300 A | 12/1989 | Press et al. |
| 5,077,288 A | 12/1991 | Lavielle et al. |
| 5,286,728 A | 2/1994 | Ferrini |
| 5,340,809 A | 8/1994 | Gaudry et al. |
| 5,380,726 A | 1/1995 | Ferrini |
| 5,384,319 A | 1/1995 | Ferrini |
| 5,397,780 A | 3/1995 | Mizuno et al. |
| 5,399,557 A | 3/1995 | Mizuno et al. |
| 5,401,743 A | 3/1995 | Rendenbach-Mueller et al. |
| 5,428,038 A | 6/1995 | Chatterjee et al. |
| 5,527,800 A | 6/1996 | Goto et al. |
| 5,591,849 A | 1/1997 | Kato et al. |
| 5,641,779 A | 6/1997 | Halazy et al. |
| 5,770,735 A | 6/1998 | Emonds-Alt et al. |
| 5,776,937 A | 7/1998 | Gante et al. |
| 5,849,745 A | 12/1998 | Wierzbicki et al. |
| 5,856,326 A | 1/1999 | Anthony et al. |
| 5,962,448 A | 10/1999 | Mizuno et al. |
| 5,977,111 A | 11/1999 | Mizuno et al. |
| 6,087,346 A | 7/2000 | Glennon et al. |
| 6,121,267 A | 9/2000 | Glase et al. |
| 6,200,989 B1 | 3/2001 | De Cillis et al. |
| 6,214,841 B1 | 4/2001 | Jackson et al. |
| 6,271,223 B1 | 8/2001 | Mizuno et al. |
| 6,331,623 B1 | 12/2001 | Mizuno et al. |
| 6,528,529 B1 | 3/2003 | Brann et al. |
| 6,562,978 B1 | 5/2003 | Imamura et al. |
| 6,693,099 B2 | 2/2004 | Degenhardt et al. |
| 7,638,531 B2 | 12/2009 | Mutahi et al. |
| 7,666,866 B2 | 2/2010 | Franciskovich et al. |
| 7,772,251 B2 | 8/2010 | Sturzebecher et al. |
| 7,968,538 B2 | 6/2011 | Becker et al. |
| 8,016,783 B2 | 9/2011 | Pastore et al. |
| 8,202,901 B2 | 6/2012 | Lopaschuk et al. |
| 8,461,117 B2 | 6/2013 | Sufi et al. |
| 8,569,495 B2 | 10/2013 | Chassaing et al. |
| 8,697,661 B2 | 4/2014 | Kritikou |
| 9,096,538 B2 | 8/2015 | Nakamura et al. |
| 9,120,801 B2 | 9/2015 | Alisi et al. |
| 10,167,258 B2 | 1/2019 | Chuang et al. |
| 10,556,013 B2 | 2/2020 | Levin |
| 10,918,728 B2 | 2/2021 | Levin |
| 10,953,102 B2 | 3/2021 | Levin |
| 11,376,330 B2 | 7/2022 | Levin |

(Continued)

FOREIGN PATENT DOCUMENTS

| | | |
|---|---|---|
| CA | 2170615 A1 | 3/1995 |
| CA | 2186010 A1 | 9/1995 |

(Continued)

OTHER PUBLICATIONS

Abrahamsson, 1998, In vitro and in vivo erosion of two different hydrophilic gel matrix tablets, European Journal of Pharmaceuticals and Biopharmaceutics, 46:69-75.
Aswathy, 2018, Formulation and Evaluaton of Mucoadhesive Buccal Tablet of Antianginal Drug, IJPPR. Human Journals, 13(1):43-71.
Bhosle, 2006, Mutual Prodrug Concept: Fundamentals and Applications, Indian Journal of Pharmaceutical Sciences, May-June, pp. 286-294.
Brand, 2013, The role of mitochondrial function and cellular bioenergetics in ageing and disease, British Journal of Dermatology, John Wiley, Hoboken, USA, 169:1-8.
Cheng, 2006, Discovery of Potent and Orally Available Malonyl-CoA Decarboxylase Inhibitors as Cardioprotective Agents, J. Med. Chem. 49:4055-4058.
Cheng, 2006, Synthesis and structure-activity relationship of small-molecule malonyl coenzyme A decarboxylase inhibitors, J. Med. Chem. 49:1517-1525.

(Continued)

*Primary Examiner* — Timothy R Rozof
(74) *Attorney, Agent, or Firm* — Brown Rudnick LLP; Adam M. Schoen

(57) ABSTRACT

The invention provides methods of treating kidney conditions using compositions that contain modified forms of trimetazidine, such as CV-8972. Providing such compositions increases energy production in the kidney. Therefore, methods of the invention are useful for treating a variety of kidney conditions, such as acute kidney disease, chronic kidney disease, chronic kidney insufficiency, diabetic kidney, or diabetic nephropathy.

20 Claims, 87 Drawing Sheets

(56) References Cited

U.S. PATENT DOCUMENTS

| | | |
|---|---|---|
| 2003/0191182 A1 | 10/2003 | Lopaschuk et al. |
| 2003/0232877 A1 | 12/2003 | Sikorski et al. |
| 2004/0082564 A1 | 4/2004 | Arrhenius et al. |
| 2005/0004121 A1 | 1/2005 | Palani et al. |
| 2007/0004750 A1 | 1/2007 | Lorsbach et al. |
| 2008/0108618 A1 | 5/2008 | Brann et al. |
| 2008/0161400 A1 | 7/2008 | Virsik et al. |
| 2009/0197891 A1 | 8/2009 | Lecanu et al. |
| 2009/0258064 A1 | 10/2009 | Newell et al. |
| 2010/0022530 A1 | 1/2010 | Schiemann et al. |
| 2011/0046370 A1 | 2/2011 | Sim et al. |
| 2011/0137362 A1 | 6/2011 | Foreman et al. |
| 2011/0212072 A1 | 9/2011 | Henkel et al. |
| 2012/0214818 A1 | 8/2012 | Dudley |
| 2016/0060530 A1 | 3/2016 | Archetti et al. |
| 2016/0346397 A1 | 12/2016 | Milne et al. |
| 2017/0008950 A1 | 1/2017 | Capon |
| 2017/0105414 A1 | 4/2017 | Nakano et al. |
| 2018/0360975 A1 | 12/2018 | Levin |
| 2019/0084917 A1 | 3/2019 | Savourey et al. |
| 2019/0216936 A1 | 7/2019 | Levin |
| 2020/0138963 A1 | 5/2020 | Levin |
| 2021/0353617 A1* | 11/2021 | Levin .................. A61K 9/0019 |
| 2022/0168431 A1* | 6/2022 | Levin .................. A61K 47/551 |
| 2022/0249463 A1 | 8/2022 | Levin et al. |

FOREIGN PATENT DOCUMENTS

| | | |
|---|---|---|
| CN | 101747292 B | 7/2011 |
| DE | 2714996 A1 | 10/1977 |
| EP | 0144991 A2 | 6/1985 |
| EP | 0251141 A1 | 1/1988 |
| EP | 615855 A1 | 9/1994 |
| EP | 661266 A1 | 7/1995 |
| EP | 749967 A1 | 12/1996 |
| EP | 1634598 A1 | 3/2006 |
| EP | 1886994 A1 | 2/2008 |
| EP | 2727916 A1 | 5/2014 |
| JP | S57131777 | 8/1982 |
| JP | 2000147773 A | 5/2000 |
| JP | 2006113343 A | 4/2006 |
| JP | 2015017236 A | 1/2015 |
| RU | 2377989 C2 | 1/2010 |
| WO | 1995000165 A1 | 1/1995 |
| WO | 9626196 A2 | 8/1996 |
| WO | 9630054 A1 | 10/1996 |
| WO | 9630343 A1 | 10/1996 |
| WO | 9728141 A1 | 8/1997 |
| WO | 9746549 A1 | 12/1997 |
| WO | 98/58638 A1 | 12/1998 |
| WO | 9950247 A1 | 10/1999 |
| WO | 2001005763 A2 | 1/2001 |
| WO | 2002058698 A2 | 8/2002 |
| WO | 2002064576 A1 | 8/2002 |
| WO | 2003006628 A2 | 1/2003 |
| WO | 2006027223 A1 | 3/2006 |
| WO | 2006117686 A2 | 11/2006 |
| WO | 2006133784 A1 | 12/2006 |
| WO | 2007075629 A2 | 7/2007 |
| WO | 2007096251 A1 | 8/2007 |
| WO | 2007/116074 A1 | 10/2007 |
| WO | 2007/116243 A2 | 10/2007 |
| WO | 2008109991 A1 | 9/2008 |
| WO | 2009015485 A1 | 2/2009 |
| WO | 2009/058818 A2 | 5/2009 |
| WO | 2009066315 A2 | 5/2009 |
| WO | 2009156479 A1 | 12/2009 |
| WO | 2011032099 A1 | 3/2011 |
| WO | 2012049101 A1 | 4/2012 |
| WO | 2015018660 A1 | 2/2015 |
| WO | 2016005576 A1 | 1/2016 |
| WO | 2016107603 A1 | 7/2016 |
| WO | 2018/236745 A1 | 12/2018 |
| WO | 2020/081361 A1 | 4/2020 |
| WO | 2020/243119 A1 | 12/2020 |
| WO | 2021/225950 A1 | 11/2021 |
| WO | 2022/150403 A1 | 7/2022 |

OTHER PUBLICATIONS

Das, 1995, Essential Fatty Acid Metabolism in Patients with Essential Hypertension, Diabetes Mellitus and Coronary Heart Disease, Prostaglandins Leukotrienes and Essential Fatty Acids, 52, 387-391.
Extended European Search Report issued European Application No. 21799968.9, date of mailing: Apr. 4, 2024, 10 pages.
Extended European Search Report issued in European Application No. 18821590.9, date of mailing: Oct. 5, 2020, 6 pages.
Extended European Search Report issued in European Application No. 19872680.4, date of mailing: Jun. 20, 2022, 7 pages.
Extended European Search Report issued in European Application No. 22169109.0, date of mailing: Aug. 30, 2022, 7 pages.
Fang, 2011. Therapeutic inhibition of fatty acid oxidation in right ventricular hypertrophy: exploiting Randle's cycle, Journal of Molecular Medicine, 90:31-43.
Fillmore, 2014, Malonyl CoA: A Promising Target for the Treatment of Cardiac Disease, Int. Union of Biochem. and Mol. Biol., 66(3):139-146.
Fillmore, 2014, Mitochondrial fatty acid oxidation alterations in heart failure, ischemic heart disease and diabetic cardiomyopathy, Brit. J. Pharmacol. 171:2080-2090.
Folmes, 2005, Fatty Acid Oxidation Inhibitors in the Management of Chronic Complications of Atherosclerosis, Current Atherosclerosis Reports 2005, 7, 63-70.
Gallaher, 1993, Viscosity and Fermentability as Attributes of Dietary Fiber Responsible of the Hypocholesterolemic Effect in Hamsters, J Nutr., 123, pp. 244-252.
Gao, 2011, Echocardiography in Mice. Curr Protoc Mouse Biol, 1:71-83.
Gibbs, 1995, Cardiac efficiency, Cardiovasc. Res. 30:627-634.
Gustafsson, 1999, Characterisation of particle properties and compaction behaviour of hydroxypropyl methylcellulose with different degrees of methoxy/hydroxypropyl substitution, European Journal of Pharmaceutical Sciences, 9(2): 171-184.
Handbook of Pharmaceutical Excipients, 6th Ed, 2009, pp. 326-329.
International Search Report and Written Opinion issued in International Application No. PCT/US2020/034611, date of mailing: Oct. 14, 2020, 45 pages.
International Search Report and Written Opinion issued in International Application No. PCT/US2020/34608, date of mailing: Oct. 14, 2020, 28 pages.
International Search Report and Written Opinion issued in International Application No. PCT/US2020/34609, date of mailing: Oct. 14, 2020, 22 pages.
International Search Report and Written Opinion issued in International Application No. PCT/US2021/039303, date of mailing: Nov. 26, 2021, 19 pages.
International Search Report and Written Opinion mailed Nov. 5, 2018, for International Patent Application PCT/US2018/038067 with International filing date Jun. 18, 2018 (11 pages).
International Search Report issued in an International Application No. PCT/US2021/030450, date of mailing: Sep. 27, 2021, 9 pages.
Kantor, 2000, The Antianginal Drug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase, Circulation Research, 86:580-588.
Kotreka, 2011, Gastroretentive Floating Drug-Delivery Systems: A Critical Review, Critical Reviews in Therapeutic Drug Carrier Systems, 28(1):47-99.
Leriche, 2012, Cleavable linkers in chemical biology, Bioorg. Med. Chem. 20:571-582.
Levy, 2014, Vasodilators in Acute Heart Failure: Review of the Latest Studies, Curr Emerg Hosp Med Rep, 2 (2): 126-134.
Lopaschuk, 2010, Myocardial Fatty Acid Metabolism in Health and Disease, Phys. Rev. 90:207-258.

(56) References Cited

OTHER PUBLICATIONS

Maskova, 2020, Hypromellose—A traditional pharmaceutical exipient with modern applications in oral and oromucosal drug delivery, Journal of Controlled Release, 324:695-727.

Morin, 1998, Evidence for the existence of [3H]-trimetazidine binding sites involved in the regulation of the mitochondrial permeability transition pore, Brit. J. Pharmacol. 123:1385-1394.

Narokha, 2014, Antioidant effect of nicotinic acid on experimental doxorubicin-induced chronic heart failure, Current Topics in Pharmacology, 18:105-111.

Non-Final Office Action issued in U.S. Appl. No. 16/722,691, date of mailing: Aug. 19, 2020, 12 pages.

Pubchem, CID 2223657, Jul. 15, 2005, pp. 1-14.

Pubchem, CID-57503849, Create Date: Aug. 8, 2012, 16 pages.

Reddy, 2006, Lipid Metabolism and Liver Inflammation. II. Fatty liver disease and fatty acid oxidation, Am J Physiol Gastrointest Liver Physiol, 290: G852-G858.

Sabbah, 2005, Metabolic Therapy for Heart Disease: Impact of Trimetazidine, Heart Failure Reviews, 10, 281-288.

Schipke, 1994, Cardiac efficiency, Basic Res. Cardiol. 89:207-40.

Spiekerkoetter, 2010, Mitochondrial fatty acid oxidation disorders: clinical presentation of long-chain fatty acid oxidation defects before and after newborn screening, J Inherit Metab Dis, 33:527-532.

Steggall, 2017, Targeting Metabolic Modulation and Mitochondrial Dysfunction in the Treatment of Heart Failure, Diseases, 5(14):1-18.

Tang, 2009, The Metabolic Approach in Patients with Heart Failure: Effects on Left Ventricle Remodeling, 15 (8):850-856.

The Merck Manual List of Diseases https://merckmanuals.com/professional (accessed Jan. 17, 2020), 4 pages.

Trammell, 2016, Nicotinamide riboside is uniquely and orally bioavailable in mice and humans, Nat. Commun. 7:12948, 14 pages.

Msser, 2008, Measuring cardiac efficiency: is it clinically useful? Heart Metab. 39:3-4.

Yong-Hu Fang, 2011, Therapeutic inhibition of fatty acid oxidation in reight ventricular hypertrophy, Journal of Molecular Medicine, Springer, Berlin, DE, 90(1):31-43.

Yuasa, 1988, Pharmacological Studies on the Actions of Trimetazidine and Its Derivatives, The Journal of Kansai Medical University, vol. 40, Issue 1, pp. 89-116.

Zhou, 2012, Trimetazidine Protects against Smoking-Induced Left Ventricular Remodeling via Attenuating Oxidative Stress, Apoptosis, and Inflammation, PLOS One, 7:1-7.

2377989, RU, Tovarystvo Z, Jan. 10, 2010.

2020/243119, WO, Imbria Pharmaceuticals, Dec. 3, 2020.

2021/225950, WO, Imbria Pharmaceuticals, Nov. 11, 2021.

2022/150403, WO, Imbria Pharmaceuticals, Jul. 14, 2022.

\* cited by examiner

FIG. 2

| | Number of subjects |
|---|---|
| Screened volunteers | 220 |
| Screening failures | |
| Vital signs | 38 |
| Medical history | 13 |
| Clinical laboratory | 8 |
| Bad venous access | 6 |
| ECG | 6 |
| BMI | 3 |
| Medication use | 2 |
| Did not finish screening | 1 |
| Extensive CYP2D6 metabolizer | 1 |
| Total screening failures | 78 |
| Approved but not receiving study drug | |
| Reserve | 24 |
| Group full | 9 |
| Personal reasons | 9 |
| Group cancelled | 8 |
| Rejected in clinic | 3 |
| Illness of volunteer | 1 |
| Total approved but not dosed | 54 |
| Subjects receiving at least 1 dose of study drug | 88 |
| Any dose of IMB-1018972 | 66 |
| Placebo dose | 14 |
| Trimetazidine dose | 8 |
| Discontinued subjects | |
| Adverse event | 2 |
| Withdrawal by subject | 1 |
| Completed subjects | 85 |

BMI=body mass index; ECG=electrocardiogram; CYP=cytochrome P450

FIG. 3

| Visit | Screening | Pretreatment | | Treatment | Posttreatment | | Follow-up |
|---|---|---|---|---|---|---|---|
| Study Day | Days -35 to -1 | Day -1 | Day 1 (Predose) | Day 1 | Day 2 | Day 3 | 10 to 17 (7 to 14 Days after the Last PK Blood Sample) |
| Confinement |  | X | X | X | X |  |  |
| Ambulatory | X |  |  |  |  | X | X |
| Admission |  | X |  |  |  |  |  |
| Discharge |  |  |  |  |  | X |  |
| Informed Consent | X |  |  |  |  |  |  |
| Medical History | X |  |  |  |  |  |  |
| Demographics | X |  |  |  |  |  |  |
| Physical Examination[a] | X | X |  |  |  | X | X |
| Height, Weight, and BMI Calculation | X |  |  |  |  |  |  |
| Serology (HBsAg, anti-HCV, and anti-HIV 1 and 2) | X |  |  |  |  |  |  |
| Drug and Alcohol Screen | X | X |  |  |  |  |  |
| Serum Pregnancy Test (Females Only) | X | X |  |  |  |  |  |
| Clinical Laboratory[b] | X | X |  |  | X |  | X |
| 12-Lead ECG[c] | X | X |  |  |  | X | X |
| Vital Signs[d] | X | X |  |  | X | X | X |
| Eligibility Check | X | X | X |  |  |  |  |
| Study Drug Administration[e] |  |  |  | X |  |  |  |
| Blood Sampling for PK[f] |  |  | X | X | X | X |  |
| Urine Collection for PK[g] |  |  | X | X | X | X |  |
| Previous and Concomitant Medication | X | X | X | X | X | X | X |
| Adverse Event Monitoring[h] |  | X | X | X | X | X | X |
| Blood Sampling for Genotyping[i] |  |  | X[j] |  |  |  |  |

FIG. 4

| Visit[b] / Study Day | Screening Days -35 to -1 | Pretreatment Day -1 | Pretreatment Day 1 (Predose) | Treatment Day 1 | Posttreatment Day 2 | Posttreatment Day 3 | Follow-up 10 to 17 (7 to 14 Days after the Last PK Blood Sample) |
|---|---|---|---|---|---|---|---|
| Confinement | | X | | | X | X | |
| Ambulatory | X | | | | | | X |
| Admission | | X | | | | | |
| Discharge | | | | | | X | |
| Informed Consent | X | | | | | | |
| Medical History | X | | | | | | |
| Demographics | X | | | | | | |
| Physical Examination[c] | X | X | | | | X | X |
| Height, Weight, and BMI Calculation | X | | | | | | |
| Serology (HBsAg, anti-HCV, and anti-HIV 1 and 2) | X | | | | | | |
| Drug and Alcohol Screen | X | X | | | | | |
| Serum Pregnancy Test (Females Only) | X | X | | | | | |
| Clinical Laboratory[d] | X | X | | | X | | X |
| 12-Lead ECG for Groups A1, A2, A3, and A4 (first period only)[e] | X | X | | | | X | X |
| 12-Lead ECG for Group A4 (second period only)[e] | | | | | X | X | X |
| Continuous Cardiac Monitoring (Telemetry; Not in the Second Period of the FE Group A4)[f] | | | X | X | X | | |
| Vital Signs[g] | X | X | X | X | X | X | X |
| Eligibility Check | X | X | X | | | | |
| Randomization | | | | X | | | |
| Study Drug Administration[h] | | | | X | | | |
| Blood Sampling for PK[i] | | | X | X | X | X | |
| Urine Collection for PK (Not in the Second Period of the FE Group A4)[j] | | | X | X | X | X | |
| Previous and Concomitant Medication | X | X | X | X | X | X | X |
| Adverse Event Monitoring[k] | | X | X | X | X | X | X |
| Blood Sampling for Genotyping[l] | | | X[j] | | | | |

FIG. 5

| Visit[a] | Screening | Pre-treatment | | Assessment Period | | | | | | | | | | | | | | | Posttreatment | | Follow-up |
|---|---|---|---|---|---|---|---|---|---|---|---|---|---|---|---|---|---|---|---|---|---|
| | | | | Treatment | | | | | | | | | | | | | | | | | |
| Study Day | -35 to -1 | -1 | 1 (Pre-dose) | 1 | 2 | 3 | 4 | 5 | 6 | 7 | 8 | 9 | 10 | 11 | 12 | 13 | 14 | 15 | 16 | 23 to 30 (7 to 14 days after the last PK blood sample) |
| Confinement | | X | X | X | X | X | X | X | X | X | X | X | X | X | X | X | X | X | X | |
| Ambulatory | X | | | | | | | | | | | | | | | | | | | X |
| Admission | | X | | | | | | | | | | | | | | | | | | | |
| Discharge | | | | | | | | | | | | | | | | | | | X | | |
| Informed Consent | X | | | | | | | | | | | | | | | | | | | | |
| Medical History | X | X | | | | | | | | | | | | | | | | | | | |
| Demographics | X | | | | | | | | | | | | | | | | | | | | |
| Physical Examination[b] | X | X | | | | | | | | | | | | | | | | | | | X |
| Height, Weight, and BMI Calculation | X | | | | | | | | | | | | | | | | | | | | |
| Serology (HBsAg, anti-HCV, and anti-HIV 1 and 2) | X | | | | | | | | | | | | | | | | | | | | |
| Drug and Alcohol Screen | X | X | | | | | | | | | | | | | | | | | | | |
| Serum Pregnancy Test (Females Only) | X | X | | | | | | | | | | | | | | | | | | | |
| Clinical Laboratory[c] | X | X | | | | | | | X | | | | | | | | | | X | | X |
| 12-Lead ECG[d] | X | X | | | X | | | | | | | X | | | | | | | | X | X |
| Continuous Cardiac Monitoring (Telemetry)[e] | | | | X | X | | | | | | | | | | | | | X | X | | |
| Vital Signs[f] | X | X | | X | X | | | | | | X | X | | | | | | X | X | X | X |
| Eligibility Check | X | X | | | | | | | | | | | | | | | | | | | |
| Randomization | | X | | | | | | | | | | | | | | | | | | | |
| Study Drug Administration[g] | | | | X | X | X | X | X | X | X | X | X | X | X | X | X | | | | | |
| Blood Sampling for PK[h] | | | | X | X | X | X | X | X | X | X | X | X | X | X | X | X | X | X | X | X |
| Previous and Concomitant Medication | X | X | | X | X | X | X | X | X | X | X | X | X | X | X | X | X | X | X | X | X |
| Adverse Event Monitoring[i] | | X | | X | X | X | X | X | X | X | X | X | X | X | X | X | X | X | X | X | X |
| Blood Sampling for Genotyping | | X | | | | | | | | | | | | | | | | | | | |

FIG. 6

| | IMB-1018972 Placebo (Pooled) (N=8) n (%) | 50 mg IMB-1018972 Fasted (N=6) n (%) | 150 mg IMB-1018972 Fasted (N=6) n (%) | 400 mg IMB-1018972 Fasted (N=6) n (%) | 150 mg IMB-1018972 Fasted-Fed (N=6) n (%) | 35 mg Trimetazidine Fasted (N=8) n (%) | Total IMB-1018972 (N=24) n (%) |
|---|---|---|---|---|---|---|---|
| Randomized | 8 (100%) | 6 (100%) | 6 (100%) | 6 (100%) | 6 (100%) | 8 (100%) | 24 (100%) |
| Safety Set | 8 (100%) | 6 (100%) | 6 (100%) | 6 (100%) | 6 (100%) | 8 (100%) | 24 (100%) |
| Pharmacokinetic Set | 0 (0%) | 6 (100%) | 6 (100%) | 6 (100%) | 6 (100%) | 8 (100%) | 24 (100%) |
| Completed Study | 8 (100%) | 6 (100%) | 6 (100%) | 6 (100%) | 4 (66.7%) | 8 (100%) | 22 (91.7%) |
| Discontinued Study | 0 (0%) | 0 (0%) | 0 (0%) | 0 (0%) | 2 (33.3%)# | 0 (0%) | 2 (8.3) |
| Reasons for Discontinuation | | | | | | | |
| Adverse Event | | | | | 1 (16.7) | | 1 (4.2) |
| Withdrawal by Subject | | | | | 1 (16.7) | | 1 (4.2) |

AE=adverse event; FE=food effect; N=total number of subjects; n=number of subjects; SAD=single ascending dose; SAE=serious adverse event
One subject discontinued due to a SAE in Period 1 of the FE arm, and 1 subject withdrew consent in Period 2 of the FE arm
Notes: The percentage is calculated as (n/N)*100%

FIG. 7

| | IMB-1018972 q12h Placebo Fed (Pooled) (N=6) n (%) | 150 mg q12h IMB-1018972 Fed (N=9) n (%) | 50 mg q12h IMB-1018972 Fed (N=9) n (%) | Total IMB-1018972 (N=18) n (%) |
|---|---|---|---|---|
| Randomized | 6 (100%) | 9 (100%) | 9 (100%) | 18 (100%) |
| Safety Set | 6 (100%) | 9 (100%) | 9 (100%) | 18 (100%) |
| Pharmacokinetic Set | 0 (0%) | 9 (100%) | 9 (100%) | 18 (100%) |
| Completed Study | 6 (100%) | 9 (100%) | 9 (100%) | 18 (100%) |

MAD=multiple ascending dose; N=total number of subjects; n=number of subjects; q12h=every 12 hours
Notes: The percentage is calculated as (n/N)*100%

FIG. 8

| Parameter | Statistic/ Category | IMB-1018972 Placebo (Pooled) (N=8) | 50 mg IMB-1018972 Fasted (N=6) | 150 mg IMB-1018972 Fasted (N=6) | 400 mg IMB-1018972 Fasted (N=6) | 150 mg IMB-1018972 Fasted-Fed (N=6) | 35 mg Trimetazidine Fasted (N=8) | Total IMB-1018972 (N=24) |
|---|---|---|---|---|---|---|---|---|
| Age (years) | Mean (SD) | 46 (18) | 46 (20) | 29 (15) | 44 (20) | 29 (11) | 32 (17) | 37 (18) |
| | Median | 55 | 46 | 22 | 51 | 27 | 24 | 29 |
| | Min - Max | 23 - 62 | 24 - 64 | 19 - 59 | 19 - 65 | 18 - 49 | 20 - 65 | 18 - 65 |
| Weight (kg) | Mean (SD) | 69.5 (6.2) | 70.1 (10.6) | 79.1 (20.5) | 67.2 (6.3) | 72.8 (7.5) | 71.3 (11.3) | 72.3 (12.5) |
| | Median | 69.4 | 71.4 | 74.3 | 66.2 | 72.8 | 66.0 | 71.1 |
| | Min - Max | 60.8 - 79.7 | 50.7 - 82.3 | 55.4 - 109.2 | 57.8 - 74.9 | 61.1 - 83.7 | 54.7 - 87.4 | 50.7 - 109.2 |
| Height (cm) | Mean (SD) | 174 (9) | 167 (5) | 171 (14) | 170 (10) | 172 (8) | 173 (8) | 170 (10) |
| | Median | 172 | 168 | 173 | 169 | 172 | 172 | 170 |
| | Min - Max | 165 - 190 | 157 - 170 | 149 - 191 | 159 - 185 | 162 - 187 | 160 - 183 | 149 - 191 |
| BMI (kg/m$^2$) | Mean (SD) | 23.0 (2.0) | 25.2 (2.9) | 26.6 (3.0) | 23.4 (2.3) | 24.6 (3.2) | 23.7 (2.5) | 24.9 (2.9) |
| | Median | 23.2 | 25.4 | 26.0 | 24.3 | 24.8 | 23.7 | 24.5 |
| | Min - Max | 19.6 - 25.3 | 20.6 - 29.2 | 23.1 - 30.3 | 19.5 - 25.9 | 20.4 - 28.3 | 19.4 - 26.7 | 19.5 - 30.3 |
| Gender, n (%) | Female | 5 (62.5%) | 6 (100%) | 5 (83.3%) | 4 (66.7%) | 3 (50.0%) | 5 (62.5%) | 18 (75.0%) |
| | Male | 3 (37.5%) | | 1 (16.7%) | 2 (33.3%) | 3 (50.0%) | 3 (37.5%) | 6 (25.0%) |
| Ethnicity, n (%) | Hispanic or Latino | | | 1 (16.7%) | | | 1 (12.5%) | 1 (4.2%) |
| | Not Hispanic or Latino | 8 (100%) | 6 (100%) | 5 (83.3%) | 6 (100%) | 6 (100%) | 7 (87.5%) | 23 (95.8%) |
| Race, n (%) | Asian | 1 (12.5%) | | | | | | |
| | Black or African American | | 1 (16.7%) | | | | | |
| | Multiple | | | | | | 1 (12.5%) | 1 (4.2%) |
| | Native Hawaiian or Other Pacific Islander | | | | | 1 (16.7%) | | 1 (4.2%) |
| | White | 7 (87.5%) | 5 (83.3%) | 6 (100%) | 6 (100%) | 5 (83.3%) | 7 (87.5%) | 22 (91.7%) |

BMI=body mass index; FE=food effect; Max=maximum; Min=minimum; N=number of subjects; SAD=single ascending dose
The summary of the PK set was identical to that of the safety set minus the pooled placebo group
Age, height, weight, and BMI were determined at screening

FIG. 9

| Parameter | Statistic/ Category | IMB-1018972 q12h Placebo Fed (Pooled) (N=6) | 150 mg q12h IMB-1018972 Fed (N=9) | 50 mg q12h IMB-1018972 Fed (N=9) | Total IMB-1018972 (N=18) |
|---|---|---|---|---|---|
| Age (years) | Mean (SD) | 38 (13) | 44 (14) | 40 (17) | 42 (15) |
|  | Median | 33 | 49 | 41 | 45 |
|  | Min - Max | 27 - 61 | 27 - 62 | 18 - 64 | 18 - 64 |
| Weight (kg) | Mean (SD) | 82.0 (18.0) | 75.2 (13.3) | 80.0 (10.9) | 77.6 (12.0) |
|  | Median | 84.9 | 79.3 | 77.6 | 78.5 |
|  | Min - Max | 50.7 - 102.0 | 53.7 - 93.5 | 67.3 - 96.8 | 53.7 - 96.8 |
| Height (cm) | Mean (SD) | 174 (9) | 172 (9) | 173 (8) | 173 (8) |
|  | Median | 175 | 174 | 176 | 175 |
|  | Min - Max | 163 - 186 | 161 - 181 | 161 - 184 | 161 - 184 |
| BMI (kg/m²) | Mean (SD) | 26.7 (4.0) | 25.2 (2.6) | 26.7 (2.7) | 25.9 (2.7) |
|  | Median | 28.2 | 25.7 | 25.9 | 25.8 |
|  | Min - Max | 19.1 - 29.7 | 20.7 - 28.5 | 23.3 - 30.9 | 20.7 - 30.9 |
| Gender, n (%) | Female | 3 (50.0%) | 5 (55.6%) | 4 (44.4%) | 9 (50.0%) |
|  | Male | 3 (50.0%) | 4 (44.4%) | 5 (55.6%) | 9 (50.0%) |
| Ethnicity, n (%) | Hispanic or Latino | | 3 (33.3%) | | 3 (16.7%) |
|  | Not Hispanic or Latino | 6 (100%) | 6 (66.7%) | 9 (100%) | 15 (83.3%) |
| Race, n (%) | American Indian or Alaska Native | | 2 (22.2%) | | 2 (11.1%) |
|  | Asian | 1 (16.7%) | | | |
|  | Black or African American | 1 (16.7%) | | | |
|  | Multiple | 1 (16.7%) | | 1 (11.1%) | 1 (5.6%) |
|  | White | 3 (50.0%) | 7 (77.8%) | 8 (88.9%) | 15 (83.3%) |

BMI=body mass index; MAD=multiple ascending dose; Max=maximum; Min=minimum; N=number of subjects; q12h=every 12 hours
The summary of the PK set was identical to that of the safety set minus the pooled placebo group
Age, height, weight, and BMI were determined at screening

FIG. 10

| Group | Subjects | Treatments | Total exposure per subject | Number of subjects exposed |
|---|---|---|---|---|
| A1 | 102, 103, 104, 105, 106, 108 | 50 mg IMB-1018972 fasted | 50 mg IMB-1018972 | N=6 |
| | 101, 107 | Placebo | Not applicable | N=2 |
| A2 | 109, 110, 111, 113, 115, 116 | 150 mg IMB-1018972 fasted | 150 mg IMB-1018972 | N=6 |
| | 112, 114 | Placebo | Not applicable | N=2 |
| A3 | 117, 118, 119, 122, 123, 124 | 400 mg IMB-1018972 fasted | 400 mg IMB-1018972 | N=6 |
| | 120, 121 | Placebo | Not applicable | N=2 |
| A4 | 126, 127, 128, 129, 132 | Period 1: 150 mg IMB-1018972 fasted Period 2: 150 mg IMB-1018972 fed | 300 mg IMB-1018972 | N=5 |
| | 131 | Period 1: 150 mg IMB-1018972 fasted | 150 mg IMB-1018972 | N=1 |
| | 125, 130 | Period 1: Placebo fasted Period 2: Placebo fed | Not applicable | N=2 |
| A5 | 133, 134, 135, 136, 137, 138, 139, 140 | 35 mg Trimetazidine fasted | 35 mg Trimetazidine | N=8 |

FE=food effect; N=number of subjects exposed; SAD=single ascending dose

FIG. 11

| Group | Subjects | Treatments | Duration | Total exposure to IMB-1018972 per subject | Number of subjects exposed |
|---|---|---|---|---|---|
| B1 | 202, 203, 204, 206, 207, 208, 209, 210, 211 | 150 mg q12h IMB-1018972 fed | 14 days/ 27 doses | 4050 mg | N=9 |
|  | 201, 205, 212 | q12h placebo fed | 14 days/ 27 doses | Not applicable | N=3 |
| B2 | 213, 215, 216, 217, 218, 219, 222, 223, 224 | 50 mg q12h IMB-1018972 fed | 14 days/ 27 doses | 1350 mg | N=9 |
|  | 214, 220, 221 | q12h placebo fed | 14 days/ 14 doses | Not applicable | N=3 |

MAD=multiple ascending dose; N=number of subjects exposed; q12h=every 12 hours

FIG. 18

| Parameter | 50 mg IMB-1018972 Fasted (N=6) | 150 mg IMB-1018972 Fasted (N=6) | 150 mg IMB-1018972 Fasted (Fasted-fed Group) (N=6) | 400 mg IMB-1018972 Fasted (N=6) | 35 mg Trimetazidine Fasted (N=8) |
|---|---|---|---|---|---|
| IMB-1028814 | | | | | |
| C$_{max}$ (ng/mL) | 104 (35.4 - 310) | 319 (125 - 699) | 275 (138 - 477) | 870 (362 - 1370) | NA |
| t$_{max}$ (h) | 1.00 (0.50 - 5.00) | 1.00 (0.50 - 3.00) | 1.02 (0.50 - 1.02) | 1.12 (0.50 - 2.02) | NA |
| AUC$_{0-t}$ (ng.h/mL) | 290 (101 - 830) | 1108 (502 - 1948) | 754 (329 - 1490) | 2795 (1243 - 4388) | NA |
| AUC$_{0-inf}$ (ng.h/mL) | 294 (103 - 837) | 1112 (504 - 1952) | 758 (332 - 1493) | 2804 (1251 - 4398) | NA |
| t$_{1/2}$ (h) | 3.02 (1.63 - 5.51) | 3.04 (2.05 - 4.50) | 2.60 (1.71 - 4.47) | 2.68 (2.21 - 3.22) | NA |
| CL/F (L/h) | 170 (59.7 - 487) | 135 (76.8 - 298) | 198 (101 - 452) | 143 (90.9 - 320) | NA |
| Trimetazidine | | | | | |
| C$_{max}$ (ng/mL) | 36.9 (16.5 - 61.5) | 97.9 (51.1 - 164) | 139 (79.2 - 203) | 274 (134 - 471) | 68.6 (49.2 - 131) |
| t$_{max}$ (h) | 2.00 (1.00 - 8.00) | 2.00 (1.00 - 4.00) | 1.51 (1.02 - 5.00) | 2.01 (1.02 - 5.00) | 5.00 (4.00 - 5.00) |
| AUC$_{0-t}$ (ng.h/mL) | 424 (163 - 892) | 1024 (561 - 1925) | 1519 (1141 - 1995) | 3305 (2097 - 4538) | 912 (589 - 1451) |
| AUC$_{0-inf}$ (ng.h/mL) | 446 (174 - 967) | 1038 (573 - 1934) | 1541 (1149 - 2014) | 3361 (2140 - 4584) | 929 (595 - 1469) |
| t$_{1/2}$ (h) | 8.00 (5.67 - 13.3) | 6.76 (5.19 - 9.65) | 7.59 (6.54 - 9.99) | 7.99 (6.69 - 9.60) | 7.49 (6.10 - 11.4) |
| IMB-1028814 + Trimetazidine | | | | | |
| C$_{max}$ (nmol/L) | 516 (308 - 1080) | 1450 (880 - 2430) | 1418 (984 - 2090) | 3839 (2700 - 5430) | NA |
| t$_{max}$ (h) | 1.00 (0.50 - 5.00) | 1.00 (1.00 - 3.00) | 1.02 (1.02 - 2.00) | 1.12 (0.50 - 2.02) | NA |
| AUC$_{0-t}$ (nmol.h/L) | 2970 (2030 - 4171) | 8262 (6994 - 10291) | 8538 (7417 - 10852) | 22365 (19230 - 27678) | NA |
| AUC$_{0-inf}$ (nmol.h/L) | 3070 (2149 - 4449) | 8305 (7049 - 10329) | 8615 (7472 - 10893) | 22561 (19386 - 28115) | NA |
| t$_{1/2}$ (h) | 7.49 (5.19 - 13.2) | 6.30 (4.87 - 8.44) | 7.47 (6.48 - 9.60) | 7.80 (6.52 - 9.19) | NA |

N=number of subjects; NA=not applicable; PK=pharmacokinetic; SAD=single ascending dose
For t$_{max}$ the median (range) is presented instead of geometric mean (range)

FIG. 19

| Analyte | PK Parameter | Slope | 95% CI Lower | 95% CI Upper | P-value |
|---|---|---|---|---|---|
| IMB-1028814 | $C_{max}$ (ng/mL) | 1.018 | 0.689 | 1.348 | 0.9094 |
| | $AUC_{0-t}$ (ng.h/mL) | 1.088 | 0.738 | 1.439 | 0.6058 |
| | $AUC_{0-inf}$ (ng.h/mL) | 1.084 | 0.735 | 1.433 | 0.6241 |
| Trimetazidine | $C_{max}$ (ng/mL) | 0.967 | 0.698 | 1.236 | 0.8026 |
| | $AUC_{0-t}$ (ng.h/mL) | 0.988 | 0.735 | 1.240 | 0.9196 |
| | $AUC_{0-inf}$ (ng.h/mL) | 0.971 | 0.718 | 1.223 | 0.8125 |

PK=pharmacokinetic

Note: Dose proportionality was explored using the power model on ln-transformed PK parameters Model: $\ln(PK) = \ln(\beta 0) + \beta 1 \cdot \ln(dose) + \epsilon$, where PK is the pharmacokinetic parameter tested (e.g., $C_{max}$ or AUC), $\ln(\beta 0)$ is the y-intercept, $\beta 1$ is the slope (a $\beta 1$ value of 1 indicates linearity), and $\epsilon$ is an error term A point estimate and 95% CI were produced for the slope. A slope of 1 (i.e., a 95% CI containing 1) means that no evidence of a deviation from dose proportionality was found

FIG. 32

| Parameter | 150 mg IMB-1018972 Fasted (Fasted-fed Group) (N=6) | 150 mg IMB-1018972 Fed (Fasted-fed Group) (N=5) |
|---|---|---|
| IMB-1028814 | | |
| $C_{max}$ (ng/mL) | 275 (138 - 477) | 180 (73.4 - 277) |
| $t_{max}$ (h) | 1.02 (0.50 - 1.02) | 2.00 (0.42 - 5.00) |
| $AUC_{0-t}$ (ng.h/mL) | 754 (329 - 1490) | 987 (409 - 1641) |
| $AUC_{0-inf}$ (ng.h/mL) | 758 (332 - 1493) | 993 (412 - 1649) |
| $t_{1/2}$ (h) | 2.60 (1.71 - 4.47) | 2.54 (1.66 - 4.20) |
| CL/F (L/h) | 198 (101 - 452) | 151 (91.0 - 364) |
| Trimetazidine | | |
| $C_{max}$ (ng/mL) | 139 (79.2 - 203) | 132 (78.6 - 182) |
| $t_{max}$ (h) | 1.51 (1.02 - 5.00) | 4.00 (1.00 - 6.00) |
| $AUC_{0-t}$ (ng.h/mL) | 1519 (1141 - 1995) | 1582 (1245 - 2125) |
| $AUC_{0-inf}$ (ng.h/mL) | 1541 (1149 - 2014) | 1606 (1255 - 2147) |
| $t_{1/2}$ (h) | 7.59 (6.54 - 9.99) | 7.50 (6.83 - 9.17) |
| IMB-1028814 + Trimetazidine | | |
| $C_{max}$ (nmol/L) | 1418 (984 - 2090) | 1065 (813 - 1400) |
| $t_{max}$ (h) | 1.02 (1.02 - 2.00) | 4.00 (1.00 - 5.00) |
| $AUC_{0-t}$ (nmol.h/L) | 8538 (7417 - 10952) | 9659 (7912 - 11513) |
| $AUC_{0-inf}$ (nmol.h/L) | 8615 (7472 - 10993) | 9740 (7949 - 11573) |
| $t_{1/2}$ (h) | 7.47 (6.48 - 9.60) | 7.25 (6.70 - 8.44) |

FE=food effect; N=number of subjects; PK=pharmacokinetic

For $t_{max}$ the median (range) is presented instead of geometric mean (range)

FIG. 33

| Analyte | PK Parameter | Test (150 mg IMB-1018972 fed) | Reference (150 mg IMB-1018972 fasted) | Estimate | Ratio Test/Reference | |
|---|---|---|---|---|---|---|
| | | | | | Lower | Upper |
| IMB-1028814 | $C_{max}$ (ng/mL) | 175 | 275 | 0.6374 | 0.3900 | 1.0417 |
| | $AUC_{0-t}$ (ng·h/mL) | 844 | 754 | 1.1192 | 1.0186 | 1.2297 |
| | $AUC_{0-inf}$ (ng·h/mL) | 849 | 758 | 1.1200 | 1.0218 | 1.2277 |
| Trimetazidine | $C_{max}$ (ng/mL) | 127 | 139 | 0.9136 | 0.8504 | 0.9814 |
| | $AUC_{0-t}$ (ng·h/mL) | 1574 | 1519 | 1.0364 | 0.9783 | 1.0980 |
| | $AUC_{0-inf}$ (ng·h/mL) | 1598 | 1541 | 1.0365 | 0.9768 | 1.0999 |

ANOVA=analysis of variance; PK=pharmacokinetic.
Note: Model: ANOVA with a fixed effect for treatment (fed, fasted) and a random effect for subject

FIG. 34

| Treatment | Ae$_{urine}$ (mg) | Fe$_{urine}$ (%) | CL$_R$# (L/h) |
|---|---|---|---|
| IMB-1028814 | | | |
| 50 mg IMB-1018972 Fasted (N=6) | 2.14 (1.79) | 5.74 (4.80) | 4.97 (3.33 – 7.58) |
| 150 mg IMB-1018972 Fasted (N=6) | 5.45 (3.81) | 4.87 (3.40) | 3.76 (2.72 – 5.88) |
| 400 mg IMB-1018972 Fasted (N=6) | 16.8 (8.05) | 5.64 (2.70) | 5.37 (3.69 – 7.23) |
| 150 mg IMB-1018972 Fasted (Fasted-fed group) (N=6) | 4.47 (2.73) | 3.99 (2.44) | 4.81 (3.69 – 6.22) |
| 35 mg Trimetazidine Fasted (N=8) | NA | NA | NA |
| Trimetazidine | | | |
| 50 mg IMB-1018972 Fasted (N=6) | 9.64 (2.75) | 30.12 (8.61) | 20.8 (12.0 – 33.7) |
| 150 mg IMB-1018972 Fasted (N=6) | 22.2 (12.6) | 23.11 (13.16) | 18.1 (10.2 – 21.7) |
| 400 mg IMB-1018972 Fasted (N=6) | 68.0 (20.0) | 26.55 (7.80) | 19.5 (14.5 – 22.4) |
| 150 mg IMB-1018972 Fasted (Fasted-fed group) (N=6) | 31.3 (9.37) | 32.55 (9.76) | 19.6 (12.3 – 25.3) |
| 35 mg Trimetazidine Fasted (N=8) | 19.1 (1.95) | 54.47 (5.56) | 20.4 (14.9 – 30.7) |

N=number of subjects; NA=not applicable, PK=pharmacokinetic
: For CL$_R$, geometric mean (range) is presented instead of arithmetic mean (SD)
Note: Fe$_{urine}$ (percentage of the dose) is calculated on mg equivalents of the analyte in the dose (ie, 100 mg IMB-1018972=75 mg IMB-1028814=64 mg trimetazidine)

FIG. 47

| Day | Parameter | 150 mg q12h IMB-1018972 Fed (N=9) | 50 mg q12h IMB-1018972 Fed (N=9) |
|---|---|---|---|
| | IMB-1028814 | | |
| 1 | $C_{max}$ (ng/mL) | 354 (224 - 597) | 89.2 (49.2 - 167) |
| | $t_{max}$ (h) | 1.02 (0.50 - 3.00) | 0.50 (0.25 - 4.00) |
| | $AUC_{0-\tau}$ (ng.h/mL) | 1202 (948 - 2327) | 276 (200 - 482) |
| 14 | $C_{max}$ (ng/mL) | 477 (226 - 784) | 100 (50.4 - 150) |
| | $C_{min}$ (ng/mL) | 12.5 (5.00 - 33.8) | 3.16 (1.24 - 10.2) |
| | $t_{max}$ (h) | 0.52 (0.50 - 2.02) | 0.52 (0.28 - 1.02) |
| | $AUC_{0-\tau}$ (ng.h/mL) | 1416 (799 - 2737) | 303 (189 - 549) |
| | $t_{1/2}$ (h) | 4.48 (3.07 - 9.19) | 2.79 (2.09 - 4.79) |
| | $R_{ac}$ | 1.18 (0.72 - 0.51) | 1.10 (0.90 - 1.47) |
| | $CL_{ss}/F$ (L/h) | 106 (54.8 - 188) | 165 (91.0 - 265) |
| | $V_z/F$ (L) | 685 (372 - 1439) | 664 (359 - 1432) |
| | Trimetazidine | | |
| 1 | $C_{max}$ (ng/mL) | 89.6 (63.9 - 147) | 35.3 (14.5 - 57.1) |
| | $t_{max}$ (h) | 3.00 (2.00 - 5.00) | 3.00 (0.50 - 6.02) |
| | $AUC_{0-\tau}$ (ng.h/mL) | 721 (539 - 1172) | 274 (112 - 428) |
| 14 | $C_{max}$ (ng/mL) | 145 (81.6 - 312) | 63.8 (32.7 - 86.5) |
| | $C_{min}$ (ng/mL) | 58.7 (32.1 - 151) | 25.9 (17.3 - 43.8) |
| | $t_{max}$ (h) | 2.00 (0.50 - 3.00) | 2.00 (1.00 - 3.12) |
| | $AUC_{0-\tau}$ (ng.h/mL) | 1175 (667 - 2820) | 519 (297 - 768) |
| | $t_{1/2}$ (h) | 9.36 (7.18 - 11.2) | 9.32 (7.11 - 11.3) |
| | $R_{ac}$ | 1.63 (1.17 - 2.41) | 1.89 (1.49 - 2.68) |
| | IMB-1028814 + Trimetazidine | | |
| 1 | $C_{max}$ (nmol/L) | 1468 (1080 - 2150) | 411 (268 - 671) |
| | $t_{max}$ (h) | 2.00 (0.50 - 3.00) | 1.00 (0.50 - 4.00) |
| | $AUC_{0-\tau}$ (nmol.h/L) | 6767 (5738 - 9590) | 1995 (1479 - 2514) |
| 14 | $C_{max}$ (nmol/L) | 2115 (1440 - 3110) | 548 (412 - 691) |
| | $C_{min}$ (nmol/L) | 275 (194 - 594) | 114 (86.0 - 174) |
| | $t_{max}$ (h) | 0.52 (0.50 - 2.02) | 0.52 (0.28 - 3.00) |
| | $AUC_{0-\tau}$ (nmol.h/L) | 9437 (7248 - 15270) | 3035 (2539 - 3881) |
| | $t_{1/2}$ (h) | 8.90 (6.55 - 10.6) | 9.08 (7.00 - 11.2) |
| | $R_{ac}$ | 1.39 (1.15 - 2.04) | 1.52 (1.32 - 2.01) |

MAD=multiple ascending dose; N=number of subjects; PK=pharmacokinetic
For $t_{max}$ the median (range) is presented instead of geometric mean (range)

FIG. 48A

| SYSTEM ORGAN CLASS/ Preferred Term | IMB-1018972 Placebo (Pooled) (N=8) E n (%) | 50 mg IMB-1018972 Fasted (N=6) E n (%) | 150 mg IMB-1018972 Fasted (N=6) E n (%) | 400 mg IMB-1018972 Fasted (N=6) E n (%) | 150 mg IMB-1018972 Fasted (Fasted-fed Group) (N=6) E n (%) | 150 mg IMB-1018972 Fed (Fasted-fed Group) (N=5) E n (%) | 35 mg Trimetazidine Fasted (N=8) E n (%) | Total IMB-1018972 (N=24) E n (%) |
|---|---|---|---|---|---|---|---|---|
| Any TEAE | 3 2 (25.0) | 3 3 (50.0) | 5 3 (50.0) | 16 6 (100) | 17 4 (66.7) | 4 1 (20.0) | 4 3 (37.5) | 45 16 (66.7) |
| GASTROINTESTINAL DISORDERS | | | 2 1 (16.7) | 2 1 (16.7) | 4 2 (33.3) | 1 1 (20.0) | 1 1 (12.5) | 9 4 (16.7) |
| Abdominal Pain | | | | | | | 1 1 (12.5) | |
| Nausea | | | | 1 1 (16.7) | 2 2 (33.3) | 1 1 (20.0) | | 4 3 (12.5) |
| Diarrhoea | | | 1 1 (16.7) | | | | | 1 1 (4.2) |
| Dry Mouth | | | | 1 1 (16.7) | | | | 1 1 (4.2) |
| Dysphagia | | | | | 1 1 (16.7) | | | 1 1 (4.2) |
| Gingival Pain | | | 1 1 (16.7) | | | | | 1 1 (4.2) |
| Vomiting | | | | | 1 1 (16.7) | | | 1 1 (4.2) |
| GENERAL DISORDERS AND ADMINISTRATION SITE CONDITIONS | | 1 1 (16.7) | | 5 3 (50.0) | 3 1 (16.7) | | | 9 5 (20.8) |
| Medical Device Site Pruritus | | | | 2 2 (33.3) | 1 1 (16.7) | | | 3 3 (12.5) |
| Influenza Like Illness | | 1 1 (16.7) | | | 1 1 (16.7) | | | 2 2 (8.3) |
| Catheter Site Related Reaction | | | | 1 1 (16.7) | | | | 1 1 (4.2) |
| Fatigue | | | | 1 1 (16.7) | | | | 1 1 (4.2) |
| Feeling Hot | | | | 1 1 (16.7) | | | | 1 1 (4.2) |
| Pyrexia | | | | | 1 1 (16.7) | | | 1 1 (4.2) |
| INFECTIONS AND INFESTATIONS | | | 1 1 (16.7) | | | 1 1 (20.0) | | 2 2 (8.3) |
| Nasopharyngitis | | | | | | 1 1 (20.0) | | 1 1 (4.2) |
| Tonsillitis | | | 1 1 (16.7) | | | | | 1 1 (4.2) |

FIG. 48B

| SYSTEM ORGAN CLASS/ Preferred Term | IMB-1018972 Placebo (Pooled) (N=8) E n (%) | 50 mg IMB-1018972 Fasted (N=6) E n (%) | 150 mg IMB-1018972 Fasted (N=6) E n (%) | 400 mg IMB-1018972 Fasted (N=6) E n (%) | 150 mg IMB-1018972 Fasted (Fasted-fed Group) (N=6) E n (%) | 150 mg IMB-1018972 Fed (Fasted-fed Group) (N=5) E n (%) | 35 mg Trimetazidine Fasted (N=8) E n (%) | Total IMB-1018972 (N=24) E n (%) |
|---|---|---|---|---|---|---|---|---|
| INJURY, POISONING AND PROCEDURAL COMPLICATIONS | | | | | | 1 1 (20.0) | | 1 1 (4.2) |
| Post Procedural Haemorrhage | | | | | | 1 1 (20.0) | | 1 1 (4.2) |
| MUSCULOSKELETAL AND CONNECTIVE TISSUE DISORDERS | | | | 1 1 (16.7) | 2 2 (33.3) | | 1 1 (12.5) | 3 3 (12.5) |
| Neck Pain | | | | | 1 1 (16.7) | | 1 1 (12.5) | |
| Back Pain | | | | 1 1 (16.7) | 1 1 (16.7) | | | 2 2 (8.3) |
| Muscle Spasms | | | | | 1 1 (16.7) | | | 1 1 (4.2) |
| NERVOUS SYSTEM DISORDERS | 2 2 (25.0) | | 1 1 (16.7) | 3 3 (50.0) | 4 3 (50.0) | 1 1 (20.0) | 1 1 (12.5) | 9 7 (29.2) |
| Dysgeusia | 1 1 (12.5) | | | | | | | |
| Dizziness | | | 1 1 (16.7) | 2 2 (33.3) | 1 1 (16.7) | | | 4 4 (16.7) |
| Headache | 1 1 (12.5) | | | 1 1 (16.7) | 1 1 (16.7) | 1 1 (20.0) | 1 1 (12.5) | 3 2 (8.3) |
| Burning Sensation | | | | | 1 1 (16.7) | | | 1 1 (4.2) |
| Somnolence | | | | | 1 1 (16.7) | | | 1 1 (4.2) |
| PSYCHIATRIC DISORDERS | | | | 1 1 (16.7) | | | | 1 1 (4.2) |
| Restlessness | | | | 1 1 (16.7) | | | | 1 1 (4.2) |
| RENAL AND URINARY DISORDERS | | | | | 1 1 (16.7) | | 1 1 (12.5) | |
| Pollakiuria | | | | | 1 1 (16.7) | | 1 1 (12.5) | |
| SKIN AND SUBCUTANEOUS TISSUE DISORDERS | 1 1 (12.5) | 2 2 (33.3) | 1 1 (16.7) | | 1 1 (16.7) | | | 4 4 (16.7) |
| Dermatitis Contact | 1 1 (12.5) | 2 2 (33.3) | 1 1 (16.7) | | | | | 3 3 (12.5) |
| Erythema | | | | | 1 1 (16.7) | | | 1 1 (4.2) |
| VASCULAR DISORDERS | | | | 4 4 (66.7) | 3 3 (50.0) | | | 7 7 (29.2) |
| Flushing | | | | 4 4 (66.7) | 2 2 (33.3) | | | 6 6 (25.0) |
| Peripheral Coldness | | | | | 1 1 (16.7) | | | 1 1 (4.2) |

FIG. 49A

| SYSTEM ORGAN CLASS/Preferred Term | IMB-1018972 q12h Placebo Fed (Pooled) (N=6) E n (%) | 150 mg q12h IMB-1018972 Fed (N=9) E n (%) | 50 mg q12h IMB-1018972 Fed (N=9) E n (%) | Total IMB-1018972 (N=18) E n (%) |
|---|---|---|---|---|
| Any TEAE | 17 5 (83.3) | 14 7 (77.8) | 21 7 (77.8) | 35 14 (77.8) |
| GASTROINTESTINAL DISORDERS | 3 2 (33.3) | | 6 4 (44.4) | 6 4 (22.2) |
| Abdominal Pain | 2 2 (33.3) | | 2 2 (22.2) | 2 2 (11.1) |
| Nausea | | | 2 2 (22.2) | 2 2 (11.1) |
| Diarrhoea | 1 1 (16.7) | | 1 1 (11.1) | 1 1 (5.6) |
| Dyspepsia | | | 1 1 (11.1) | 1 1 (5.6) |
| GENERAL DISORDERS AND ADMINISTRATION SITE CONDITIONS | 4 2 (33.3) | 5 4 (44.4) | 2 1 (11.1) | 7 5 (27.8) |
| Catheter Site Pain | 4 2 (33.3) | | | |
| Catheter Site Haematoma | | 1 1 (11.1) | | 1 1 (5.6) |
| Chest Discomfort | | 1 1 (11.1) | | 1 1 (5.6) |
| Fatigue | | | 1 1 (11.1) | 1 1 (5.6) |
| Feeling Hot | | | 1 1 (11.1) | 1 1 (5.6) |
| Medical Device Site Erythema | | 1 1 (11.1) | | 1 1 (5.6) |
| Medical Device Site Irritation | | 1 1 (11.1) | | 1 1 (5.6) |
| Vessel Puncture Site Haematoma | | 1 1 (11.1) | | 1 1 (5.6) |
| INFECTIONS AND INFESTATIONS | 1 1 (16.7) | | 1 1 (11.1) | 1 1 (5.6) |
| Nasopharyngitis | 1 1 (16.7) | | 1 1 (11.1) | 1 1 (5.6) |
| MUSCULOSKELETAL AND CONNECTIVE TISSUE DISORDERS | 2 2 (33.3) | 1 1 (11.1) | 6 4 (44.4) | 7 5 (27.8) |
| Musculoskeletal Stiffness | 2 2 (33.3) | | | |
| Myalgia | | 1 1 (11.1) | 1 1 (11.1) | 2 2 (11.1) |
| Muscle Twitching | | | 1 1 (11.1) | 1 1 (5.6) |
| Muscular Weakness | | | 1 1 (11.1) | 1 1 (5.6) |
| Musculoskeletal Pain | | | 1 1 (11.1) | 1 1 (5.6) |
| Neck Pain | | | 1 1 (11.1) | 1 1 (5.6) |
| Pain In Extremity | | | 1 1 (11.1) | 1 1 (5.6) |

FIG. 49B

| SYSTEM ORGAN CLASS/Preferred Term | IMB-1018972 q12h Placebo Fed (Pooled) (N=6) E n (%) | 150 mg q12h IMB-1018972 Fed (N=9) E n (%) | 50 mg q12h IMB-1018972 Fed (N=9) E n (%) | Total IMB-1018972 (N=18) E n (%) |
|---|---|---|---|---|
| NERVOUS SYSTEM DISORDERS | 3 2 (33.3) | 1 1 (11.1) | 6 3 (33.3) | 7 4 (22.2) |
| Dizziness | | 1 1 (11.1) | 1 1 (11.1) | 2 2 (11.1) |
| Headache | 3 2 (33.3) | | 1 1 (11.1) | 1 1 (5.6) |
| Hypoaesthesia | | | 2 1 (11.1) | 2 1 (5.6) |
| Myoclonus | | | 1 1 (11.1) | 1 1 (5.6) |
| Paraesthesia | | | 1 1 (11.1) | 1 1 (5.6) |
| REPRODUCTIVE SYSTEM AND BREAST DISORDERS | 1 1 (16.7) | | | |
| Dysmenorrhoea | 1 1 (16.7)* | | | |
| RESPIRATORY, THORACIC AND MEDIASTINAL DISORDERS | 2 2 (33.3) | | | |
| Oropharyngeal Pain | 2 2 (33.3) | | | |
| SKIN AND SUBCUTANEOUS TISSUE DISORDERS | 1 1 (16.7) | | | |
| Dermatitis Contact | 1 1 (16.7) | | | |
| VASCULAR DISORDERS | | 7 6 (66.7) | | 7 6 (33.3) |
| Flushing | | 7 6 (66.7) | | 7 6 (33.3) |

%=number of subjects (n) as a percentage of number of subjects (N) per treatment; AE=adverse event; E=number of AEs; MAD=multiple ascending dose; MedDRA=Medical Dictionary for Regulatory Activities; N=number of subjects exposed; n=number of subjects that experienced the AE; q12h=every 12 hours; TEAE=treatment-emergent adverse event
*: No distinction between gender is made
Adverse events were classified according to MedDRA 22.0
Subjects were counted once, per preferred term, for multiple occurrences of a specific MedDRA term

FIG. 50

| Treatment | All TEAEs | | | | Related TEAEs | | | | Not Related TEAEs | | |
|---|---|---|---|---|---|---|---|---|---|---|---|
| | All severities E n (%) | Mild E n (%) | Moderate E n (%) | All severities E n (%) | Mild E n (%) | Moderate E n (%) | All severities E n (%) | Mild E n (%) | Moderate E n (%) |
| IMB-1018972 Placebo (Pooled) (N=8) | 3 2 (25.0) | 3 2 (25.0) | | | | | 3 2 (25.0) | 3 2 (25.0) | |
| 50 mg IMB-1018972 Fasted (N=6) | 3 3 (50.0) | 3 3 (50.0) | | | | | 3 3 (50.0) | 3 3 (50.0) | |
| 150 mg IMB-1018972 Fasted (N=6) | 5 3 (50.0) | 5 3 (50.0) | | | | | 5 3 (50.0) | 5 3 (50.0) | |
| 400 mg IMB-1018972 Fasted (N=6) | 16 6 (100) | 9 5 (83.3) | 7 4 (66.7) | 10 4 (66.7) | 3 2 (33.3) | 7 4 (66.7) | 6 3 (50.0) | 6 3 (50.0) | |
| 150 mg IMB-1018972 Fasted (Fasted-fed group) (N=6) | 17 4 (66.7) | 15 4 (66.7) | 2 2 (33.3) | 9 3 (50.0) | 8 2 (33.3) | 1 1 (16.7) | 8 4 (66.7) | 7 4 (66.7) | 1 1 (16.7) |
| 150 mg IMB-1018972 Fed (Fasted-fed group) (N=5) | 4 1 (20.0) | 2 1 (20.0) | 2 1 (20.0) | 2 1 (20.0) | 2 1 (20.0) | | 2 1 (20.0) | | 2 1 (20.0) |
| 35 mg Trimetazidine Fasted (N=8) | 4 3 (37.5) | 4 3 (37.5) | | | | | 4 3 (37.5) | 4 3 (37.5) | |
| Total IMB-1018972 (N=24) | 45 16 (66.7) | 34 15 (62.5) | 11 7 (29.2) | 21 7 (29.2) | 13 4 (16.7) | 8 5 (20.8) | 24 13 (54.2) | 21 13 (54.2) | 3 2 (8.3) |

%=number of subjects (n) as a percentage of number of subjects (N) per treatment; AE=adverse event; E=number of AEs; FE=food effect; N=number of subjects exposed; n=number of subjects that experienced the AE; SAD=single ascending dose; TEAE=treatment-emergent adverse event Adverse events that were assessed as possibly, likely, or definitely were considered related to the study drug whereas AEs that were assessed as none or unlikely were considered not related to the study drug Subjects were counted once, per preferred term, for multiple occurrences of a specific MedDRA term

FIG. 51

| Treatment | All TEAEs | | | Related TEAEs | | | Not Related TEAEs | | |
|---|---|---|---|---|---|---|---|---|---|
| | All severities E n (%) | Mild E n (%) | Moderate E n (%) | All severities E n (%) | Mild E n (%) | Moderate E n (%) | All severities E n (%) | Mild E n (%) | Moderate E n (%) |
| IMB-1018972 q12h Placebo Fed (Pooled) (N=6) | 17 5 (83.3) | 17 5 (83.3) | | | | | 17 5 (83.3) | 17 5 (83.3) | |
| 150 mg q12h IMB-1018972 Fed (N=9) | 14 7 (77.8) | 14 7 (77.8) | | 7 6 (66.7) | 7 6 (66.7) | | 7 4 (44.4) | 7 4 (44.4) | |
| 50 mg q12h IMB-1018972 Fed (N=9) | 21 7 (77.8) | 21 7 (77.8) | | | | | 21 7 (77.8) | 21 7 (77.8) | |
| Total IMB-1018972 (N=18) | 35 14 (77.8) | 35 14 (77.8) | | 7 6 (33.3) | 7 6 (33.3) | | 28 11 (61.1) | 28 11 (61.1) | |

%=number of subjects (n) as a percentage of number of subjects (N) per treatment; AE=adverse event; E=number of AEs; MAD=multiple ascending dose; N=number of subjects exposed; n=number of subjects that experienced the AE; q12h=every 12 hours; TEAE=treatment-emergent adverse event
Adverse events that were assessed as possibly, likely, or definitely were considered related to the study drug whereas AEs that were assessed as none or unlikely were considered not related to the study drug
Subjects were counted once, per preferred term, for multiple occurrences of a specific MedDRA term

FIG. 52

| Visit | Screening | Pre-treatment | | Assessment Period Treatment | | | | | | | | | | | | | | Posttreatment | | | Follow-up |
|---|---|---|---|---|---|---|---|---|---|---|---|---|---|---|---|---|---|---|---|---|---|
| Study Day | -35 to -1 | -1 | 1 (Pre-dose) | 1 | 2 | 3 | 4 | 5 | 6 | 7 | 8 | 9 | 10 | 11 | 12 | 13 | 14 | 15 | 16 | 23 to 30 (7 to 14 days after the last PK blood sample) |
| Confinement | | X | X | X | X | X | X | X | X | X | X | X | X | X | X | X | X | X | X | |
| Ambulatory | X | | | | | | | | | | | | | | | | | | | | X |
| Admission | | X | | | | | | | | | | | | | | | | | | | |
| Discharge | | | | | | | | | | | | | | | | | | | | X | |
| Informed Consent | X | | | | | | | | | | | | | | | | | | | | |
| Medical History | X | | | | | | | | | | | | | | | | | | | | |
| Demographics | X | | | | | | | | | | | | | | | | | | | | |
| Physical Examination[c] | X | X | | | | | | | | | | | | | | | | | | | X |
| Height, Weight, and BMI Calculation | X | | | | | | | | | | | | | | | | | | | | |
| Serology (HBsAg, anti-HCV, and anti-HIV 1 and 2) | X | | | | | | | | | | | | | | | | | | | | |
| Drug and Alcohol Screen | X | | | | | | | | | | | | | | | | | | | | |
| Serum Pregnancy Test (Females Only) | X | | | | | | | | | | | | | | | | | | | | |
| Clinical Laboratory[b] | X | X | | X | | | | X | | | X | | | X | | X | | X | | | X |
| 12-Lead ECG[d] | X | X | | X | X | X | X | X | X | X | X | X | X | X | X | X | X | X | X | X | X |
| Vital Signs[d] | X | X | | X | X | X | X | X | X | X | X | X | X | X | X | X | X | X | X | X | X |
| Eligibility Check | X | X | | | | | | | | | | | | | | | | | | | |
| Randomization | | X | | | | | | | | | | | | | | | | | | | |
| Study Drug Administration[e] | | | X | X | X | X | X | X | X | X | X | X | X | X | | | | | | | |
| Blood Sampling for PK[f] | | | | X | X | X | X | X | X | X | X | X | X | X | X | X | X | X | X | X | X |
| Previous and Concomitant Medication | X | X | | X | X | X | X | X | X | X | X | X | X | X | X | X | X | X | X | X | X |
| Adverse Event Monitoring[g] | | X | | X | X | X | X | X | X | X | X | X | X | X | X | X | X | X | X | X | X |
| Blood Sampling for Genotyping[h] | | | X | | | | | | | | | | | | | | | | | | |

BMI=body mass index; ECG=electrocardiogram; HBsAg=hepatitis B surface antigen; HCV=hepatitis C virus; MR=modified release; PK=pharmacokinetic(s)

FIG. 53

| Visit | Screening | Pre-treatment | | Assessment Period - Treatment | | | | | Post-treatment | | Follow-up |
|---|---|---|---|---|---|---|---|---|---|---|---|
| Study Day | -35 to -1 | -1 | 1 (Predose) | 1 | 2 | 3 | 4 | 5 | 6 | 7 | Day 14 ± 1 day (6 to 8 days after the last PK blood sample) |
| Confinement | | X | X | | | | | | | | |
| Ambulatory | | | | | | | | | X | | X |
| Admission | | X | | | | | | | | | |
| Discharge | | | | | | | | | | X | |
| Informed Consent | X | | | | | | | | | | |
| Medical History | X | | | | | | | | | | |
| Demographics | X | | | | | | | | | | |
| Physical Examination[a] | X | X | | | | | | | | | X |
| Height, Weight, and BMI Calculation | X | | | | | | | | | | |
| Serology (HBsAg, anti-HCV, and anti-HIV 1 and 2) | X | | | | | | | | | | |
| Drug and Alcohol Screen | X | X | | | | | | | | | |
| Serum Pregnancy Test (Females Only) | X | X | | | | | | | | | |
| Clinical Laboratory[b] | X | X | | | | | | | X | | X |
| 12-Lead ECG[c] | X | X | | X | X | X | X | X | X | X | X |
| Vital Signs[d] | X | X | | X | X | X | X | X | X | X | X |
| Eligibility Check | X | X | | | | | | | | | |
| Randomization | | X | | | | | | | | | |
| Study Drug Administration[e] | | | | X | | | | | | | |
| Blood Sampling for PK Profiles[f] | | | | X | X | X | X | X | X | X | |
| Previous and Concomitant Medication | X | X | | X | X | X | X | X | X | X | X |
| Adverse Event Monitoring[g] | | X | | X | X | X | X | X | X | X | X |
| Blood Sampling for Genotyping[h] | | X | | | | | | | | | |

BMI=body mass index; ECG=electrocardiogram; HBsAg=hepatitis B surface antigen; HCV=hepatitis C virus; MR=modified release; PK=pharmacokinetic(s)

FIG. 54

| | MR IMB-1018972*<br>(N=12)<br>n (%) |
|---|---|
| Randomized | 12 (100%) |
| Safety Set | 12 (100%) |
| Pharmacokinetic Set | 12 (100%) |
| Completed Study | 11 (91.7%) |
| Discontinued Study | 1 (8.3)# |
| Reason for Discontinuation | |
| Adverse Event | 1 (8.3) |

AE=adverse event; MR=modified release; N=total number of subjects; n=number of subjects

*: Day 1: 50 mg 8h fasted, Day 4: 50 mg 4h fasted, Day 7: 200 mg 8h fasted, Day 10: 200 mg 4h fasted, Day 13: 200 mg 8h fed

: One subject discontinued due to an AE and did not receive the last dose on Day 13.

Notes: The percentage is calculated as (n/N)*100%

FIG. 55

| | 200 mg 8-hour q12h MR IMB-1018972 Fed (N=12) n (%) |
|---|---|
| Randomized | 12 (100%) |
| Safety Set | 12 (100%) |
| Pharmacokinetic Set | 12 (100%) |
| Completed Study | 12 (100%) |

MR=modified release; N=total number of subjects; n=number of subjects
Notes: The percentage is calculated as (n/N)*100%

FIG. 56

| Parameter | Statistic/Category | MR IMB-1018972* (N=12) |
|---|---|---|
| Age (years) | Mean (SD) | 32 (16) |
| | Median | 26 |
| | Min - Max | 19 - 62 |
| Weight (kg) | Mean (SD) | 80.5 (14.1) |
| | Median | 82.1 |
| | Min - Max | 59.3 - 110.4 |
| Height (cm) | Mean (SD) | 177 (14) |
| | Median | 173 |
| | Min - Max | 161 - 204 |
| BMI (kg/m²) | Mean (SD) | 25.8 (3.6) |
| | Median | 25.2 |
| | Min - Max | 21.5 - 31.0 |
| Gender, n (%) | Female | 6 (50.0%) |
| | Male | 6 (50.0%) |
| Ethnicity, n (%) | Hispanic or Latino | 1 (8.3%) |
| | Not Hispanic or Latino | 11 (91.7%) |
| Race, n (%) | Black or African American | 1 (8.3%) |
| | White | 11 (91.7%) |

BMI=body mass index; Max=maximum; Min=minimum; MR=modified release; N=number of subjects
*: Day 1: 50 mg 8h fasted, Day 4: 50 mg 4h fasted, Day 7: 200 mg 8h fasted, Day 10: 200 mg 4h fasted, Day 13: 200 mg 8h fed
Age, height, weight, and BMI were determined at screening
The summary of the PK set was identical to that of the safety set

FIG. 57

| Parameter | Statistic/Category | 200 mg 8-hour q12h MR IMB-1018972 Fed (N=12) |
|---|---|---|
| Age (years) | Mean (SD) | 45 (15) |
| | Median | 42 |
| | Min - Max | 24 - 64 |
| Weight (kg) | Mean (SD) | 76.1 (10.7) |
| | Median | 74.4 |
| | Min - Max | 59.9 - 96.6 |
| Height (cm) | Mean (SD) | 174 (5) |
| | Median | 175 |
| | Min - Max | 163 - 182 |
| BMI (kg/m$^2$) | Mean (SD) | 25.1 (2.7) |
| | Median | 25.6 |
| | Min - Max | 20.0 - 29.2 |
| Gender, n (%) | Female | 6 (50.0%) |
| | Male | 6 (50.0%) |
| Ethnicity, n (%) | Not Hispanic or Latino | 12 (100%) |
| Race, n (%) | Asian | 1 (8.3%) |
| | White | 11 (91.7%) |

BMI=body mass index; Max=maximum; Min=minimum; MR=modified release; N=number of subjects
Age, height, weight, and BMI were determined at screening
The summary of the PK set was identical to that of the safety set

FIG. 58

| Subjects | Treatments | Duration | Total exposure to IMB-1018972 per subject | Number of subjects exposed |
|---|---|---|---|---|
| 501, 502, 503, 504, 506, 507, 508, 509, 510, 511, 512 | Day 1: 50 mg 8-hour MR formulation of IMB-1018972 fasted<br>Day 4: 50 mg 4-hour MR formulation of IMB-1018972 fasted<br>Day 7: 200 mg 8-hour MR formulation of IMB-1018972 fasted<br>Day 10: 200 mg 4-hour MR formulation of IMB-1018972 fasted<br>Day 13: 200 mg 8-hour MR formulation of IMB-1018972 fed | 13 days/ 5 doses | 700 mg | N=11 |
| 505 | Day 1: 50 mg 8-hour MR formulation of IMB-1018972 fasted<br>Day 4: 50 mg 4-hour MR formulation of IMB-1018972 fasted<br>Day 7: 200 mg 8-hour MR formulation of IMB-1018972 fasted<br>Day 10: 200 mg 4-hour MR formulation of IMB-1018972 fasted | 10 days/ 4 doses | 500 mg | N=1 |

MR=modified release; N=number of subjects exposed

FIG. 59

Table 21 Extent of Exposure – Multiple-Dose MR Part (Safety Set)

| Subjects | Treatments | Duration | Total exposure to IMB-1018972 per subject | Number of subjects exposed |
|---|---|---|---|---|
| 513, 514, 515, 516, 517, 518, 519, 520, 521, 522, 523, 524 | 200 mg 8-hour MR formulation of IMB-1018972 q12h fed | 5 days/ 9 doses | 1800 mg | N=12 |

MR=modified release; N=number of subjects exposed

FIG. 66

Table 28 Summary Statistics (Geometric Mean [Range]) of IMB-1028814, Trimetazidine, and IMB-1028814 + Trimetazidine Pla Pharmacokinetic Parameters - Single-Dose MR Part (PK Set)

| Parameter | 50 mg 8-hour MR IMB-1018972 Fasted (N=12) | 50 mg 4-hour MR IMB-1018972 Fasted (N=12) | 200 mg 8-hour MR IMB-1018972 Fasted (N=12) | 200 mg 4-hour MR IMB-1018972 Fasted (N=12) | 200 mg 8-hour MR IMB-1018972 Fed (N=11) |
|---|---|---|---|---|---|
| | | | IMB-1028814 | | |
| $C_{max}$ (ng/mL) | 26.7 (14.8 - 53.3) | 41.0 (16.1 - 82.7) | 205 (91.9 - 379) | 303 (163 - 538) | 302 (121 - 462) |
| $t_{max}$ (h) | 2.00 (1.00 - 10.00) | 5.00 (4.00 - 6.00) | 2.00 (1.00 - 4.00) | 3.00 (2.00 - 4.00) | 3.00 (2.00 - 5.00) |
| $AUC_{0-t}$ (ng·h/mL) | 268 (110 - 577) | 360 (178 - 657) | 1488 (635 - 2703) | 1410 (549 - 2518) | 1797 (728 - 3058) |
| $AUC_{0-\infty}$ (ng·h/mL) | 279 (115 - 583) | 369 (183 - 665) | 1561 (646 - 2711) | 1421 (552 - 2522) | 1836 (732 - 3061) |
| $t_{1/2}$ (h) | 4.27 (2.97 - 8.16) | 3.35 (2.54 - 5.65) | 4.03 (3.30 - 7.25) | 3.46 (1.90 - 14.8) | 4.50 (2.68 - 22.9) |
| CL/F (L/h) | 179 (85.7 - 434) | 135 (75.2 - 273) | 133 (73.8 - 310) | 141 (79.3 - 362) | 111 (65.3 - 273) |
| $V_z/F$ (L) | 1102 (475 - 2823) | 654 (357 - 1642) | 775 (394 - 1720) | 703 (310 - 1966) | 718 (363 - 2583) |
| | | | Trimetazidine | | |
| $C_{max}$ (nmol/L) | 16.1 (7.63 - 32.7) | 20.2 (7.81 - 47.0) | 84.0 (28.5 - 201) | 111 (30.2 - 265) | 93.1 (29.4 - 219) |
| $t_{max}$ (h) | 8.00 (5.00 - 12.02) | 6.00 (4.00 - 10.00) | 5.00 (1.05 - 12.80) | 3.00 (2.00 - 5.00) | 5.00 (4.00 - 12.00) |
| $AUC_{0-t}$ (ng·h/mL) | 333 (154 - 835) | 379 (168 - 795) | 1512 (635 - 3963) | 1447 (624 - 3385) | 1527 (596 - 3482) |
| $AUC_{0-\infty}$ (ng·h/mL) | 351 (164 - 873) | 394 (179 - 810) | 1565 (683 - 4037) | 1488 (641 - 3447) | 1549 (606 - 3497) |
| $t_{1/2}$ (h) | 9.35 (7.02 - 19.3) | 8.13 (5.81 - 13.4) | 8.44 (6.45 - 15.4) | 8.11 (6.23 - 15.2) | 9.23 (6.27 - 15.0) |
| | | | IMB-1028814 + Trimetazidine | | |
| $C_{max}$ (nmol/L) | 146 (92.5 - 206) | 218 (110 - 331) | 974 (644 - 1440) | 1455 (924 - 2030) | 1342 (806 - 1770) |
| $t_{max}$ (h) | 5.00 (2.00 - 10.00) | 5.00 (4.00 - 6.00) | 2.52 (1.05 - 5.00) | 3.00 (2.00 - 4.00) | 4.00 (2.00 - 5.00) |
| $AUC_{0-t}$ (nmol·h/L) | 2263 (1032 - 3784) | 2774 (1833 - 4045) | 11292 (6200 - 18222) | 10769 (7113 - 15875) | 12454 (8739 - 17263) |
| $AUC_{0-\infty}$ (nmol·h/L) | 2320 (1068 - 3846) | 2822 (1963 - 4286) | 11462 (6345 - 18494) | 10926 (7156 - 16110) | 12537 (8781 - 17319) |
| $t_{1/2}$ (h) | 7.96 (6.20 - 13.9) | 6.95 (5.00 - 11.1) | 7.31 (5.94 - 12.0) | 7.71 (5.65 - 13.5) | 8.86 (5.47 - 14.6) |

MR=modified release; N=number of subjects; PK=pharmacokinetic
For $t_{max}$ the median (range) is presented instead of geometric mean (range)

FIG. 67

| Analyte | PK Parameter | Test (200 mg 8-hour MR IMB-1018972 fed) | Reference (200 mg 8-hour MR IMB-1018972 fasted) | Estimate | Ratio Test/Reference | |
|---|---|---|---|---|---|---|
| | | | | | Lower | Upper |
| IMB-1028814 | $C_{max}$ (ng/mL) | 292 | 205 | 1.4239 | 1.2435 | 1.6306 |
| | $AUC_{0-t}$ (ng·h/mL) | 1731 | 1488 | 1.1636 | 1.0539 | 1.2848 |
| | $AUC_{0-inf}$ (ng·h/mL) | 1744 | 1501 | 1.1619 | 1.0512 | 1.2844 |
| Trimetazidine | $C_{max}$ (ng/mL) | 92.2 | 84.0 | 1.0978 | 0.9946 | 1.2116 |
| | $AUC_{0-t}$ (ng·h/mL) | 1503 | 1512 | 0.9941 | 0.9076 | 1.0887 |
| | $AUC_{0-inf}$ (ng·h/mL) | 1521 | 1565 | 0.9716 | 0.8842 | 1.0676 |

ANOVA=analysis of variance; PK=pharmacokinetic
Note: Model: ANOVA with a fixed effect for treatment (fed, fasted) and a random effect for subject

FIG. 80

| Day | Parameter | 200 mg 8-hour q12h MR IMB-1018972 Fed (N=12) |
|---|---|---|
| | IMB-1028814 | |
| 1 | $C_{max}$ (ng/mL) | 191 (82.3 - 341) |
| | $t_{max}$ (h) | 2.00 (0.50 - 5.00) |
| | $AUC_{0-\tau}$ (ng.h/mL) | 1203 (426 - 2097) |
| 5 | $C_{max}$ (ng/mL) | 213 (105 - 375) |
| | $C_{min}$ (ng/mL) | 41.4 (13.2 - 109) |
| | $t_{max}$ (h) | 2.00 (0.55 - 5.00) |
| | $AUC_{0-\tau}$ (ng.h/mL) | 1471 (634 - 2574) |
| | $t_{1/2}$ (h) | 3.85 (2.73 - 7.01) |
| | $R_{ac}$ | 1.22 (0.87 - 1.56) |
| | $CL_{ss}/F$ (L/h) | 136 (77.7 - 315) |
| | $V_z/F$ (L) | 756 (441 - 1512) |
| | Trimetazidine | |
| 1 | $C_{max}$ (ng/mL) | 75.5 (6.48 - 168) |
| | $t_{max}$ (h) | 5.50 (5.00 - 11.92) |
| | $AUC_{0-\tau}$ (ng.h/mL) | 707# (52.8 - 1497) |
| 5 | $C_{max}$ (ng/mL) | 146 (11.1 - 457) |
| | $C_{min}$ (ng/mL) | 92.0 (7.71 - 320) |
| | $t_{max}$ (h) | 5.00 (2.00 - 6.00) |
| | $AUC_{0-\tau}$ (ng.h/mL) | 1484 (113 - 4874) |
| | $t_{1/2}$ (h) | 9.52 (7.13 - 15.0) |
| | $R_{ac}$ | 2.28# (1.59 - 3.26) |
| | IMB-1028814 + Trimetazidine | |
| 1 | $C_{max}$ (nmol/L) | 948 (660 - 1540) |
| | $t_{max}$ (h) | 5.00 (0.50 - 5.00) |
| | $AUC_{0-\tau}$ (nmol.h/L) | 7226 (5252 - 10741) |
| 5 | $C_{max}$ (nmol/L) | 1386 (994 - 2150) |
| | $C_{min}$ (nmol/L) | 583 (381 - 1290) |
| | $t_{max}$ (h) | 4.00 (1.00 - 5.00) |
| | $AUC_{0-\tau}$ (nmol.h/L) | 12021 (7793 - 21671) |
| | $t_{1/2}$ (h) | 8.64 (6.94 - 14.6) |
| | $R_{ac}$ | 1.66 (1.20 - 2.54) |

MR=modified release; N=number of subjects; PK=pharmacokinetic
: N=11 subjects
For $t_{max}$ the median (range) is presented instead of geometric mean (range)

FIG. 81A

| SYSTEM ORGAN CLASS/ Preferred Term | 50 mg 8-hour MR IMB-1018972 Fasted (N=12) E n (%) | 50 mg 4-hour MR IMB-1018972 Fasted (N=12) E n (%) | 200 mg 8-hour MR IMB-1018972 Fasted (N=12) E n (%) | 200 mg 4-hour MR IMB-1018972 Fasted (N=12) E n (%) | 200 mg 8-hour MR IMB-1018972 Fed (N=11) E n (%) | Total MR IMB-1018972 (N=12) E n (%) |
|---|---|---|---|---|---|---|
| Any TEAE | 6 4 (33.3) | 9 6 (50.0) | 6 5 (41.7) | 11 8 (66.7) | 5 2 (18.2) | 37 10 (83.3) |
| EYE DISORDERS | | | | | | 1 1 (8.3) |
| Eyelid Irritation | | | | | 1 1 (9.1) | 1 1 (8.3) |
| GASTROINTESTINAL DISORDERS | | | 1 1 (8.3) | 3 3 (25.0) | 1 1 (9.1) | 5 4 (33.3) |
| Abdominal Pain | | | | 1 1 (8.3) | | 2 2 (16.7) |
| Abdominal Pain Upper | | | 1 1 (8.3) | | 1 1 (9.1) | 1 1 (8.3) |
| Aphthous Ulcer | | | | 1 1 (8.3) | | 1 1 (8.3) |
| Diarrhoea | | | | 1 1 (8.3) | | 1 1 (8.3) |
| GENERAL DISORDERS AND ADMINISTRATION SITE CONDITIONS | 1 1 (8.3) | 3 3 (25.0) | 2 2 (16.7) | 3 3 (25.0) | 2 2 (18.2) | 11 7 (58.3) |
| Catheter Site Related Reaction | | | 2 2 (16.7) | 2 2 (16.7) | | 5 4 (33.3) |
| Catheter Site Haematoma | | | | | | 2 2 (16.7) |
| Catheter Site Pain | | 1 1 (8.3) | | | | 1 1 (8.3) |
| Malaise | | 1 1 (8.3) | | | 1 1 (9.1) | 1 1 (8.3) |
| Medical Device Site Dryness | | 1 1 (8.3) | | | 1 1 (9.1) | 1 1 (8.3) |
| Medical Device Site Irritation | | | | 1 1 (8.3) | | 1 1 (8.3) |
| INFECTIONS AND INFESTATIONS | | | | | 1 1 (9.1) | 1 1 (8.3) |
| Nasopharyngitis | | | | | 1 1 (9.1) | 1 1 (8.3) |
| INJURY, POISONING AND PROCEDURAL COMPLICATIONS | | 1 1 (8.3) | | | | 1 1 (8.3) |
| Arthropod Bite | | 1 1 (8.3) | | | | 1 1 (8.3) |
| INVESTIGATIONS | | 1 1 (8.3) | | | | 1 1 (8.3) |
| Alanine Aminotransferase Increased | | 1 1 (8.3) | | | | 1 1 (8.3) |

FIG. 81B

| SYSTEM ORGAN CLASS/ Preferred Term | 50 mg 8-hour MR IMB-1018972 Fasted (N=12) E n (%) | 50 mg 4-hour MR IMB-1018972 Fasted (N=12) E n (%) | 200 mg 8-hour MR IMB-1018972 Fasted (N=12) E n (%) | 200 mg 4-hour MR IMB-1018972 Fasted (N=12) E n (%) | 200 mg 8-hour MR IMB-1018972 Fed (N=11) E n (%) | Total MR IMB-1018972 (N=12) E n (%) |
|---|---|---|---|---|---|---|
| MUSCULOSKELETAL AND CONNECTIVE TISSUE DISORDERS | 1 1 (8.3) | | | | | 1 1 (8.3) |
| Back Pain | 1 1 (8.3) | | | | | 1 1 (8.3) |
| NERVOUS SYSTEM DISORDERS | 1 1 (8.3) | 2 2 (16.7) | 1 1 (8.3) | 4 4 (33.3) | | 8 7 (58.3) |
| Headache | 1 1 (8.3) | 2 2 (16.7) | | 3 3 (25.0) | | 6 5 (41.7) |
| Dizziness | | | 1 1 (8.3) | 1 1 (8.3) | | 2 2 (16.7) |
| RENAL AND URINARY DISORDERS | 1 1 (8.3) | 2 2 (16.7) | 1 1 (8.3) | 1 1 (8.3) | | 5 2 (16.7) |
| Pollakiuria | 1 1 (8.3) | 2 2 (16.7) | 1 1 (8.3) | 1 1 (8.3) | | 5 2 (16.7) |
| SKIN AND SUBCUTANEOUS TISSUE DISORDERS | 2 1 (8.3) | | 1 1 (8.3) | | | 3 2 (16.7) |
| Dermatitis Contact | 1 1 (8.3) | | | | | 2 2 (16.7) |
| Skin Exfoliation | 1 1 (8.3) | | | | | 1 1 (8.3) |

%=number of subjects (n) as a percentage of number of subjects (N) per treatment; AE=adverse event; E=number of AEs; MedDRA=Medical Dictionary for Regulatory Activities; MR=modified release; N=number of subjects exposed, n=number of subjects that experienced the AE; TEAE=treatment-emergent adverse event
Adverse events were classified according to MedDRA 22.0
Subjects were counted once, per preferred term, for multiple occurrences of a specific MedDRA term

FIG. 82

| SYSTEM ORGAN CLASS/ Preferred Term | 200 mg 8-hour q12h MR IMB-1018972 Fed (N=12) E n (%) |
|---|---|
| Any TEAE | 40 12 (100) |
| EYE DISORDERS | 2 2 (16.7) |
| Eye Pain | 1 1 (8.3) |
| Ocular Discomfort | 1 1 (8.3) |
| GASTROINTESTINAL DISORDERS | 9 5 (41.7) |
| Abdominal Pain | 2 2 (16.7) |
| Diarrhoea | 1 1 (8.3) |
| Dyspepsia | 1 1 (8.3) |
| Faeces Pale | 1 1 (8.3) |
| Flatulence | 1 1 (8.3) |
| Gingival Pain | 1 1 (8.3) |
| Oral Discomfort | 1 1 (8.3) |
| Toothache | 1 1 (8.3) |
| GENERAL DISORDERS AND ADMINISTRATION SITE CONDITIONS | 4 4 (33.3) |
| Catheter Site Pain | 1 1 (8.3) |
| Influenza Like Illness | 1 1 (8.3) |
| Medical Device Site Irritation | 1 1 (8.3) |
| Thirst | 1 1 (8.3) |
| INFECTIONS AND INFESTATIONS | 1 1 (8.3) |
| Nasopharyngitis | 1 1 (8.3) |
| INJURY, POISONING AND PROCEDURAL COMPLICATIONS | 1 1 (8.3) |
| Arthropod Bite | 1 1 (8.3) |
| MUSCULOSKELETAL AND CONNECTIVE TISSUE DISORDERS | 4 4 (33.3) |
| Myalgia | 2 2 (16.7) |
| Neck Pain | 1 1 (8.3) |
| Pain In Extremity | 1 1 (8.3) |
| NERVOUS SYSTEM DISORDERS | 9 7 (58.3) |
| Headache | 6 5 (41.7) |
| Dizziness | 2 2 (16.7) |
| Dizziness Postural | 1 1 (8.3) |
| RENAL AND URINARY DISORDERS | 4 4 (33.3) |
| Pollakiuria | 4 4 (33.3) |
| RESPIRATORY, THORACIC AND MEDIASTINAL DISORDERS | 1 1 (8.3) |
| Oropharyngeal Pain | 1 1 (8.3) |
| SKIN AND SUBCUTANEOUS TISSUE DISORDERS | 2 2 (16.7) |
| Dermatitis Contact | 1 1 (8.3) |
| Erythema | 1 1 (8.3) |
| VASCULAR DISORDERS | 3 2 (16.7) |
| Flushing | 2 2 (16.7) |
| Haematoma | 1 1 (8.3) |

%=number of subjects (n) as a percentage of number of subjects (N) per treatment; AE=adverse event; E=number of AEs; MedDRA=Medical Dictionary for Regulatory Activities; MR=modified release; N=number of subjects exposed, n=number of subjects that experienced the AE; q12h=every 12 hours; TEAE=treatment-emergent adverse event
Adverse events were classified according to MedDRA 22.0
Subjects were counted once, per preferred term, for multiple occurrences of a specific MedDRA term

FIG. 83

| Treatment | All TEAEs | | | Related TEAEs | | | Not Related TEAEs | | |
|---|---|---|---|---|---|---|---|---|---|
| | All severities E n (%) | Mild E n (%) | Moderate E n (%) | All severities E n (%) | Mild E n (%) | Moderate E n (%) | All severities E n (%) | Mild E n (%) | Moderate E n (%) |
| 50 mg 8-hour MR IMB-1018972 Fasted (N=12) | 6 4 (33.3) | 6 4 (33.3) | | 2 2 (16.7) | 2 2 (16.7) | | 4 2 (16.7) | 4 2 (16.7) | |
| 50 mg 4-hour MR IMB-1018972 Fasted (N=12) | 9 6 (50.0) | 8 5 (41.7) | 1 1 (8.3) | 3 3 (25.0) | 2 2 (16.7) | 1 1 (8.3) | 6 5 (41.7) | 6 5 (41.7) | |
| 200 mg 8-hour MR IMB-1018972 Fasted (N=12) | 6 5 (41.7) | 6 5 (41.7) | | 1 1 (8.3) | 1 1 (8.3) | | 5 4 (33.3) | 5 4 (33.3) | |
| 200 mg 4-hour MR IMB-1018972 Fasted (N=12) | 11 8 (66.7) | 11 8 (66.7) | | 1 1 (8.3) | 1 1 (8.3) | | 10 8 (66.7) | 10 8 (66.7) | |
| 200 mg 8-hour MR IMB-1018972 Fed (N=11) | 5 2 (18.2) | 5 2 (18.2) | | | | | 5 2 (18.2) | 5 2 (18.2) | |
| Total MR IMB-1018972 (N=12) | 37 10 (83.3) | 36 10 (83.3) | 1 1 (8.3) | 7 4 (33.3) | 6 3 (25.0) | 1 1 (8.3) | 30 10 (83.3) | 30 10 (83.3) | |

%=number of subjects (n) as a percentage of number of subjects (N) per treatment; AE=adverse event; E=number of AEs; MR=modified release; N=number of subjects exposed; n=number of subjects that experienced the AE; TEAE=treatment-emergent adverse event Adverse events that were assessed as possibly, likely, or definitely were considered related to the study drug whereas AEs that were assessed as none or unlikely were considered not related to the study drug Subjects were counted once, per preferred term, for multiple occurrences of a specific MedDRA term

FIG. 84

| Treatment | All TEAEs | | | Related TEAEs | | | Not Related TEAEs | | |
|---|---|---|---|---|---|---|---|---|---|
| | All severities E n (%) | Mild E n (%) | Moderate E n (%) | All severities E n (%) | Mild E n (%) | Moderate E n (%) | All severities E n (%) | Mild E n (%) | Moderate E n (%) |
| 200 mg 8-hour q12h MR IMB-1018972 Fed (N=12) | 40 12 (100) | 40 12 (100) | | 10 7 (58.3) | 10 7 (58.3) | | 30 9 (75.0) | 30 9 (75.0) | |

%=number of subjects (n) as a percentage of number of subjects (N) per treatment; AE=adverse event; E=number of AEs; MR=modified release; N=number of subjects exposed; n=number of subjects that experienced the AE; q12h=every 12 hours; TEAE=treatment-emergent adverse event Adverse events that were assessed as possibly, likely, or definitely were considered related to the study drug whereas AEs that were assessed as none or unlikely were considered not related to the study drug Subjects were counted once, per preferred term, for multiple occurrences of a specific MedDRA term

METHODS OF TREATING KIDNEY CONDITIONS USING MODIFIED FORMS OF TRIMETAZIDINE

CROSS-REFERENCE TO RELATED APPLICATIONS

This application is a continuation of U.S. application Ser. No. 17/735,594, filed May 3, 2022, which claims the benefit of, and priority to, U.S. Provisional Patent Application No. 63/183,303, filed May 3, 2021, the contents of each of which are incorporated herein by reference.

FIELD OF THE INVENTION

The invention relates to methods of treating kidney conditions using modified forms of trimetazidine.

BACKGROUND

Kidney conditions afflict millions of people worldwide. For example, about one in eight Americans has chronic kidney disease, and the incidence of chronic kidney disease is increasing over time. Other widespread kidney conditions include acute kidney disease, chronic kidney insufficiency, diabetic kidney, and diabetic nephropathy. The primary treatment for serious kidney conditions is dialysis, which imposes severe limitations on the patient's activities. Kidney transplantation is recommended for patients with end-stage kidney disease. However, the number of patients who need kidney transplants exceeds the organ supply, and many patients die while waiting for a transplant.

SUMMARY

The invention provides methods of treating kidney conditions using compositions that contain CV-8972. CV-8972, a modified form of trimetazidine, has the IUPAC name 2-[4-[(2,3,4-trimethoxyphenyl)methyl]piperazin-1-yl]ethyl pyridine-3-carboxylate and the following structure:

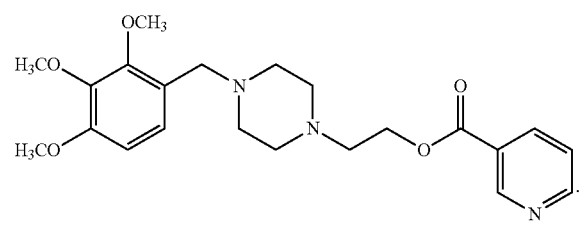 [SMILES: COc1ccc(CN2CCN(CCOC(=O)c3cccnc3)CC2)c(OC)c1OC]

The invention is based on the recognition that the kidney has a high energy demand and that CV-8972 stimulates production of ATP by multiple mechanisms. Therefore, by providing CV-8972 to patients, energy production in the kidney is increased. The methods of the invention are useful for treating a variety of kidney conditions, such as acute kidney disease, chronic kidney disease, chronic kidney insufficiency, diabetic kidney, or diabetic nephropathy.

In an aspect, the invention provides methods of increasing ATP production in a kidney of a subject by providing to a subject having a kidney condition a composition comprising a compound of formula (X):

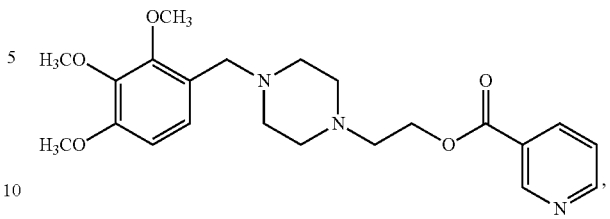

(X)

or a pharmaceutically acceptable salt thereof.

The kidney condition may be accumulation of mesangial matrix, acute interstitial nephritis, acute kidney disease, acute kidney injury (AKI), acute tubular necrosis (ATN), Alport syndrome, atherosclerosis, atherosclerotic renal artery stenosis, an autoimmune disorder, such us systemic lupus erythematosus, autosomal dominant polycystic kidney disease (ADPKD), benign prostatic hyperplasia, bladder stones, cancer, including cancer of the bladder, ureters, or prostate, cardiac surgery, cell apoptosis, chronic kidney disease, chronic kidney insufficiency, chronic tubulointerstitial nephritis, delayed graft function (DGF), including DGF-renal, diabetes, diabetic kidney, diabetic nephropathy, including type 1 diabetic nephropathy (T1D nephropathy), end-stage renal disease, Focal segmental glomerulosclerosis (FSGS), glomerular basement membrane thickening, glomerular hyperfiltration, glomerular and tubular epithelial hypertrophy, glomerulonephritis, glomerulosclerosis, heart failure, hemolytic-uremic syndrome, hypertension, IgA nephropathy (also called Berger's disease), infection, injury, ischemia, ischemia/reperfusion injury, ischemic nephropathy, kidney hypoxia, kidney stones, kidney transplantation, liver cirrhosis, methyl melonic acidosis (MMA), microalbuminuria, obstructed urinary catheter, proteinuria, reduced creatinine clearance, reduced glomerular filtration rate, reflux nephropathy, renal vein thrombosis, rhabdomyolysis, tumor lysis syndrome, vascular occlusion, or vasculitis.

The composition may be provided by any suitable route or mode of administration. The dose may be provided orally, intravenously, enterally, parenterally, dermally, buccally, topically, transdermally, by injection, subcutaneously, nasally, pulmonarily, or with or on an implantable medical device (e.g., stent or drug-eluting stent or balloon equivalents).

The composition may be provided in a single dose per day. The composition may be provided in multiple doses per day. The composition may be provided in 2, 3, 4, 5, 6, or more doses per day.

The composition may be provided to the subject to deliver a defined daily dose of the compound of formula (X). The dose may contain from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of the compound. The dose may contain about 10 mg, about 25 mg, about 50 mg, about 100 mg, about 200 mg, about 300 mg, or about 400 mg of the compound.

The composition may be formulated for immediate release of the compound of formula (X). The composition may be formulated for modified release of the compound of formula (X).

In another aspect, the invention provides methods of treating kidney conditions in a subject by providing to a subject having a kidney condition a composition comprising a compound of formula (X):

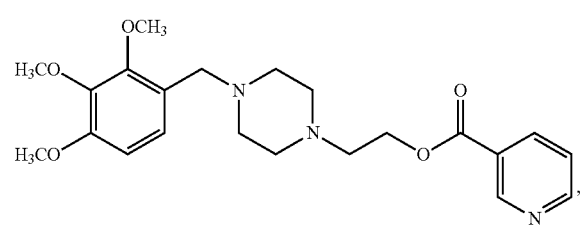

(X)

or a pharmaceutically acceptable salt thereof.

The kidney condition may be any of those described above.

The composition may be provided by any suitable route or mode of administration, such as any of those described above.

The composition may be provided in a single dose per day. The composition may be provided in multiple doses per day. The composition may be provided in 2, 3, 4, 5, 6, or more doses per day.

The composition may be provided to the subject to deliver a defined daily dose of the compound of formula (X), such as any of those described above.

The composition may be formulated for immediate release of the compound of formula (X). The composition may be formulated for modified release of the compound of formula (X).

BRIEF DESCRIPTION OF THE DRAWINGS

FIG. 2 is a table of the disposition of subjects of an FIH study of IMB-1018972.

FIG. 3 is a Schedule of Assessments for SAD part Group A5 of an FIE study of IMB-1018972.

FIG. 4 is a table of assessments given for the SAD part (and integrated FE arm) Groups A1 to A4 of an FIH study of IMB-1018972.

FIG. 5 is a table of assessments given for the MAD part of an FIH study of IMB-1018972.

FIG. 6 is a table of analysis data sets for the SAD Part (and integrated FE Arm) per dose level and total for IMB-1018972 of an FIH study of IMB-1018972.

FIG. 7 is a table of analysis data sets for the MAD Part per dose level and total for IMB-1018972 of an FIH study of IMB-1018972.

FIG. 8 is a table of a summary of demographic characteristics—SAD Part (and Integrated FE Arm) (Safety Set) of an FIH study of IMB-1018972.

FIG. 9 is a table of a summary of demographic characteristics—MAD Part (Safety Set) of an FIH study of IMB-1018972.

FIG. 10 is a table of the Extent of Exposure—SAD Part (and Integrated FE Arm) (Safety Set) of an FIH study of IMB-1018972.

FIG. 11 is a table of the Extent of Exposure—MAD Part of an FIE study of IMB-1018972.

FIG. 18 is a table of Summary Statistics (Geometric Mean [Range]) of IMB-1028814, Trimetazidine, and IMB-1028814+Trimetazidine Plasma Pharmacokinetic Parameters—SAD Part (PK Set) of an FIH study of IMB-1018972.

FIG. 19 is a table of Exploratory Analysis of Dose Proportionality for IMB-1028814 and Trimetazidine over the Dose Range of 50 mg to 400 mg IMB-1018972 under Faster Conditions—SAD Part (PK Set) of an FIH study of IMB-1018972.

FIG. 32 is a table of Summary Statistics (Geometric Mean [Range]) of IMB-1028814, Trimetazidine, and IMB-128814+Trimetazidine, and IMB-1028814+Trimetazidine Plasma Pharmacokinetic Parameters—FE Arm of SAD Part (PK Set) of an FIH study of IMB-1018972.

FIG. 33 is a table of Exploratory Analysis of Food Effect for IMB-1028814 and Trimetazidine following Administration of 150 mg IMB-1018972—FE Arm of SAD Part (PK Set) of an FIH study of IMB-1018972.

FIG. 34 is a table of Summary Statistics (Arithmetic Mean [SD]) of Urine Pharmacokinetic Parameters for IMB-1028814, Trimetazidine, and IMB-1028814+Trimetazidine—SAD Part (PK Set) of an FIE study of IMB-1018972.

FIG. 47 is a table of Summary Statistics (Geometric Mean [Range]) of IMB-1028814, Trimetazidine, and IMB-1028814+Trimetazidine Plasma Pharmacokinetic Parameters—MAD Part (PK Set) of an FIE study of IMB-1018972.

FIG. 48A and FIG. 48B is a table Summary of All TEAEs by System Organ Class, Preferred Term and Treatment—SAD Part (and integrated FE Arm) (Safety Set) with the following notifications: of an FIH study of IMB-1018972.

FIG. 49A and FIG. 49B is a table Summary of All TEAEs by System Organ Class, Preferred Term and Treatment—MAD Part (Safety Set) of an FIH study of IMB-1018972.

FIG. 50 is a table Summary of All TEAEs by Treatment, Relationship, and Severity-SAD Part (and Integrated FE Arm) (Safety Set) of an FIH study of IMB-1018972.

FIG. 51 is a table Summary of All TEAEs by Treatment, Relationship, and Severity—MAD Part (Safety Set) of an FIE study of IMB-1018972.

FIG. 52 is a table of assessments given for the Single-Dose MR Part of an FIH study of IMB-1018972.

FIG. 53 is a table of assessments given for the Multiple-Dose MR part of an FIE study of IMB-1018972.

FIG. 54 is a table of analysis data sets for the Single-Dose MR Part of an FIH study of IMB-1018972.

FIG. 55 a table of analysis data sets for the Multiple-Dose MR Part of an FIE study of IMB-1018972.

FIG. 56 is a table of a summary of demographic characteristics—Single-Dose MR Part (Safety Set) of an FIH study of IMB-1018972.

FIG. 57 is a table of a summary of demographic characteristics—Multiple-Dose MR Part (Safety Set) of an FIH study of IMB-1018972.

FIG. 58 is a table of the Extent of Exposure—Single-Dose MR Part (Safety Set) of an FIE study of IMB-1018972.

FIG. 59 is a table of the Extent of Exposure—Multiple-Dose MR Part (Safety Set) of an FIE study of IMB-1018972.

FIG. 66 is a table of Summary Statistics Geometric Mean [Range]) of IMB-1028814, Trimetazidine, and IMB-1028814+Trimetazidine Plasma Pharmacokinetic Parameters—Single-Dose MR Part (PK Set) of an FIH study of IMB-1018972.

FIG. 67 is a table of Exploratory Analysis of Food Effect for IMB-1028814 and Trimetazidine following Administration of 200 mg 8-hour MR IMB-1018972—Single-Dose MR Part (PK Set) of an FIE study of IMB-1018972.

FIG. 80 is a table of Summary Statistics Geometric Mean [Range]) of IMB-1028814, Trimetazidine, and IMB-1028814+Trimetazidine Plasma Pharmacokinetic Parameters-Multiple-Dose MR Part (PK Set) of an FIH study of IMB-1018972.

FIG. 81A and FIG. 81B is a table Summary of All TEAEs by System Organ Class, Preferred Term and Treatment—Single-Dose MR Part (Safety Set) of an FIH study of IMB-1018972.

FIG. 82 is a table Summary of All TEAEs by System Organ Class, Preferred Term and Treatment—Single-Dose MR Part (Safety Set) of an FIH study of IMB-1018972.

FIG. 83 is a table Summary of All TEAEs by Treatment, Relationship, and Severity-Single-Dose MR Part (Safety Set) of an FIH study of IMB-1018972.

FIG. 84 is a table Summary of All TEAEs by Treatment, Relationship, and Severity—Multiple-Dose MR Part (Safety Set) of an FIH study of IMB-1018972.

DETAILED DESCRIPTION

Figure 1:
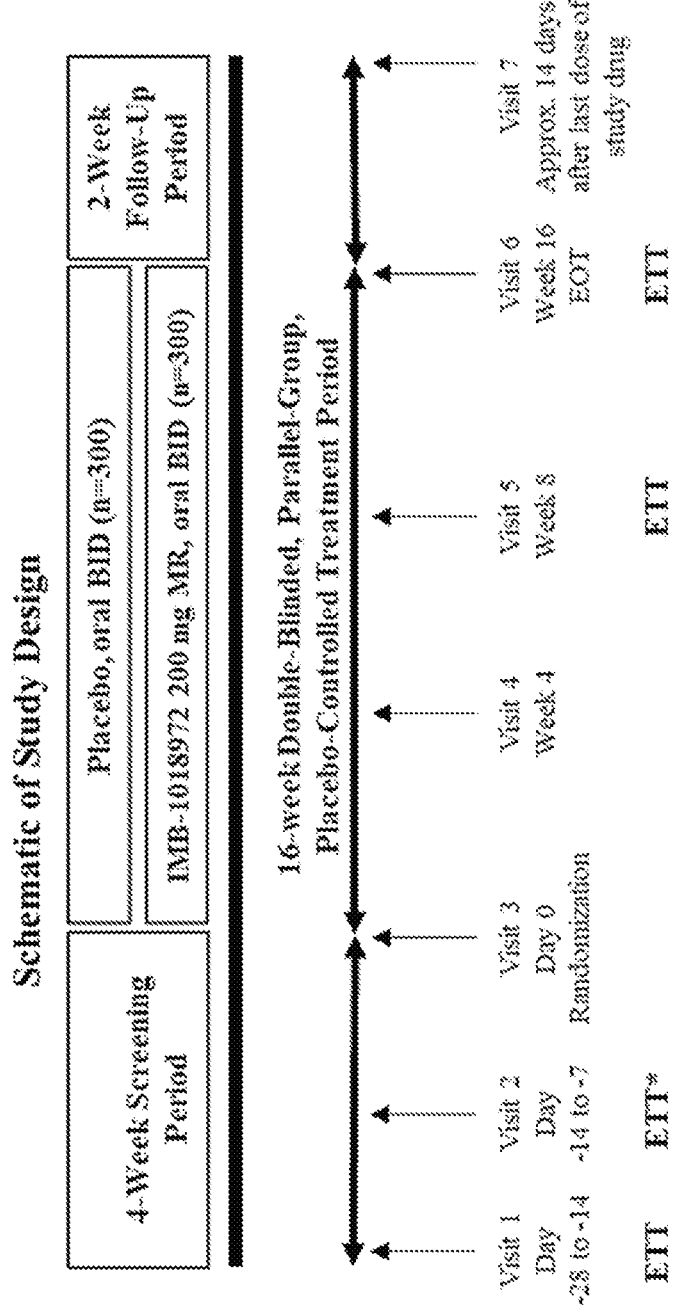
FIG. 1 a table of the disposition of subjects of an FIE study of IMB-1018972.

The invention provides methods of increase energy production in the kidney. The invention is based on the recognition that the kidney has a high demand for energy and that CV-8972, which has been previously described as improving energy production in the heart, promotes ATP synthesis in the kidney as well. Therefore, the methods are useful for treating a variety of kidney conditions for which increased energy production provides a therapeutic benefit.

Modified Forms of Trimetazidine

The invention provides compositions that contain mixtures that include modified forms of trimetazidine. Trimetazidine has the following structure:

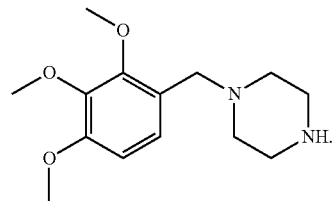 [SMILES: COc1ccc(CN2CCNCC2)c(OC)c1OC]

Trimetazidine is described as the first cytoprotective anti-ischemic agent developed and has long been used to treat angina.

Trimetazidine promotes glucose oxidation by inhibiting oxidation of fatty acids. Glucose oxidation and fatty acid oxidation are energy-producing metabolic pathways that compete with each other for substrates. In glucose oxidation, glucose is broken down to pyruvate via glycolysis in the cytosol of the cell. Pyruvate then enters the mitochondria, where it is converted to acetyl coenzyme A (acetyl-CoA). In beta-oxidation of fatty acids, which occurs in the mitochondria, two-carbon units from long-chain fatty acids are sequentially converted to acetyl-CoA. The remaining steps in energy production from oxidation of glucose or fatty acids are common to the two pathways. Briefly, they include breakdown of acetyl-CoA to carbon dioxide via the citric acid cycle, the concomitant generation of a proton gradient across the mitochondrial inner membrane via a series of oxygen-dependent electron transport reactions, and the use of the energy potential in the proton gradient to drive ATP synthesis. Trimetazidine inhibits oxidation of fatty acids by blocking long-chain 3-ketoacyl-CoA thiolase, thus causing cells to rely on glucose oxidation to support energy production.

Forcing cardiac mitochondria to rely on oxidation of glucose rather fatty acids as an energy source provides a therapeutic benefit for many patients with cardiovascular conditions. In certain types of heart disease, the overall efficiency of energy production by cardiac mitochondria is diminished due in part to an increased reliance on fatty acid oxidation over glucose oxidation. Glucose oxidation is a more efficient pathway for energy production, as measured by the number of ATP molecules produced per O2 molecule consumed, than is fatty acid oxidation. Thus, overall cardiac efficiency can be increased by agents that promote glucose oxidation, such as trimetazidine.

CV-8972 was recently identified as a trimetazidine-derivative having improved pharmacological properties. CV-8972 has the IUPAC name 2-[4-[(2,3,4-trimethoxyphenyl)methyl]piperazin-1-yl]ethyl pyridine-3-carboxylate and the structure of Formula (X):

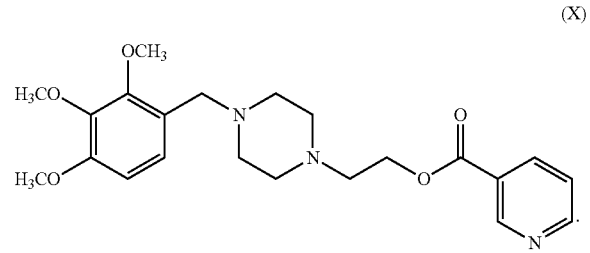 [SMILES: COc1ccc(CN2CCN(CCOC(=O)c3cccnc3)CC2)c(OC)c1OC]

(X)

When CV-8972 is administered to a subject, it is initially broken into nicotinic acid and CV-8814, which has the IUPAC name 2-[4-[(2,3,4-trimethoxyphenyl)methyl]piperazin-1-yl]ethanol and the structure of Formula (IX):

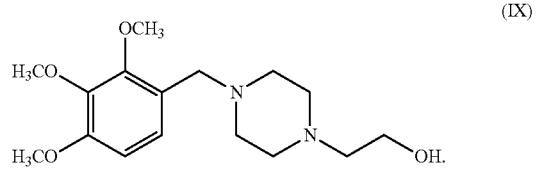 [SMILES: COc1ccc(CN2CCN(CCO)CC2)c(OC)c1OC]

(IX)

CV-8814 is a hydroxyethyl derivative of trimetazidine, and the hydroxyethyl group is subsequently removed in the body to provide trimetazidine. CV-8972 and its metabolic products are described in U.S. Pat. No. 10,556,013, the contents of which are incorporated herein by reference.

The improved therapeutic properties of CV-8972 are due in part to the effect of nicotinic acid. Nicotinic acid serves as a precursor for synthesis of nicotinamide adenine dinucleotide ($NAD^+$), the oxidized form of an essential coenzyme in the mitochondrial electron transport reaction. Supplying a $NAD^+$ precursor ensures that mitochondrial redox reactions occur robustly to drive ATP synthesis, regardless of whether oxidation of glucose or fatty acids is used to feed the citric acid cycle. Thus, the nicotinic acid product of CV-8972 promotes mitochondrial respiration.

The stepwise breakdown of CV-8972 to CV-8814 and then to trimetazidine also contributes to the improved therapeutic properties of CV-8972. Like trimetazidine, CV-8814 inhibits 3-ketoacyl-CoA thiolase, so CV-8972 delivers two different active pharmaceutical ingredients (APIs). However, CV-8814 does not produce the same undesirable side effects as trimetazidine. In addition, due to the sequential metabolism of CV-8972, the level of circulating trimetazidine following a dose of CV-8972 is much lower than the level following of comparable dose of trimetazidine itself. Therefore, compared to unadulterated trimetazidine, CV-8972 provides a more sustained level of circulating API and fewer side effects.

Other modified forms of trimetazidine that may be used in compositions of the invention are described in, for example, U.S. Pat. Nos. 4,100,285 and 4,574,156, the contents of each of which are incorporated herein by reference.

Kidney Conditions

The invention provides methods of treating kidney conditions associated with renal inflammation by providing to a subject a composition containing a modified form of trimetazidine, such as the compound of formula (X). For example and without limitation, the disease, disorder, or condition may be or include accumulation of mesangial matrix, acute interstitial nephritis, acute kidney injury (AKI), including AKI associated with cardiac surgery, acute tubular necrosis (ATN), Alport syndrome, atherosclerosis, atherosclerotic renal artery stenosis, an autoimmune disorder, such us systemic lupus erythematosus, autosomal dominant polycystic kidney disease (ADPKD), benign prostatic hyperplasia, bladder stones, cancer, including cancer of the bladder, ureters, or prostate, cardiac surgery, cell apoptosis, chronic kidney disease, chronic tubulointerstitial nephritis, delayed graft function (DGF), including DGF-renal, diabetes, diabetic nephropathy, including type 1 diabetic nephropathy (T1D nephropathy), end-stage renal disease, Focal segmental glomerulosclerosis (FSGS), glomerular basement membrane thickening, glomerular hyperfiltration, glomerular and tubular epithelial hypertrophy, glomerulonephritis, glomerulosclerosis, heart failure, hemolytic-uremic syndrome, hypertension, IgA nephropathy (also called Berger's disease), infection, injury, ischemia, ischemia/reperfusion injury, ischemic nephropathy, kidney hypoxia, kidney stones, kidney transplantation, liver cirrhosis, methyl melonic acidosis (MMA), microalbuminuria, obstructed urinary catheter, proteinuria, reduced creatinine clearance, reduced glomerular filtration rate, reflux nephropathy, renal vein thrombosis, rhabdomyolysis, tumor lysis syndrome, vascular occlusion, or vasculitis.

The methods may treat or prevent renal inflammation associated with a kidney condition, such as any of those described above.

The kidney condition may be acute kidney injury. AKI may be assessed by any suitable standard. Several standards for acute kidney injury are known in the art, such as the criteria provided by the Acute Kidney Injury Network (AKIN); Kidney Disease Improving Global Outcomes (KDIGO); and Risk, Injury, Failure, Loss, and End-stage Kidney (RIFLE). AKI may be categorized or staged according to the AKI, KDIGO, or RIFLE criteria. For example, a subject may be deemed to have stage 1, stage 2, or stage 3 AKI, or a subject may be deemed to have risk, injury, failure, or loss. The standard may apply to an adult, pediatric, newborn, neonatal, infant, child, adolescent, pre-teen, teenage, or elderly subject.

Standards typically include measurements of serum creatinine (SCr) concentrations, urine output, or glomerular filtration rate (GFR). Standards may include multiple parameters, e.g., combinations of the aforementioned standards. A subject may be deemed to have AKI, or a stage or category thereof, when she has abnormally high SCr concentration, abnormally low urine output, abnormally low GFR, or any combination thereof. Standards may be absolute, e.g., they may require a value above or below a defined threshold value. Alternatively, standards may be relative, e.g., they may require an increase or decrease relative to a baseline value. Standards for different parameters, e.g., abnormally high SCr concentration abnormally low urine output, or abnormally low GFR, may independently be absolute or relative.

Standards for acute kidney injury may include a temporal component. For example, a subject may be deemed to have AKI when an elevated SCr concentration is measured at some interval following a preceding event. The preceding event may be cardiac surgery, cardiac arrest, admission to a hospital, clinic, medical facility, or any unit thereof. The interval may be 1 hour, 2 hours, 4 hours, 6 hours, 8 hours, 12 hours, 24 hours, 36 hours, 48 hours, or 72 hours. A subject may be deemed to have AKI when urine output is measured across some interval, such as 1 hour, 2 hours, 4 hours, 6 hours, 8 hours, 12 hours, 24 hours, 36 hours, 48 hours, or 72 hours.

For example and without limitation, a standard for reduced urine output associated with AKI may be less than 0.5 mL/kg/h for 6-12 hours, less than 0.5 mL/kg/h for at least 12 hours, or less than 0.3 mL/kg/h for 24 hours, or anuria for at least 12 hours.

For example and without limitation, a standard for elevated SCr concentration associated with AKI may be a SCr concentration of at least 0.3 mg/dl, a SCr concentration of at least 1 mg/dl, a SCr concentration of at least 4 mg/dl, a SCr concentration of at least 26.5 µmol/l, or a SCr concentration of at least 353.6 µmol/l. For example and without limitation, a standard for elevated SCr concentration associated with AKI may be an increase of 50% over baseline, an increase of 100% over baseline, or an increase of 200% over baseline.

For example and without limitation, a standard for GFR associated with AKI may be a GFR of less than 35 ml/min per 1.73 mm$^2$. For example and without limitation, a standard for GFR associated with AKI may be a decrease of at least at least 25% relative to a baseline, a decrease of at least at least 50% relative to a baseline, or a decrease of at least at least 75% relative to a baseline.

The methods may treat or prevent a kidney condition associated with reperfusion injury. Reperfusion injury, which is also called reperfusion insult, ischemia-reperfusion injury, and reoxygenation injury, is the tissue damage that results when blood supply to the tissue is restored after a period of ischemia or lack of oxygen. The sudden influx of nutrients and oxygen after a bout of ischemia, anoxia, or hypoxia produces a high level of reactive oxygen species that exceeds the tissue's detoxification capacity. The oxidative stress is associated with microvascular injury due to increased permeability of capillaries and arterioles that allows fluid to penetrate the tissue more readily. In addition, white blood cells in the returning blood respond to damaged tissue by releasing inflammatory factors.

Reperfusion injury can occur following any surgery that limits blood supply to an organ. In particular, reperfusion injury is a risk following cardiac procedures due to changes in blood during the procedure. Reperfusion injury is also a major concern in organ transplantation procedures due to the lack of blood flow to the organ while it is being transported.

Methods of Providing Compositions

Providing the composition to the subject may include administering it to the subject. The composition may be administered by any suitable means. For example and without limitation, the composition may be administered buccally, by injection or infusion, dermally, enterally, enterally, intraarterially, intravenously, nasally, orally, parenterally, pulmonarily, rectally, subcutaneously, topically, transdermally, vaginally, or with or on an implantable medical device (e.g. stent or drug-eluting stent or balloon equivalents). The compositions may be provided directly to the kidney via in vitro perfusion of the renal artery.

The composition may be provided according to a dosing regimen. The dosing regimen may include a dose, a dosing interval, or both.

The composition may be provided in a single dose per day. The composition may be provided in multiple doses per day. The composition may be provided in 2, 3, 4, 5, 6, or more doses per day.

The composition may be provided to the subject to deliver a defined daily dose of the compound of formula (X). The dose may contain from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of the compound. The dose may contain about 10 mg, about 25 mg, about 50 mg, about 100 mg, about 200 mg, about 300 mg, or about 400 mg of the compound.

The interval between doses may be about 4 hours, about 6 hours, about 8 hours, about 12 hours, about 24 hours, about 36 hours, or about 48 hours The composition may be formulated for immediate release of the compound of formula (X). The composition may be formulated for modified release of the compound of formula (X).

In certain embodiments, modified-release formulations contain mixtures that include erodible polymers that promote swelling of the mixture in an aqueous environment. An erodible polymer is any polymer that breaks down inside the body within a physiologically relevant time frame. The erodible polymer may have other characteristics that promote the gradual release of the modified form of trimetazidine from the mixture. For example and without limitation, the polymer may be one or more of the following: biocompatible, i.e., not harmful to living tissue; hydrophilic; hygroscopic; tending to form a hydrogel.

Without wishing to be bound by theory, the polymer-containing mixtures may promote gradual release by one or more mechanisms. For example, swelling of the mixture by absorption of water may facilitate diffusion of the modified form of trimetazidine from the mixture. Degradation of the polymer may also allow the modified form of trimetazidine to be released from the mixture. Osmotic pressure due the high concentration gradient of compound between the inside and outside of the mixture may also contribute to diffusion of the modified form of trimetazidine from the mixture.

For example and without limitation, the polymer may be a cellulose derivative, a gelatin derivative, e.g., a cross-linked gelatin derivative, or a polyester derivative.

Derivatives of cellulose, is a linear chain β(1→4) linked D-glucose units, include polymers that contain substitutions on one of more of the hydroxyl groups of each glucose unit. Substituents may be organic or inorganic and are typically attached via ester or ether linkages. Cellulose ester derivatives include carboxymethyl cellulose (CMC), e.g., sodium carboxymethyl cellulose, ethyl cellulose, ethyl hydroxyethyl cellulose, ethyl methyl cellulose, hydroxyethyl cellulose, hydroxyethyl methyl cellulose, hydroxypropyl cellulose (HPC), hydroxypropyl methylcellulose (HPMC), and methylcellulose. Cellulose ether derivatives include cellulose acetate, cellulose acetate butyrate, cellulose acetate propionate, cellulose propionate, cellulose sulfate, cellulose triacetate, and nitrocellulose. The use of cellulose-based polymers to form biodegradable hydrogels is known in the art and described in, for example, Sannino, et al., Biodegradable Cellulose-based Hydrogels: Design and Applications, Materials 2009, 2, 353-373; doi:10.3390/ma2020353, the contents of which are incorporated herein by reference.

The mixture may contain multiple polymers or multiple polymeric forms of the same polymer. For example, HPMC polymeric forms may differ in a variety of physical properties, including viscosity, degree of methoxyl substitution, degree of hydroxypropoxyl substitution, or average molecule weight.

The viscosity of a HMPC polymeric form may be determined by testing under standard conditions, including the concentration of HMPC in the solution and the temperature of the solution. For example and without limitation, the HPMC concentration may be may be 1%, 1.5%, 2%, 2.5%, or 3%. For example and without limitation, the temperature of the solution may be 15° C., 16° C., 17° C., 18° C., 19° C., 20° C., 21° C., 22° C., 23° C., 24° C., or 25° C.

A polymeric form of a cellulose derivative, such as HPMC, may have a defined viscosity. For example and without limitation, a polymeric form of HPMC may have a viscosity of from about 2 cP to about 4 cP, from about 4 cP to about 6 cP, from about 5 cP to about 8 cP, from about 12 cP to about 18 cP, from about 40 cP to about 60 cP, from about 80 cP to about 120 cP, from about 300 cP to about 500 cP, from about 1200 cP to about 2400 cP, from about 2500 cP to about 5000 cP, from about 9000 cP to about 18,000 cP, from about 12,000 cP to about 24,000 cP, from about 12,000 cP to about 24,000 cP, from about 75,000 cP to about 150,000 cP, at least about 2 cP at least about 4 cP at least about 5 cP at least about 12 cP at least about 40 cP at least about 80 cP at least about 300 cP at least about 1200 cP at least about 2500 cP at least about 9000 cP at least about 12,000 cP at least about 12,000 cP at least about 75,000 cP less than about 4 cP, less than about 6 cP, less than about 8 cP, less than about 18 cP, less than about 60 cP, less than about 120 cP, less than about 500 cP, less than about 2400 cP, less than about 5000 cP, less than about 18,000 cP, less than about 24,000 cP, less than about 24,000 cP, or less than about 150,000 cP for a 2% aqueous solution of the polymeric form at 20° C.

Polymeric forms of cellulose derivatives, such as HPMC, may vary in their degree of substitution of the glucose units. The degree of substitution may be expressed as a weight percentage of the substituent or as a molar ratio of substituent to glucose unit. For a cellulose derivative that has two different substituents, such as HPMC, the polymeric form may be described by the degree of substitution for each substituent.

Each polymeric form of HPMC may independently have a defined degree of methoxyl substitution. For example and without limitation, the degree of methoxyl substitution may be from about 19% to about 24%, from about 22% to about 24%, from about 27% to about 30%, from about 27% to about 30%, or from about 28% to about 32%.

Each polymeric form of HPMC may independently have a defined degree of hydroxypropoxyl substitution. For example and without limitation, the degree of hydroxypropoxyl substitution may be from about 4% to about 8%, from about 7% to about 10%, from about 7% to about 12%, from about 8% to about 10%, from about 8% to about 11%, or from about 9% to about 12%.

Each polymeric form of HPMC may independently have a defined average molecular weight. The average molecular weight may be about 10 kDa, about 13 kDa, about 20 kDa, about 26 kDa, about 41 kDa, about 63 kDa, about 86 kDa, about 110 kDa, about 120 kDa, about 140 kDa, about 180 kDa, or about 220 kDa.

When multiple forms of a polymer, such as HPMC, are present, one or more polymeric forms may be present in a defined amount. For example and without limitation, a polymer, such as HPMC, may contain about 50%, about 60%, about 70%, about 80%, about 90%, about 95%, about 96%, about 97%, about 98%, about 99%, at least 50%, at least 60%, at least 70%, at least 80%, at least 90%, at least 95%, at least 96%, at least 97%, at least 98%, or at least 99% by weight of one polymeric form.

Modified-release formulations of CV-8972 are described in co-owned, co-pending U.S. Application Nos. 63/046,115 and 63/046,117, the contents of which are incorporated herein by reference.

Methods of the invention may include providing a crystal form of CV-8972. Crystals of CV-8972 may exist in at least five polymorphic forms: Form A, Form B, Form C, Form D, and Form E. Form A is monohydrate, and Forms B, D, and E are anhydrous. Crystal forms of CV-8972 and methods of preparing them are described in co-owned, co-pending U.S. Application Nos. 63/046,120 and 63/046,123, the contents of which are incorporated herein by reference.

In certain embodiments, methods of the invention include providing pharmaceutical compositions containing a compound in a form suitable for oral use, for example, as tablets, troches, lozenges, fast-melts, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. Preparation and administration of compounds is discussed in U.S. Pat. No. 6,214,841 and U.S. Patent Publication No. 2003/0232877, the contents of each of which are incorporated by reference herein.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions use in methods of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol, or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Providing a composition to a subject may improve renal function. For example, renal function may be improved by at least 10%, at least 20%, at least 30%, at least 40%, at least 50%, at least 60%, at least 70%, at least 80%, at least 90%, at least 100%, at least 200%, or at least 300%. Measurable markers of renal function, are well known in the medical and veterinary literature and to those of skill in the art, and include, but are not limited to, blood urea nitrogen or "BUN" levels (both static measurements and measurements of rates of increase or decrease in BUN levels), serum creatinine levels (both static measurements and measurements of rates of increase or decrease in serum creatinine levels), measurements of the BUN/creatinine ratio (static measurements of measurements of the rate of change of the BUN/creatinine ratio), urine/plasma ratios for creatinine, urine/plasma ratios for urea, glomerular filtration rates (GFR), serum concentrations of sodium (Na t), urine osmolarity, daily urine output, albuminuria, proteinuria, and the like. Of the above, measurements of the plasma concentrations of creatinine and/or urea or BUN are particularly important and useful readouts of renal function.

EXAMPLES

Example 1

Study Design

A Phase 1 first-in-human, randomized, double-blind, placebo-controlled single ascending dose and multiple ascending dose study to investigate the safety, tolerability, and pharmacokinetics (including food effect) or IMB-1018972 in healthy subjects.

Objectives

The primary objective is to assess the safety and tolerability of single and multiple ascending oral doses of IMB-1018972, single oral doses of trimetazidine, single oral doses of modified-release (MR) formulations of IMB-1018972, and multiple oral doses of the 200 mg 8-hour MR formulation of IMB-1018972 in healthy subjects.

Secondary objectives include: To assess the pharmacokinetic (PK) profile of single and multiple ascending oral doses of IMB-1018972, single oral doses of trimetazidine, single oral doses of MR formulations of IMB-1018972, and multiple oral doses of the 200 mg 8-hour MR formulation of IMB-1018972 in healthy subjects; To assess the effect of food on the absorption and the PK profile of IMB-1018972 following a single oral dose of IMB-1018972 in healthy subjects; To evaluate the effect of food on the safety and tolerability of IMB-1018972 following a single oral dose of IMB-1018972 in healthy subjects; To assess the absorption and PK profile of the 200 mg 8-hour MR formulation of IMB-1018972 following multiple oral doses taken with food in healthy subjects; and To evaluate the safety and tolerability of the 200 mg 8-hour MR formulation of IMB-1018972 following multiple oral doses taken with food in healthy subjects.

Design and Treatments

This was a double-blind, randomized, placebo-controlled study, consisting of a single ascending dose (SAD) part with integrated food effect (FE) arm, a multiple ascending dose (MAD) part, and single-dose and multiple-dose MR parts to assess the safety, tolerability, and PK of ascending single and multiple oral doses of IMB-1018972 (immediate-release [IR] formulation in the SAD and MAD parts), single oral doses of a MR formulation of trimetazidine, single oral doses of MR formulations of IMB-1018972, and multiple oral doses of the 200 mg 8-hour MR formulation of IMB-1018972. The study started with the SAD part.

SAD Part (and Integrated FE Arm)

In the SAD part, 5 groups of 8 healthy subjects (6 subjects on active drug and 2 on placebo in Groups A1, A2, A3, and A4, and 8 subjects on active drug in Group A5) were included. In Groups A1, A2, A3, and A4, subjects received a single oral dose of an IR formulation of IMB-1018972 or placebo under fasted conditions (an overnight fast of at least 10 hours). In Group A5, all subjects received a single oral dose of a MR formulation of trimetazidine under fasted conditions (an overnight fast of at least 10 hours). Each subject participated in only 1 group during the study.

Subjects assigned to Group A4 also participated in the FE arm and received the same single dose of IMB-1018972 or placebo under fed conditions (Food and Drug Administration [FDA]-defined high-fat breakfast after an overnight fast of at least 10 hours) in a second period at least 1 week after drug administration under fasted conditions in the SAD part.

The following treatments were administered in the SAD part under fasted conditions:
Group A1: single oral dose of 50 mg IR formulation of IMB-1018972 (n=6) or matching placebo (n=2) on Day 1
Group A2: single oral dose of 150 mg IR formulation of IMB-1018972 (n=6) or matching placebo (n=2) on Day 1
Group A3: single oral dose of 400 mg IR formulation of IMB-1018972 (n=6) or matching placebo (n=2) on Day 1
Group A4: single oral dose of 150 mg IR formulation of IMB-1018972 (n=6) or matching placebo (n=2) on Day 1 (FE group)
Group A5: single oral dose of 35 mg MR formulation of trimetazidine (Vastarel; n=8) on Day 1

The following treatment was administered in the FE arm under fed conditions (FDA-defined high-fat breakfast):
Group A4: single oral dose of 150 mg IR formulation of IMB-1018972 (n=5) or matching placebo (n=2) on Day 1 (same dose as in SAD part)

IMB-1018972 dose-escalation was based on the available safety, tolerability, and PK results of at least 5 dosed subjects in the preceding group. A dose-escalation meeting was held between the Investigator and the Sponsor. Further, a dose-escalation report (DER) was provided by the Investigator to the Independent Ethics Committee (IEC) following completion of each dose level. Escalation to the next higher dose only proceeded when none of the stopping criteria had been reached and if the available safety, tolerability, and PK results (results up to 48 hours postdose) of at least 5 dosed subjects in the preceding group were acceptable to the Investigator and the Sponsor and after a statement of no objection of the DER from the IEC.

In this first-in-human (FIH) study, the subjects participating at the lowest dose level, subjects of Group A1, were dosed according to a sentinel dosing design to ensure optimal safety. This means that initially, 2 subjects were dosed: 1 subject with IMB-1018972 and 1 subject with placebo. Since the safety and tolerability results of the first 24 hours following dosing for the initial 2 subjects were acceptable to the Investigator, the other 6 subjects (5 active drug and 1 placebo) of the lowest dose level were also dosed.

MAD Part

In the MAD part, 2 groups of 12 healthy subjects (9 subjects on active drug and 3 on placebo in each group) were included. Subjects received multiple oral doses of an IR formulation of IMB-1018972 or placebo once every 12 hours (q12h) for 14 consecutive days. Each subject participated in only 1 group during the study.

The following treatments were administered under fed conditions as determined based on the results of Group A4 in the FE arm. The doses were selected based upon the safety, tolerability, and PK data from the SAD part:
Group B1 multiple oral doses of an IR formulation of 150 mg IMB-1018972 (n=9) or matching placebo (n=3) twice daily (q12h) for 14 days; on Day 14 only a single morning dose was administered
Group B2: multiple oral doses of an IR formulation of 50 mg IMB-1018972 (n=9) or matching placebo (n=3) q12h for 14 days; on Day 14 only a single morning dose was administered IMB-1018972 dose escalation was based on the available safety, tolerability, and PK results of at least 8 dosed subjects in the preceding group. A dose-escalation meeting was held between the Investigator and the Sponsor. Further, a DER was provided by the Investigator to the IEC following completion of each dose level. Escalation to the next higher dose only proceed when none of the stopping criteria had been reached and if the available safety, tolerability, and PK results (results up to 48 hours after the final morning dose on Day 14) of at least 8 dosed subjects in the preceding group were acceptable to the Investigator and the Sponsor and after a statement of no objection of the DER from the IEC.

Single-Dose MR Part

In the single-dose MR part, 1 group of 12 healthy subjects (all on active drug) was included. The subjects received a single oral dose of 1 of 4 MR formulations of IMB-1018972 under fasted conditions (an overnight fast of at least 10 hours) on Days 1, 4, 7, and 10 in a fixed order that was the same for all subjects. The MR formulation of IMB-1018972 to be administered on Day 13 under fed conditions was 1 of the 4 MR formulations administered on Days 1, 4, 7, and 10 under fasted conditions. The formulation chosen for administration on Day 13 was the 200 mg 8-hour MR formulation as determined by the Sponsor based on the available safety, tolerability, and PK results of the 4 MR formulations.

The following treatments were administered in the single-dose MR part:
Day 1: single oral dose of 50 mg 8-hour MR formulation of IMB-1018972 (n=12) under fasted conditions
Day 4: single oral dose of 50 mg 4-hour MR formulation of IMB-1018972 (n=12) under fasted conditions
Day 7: single oral dose of 200 mg 8-hour MR formulation of IMB-1018972 (n=12) under fasted conditions Day 10: single oral dose of 200 mg 4-hour MR formulation of IMB-1018972 (n=12) under fasted conditions Day 13: single oral dose of 200 mg 8-hour MR formulation of IMB-1018972 (n=12) under fed conditions Multiple-Dose MR Part In the multiple-dose MR part, 1 group of 12 healthy subjects (all on active drug) was included. Subjects received multiple oral doses of the 200 mg 8-hour MR formulation of IMB-1018972 q12h under fed conditions for 5 consecutive days; on Day 5 only a single morning dose was administered.

Study Schedule

Screening: Between Day −35 and Day −1 (admission)

Confinement period: SAD part: 1 period in the clinic from Day −1 (admission) to approximately 48 hours after study drug administration (Day 3); an exception was Group A4 also participating in the FE arm in which subjects were in the clinic for 2 periods, each being from Day −1 (admission) to approximately 48 hours after study drug administration (Day 3) MAD part: 1 period in the clinic from Day −1 (admission) to approximately 48 hours after the last study drug administration on Day 14 (Day 16) Single-dose MR part: 1 period in the clinic from Day −1 (admission) to approximately 72 hours after study drug administration on Day 13 (Day 16) Multiple-dose MR part: 1 period in the clinic from Day −1 (admission) to approximately 48 hours after study drug administration on Day 5 (Day 7)

Follow-up: SAD part: 7 to 14 days after the last PK blood sample (between Day 10 and Day 17); FE arm: 7 to 14 days after the last PK blood sample in the second period (between Day 10 and Day 17); MAD part: 7 to 14 days after the last PK blood sample (between Day 23 and Day 30); Single-dose MR part: 7 to 14 days after the last PK blood sample (between Day 23 and Day 30); Multiple-dose MR part: 6 to 8 days after the last PK blood sample (Day 14±1 day)

Subjects

SAD part: 40 healthy male or female subjects (this included 8 subjects also participating in the FE arm); from Group A4 onwards, all efforts were made to have a ratio of 50:50 for male and female subjects per group, but at minimum at least 3 subjects of each gender were dosed per group MAD part: 24 healthy male or female subjects; for each group, all efforts were made to have a ratio of 50:50 for male and female subjects, but at minimum at least 4 subjects of each gender were dosed per group Single-dose MR part: 12 healthy male or female subjects; for this group, all efforts were made to have a ratio of 50:50 for male and female subjects, but at minimum at least 4 subjects of each gender were dosed Multiple-dose MR part: 12 healthy male or female subjects; for this group, all efforts were made to have a ratio of 50:50 for male and female subjects, but at minimum at least 4 subjects of each gender were dosed Main Criteria for Inclusion Age: 18 years to 65 years, inclusive, at screening Body mass index (BMI): 18.0 kg/m$^2$ to 32.0 kg/m$^2$, inclusive Status: Healthy subjects Study Drug Active medication Drug product: IMB-1018972

Activity: Fatty acid oxidation inhibitor In development for: Ischemic cardiovascular disease Strength: 25 mg, 100 mg, and 200 mg IR formulations (based on free base); 50 mg MR formulation and 200 mg MR formulation with 4-hour and 8-hour dissolution profile (based on free base)

Dosage form: Oral IR capsule(s) to be used in the SAD and MAD parts and oral MR tablet(s) to be used in the MR parts Manufacturer: Pharmacy at PRA Batch number: 2479-1810-00441 (drug substance)

IMB-1018972 Placebo (Visually Matching Active Medication)

Active substance: Not applicable

Activity: Not applicable

Strength: Not applicable

Dosage form: Oral capsule(s)

Manufacturer: Pharmacy at PRA

Batch number: Not applicable

Active Medication

Drug product: Vastarel MR (trimetazidine dihydrochloride)

Activity: Fatty acid oxidation inhibitor

In development for: Angina pectoris

Strength: 35 mg

Dosage form: Oral modified-release tablet

Manufacturer: Server Research & Pharmaceuticals (Pakistan) (Pvt.) Ltd.

Batch number: 273782 (drug product)

Variables

Safety: Adverse events, clinical laboratory, vital signs, 12-lead electrocardiogram, continuous cardiac monitoring (telemetry), and physical examination Pharmacokinetics: Plasma concentrations of IMB-1018972, IMB-1028814, and trimetazidine Urine concentrations of IMB-1018972, IMB-1028814, and trimetazidine (SAD part only) Plasma PK parameters estimated using noncompartmental analysis, as appropriate. SAD part, integrated FE arm, and single-dose MR part: $C_{max}$, $t_{max}$, $AUC_{0-t}$, $AUC_{0-inf}$, % $AUC_{extra}$, $k_{el}$, $t_{1/2}$, CL/F (IMB-1028814 only), and $V_z/F$ (IMB-1028814 only). Day 1 of MAD part and multiple-dose MR part: $C_{max}$, $t_{max}$, and $AUC_{0-T}$. Day 14 of MAD part and Day 5 of multiple-dose MR part: $C_{max}$, $t_{max}$, $C_{min}$, $k_{el}$, $t_{1/2}$, $AUC_{0-T}$, $CL_{ss}/F$ (IMB-1028814 only), $V_z/F$ (IMB-1028814 only), and Rae Urine PK parameters estimated using noncompartmental analysis, as appropriate: $Ae_{urine}$, $Fe_{urine}$, and $CL_R$ Statistical Methods Sample size calculation: For this FIH study, no prospective calculations of statistical power were made. The sample size was selected to provide information on safety, tolerability, and PK following single and multiple doses of IMB-1018972, single doses of trimetazidine, single doses of MR formulations of IMB-1018972, and multiple doses of the 200 mg 8-hour MR formulation of IMB-1018972, and is typical for a FIE study. Any p-values to be calculated according to the statistical analysis plan were interpreted in the perspective of the exploratory character of this study.

Safety parameters: Descriptive statistics

PK parameters: Descriptive statistics for all relevant PK parameters: n, mean, SD, minimum, median, maximum, geometric mean, and coefficient of variation; analysis of variance on $C_{max}$ and AUC parameters to determine dose proportionality and FE Results
Subject Disposition Of the 220 subjects who were screened, 88 subjects were included in the study and received the study drug. Sixty-six subjects received a dose of IMB-1018972, 8 received trimetazidine, and 14 received placebo. Eighty-five of 88 subjects completed the study. One subject of the FE arm Group A4 withdrew consent on Day 1 of the second period after receiving the single oral dose of 150 mg IMB-1018972 under fed conditions. Another subject of the FE arm Group A4 was withdrawn from the study due to a serious adverse event (SAE) of influenza like illness (of moderate severity and unlikely related) in the first period and only received the single oral dose of 150 mg IMB-1018972 under fasted conditions and not the fed dose in the second treatment period. One subject of the single-dose MR part was withdrawn from the study due to a moderate treatment-emergent adverse event (TEAE) of alanine aminotransferase (ALT) increased (possibly related; up to 149 IU/L on Day 11) and did not receive the last single oral dose of 200 mg 8-hour MR formulation of IMB-1018972 under fed conditions on Day 13. None of these discontinued subjects were replaced. All 88 subjects were included in the PK and safety sets.

FIG. 1 is a table of the disposition of subjects.

Demographics
SAD Part (and Integrated FE Arm)
IMB-10108972 and Placebo

Thirty-two subjects were included of whom 23 were female and 9 were male. Mean age ranged between 29 and 46 years and mean BMI ranged between 23.0 and 26.6 kg/m2 over all treatments, including placebo. Individual age ranged between 18 and 65 years and individual BMI ranged between 19.5 and 30.3 kg/m2. Twenty-nine subjects were of white race, 1 subject was Asian, 1 subject was Black or African American, and 1 subject was Native Hawaiian or Other Pacific Islander.

Trimetazidine Group

Eight subjects were included of whom 5 were female and 3 were male. Mean age was 32 years and mean BMI was 23.7 kg/m2. Individual age ranged between 20 and 65 years and individual BMI ranged between 19.4 and 26.7 kg/m2. Seven subjects were of white race and 1 subject was of multiple race.

MAD Part

Twenty-four subjects were included of whom 12 were female and 12 were male. Mean age ranged between 38 and 44 years and mean BMI ranged between 25.2 and 26.7 kg/m2 over all treatments, including placebo. Individual age ranged between 18 and 64 years and individual BMI ranged between 19.1 and 30.9 kg/m2. Eighteen subjects were of white race, 2 subjects were of multiple race, 2 subjects were American Indian or Alaska Native, 1 subject was Asian, and 1 subject was Black or African American.

Single-Dose MR Part

Twelve subjects were included of whom 6 were female and 6 were male. Mean age was 32 years and mean BMI was 25.8 kg/m2. Individual age ranged between 19 and 62 years and individual BMI ranged between 21.5 and 31.0 kg/m2. Eleven subjects were of white race and 1 subject was Black or African American.

Multiple-Dose MR Part

Twelve subjects were included of whom 6 were female and 6 were male. Mean age was years and mean BMI was 25.1 kg/m2. Individual age ranged between 24 and 64 years and individual BMI ranged between 20.0 and 29.2 kg/m2. Eleven subjects were of white race and 1 subject was Asian.

Safety

In the SAD part, treatment with single oral doses of 50 mg, 150 mg, and 400 mg 1 MB-1018972 under fasted conditions, treatment with single oral doses of 150 mg IMB-1018972 under fed conditions, and treatment with single oral doses of 35 mg trimetazidine were well tolerated by healthy male and female subjects. During the SAD part, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions. These TEAEs were all considered by the Investigator to be related to the study drug. No subjects dropped out due to flushing and flushing was not considered a safety issue. There were no clinically important trends in the physical examinations, vital signs, clinical laboratory, or ECG results. Dose escalation beyond 400 mg IMB-1018972 IR did not proceed as planned based on the PK exposure levels of IMB-1028814 and trimetazidine exceeding the target exposure levels in the 400 mg group and the findings of flushing at that dose. The predefined target exposure level was approximately 3 to 4 'trimetazidine equivalents', ie, the ratio of the combined exposure of the active metabolites of IMB-1018972 to the single oral doses of 35 mg MR trimetazidine as seen in published literature.

In the MAD part, 14-day treatment with oral q12h doses of 50 mg and 150 mg IMB-1018972 under fed conditions was well tolerated by healthy male and female subjects. The most common AEs were 7 incidental and mild TEAEs of flushing that occurred in 6 subjects who had received 150 mg IMB-1018972 q12h. Five of these 6 subjects reported only a single TEAE of flushing during the 14 days dosing period. One subject reported flushing twice, on Day 2 and on Day 14. No TEAEs of flushing were reported following administration of 50 mg IMB-1018972 q12h. No subjects dropped out and no modification of the dose was needed due to the TEAEs of flushing.

In the single-dose MR part, treatment with the 50 mg MR formulation and 200 mg MR formulation with 4-hour and 8-hour dissolution profile under fasted conditions, and subsequently, the 200 mg 8-hour MR formulation of IMB-1018972 under fed conditions was well tolerated by healthy male and female subjects, except for 1 subject in which ALT was elevated (up to 149 IU/L) after 2 single doses of 50 mg MR formulation and 2 doses of 200 mg MR formulation. No TEAEs of flushing were reported in the single-dose MR part.

In the multiple-dose MR part, 5-day treatment with multiple oral doses of the 200 mg 8-hour MR formulation of IMB-1018972 q12h under fed conditions was well tolerated by healthy male and female subjects. Flushing of mild severity was reported by 2 subjects who were post-menopausal females and 1 of whom had reported ongoing "hot flushes" as part of medical history. No subjects dropped out and no modification of the dose was needed due to the TEAEs of flushing.

Overall, no deaths were reported during the study. The majority of the reported TEAEs were transient and resolved without sequelae by follow-up. Most TEAEs were of mild severity and no severe TEAEs were reported during the study. TEAEs of moderate severity were the 5 TEAEs of flushing mentioned above and 1 TEAE each of restlessness, back pain, nausea, tonsillitis, post procedural hemorrhage, ALT increased, and influenza like illness. The moderate TEAE of ALT increased was reported by a subject of the single-dose MR part. This subject was withdrawn from the study as a result of this TEAE. The TEAE of ALT increased (up to 149 IU/L on Day 11) was considered by the Investigator to be possibly related to the study drug. The moderate TEAE of influenza like illness was considered to be an SAE and was reported by a subject in the SAD part who had received a single dose of 150 mg IMB-1018972 under fasted conditions in the SAD part. The subject was withdrawn from the study as a result of this SAE. The SAE was considered by the Investigator unlikely to be related to the study drug.

In both the SAD part and MAD part, there was no clear dose dependency of the number and incidence of TEAEs. In the FE arm of the SAD part, dosing under fed conditions appeared to attenuate the number and incidence of TEAEs. In the single-dose MR part, there was no clear difference between fasted and fed IMB-1018972 administration for the number and incidence of TEAEs.

The most frequently reported TEAEs during the study were of the system organ class vascular disorders (mainly TEAEs of flushing), general disorders and administration site conditions, nervous system disorders, gastrointestinal disorders, and musculoskeletal and connective tissue disorders.

The majority of the TEAEs reported during the study were considered by the Investigator not to be related to the study drug.

There were no findings of clinical relevance with respect to clinical laboratory, vital signs, 12-lead ECG, continuous cardiac monitoring (telemetry), or physical examination.

Pharmacokinetics

All blood samples of subjects that received IMB-1018972 in this study were analyzed for IMB-1018972 in plasma, but IMB-1018972 could be measured in only few plasma samples. Therefore, the IMB-1018972 concentrations have only been listed and no descriptive statistics or concentration-time profiles have been presented in this clinical study report. In addition, no PK parameters have been calculated for plasma IMB-1018972. As a result, urine samples were not analyzed for IMB-1018972 concentrations.

Since the pharmacodynamic effect of IMB-1028814 and trimetazidine is the same, data are presented for IMB-1028814 and trimetazidine individually, as well as for the sum of IMB-1028814 and trimetazidine concentrations.

SAD Part (and Integrated FE Arm)

PK in Plasma Following Administration of IMB-1018972 Under Fasted Conditions

The initial hydrolysis of IMB-1018972 to IMB-1028814 and subsequent systemic bioavailability of IMB-1028814 was relatively rapid with median tmax around 1 hour postdose for IMB-1028814, and between 1.5 hours and 2 hours postdose for trimetazidine over the studied single-dose range of 50 mg to 400 mg IMB-1018972 under fasted conditions. Median tmax did not increase with increasing IMB-1018972 dose.

The geometric mean Cmax increased with dose and ranged between 104 ng/mL and 870 ng/mL for IMB-1028814, between 36.9 ng/mL and 274 ng/mL for trimetazidine, and between 516 nmol/L and 3,839 nmol/L (molar units to account for differences in molecular weight) for IMB-1028814+trimetazidine over the studied single-dose range of 50 mg to 400 mg IMB-1018972 under fasted conditions. Similarly, the geometric mean $AUC_{0-t}$ increased with dose and ranged between 290 ng·h/mL and 2,795 ng·h/mL for IMB-1028814, between 424 ng·h/mL and 3,305 ng·h/mL for trimetazidine, and between 2,970 nmol·h/L and 22,365 nmol·h/L for IMB-1028814+trimetazidine over the studied single-dose range of 50 mg to 400 mg IMB-1018972 under fasted conditions. The predefined stopping criterion for IMB-1028814 plasma exposure of 417,733 and 652,849 ng·h/mL for males and females, respectively, was not reached by any of the subjects during the SAD part.

Dose proportionality of IMB-1028814 and trimetazidine was explored for Cmax, AUC0-t, and AUC0-inf. The 95% CIs of the slopes of all 3 exposure parameters included 1 for both IMB-1028814 and trimetazidine indicating no evidence of a deviation from dose proportionality of IMB-1028814 and trimetazidine over the IMB-1018972 single-dose range of 50 to 400 mg under fasted conditions.

The geometric mean $t_{1/2}$ of IMB-1028814 was relatively short, ranging between 2.6 hours and 3 hours over the IMB-1018972 single-dose range under fasted conditions. For metabolite trimetazidine, geometric mean $t_{1/2}$ was longer, ranging between 6.76 hours and 8 hours over the IMB-1018972 single-dose range under fasted conditions. Geometric mean $t_{1/2}$ of IMB-1028814 and trimetazidine did not increase with increasing IMB-1018972 dose indicating that the PK of the 2 moieties was linear.

PK in Plasma Following Administration of Trimetazidine

Following administration of a single oral dose of 35 mg trimetazidine, median trimetazidine tmax was 5 hours, and geometric mean values were 68.6 ng/mL for Cmax, 912 ng·h/mL for $AUC_{0-t}$, and 929 ng·h/mL for $AUC_{0-inf}$. The geometric mean t½ of trimetazidine was 7.49 hours.

Effect of Food

The possible effect of food on the PK of IMB-1028814 and trimetazidine was explored by comparing administration of single oral doses of 150 mg IMB-1018972 after an FDA-defined high-fat breakfast and under fasted conditions.

Median IMB-1028814 $t_{max}$ in plasma was reached at 2 hours postdose under fed conditions relative to 1 hour postdose under fasted conditions. Median trimetazidine $t_{max}$ in plasma was reached at 4 hours postdose under fed conditions relative to 1.5 hours postdose under fasted conditions.

The effect of food of IMB-1028814 and trimetazidine was explored for Cmax, AUC0-t, and $AUC_{0-inf}$. No evidence for an effect of food was observed on the IMB-1028814 exposure parameters $AUC_{0-t}$ and $AUC_{0-inf}$ (both with an estimate of 1.12 and 90% CI ranging from 1.02 to 1.23). However, $C_{max}$ was approximately 36% lower following administration of a single dose of 150 mg IMB-1018972 after an FDA-defined high-fat breakfast relative to administration under fasted conditions (estimate of 0.64; 90% CI ranging from 0.39 to 1.04).

No evidence for an effect of food was observed on the trimetazidine exposure parameters $C_{max}$ (estimate of 0.91; 90% CI ranging from 0.85 to 0.98), and AUC0-t and AUC0-inf (both with an estimate of 1.04 and 90% CI ranging from 0.98 to 1.10) following administration of a single dose of 150 mg IMB-1018972.

PK in Urine

The arithmetic mean percent of the dose excreted in urine ranged between 3.99% and 5.74% for IMB-1028814, and between 23.11% and 32.55% for trimetazidine within 48 hours after a single oral IMB-1018972 dose over the studied dose range of 50 mg to 400 mg. Within 48 hours following administration of a single oral dose of 35 mg trimetazidine, an arithmetic mean of 54.47% was excreted in urine as trimetazidine. These results indicate that metabolism is the primary clearance mechanism for IMB-1028814 while renal excretion is the primary clearance mechanism for trimetazidine.

The geometric mean renal clearance (CLR) ranged between 3.76 L/h and 5.37 L/h for IMB-1028814, and between 18.1 L/h and 20.8 L/h for trimetazidine over the studied single-dose range of 50 mg to 400 mg IMB-1018972. Geometric mean CLR for trimetazidine was 20.4 L/h following administration of a single oral dose of 35 mg trimetazidine. The renal clearance of trimetazidine is greater than the glomerular filtration rate (125 mL/min or 7.5 L/h), indicating that trimetazidine undergoes net tubular secretion.

MAD Part

Over the 2 multiple-dose levels, median $t_{max}$ ranged between 0.5 hours and 1 hours postdose for IVB-1028814 on Day 1, and was 3 hours postdose for trimetazidine on Day 1. On Day 14, median $t_{max}$ was 0.5 hours postdose for IMB-1028814 and 2 hours postdose for trimetazidine.

Exposure Parameters on Day 1

No dose-proportionality analysis was done since there were only 2 IMB-1018972 dose levels in the MAD part: multiple oral doses of 50 mg or 150 mg q12h for 14 days under fed conditions.

The geometric mean $C_{max}$ and $AUC0_{-T}$ were higher after 150 mg fed than after 50 mg fed for IMB-1028814 (297% and 336% higher for $C_{max}$ and $AUC_{0-T}$, respectively), trimetazidine (154% and 163% higher for $C_{max}$ and $AUC_{0-T}$ respectively), and IVB-1028814+trimetazidine (257% and 239% higher for $C_{max}$ and $AUC_{0-T}$, respectively).

When comparing the MAD and SAD parts, geometric mean $C_{max}$ was 97% higher on Day 1 after 150 mg fed in the MAD part than after a single dose of 150 mg fed in the SAD part for IMB-1028814. For trimetazidine however, geometric mean $C_{max}$ was 32% lower on Day 1 after 150 mg fed in the MAD part than after a single dose of 150 mg fed in the SAD part.

Exposure Parameters on Day 14 Following Repeated q12h Dosing

The geometric mean $C_{max}$ and $AUC_{0-T}$ were higher after 150 mg fed than after 50 mg fed for IMB-1028814 (377% and 367% higher for $C_{max}$ and $AUC_{0-T}$, respectively), trimetazidine (127% and 126% higher for $C_{max}$ and $AUC_{0-T}$, respectively), and IMB-1028814+trimetazidine (286% and 211% higher for $C_{max}$ and $AUC_{0-T}$, respectively).

The predefined stopping criterion for IMB-1028814 plasma exposure of 417,733 and 652,849 ng·h/mL for males and females, respectively, was not reached by any of the subjects during the MAD part.

Trough Concentrations Following Repeated q12h Dosing

Based upon visual inspection of the geometric mean plasma concentration-time profiles and the geometric mean trough concentrations, it can be concluded that for both 150 mg fed and 50 mg fed, the Day 14 IMB-1018972 dose was administered under steady-state conditions of IMB-1028814 and trimetazidine concentrations.

Accumulation Following Repeated q12h Dosing

For both the 50 mg and 150 mg fed dose levels, geometric mean $AUC_{0-T}$ values of IMB-1028814, trimetazidine, and IMB-1028814+trimetazidine were higher on Day 14 relative to Day 1. Geometric mean Rac for IVB-1028814 was 1.18 and 1.10 after the 150 mg fed dose and 50 mg fed dose, respectively, indicating minimal accumulation of IMB-1028814 in plasma. Geometric mean Rac for trimetazidine was 1.63 and 1.89 after the 150 mg fed dose and 50 mg fed dose, respectively, indicating modest accumulation of trimetazidine in plasma. Geometric mean Rac for IMB-1028814+trimetazidine was 1.39 and 1.52 after the 150 mg fed dose and 50 mg fed dose, respectively, indicating modest accumulation of IMB-1028814+trimetazidine in plasma.

Terminal Elimination Half-Life Following Repeated q12h Dosing

For IMB-1028814, the geometric mean t½ of 4.48 hours after 150 mg fed was longer than that of 2.79 hours after 50 mg fed. For trimetazidine, the geometric mean t½ of 9.36 hours after 150 mg fed was similar to that of 9.32 hours after 50 mg fed. For IMB-1028814+trimetazidine, the geometric mean $t_{1/2}$ of 8.90 hours for IMB-1028814 after 150 mg fed was similar to that of 9.08 hours after 50 mg fed.

Single-Dose MR Part

Following administration of both the 50-mg and 200-mg single oral fasted doses of IMB-1018972, $t_{max}$ for IMB-1028814 was earlier with the 8-hour MR formulation (2 hours for 50 mg and 200 mg IMB-1018972) than with the 4-hour MR formulation (5 hours for 50 mg IMB-1018972 and 3 hours for 200 mg IMB-1018972). Following administration of both the 50-mg and 200-mg single oral fasted doses of IMB-1018972, $t_{max}$ for trimetazidine was later with the 8-hour MR formulation (8 hours for 50 mg IMB-1018972 and 5 hours for 200 mg IMB-1018972) than with the 4-hour MR formulation (6 hours for 50 mg IMB-1018972 and 3 hours for 200 mg IMB-1018972). Following administration of both the 50-mg and 200-mg single oral fasted doses of IMB-1018972, $t_{max}$ for IMB-1028814+trimetazidine was similar for the 8-hour MR formulation (5 hours for 50 mg IMB-1018972 and 2.5 hours for 200 mg IMB-1018972) and the 4-hour MR formulation (5 hours for 50 mg IMB-1018972 and 3 hours for 200 mg IMB-1018972).

Following administration of the 50-mg and 200-mg single oral fasted doses of IMB-1018972, $C_{max}$ for IMB-1028814 was 35% and 32% lower, respectively, $C_{max}$ for trimetazidine was 20% and 24% lower, respectively, and $C_{max}$ for IMB-1028814+trimetazidine was 21% and 34% lower, respectively, for the 8-hour MR formulation relative to the 4-hour MR formulation.

Following administration of the 50-mg single oral fasted dose of IMB-1018972, $AUC_{0-t}$ for IMB-1028814 was 26% lower, $AUC_{0-t}$ for trimetazidine was 12% lower, and $AUC_{0-t}$ for IMB-1028814+trimetazidine was 18% lower after the 8-hour MR formulation than after the 4-hour MR formulation. Following the 200-mg single oral fasted dose of IMB-1018972, $AUC_{0-t}$ for IMB-1028814 was 6% higher, $AUC_{0-t}$ for trimetazidine was 4% higher, and $AUC_{0-t}$ for IMB-1028814+trimetazidine was 5% higher after the 8-hour MR formulation than after the 4-hour MR formulation.

Following administration of the 50-mg MR formulation and 200 mg MR formulation with 4-hour and 8-hour dissolution profile under fasted conditions, geometric mean t½ ranged between 3.35 hours and 4.27 hours for IMB-1028814, between 8.11 hours and 9.35 hours for trimetazidine, and between 6.95 hours and 7.96 hours for IMB-1028814+trimetazidine. Thus, for each of the analytes, no difference was observed in t½ was between the 4 fasted treatments.

Effect of Food

The possible effect of food on the PK of IMB-1028814 and trimetazidine was explored by comparing administration of single oral doses of 200 mg MR formulation of IMB-1018972 with 8-hour dissolution profile after an FDA-defined high-fat breakfast and under fasted conditions.

Median IMB-1028814 $t_{max}$ was reached at 3 hours postdose under both conditions. Median trimetazidine $t_{max}$ was reached at 5 hours postdose relative to 3 hours postdose under fasted conditions.

The effect of food of IMB-1028814 and trimetazidine was explored for $C_{max}$, $AUC_{0-t}$, and $AUC_{0-inf}$. No evidence for an effect of food was observed on the IMB-1028814 exposure parameters $AUC_{0-t}$ and $AUC_{0-inf}$ (both with an estimate of 1.16 and 90% CI ranging from 1.05 to 1.28). However, $C_{max}$ was approximately 42% higher following administration of a single dose of 200 mg 8-hour MR IMB-1018972 after an FDA-defined high-fat breakfast relative to administration under fasted conditions (estimate of 1.42; 90% CI ranging from 1.24 to 1.63).

No evidence for an effect of food was observed on the trimetazidine exposure parameters $C_{max}$ (estimate of 1.10; 90% CI ranging from 0.99 to 1.21), $AUC_{0-t}$ (estimate of 0.99; 90% CI ranging from 0.91 to 1.09), and $AUC_{0-inf}$ (estimate of 0.97; 90% CI ranging from 0.88 to 1.07) following administration of a single dose of 200 mg 8-hour MR IMB-1018972.

Multiple-Dose MR Part

Following administration of the 200 mg 8-hour MR IMB-1018972 dose, median IMB-1028814 $t_{max}$ was 2 hours on Day 1 and Day 5, and median $t_{max}$ was 5.5 hours and 5 hours for trimetazidine on Day 1 and Day 5, respectively.

Based upon visual inspection of the geometric mean plasma concentration-time profiles and the geometric mean trough concentrations, it can be concluded that steady state for both IMB-1028814 and trimetazidine concentrations was reached by Day 5 following multiple dose administration of 200 mg 8-hour MR IMB-1018972.

Geometric mean $R_{ac}$ for IMB-1028814, trimetazidine, and IMB-1028814+trimetazidine were 1.22, 2.28, and 1.66 on Day 5 relative to Day 1. This indicates minimal accumulation of IMB-1028814 in plasma, moderate accumulation of trimetazidine in plasma, and moderate accumulation of IMB-1028814+trimetazidine in plasma. The geometric mean half-life of the 200 mg 8-hour MR IMB-1018972 dose was 3.85 hours, 9.52 hours, and 8.64 hours for IMB-1028814, trimetazidine, and IMB-1028814+trimetazidine, respectively.

Conclusions

Safety

Overall, single oral IMB-1018972 doses and multiple oral IMB-1018972 doses of an IR formulation, and single and multiple doses of MR formulations, were generally well tolerated by healthy male and female subjects. There were no findings of clinical relevance with respect to clinical laboratory, vital signs, 12-lead ECG, continuous cardiac monitoring (telemetry), or physical examination. Of note, there were no findings of hemodynamic changes, nor changes in the QTc-interval, after administration of IMB-1018972 either as the IR or MR formulations.

During the SAD part, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions. These TEAEs were all considered by the Investigator to be related to the study drug. No subjects dropped out due to flushing and flushing was not considered a safety issue. Dose escalation beyond 400 mg IMB-1018972 IR did not proceed as planned based on the PK exposure levels of IMB-1028814 and trimetazidine exceeding the target exposure levels in the 400 mg group and the findings of flushing at that dose. The predefined target exposure level was approximately 3 to 4 'trimetazidine equivalents', ie, the ratio of the combined exposure of the active metabolites of IMB-1018972 to the single oral doses of 35 mg MR trimetazidine as seen in published literature.

There were no deaths reported during the study. Most TEAEs were of mild severity and no severe TEAEs were reported during the study. Overall, 12 of a total of 181 TEAEs were of moderate severity.

Two subjects were withdrawn from the study: 1 subject due to a moderate SAE of influenza like illness (unlikely related) and 1 due to a moderate TEAE of ALT increased (possibly related).

Overall, there was no clear dose dependency of the number and incidence of TEAEs.

Dosing under fed conditions appeared to attenuate the number and incidence of TEAEs in the FE arm of the SAD part, whereas no clear difference between fasted and fed IMB-1018972 administration for the number and incidence of TEAEs was observed in the single-dose MR part.

Pharmacokinetics

IMB-1018972 could be measured in only few plasma samples taken during this study.

When combining the single and multiple IMB-1018972 dose results under fasted and fed conditions, including those of the MR formulations, the initial hydrolysis of IMB-1018972 to IMB-1028814 and subsequent systemic bioavailability of IMB-1028814 was relatively rapid with median tmax ranging between 0.5 hours and 5 hours postdose for IMB-1028814, and between 1.5 hours and 8 hours postdose for trimetazidine. Median tmax did not increase with increasing IMB-1018972 dose The predefined stopping criterion for IMB-1028814 plasma exposure of 417,733 and 652,849 ng·h/mL for males and females, respectively, was not reached by any of the subjects during the SAD part or MAD part.

Following single oral IMB-1018972 doses in the range of 50 to 400 mg under fasted conditions, systemic exposure to IMB-1028814 and trimetazidine was dose proportional for $C_{max}$, $AUC_{0-t}$, and $AUC_{0-inf}$.

No evidence for an effect of food was observed on the IMB-1028814 exposure parameters $AUC_{0-t}$ and $AUC_{0-inf}$ following administration of a single dose of 150 mg IMB-1018972. However, $C_{max}$ was approximately 36% lower following administration of a single dose of 150 mg IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 150 mg IMB-1018972.

No evidence for an effect of food was observed on the IMB-1028814 exposure parameters $AUC_{0-t}$ and $AUC_{0-inf}$ following administration of a single dose of 200 mg 8-hour MR IMB-1018972. However, $C_{max}$ was approximately 42% higher following administration of a single dose of 200 mg 8-hour MR IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 200 mg 8-hour MR IMB-1018972.

When combining the single and multiple IMB-1018972 dose results under fasted and fed conditions, including those of the MR formulations, the geometric mean t½ ranged between 2.5 hours and 4.5 hours for IMB-1028814, and between 6.5 hours and 9.5 hours for trimetazidine. Geometric mean $t_{1/2}$ did not increase with increasing IMB-1018972 dose.

Within 48 hours following administration of a single oral dose of IMB-1018972 over the range of 50 mg to 400 mg, on average between 3.99% and 5.74% of the dose was excreted in urine as IMB-1028814, and on average between 23.11% and 32.55% of the dose was excreted as trimetazidine.

Within 48 hours following administration of a single oral dose of 35 mg trimetazidine, on average 54.47% of the dose was excreted in urine as trimetazidine.

Following 14 days of twice daily dosing with 150 mg and 50 mg IMB-1018972 under fed conditions, no relevant accumulation was observed of IMB-1028814 (Rac of 1.18 and 1.10 for 150 mg and 50 mg, respectively) and accumulation of trimetazidine was modest (Rac of 1.63 and 1.89 for 150 mg and 50 mg, respectively).

Following 5 days of twice daily dosing with 200 mg 8-hour MR IMB-1018972 under fed conditions, no relevant accumulation of IMB-1028814 (Rac of 1.22) was observed, whereas accumulation of trimetazidine was moderate (Rac of 2.28).

Overall

In view of the positive risk/benefit profile and the observed PK characteristics of the IMB-1018972 metabolitescIMB-1028814 and trimetazidine in this single-dose and multiple-dose FIE study, further clinical development of IMB-1018972 is warranted.

Introduction

IMB-1018972 is an orally administered small molecule that is being developed as a treatment for ischemic cardiovascular disease and the associated abnormal cellular energetics. Potential indications include angina pectoris, heart failure, and peripheral vascular disease. IMB-1018972 is a new chemical entity (NCE) of the drug class partial fatty acid oxidation (pFOX) inhibitors that acts to preserve or enhance energy metabolism in cells exposed to hypoxia or ischemia. Other pFOX inhibitors include ranolazine (Ranexa), perhexiline, and trimetazidine. Glucose oxidation is a more efficient producer of adenosine triphosphate per oxygen molecule consumed compared to fatty acid oxidation.

IMB-1018972 undergoes hydrolysis after administration, and the hydrolysis products are nicotinic acid (also known as niacin or vitamin B3) and an inhibitor of 3-ketoacyl CoA thiolase (3-KAT) named IMB-1028814. In addition to IMB-1018972, IMB-1028814 has been studied and characterized extensively in nonclinical studies. IMB-1028814 undergoes further metabolism and 1 metabolite is trimetazidine, a drug marketed in Europe since 1987 for the treatment of angina pectoris.

The primary mechanism of action of IMB-1028814 is thought to be competitive inhibition of 3-KAT that results in the shift of substrate utilization in the myocardium from fatty acid oxidation to glucose oxidation. The delivery of nicotinic acid may serve to additionally enhance cellular energetics.

A detailed description of the chemistry, pharmacology, efficacy, and safety of IMB-1018972 is provided in the IMB-1018972 investigator's brochure. The nonclinical pharmacology and toxicology data collected at the time the CSP was finalized supported conducting clinical studies that administer IMB-1018972 for up to 4 weeks to assess its safety, tolerability, PK, and pharmacodynamics in humans.

Trimetazidine administered in this study is a drug marketed in Europe since 1978 for the treatment of angina pectoris.

Study Rationale

No clinical studies with IMB-1018972 had been performed prior to the study described in this CSR. Therefore, this first-in-human study (FIH), with single-dose and multiple-dose escalation designs (single ascending dose [SAD] part and multiple ascending dose [MAD] part) and a single-dose food effect (FE) study was conducted to assess the safety, tolerability, and PK of IMB-1018972 as an immediate-release (IR) formulation following administration of single and multiple ascending doses.

During the study, a group was added to the SAD part testing a single 35-mg modified-release (MR) dose of trimetazidine (Vastarel). The primary rationale for adding this group was to study the PK profile of commercially available trimetazidine with the same analytical assays utilized in the current study, which would enable a direct comparison of the PK profiles of trimetazidine generated from Vastarel and that generated from the metabolism of IMB-1028814. The analytical assays include detection of trimetazidine in blood and urine, which is the primary route of elimination. These data, together with the data generated from the MAD part would help the Sponsor select doses for further investigation in the Phase 2 proof-of-concept study in patients with refractory angina.

During the study, a single-dose MR part was added assessing the safety, tolerability, and PK profile of single oral doses of newly developed MR formulations of IMB-1018972. These concerned 4 MR formulations: 50 mg and 200 mg dose strengths of IMB-1018972, each with a 4-hour dissolution profile and an 8-hour dissolution profile. The objectives of these MR formulations were two-fold: the first objective was to lower the $C_{max}$ of IMB-1018972 and its subsequent metabolites; the second was to extend the absorption time and preserve total exposure as measured by the AUCs. The expectation was that lower $C_{max}$ would improve overall tolerability and extended absorption time with preserved AUCs was expected to decrease the variability seen in the exposures of the IR formulation. Based on the available safety, tolerability, and PK results of the 4 MR formulations administered under fasted conditions in the single-dose MR part, the formulation chosen by the Sponsor for administration under fed conditions in the single-dose MR part was the 200 mg 8-hour MR formulation. This MR formulation testing was important as it was planned to use this formulation in the Phase 2 proof-of-concept studies planned to commence in the year 2020.

A final part (multiple-dose MR part) was added assessing the safety, tolerability, and PK profile of multiple doses (every 12 hours [q12h] for 5 consecutive days) of the MR formulation with a 200 mg dose strength and an 8-hour dissolution profile (200 mg 8-hour MR formulation), taken with food. This dose and formulation were tested in the fasted and fed states in the single-dose MR part. This dose and formulation are targeted for use in a patient population in later studies, and data collected from the subject cohort in this final part would inform that decision.

Study Objectives

Primary

To assess the safety and tolerability of single and multiple ascending oral doses of IMB-1018972, single oral doses of trimetazidine, single oral doses of MR formulations of IMB-1018972, and multiple oral doses of the 200 mg 8-hour MR formulation of IMB-1018972 in healthy subjects.

Secondary
    To assess the PK profile of single and multiple ascending oral doses of IMB-1018972, single oral doses of trimetazidine, single oral doses of MR formulations of IMB-1018972, and multiple oral doses of the 200 mg 8-hour MR formulation of IMB-1018972 in healthy subjects
    To assess the effect of food on the absorption and the PK profile of IMB-1018972 following a single oral dose of IMB-1018972 in healthy subjects
    To evaluate the effect of food on the safety and tolerability of IMB-1018972 following a single oral dose of IMB-1018972 in healthy subjects
    To assess the absorption and PK profile of the 200 mg 8-hour MR formulation of IMB-1018972 following multiple oral doses taken with food in healthy subjects
    To evaluate the safety and tolerability of the 200 mg 8-hour MR formulation of IMB-1018972 following multiple oral doses taken with food in healthy subjects Investigational Plan
Overall Study Design and Plan
Type of Study This was a double-blind, randomized, placebo-controlled study, consisting of a SAD part with integrated FE arm, a MAD part, and single-dose and multiple-dose MR parts to assess the safety, tolerability, and PK of ascending single and multiple oral doses of IMB-1018972 (IR formulation in the SAD and MAD parts), single oral doses of a MR formulation of trimetazidine, single oral doses of MR formulations of IMB-1018972, and multiple oral doses of the 200 mg 8-hour MR formulation of IMB-1018972. The study started with the SAD part.

SAD Part (and Integrated FE Arm)

In the SAD part, 5 groups of 8 healthy subjects (6 subjects on active drug and 2 on placebo in Groups A1, A2, A3, and A4, and 8 subjects on active drug in Group A5) were included. In Groups A1, A2, A3, and A4, subjects received a single oral dose of an IR formulation of IMB-1018972 or placebo under fasted conditions (an overnight fast of at least 10 hours). In Group A5, all subjects received a single oral dose of a MR formulation of trimetazidine under fasted conditions (an overnight fast of at least 10 hours). Each subject participated in only 1 group during the study Subjects assigned to Group A4 also participated in the FE arm and received the same single dose of IMB-1018972 or placebo under fed conditions (Food and Drug Administration [FDA]-defined high-fat breakfast after an overnight fast of at least 10 hours) in a second period at least 1 week after drug administration under fasted conditions in the SAD part.

In this first-in-human (FIH) study, the subjects participating at the lowest dose level, subjects of Group A1, were dosed according to a sentinel dosing design to ensure optimal safety. This means that initially, 2 subjects were dosed: 1 subject with IMB-1018972 and 1 subject with placebo. Since the safety and tolerability results of the first 24 hours following dosing for the initial 2 subjects were acceptable to the Investigator, the other 6 subjects (5 active drug and 1 placebo) of the lowest dose level were also dosed. Depending on emerging safety data, it could have been decided to implement this sentinel dosing design for other groups as well; however, this was not done.

The SAD part consisted of:
    An eligibility screening period of up to 35 days
    One study period involving administration of a single dose of IMB-1018972 or placebo (or trimetazidine in Group A5); this was 2 periods for subjects of Group A4 also participating in the FE arm
    Safety assessments and blood sampling for PK purposes from predose up to 48 hours after drug administration
    Discharge at 48 hours after study drug administration (in each period for subjects of Group A4 also participating in the FE arm)
    A follow-up visit 7 to 14 days after the last PK blood sample; this was 7 to 14 days after the last PK blood sample in the second period for subjects of Group A4 also participating in the FE arm MAD Part In the MAD part, 2 groups of 12 healthy subjects (9 subjects on active drug and 3 on placebo in each group) were included. Subjects received multiple oral doses of an IR formulation of IMB-1018972 or placebo once q12h for 14 consecutive days. Each subject participated in only 1 group during the study.

Study drug administration was under fed conditions as determined based on the results of Group A4 in the FE arm.

The MAD part consisted of:
    An eligibility screening period of up to 35 days
    One study period involving administration of multiple doses of IMB-1018972 or placebo for 14 consecutive days
    Safety assessments and blood sampling for PK purposes from predose up to 48 hours after the last study drug administration
    Discharge at 48 hours after the last study drug administration
    A follow-up visit 7 to 14 days after the last PK blood sample Single-Dose MR Part In the single-dose MR part, 1 group of 12 healthy subjects (all on active drug) was included. The subjects received a single oral dose of 1 of 4 MR formulations of IMB-1018972 under fasted conditions (an overnight fast of at least 10 hours) on Days 1, 4, 7, and 10 in a fixed order that was the same for all subjects. The MR formulation of IMB-1018972 to be administered on Day 13 under fed conditions was 1 of the 4 MR formulations administered on Days 1, 4, 7, and 10 under fasted conditions as determined by the Sponsor based on the available safety, tolerability, and PK results of the 4 MR formulations.

The single-dose MR part consisted of:
    An eligibility screening period of up to 35 days
    One study period involving administration of single doses of IMB-1018972 on Days 1, 4, 7, 10, and 13
    Safety assessments and blood sampling for PK purposes from predose on Day 1 up to 48 hours after the last drug administration
    Discharge at 72 hours after the last study drug administration
    A follow-up visit 7 to 14 days after the last PK blood sample Multiple Dose MR Part In the multiple-dose MR part, 1 group of 12 healthy subjects (all on active drug) was included. Subjects received multiple oral doses of the MR formulation of IMB-1018972 q12h under fed conditions for 5 consecutive days; on Day 5 only a single morning dose was administered. The MR formulation of IMB-1018972 administered was the same as that administered in the single-dose MR part under both fasted and fed conditions.

The multiple-dose MR part consists of:
    An eligibility screening period of up to 35 days
    One study period involving administration of multiple doses of the 200 mg 8-hour MR formulation of IMB-1018972 from Day 1 to Day 5

Safety assessments and blood sampling for PK purposes from predose on Day 1 up to 48 hours after the last drug administration Discharge at 48 hours after the last drug administration A follow-up visit 6 to 8 days after the last PK blood sample Screen Period Subjects reported to the medical screening facility for the eligibility screening within 5 weeks prior to (the first) study drug administration.

Subjects signed the study-specific ICF prior to any study-specific screening procedures being performed. The written informed consent was obtained for all subjects, regardless of their eligibility for the study. The signed ICFs were retained and archived at PRA and a copy was provided to the subject.

Treatment Period

Subjects were in the clinic for 1 treatment period (2 treatment periods for subjects of Group A4 also participating in the FE arm). The subjects were admitted to the clinical research center in the afternoon of Day −1. Day 1 was the day of (the first) drug administration.

Subjects of the SAD part were discharged on Day 3 (48 hours after study drug administration) after completion of the assessments; discharge was on Day 3 of each period for subjects of Group A4 also participating in the FE arm. Subjects of the MAD part were discharged on Day 16 (48 hours after the last study drug administration on Day 14) after completion of the assessments. Subjects of the single-dose MR part were discharged on Day 16 (72 hours after the last study drug administration on Day 13) after completion of the assessments. Subjects of the multiple-dose MR part were discharged on Day 7 (48 hours after the last study drug administration on Day 5) after completion of the assessments Follow-Up For the SAD part, the follow-up assessments were performed 7 to 14 days after the last PK blood sample (between Day 10 and Day 17). For the FE arm, the follow-up assessments were performed 7 to 14 days after the last PK blood sample in the second period (between Day 10 and Day 17). For the MAD part, the follow-up assessments were performed 7 to 14 days after the last PK blood sample (between Day 23 and Day 30). For the single-dose MR part, the follow-up assessments were performed 7 to 14 days after the last PK blood sample (between Day 23 and Day 30). For the multiple-dose MR part, the follow-up assessments were performed 6 to 8 days after the last PK blood sample (Day 14±1 day).

Discussion of Study Design

Dose Escalation within a Study Part

An escalating-dose study design was chosen for the SAD and MAD parts to allow careful increase of the IMB-1018972 dose after assessment of the available safety, tolerability, and PK results of the preceding group.

A dose-escalation meeting was held between the Investigator and the Sponsor. Further, a dose-escalation report (DER) was provided by the Investigator to the IEC following completion of each dose level. Escalation to the next higher dose only proceeded when none of the stopping criteria had been reached and if the available safety, tolerability, and PK results of the preceding group were acceptable to the Investigator and the Sponsor and after a statement of no objection of the DER from the IEC. The safety, tolerability, and PK results had to be available up to 48 hours postdose for the SAD part and up to 48 hours after the final morning dose on Day 14 for the MAD part. In addition, these results had to be available from at least 5 dosed subjects of the preceding group in the SAD part and at least 8 dosed subjects of the preceding group in the MAD part The planned dose levels to be administered could be changed based on the safety, tolerability, and plasma PK results of the previous group(s).

Dose levels in the MAD part could not exceed dose levels that were well tolerated in the SAD part.

The increase from one dose level to the next dose level could not be more than 3-fold.

Although this was an ascending dose study, if safety or tolerability issues were experienced, a lower dose could be administered in the next groups. Also, the same dose could be tested in 2 groups or an intermediate dose could by tested to gain more information on safety, tolerability, and/or PK.

Stopping Rules for Dose Escalation

Dosing within a group and dose escalation to a next group was halted at any time if 1 of the following circumstances occurred:

A drug-related serious adverse reaction (ie, a serious adverse event [SAE] considered at least possibly related to the study drug administration) in 1 subject.

Drug-related severe adverse reactions (ie, severe adverse events [AEs] considered at least possibly related to the study drug administration) in 2 subjects in the same group, or in 1 subject in the sentinel group of a group.

Other findings that, at the discretion of the Investigator and/or Sponsor's Medical Monitor, indicated that further dosing had to be stopped.

When stopping rules for a group were met, the randomization code for subjects meeting the stopping rules was to be unblinded. If after unblinding it was concluded that subjects on active medication met the stopping rules, dosing in the group was to be stopped, and no further dose escalation was to be performed. If a subsequent integrated analysis of available data led to the conclusion that further careful escalation was warranted, a substantial amendment was needed before continuation of the study. Dose escalation in a study part (SAD, MAD) was permanently stopped if:

Blinded PK data indicated that after dose escalation it was anticipated that individual subjects would exceed the predefined maximum exposure level of $AUC_{0-8\times2}$ for IMB-1028814 of 417,733 and 652,849 ng·h/mL for males and females, respectively Sentinel Dosing IMB-1018972 is in the early stage of clinical development, with the SAD part of the study being the first time the compound was administered to man. In this FIH study, the subjects participating at the lowest dose level of the SAD part, subjects of Group A1, were dosed according to a sentinel dosing design to ensure optimal safety. This means that initially, 2 subjects were dosed. One of these subjects received the active medication IMB-1018972, and the other subject received placebo. The subjects were closely observed by the Investigator for the first 24 hours following drug administration. The general tolerability of the study drug was monitored during this time, and the electrocardiogram (ECG) and vital signs recordings were reviewed. Any reported AEs were also considered in the Investigator's evaluation. If the safety and tolerability results of the first 24 hours following dosing for the initial 2 subjects were acceptable to the Investigator, the other subjects of the lowest dose level could be dosed in a placebo-controlled randomized manner (5 active and 1 placebo). Depending on emerging safety data, it could have been decided to implement this sentinel dosing design for other SAD groups as well (except for the second period of Group A4 in the FE arm and except for Group A5; all subjects of these 2 groups could be dosed on the same day).

Effect of Food

Subjects from Group A4 of the SAD part were assigned to the integrated FE arm. After administration of the drug to fasting subjects in the SAD part, the FE arm used the same subjects and experimental procedures. An exception was that subjects consumed an FDA-defined high-fat breakfast prior to dosing to evaluate the possible effect of food on the PK of IMB-1018972. This allowed for a within-subject comparison of the PK of IMB-1018972 in plasma and tolerability after administration in fasted and fed conditions.

In the single-dose MR part, 12 healthy subjects (all on active drug) received a single oral dose of 1 of 4 MR formulations of IMB-1018972 under fasted conditions (an overnight fast of at least 10 hours) on Days 1, 4, 7, and 10 in a fixed order that was the same for all subjects. On Day 13, 1 of these 4 MR formulations was chosen to be administered to the same subjects under fed conditions (FDA-defined high-fat breakfast prior to dosing) to evaluate the possible effect of food on the PK of IMB-1018972). This allowed for a within-subject comparison of the PK of IMB-1018972 in plasma and tolerability after administration of this MR formulation in fasted and fed conditions.

In the multiple-dose MR part, 12 healthy subjects received multiple oral doses of the MR formulation of IMB-1018972 q12h under fed conditions for 5 consecutive days; on Day 5 only a single morning dose was administered. The MR formulation of IMB-1018972 administered was the same as that administered in the single-dose MR part. The safety, tolerability, and PK of multiple doses of this MR formulation taken with food were evaluated.

Continuation to the MAD Part of the Study

The MAD part could start after the results from the FE arm were available. The first group of the MAD part could start when a DER, summarizing safety and available PK data of previous SAD groups, concluded that a single dose with an exposure at/above the expected steady-state exposure in the first MAD group was well tolerated.

In the MAD part, subjects received twice daily dosing, which was the anticipated clinical dosing regimen considering the anticipated short human half-life and absence of prolonged duration of action. Doses were given q12h. In the MAD part, dosing continued for 14 days, which was anticipated to result in steady state of exposure.

The highest multiple-dose group planned could not exceed the highest planned single dose of 1600 mg/day or the highest tolerated dose in the SAD part. This was predicted to sufficiently cover doses in future dose-finding studies in patients.

Other

The planned confinement period, day of discharge, and follow-up period could be adapted depending on emerging study results. Also, the timing, type, and number of safety and PK assessments could be changed during the study.

The purpose of including placebo-treated subjects in each group (except Group A5 and the single-dose and multiple-dose MR parts in which no placebo was administered) was to assist the medical assessment of whether or not any abnormalities observed were due to the study drug or to study procedures, and not for a formal statistical comparison between active and placebo subjects.

There was no indication from in vitro studies (cytochrome P450 [CYP]3A4/GT1A1/CYP2C19/CYP2C9) for interaction with oral contraceptives. Women of childbearing potential who were using adequate contraception were included in the present study, in order to make the outcome of this FIH study relevant for the female target patient population.

The use of healthy subjects as opposed to patients allowed a clearer interpretation of the study results, as there were no confounding factors resulting from changes in disease state and/or concomitant medications.

The study was performed in different groups of subjects since the number of doses to be tested, and all assessments associated with these sessions, were regarded as too extensive to be performed in a single group of subjects participating repeatedly.

The Investigator took all the usual precautions necessary for studies at an early stage in the development of a new drug.

Selection of Study Population

The overall study population consisted of 88 subjects.

In the SAD part (and integrated FE part), a total of 40 healthy male or female subjects were included. Eight subjects from Group A4 in the SAD part participated in the FE arm. From Group A4 onwards, all efforts were made to have a ratio of 50:50 for male and female subjects per group, but at minimum at least 3 subjects of each gender were dosed per group.

In the MAD part, a total of 24 healthy male or female subjects were included. For each group, all efforts were made to have a ratio of 50:50 for male and female subjects, but at minimum at least 4 subjects of each gender were dosed per group.

In the single-dose and multiple-dose MR parts, a total of 24 healthy male or female subjects (12 in each part) were included. All efforts were made to have a ratio of 50:50 for male and female subjects, but at minimum at least 4 subjects of each gender were dosed in each part.

Inclusion Criteria

Subjects were eligible for inclusion in the study if they met all the following inclusion criteria:
1. Gender: male or female.
2. Age: 18 years to 65 years, inclusive, at screening.
3. Body mass index (BMI): 18.0 kg/m2 to 32.0 kg/m2, inclusive.
4. Status: healthy subjects.
5. At screening, females could be of childbearing potential (but not pregnant or lactating), or of nonchildbearing potential (either surgically sterilized or physiologically incapable of becoming pregnant, or at least 1 year postmenopausal [amenorrhea duration of 12 consecutive months]); nonpregnancy was confirmed for all females by a serum pregnancy test conducted at screening and each admission.
6. Female subjects of childbearing potential who had a fertile male sexual partner had to agree to use adequate contraception from screening until 90 days after the follow-up visit. Adequate contraception was defined as using hormonal contraceptives or an intrauterine device combined with at least 1 of the following forms of contraception: a diaphragm, a cervical cap, or a condom. Total abstinence, in accordance with the lifestyle of the subject, was also acceptable.
7. Male subjects, if not surgically sterilized, had to agree to use adequate contraception and not donate sperm from (first) admission to the clinical research center until 90 days after the follow-up visit. Adequate contraception for the male subject (and his female partner) was defined as using hormonal contraceptives or an intrauterine device combined with at least 1 of the following forms of contraception: a diaphragm, a cervical cap, or a condom. Total abstinence, in accordance with the lifestyle of the subject, was also acceptable.
8. All prescribed medication had to be stopped at least 30 days prior to (first) admission to the clinical research center. An exception was made for hormonal contraceptives, which could be used throughout the study.
9. All over-the-counter medication, vitamin preparations and other food supplements, or herbal medications (eg, St. John's Wort) had to be stopped at least 14 days prior to (first) admission to the clinical research center. An exception was made for paracetamol, which was allowed up to admission to the clinical research center.
10. Willingness to abstain from alcohol, methylxanthine-containing beverages or food (coffee, tea, cola, chocolate, energy drinks), grapefruit (juice), and tobacco products from 48 hours prior to (each) admission to the clinical research center.
11. Good physical and mental health on the basis of medical history, physical examination, clinical laboratory, and vital signs, as judged by the Investigator.
12. Had no clinically significant abnormal 12-lead ECG (incomplete right bundle branch block could be accepted) at screening: PR-interval <210 ms, QRS-duration <120 ms, and QTc-interval (Fridericia's)<450 msec for males and females.
13. Willing and able to sign the ICF.

Exclusion Criteria

Subjects were excluded from participation if any of the following exclusion criteria applied:
1. Previous participation in the current study.
2. Employee of PRA or the Sponsor.
3. History of relevant drug and/or food allergies.
4. Using tobacco products within 3 months prior to (the first) drug administration.
5. History of alcohol abuse or drug addiction (including soft drugs like cannabis products).
6. Positive drug and alcohol screen (opiates, methadone, cocaine, amphetamines [including ecstasy], cannabinoids, barbiturates, benzodiazepines, tricyclic antidepressants, and alcohol) at screening and (each) admission to the clinical research center.
7 Average intake of more than 24 units of alcohol per week (1 unit of alcohol equals approximately 250 mL of beer, 100 mL of wine, or 35 mL of spirits).
8. Positive screen for hepatitis B surface antigen (HBsAg), anti-hepatitis C virus (HCV) antibodies, or anti-HIV 1 and 2 antibodies.
9. Participation in a drug study within 60 days prior to (the first) drug administration in the current study. Participation in more than 4 other drug studies in the 12 months prior to (the first) drug administration in the current study.
10. Donation or loss of more than 100 mL of blood within 60 days prior to (the first) drug administration. Donation or loss of more than 1.5 liters of blood (for male subjects)/more than 1.0 liters of blood (for female subjects) in the 10 months prior to (the first) drug administration in the current study.
11. Significant and/or acute illness within 5 days prior to (the first) drug administration that could impact safety assessments, in the opinion of the Investigator.
12. Unsuitable veins for infusion or blood sampling.
13. For FE Group A4 and the single-dose MR part only: Unwillingness to consume the FDA breakfast.

Please note that subjects were to refrain from consumption of any foods containing poppy seeds within 48 hours (2 days) prior to screening to the clinical research center to avoid false positive drug screen results. In addition, they were to refrain from strenuous exercise within 96 hours (4 days) prior to screening as this could result in abnormal clinical laboratory values.

Removal of Subject from Assessment

Participation in the study was strictly voluntary. A subject had the right to withdraw from the study at any time for any reason.

The Investigator had the right to terminate participation of a subject for any of the following reasons: difficulties in obtaining blood samples, violation of the protocol, severe AEs or SAEs, or for any other reason relating to the subject's safety or the integrity of the study data.

If a subject was withdrawn from the study, the Sponsor was to be informed immediately. If there was a medical reason for withdrawal, the subject remained under the supervision of the Investigator until satisfactory health had returned.

Subjects who dropped out or withdrew for any reason without completing all screening evaluations successfully, were considered screening failures.

A subject who was withdrawn or voluntarily withdrew from the study for any reason, whether related to the study drug or not, after having received a subject number, was considered an early-termination subject. If a subject was withdrawn for a reason related to the study drug, according to the judgment of the Investigator, the early-termination subject was not replaced. If a subject did not complete the study for a reason not related to the study drug, the early-termination subject could be replaced after mutual agreement between the Sponsor and PRA.

The decision regarding the replacement of subjects was documented.

PRA made every effort to ensure that early-termination subjects who had received study drug completed the safety follow-up assessments.

Stopping Rules for Individual Subjects

Dosing of a subject was stopped at any time during the study if any of the following circumstances occurred:
A serious adverse reaction (ie, an SAE considered at least possibly related to the study drug administration).
An overall pattern of clinically significant changes in any safety parameter (eg, moderate or severe AEs in >1 subject) that could appear to be minor in terms of an individual event but, in the opinion of the Sponsor or Investigator, collectively represented a safety concern.
Other findings that, at the discretion of the Investigator and/or Sponsor's Medical Monitor, indicated that further dosing should be stopped.

Treatments

SAD Part (and Integrated FE Arm)

The following treatments were administered under fasted conditions according to the randomization code:
Group A1 single oral dose of 50 mg IR formulation of IMB-1018972 (n=6) or matching placebo (n=2) on Day 1
Group A2 single oral dose of 150 mg IR formulation of IMB-1018972 (n=6) or matching placebo (n=2) on Day 1
Group A3: single oral dose of 400 mg IR formulation of IMB-1018972 (n=6) or matching placebo (n=2) on Day 1
Group A4: single oral dose of 150 mg IR formulation of IMB-1018972 (n=6) or matching placebo (n=2) on Day 1 (FE group)
Group A5: single oral dose of 35 mg MR formulation of trimetazidine (Vastarel; n=8) on Day 1

The following treatment was administered in the FE arm under fed conditions (FDA-defined high-fat breakfast) according to the randomization code Group A4: single oral dose of 150 mg IR formulation of IMB-1018972 (n=5) or matching placebo (n=2) on Day 1 (same dose as in SAD part)

Up to 2 additional SAD groups could be included to evaluate a lower, intermediate, or repeat dose level(s), or, provided that dose-escalation termination criteria had not been met, a higher dose level.

MAD Part

The following treatments were administered according to the randomization code under fed conditions as determined based on the results of Group A4 in the FE arm. The doses were selected based upon the safety, tolerability, and PK data from the SAD part:

Group B1: multiple oral doses of an IR formulation of 150 mg IMB-1018972 (n=9) or matching placebo (n=3) twice daily (q12h) for 14 days; on Day 14 only a single morning dose was administered Group B2: multiple oral doses of an IR formulation of 50 mg IMB-1018972 (n=9) or matching placebo (n=3) q12h for 14 days; on Day 14 only a single morning dose was administered Up to 2 additional MAD groups could be included to evaluate a lower, intermediate, or repeat dose level(s), or, provided that dose-escalation termination criteria had not been met, a higher dose level.

Single-Dose MR Part

The formulation chosen for administration on Day 13 was the 200 mg 8-hour MR formulation as determined by the Sponsor based on the available safety, tolerability, and PK results of the 4 MR formulations administered on Days 1, 4, 7, and 10 under fasted conditions.

The following treatments were administered in the single-dose MR part:

Day 1: single oral dose of 50 mg 8-hour MR formulation of IMB-1018972 (n=12) under fasted conditions Day 4: single oral dose of 50 mg 4-hour MR formulation of IMB-1018972 (n=12) under fasted conditions Day 7: single oral dose of 200 mg 8-hour MR formulation of IMB-1018972 (n=12) under fasted conditions Day 10: single oral dose of 200 mg 4-hour MR formulation of IMB-1018972 (n=12) under fasted conditions Day 13: single oral dose of 200 mg 8-hour MR formulation of IMB-1018972 (n=12) under fed conditions Multiple-Dose MR Part Twelve subjects received multiple oral doses of the 200 mg 8-hour MR formulation of IMB-1018972 q12h under fed conditions for 5 consecutive days; on Day 5 only a single morning dose was administered.

Identity of Investigational Products

Active Medication

Drug product: IMB-1018972
Activity: Fatty acid oxidation inhibitor
In development for: Ischemic cardiovascular disease
Strength: 25 mg, 100 mg, and 200 mg IR formulations (based on free base); 50 mg MR formulation and 200 mg MR formulation with 4-hour and 8-hour dissolution profile (based on free base)
Dosage form: Oral IR capsule(s) to be used in the SAD and MAD parts and oral MR tablet(s) to be used in the MR parts
Manufacturer: Pharmacy at PRA
Batch number: 2479-1810-00441 (drug substance)

IMB-1018972 Placebo (Visually Matching Active Medication)

Active substance: Not applicable
Activity: Not applicable
Strength: Not applicable
Dosage form: Oral capsule(s)
Manufacturer: Pharmacy at PRA
Batch number: Not applicable Active Medication Drug product: Vastarel MR (trimetazidine dihydrochloride)
Activity: Fatty acid oxidation inhibitor
In development for: Angina pectoris
Strength: 35 mg
Dosage form: Oral MR tablet
Manufacturer: Server Research & Pharmaceuticals (Pakistan) (Pvt.) Ltd.
Batch number: 273782 (drug product)

The study drug was stored in the pharmacy at PRA in a locked facility under the required storage conditions with continuous monitoring. The study drug was dispensed by the pharmacist to the Investigator or authorized designee.

The total number of IMB-1018972 capsules given per dose level in the SAD part (and integrated FE arm) and MAD part is given in Table 1. The number of placebo capsules that was administered to a placebo subject in a specific group was the same as the number of IMB-1018972 capsules that was given to an IMB-1018972 subject in that group.

TABLE 1

Number of IMB-1018972 Capsules Given per Dose Level in the SAD Part (and Integrated FE Arm) and MAD Part

| IMB-1018972 dose level | Number of 25-mg (free base) IMB-1018972 capsules | Number of 100-mg (free base) IMB-1018972 capsules | Number of 200-mg (free base) IMB-1018972 capsules | Total number of IMB-1018972 capsules |
|---|---|---|---|---|
| 50 | 2 | 0 | 0 | 2 |
| 150 | 2 | 1 | 0 | 3 |
| 400 | 0 | 0 | 2 | 2 |

Method of Assignment Subjects to Treatment Groups

After obtaining informed consent, subjects were screened according to the inclusion and exclusion criteria. Subjects who met all eligibility criteria received a subject number upon inclusion in the study. They received the subject number just prior to dosing according to the randomization code generated by the Biostatistics Department of PRA. The subject number ensured identification throughout the study.

Subject numbers were 101 to 140 for the SAD part, 201 to 224 for the MAD part, 501 to 512 for the single-dose MR part, and 513 to 524 for the multiple-dose MR part. Any additional subjects to be included in the SAD part were to be numbered starting from subject number 141 and any additional subjects in the MAD part were to be numbered starting from subject number 225.

Any replacement subject was to receive the number of the subject to be replaced, increased by 200, and was to be administered the same treatment(s). Subjects were assigned to a study part and group based on their availability. Treatments within a group were assigned according to the randomization code generated by the Biostatistics Department of PRA.

In each SAD group, except for Group A5, 6 subjects were randomly assigned to receive IMB-1018972 and 2 subjects were randomly assigned to receive placebo. In Group A5, all 8 subjects received trimetazidine. In each MAD group, 9 subjects were randomly assigned to receive IMB-1018972 and 3 subjects were randomly assigned to receive placebo. In both MR parts, all 12 subjects received IMB-1018972.

For the 2 sentinel subjects in Group A1 of the SAD part, randomization ensured that 1 subject received IMB-1018972 and the other subject received placebo. For the remaining 6 subjects of Group A1, randomization ensured that 5 received IMB-1018972 and 1 received placebo. Depending on emerging safety data, it could be decided to implement this sentinel dosing design for other SAD groups as well (except for the second period of Group A4 in the FE arm and except for Group A5; all subjects of these 2 groups could be dosed on the same day).

Subjects who dropped out or withdrew for any reason without completing all screening evaluations successfully were considered screening failures. Such subjects, and also subjects who were eligible for inclusion in the study but did not receive the study drug, received no subject number, and only applicable data were entered in the eCRFs.

Selection of Doses in the Study

Based on the nonclinical toxicology data, it was considered that subjects in this clinical study were not at unreasonable risk of adverse effects. Based on the 28-day dog no observed adverse effect level (NOAEL) of 200 mg/kg/day (oral), the calculated human equivalent dose (HED) is 108 mg/kg/day. For a 60-kg individual, the NOAEL dose would be 6480 mg. With a 10-fold safety factor applied, this would allow for a maximum recommended starting dose (MRSD) of 648 mg/day.7,8 The planned starting dose in the current Phase 1 study was 50 mg, equivalent to 0.83 mg/kg/day for a 60-kg subject. This starting dose is less than 10% of the MRSD determined from the dog NOAEL and less than 1% of the dog NOAEL The maximum planned dose in this study of 1600 mg in healthy volunteers was 25% of the HED NOAEL dose of 6480 mg and only 2.5 fold higher than the MRSD. The conservative dosing margin was expected to cover potential supratherapeutic exposures, for instance in patients with renal or hepatic impairment, or in case of potential drug interactions with IMB-1018972. This risk for healthy volunteers at these exposure levels was determined to be acceptable based on the absence of irreversible or significant toxicities without sentinel safety biomarkers.

The relevant animal study was the 28-day dog study where the NOAEL for IMB-1018972 was 200 mg/kg/day. The $AUC_{0-8\times2}$ for IMB-1028814 on Day 26 at this dose was 417,733 and 652,849 ng·h/mL for males and females, respectively. The $AUC_{0-8\times2}$ for trimetazidine on Day 26 at this dose was 15,042, and 13,834 ng·h/mL for males and females, respectively.

A cohort was added by the Sponsor that was testing a single 35 mg MR dose of trimetazidine (Vastarel). This dose was selected as it is the most commonly used dose of trimetazidine in treating angina and it was therefore known that it has an efficacious PK profile.

Timing of Doses in the Study

The study drug was administered with 240 mL of tap water to the subject in the upright position. If needed, an additional volume of water was allowed to consume the capsules/tablets comfortably; this additional volume was documented in the eCRF. The dose was given between 08:00 h and 11:00 h, and between 20:00 h and 23:00 h for the afternoon/evening dose. Dosing for each individual subject was at around the same time (±15 min) on each dosing day. The study drug was not chewed.

Administration of the study drug was supervised by the Investigator or authorized designee. After drug administration, a mouth and hand inspection took place.

Dosing Under Fasted Conditions

SAD Part 9 and Integrated FE Arm) and Single-Dose MR Part

Before dosing (on Days 1, 4, 7, and 10 in the single-dose MR part), subjects fasted overnight for at least 10 hours following a light supper on the evening before. Following dosing, subjects fasted for 4 hours until lunch. During fasting, fluids other than water were not allowed; however, water was not allowed from 2 hours predose until 1 hour postdose (apart from the water taken with the dose).

Subjects of Group A4, also participating in the FE arm, and subjects of the single-dose MR part were not allowed to lie down for 4 hours after dosing, except when required for assessments that needed to be performed.

Dosing Under Fed Conditions

FE Arm

Before dosing, subjects fasted overnight for at least 10 hours following a snack on the evening before. Then, subjects received an FDA-defined high-fat breakfast that had to be consumed within 20 minutes. The entire breakfast had to be consumed by the subjects. Dosing occurred at 30 minutes after the start of breakfast. Following dosing, subjects fasted for 4 hours until lunch. During fasting, fluids other than water were not allowed.

Subjects of Group A4 also participating in the FE arm were not allowed to lie down for 4 hours after dosing, except when required for assessments that needed to be performed.

MAD Arm

Morning Dose

Before each morning dose, subjects fasted overnight for at least 10 hours following a snack on the evening before. On Days 1 and 14, subjects received a standardized breakfast that had to be consumed within 20 minutes. Dosing occurred at 30 minutes after the start of breakfast. Following dosing, subjects fasted for 4 hours until lunch. During fasting, fluids other than water were not allowed. On Days 2 to 13, breakfast was not standardized and was given within maximally 1 hour before dosing and consumed before dosing. No fasting after dosing was applicable on these days.

Evening Dose

On all dosing days, an evening snack was given within maximally 1 hour before dosing and consumed before dosing.

Single-Dose MR Part

Before dosing on Day 13, subjects fasted overnight for at least 10 hours following a snack on the evening before. On Day 13, subjects received a FDA-defined high-fat breakfast that had to be consumed within 20 minutes. Dosing occurred at 30 minutes after the start of breakfast. Following dosing, subjects fasted for 4 hours until lunch. During fasting, fluids other than water were not allowed. Subjects were not allowed to lie down for 4 hours after dosing, except when required for assessments that needed to be performed.

Multiple-Dose MR Part

Morning Dose

Before each morning dose, subjects fasted overnight for at least 10 hours following a snack the evening before. On Days 1 and 5, subjects received a standardized breakfast that had to be consumed within 20 minutes. Dosing took place 30 minutes after the start of breakfast. After dosing, subjects fasted for 4 hours until lunch. During fasting, fluids other than water were not allowed. On Days 2 to 4, breakfast was not standardized, and was given maximally within 1 hour before dosing and consumed before dosing. Subjects did not fast after dosing on these days.

Evening Dose

From Day 1 to Day 4, an evening snack was given maximally within 1 hour before dosing and consumed before dosing. Subjects fasted overnight for at least 10 hours after consuming the snack.

Subjects were not allowed to lie down for 4 hours after morning or evening dosing, except when required for assessments that needed to be performed.

Meals During the Study

A fasting period of at least 4 hours was required before obtaining clinical laboratory samples at all time points.

When not fasting, meals and snacks (such as decaffeinated coffee, herbal tea, fruit, and biscuits) were provided according to PRA standard operating procedures (SOPs). A light supper was provided on the evening before those days where fasting was required until lunch time (fasted conditions); a snack was provided on the evening before those days where fasting was required until the FDA-defined high-fat breakfast or breakfast (fed conditions).

For the second period of Group A4 in the FE arm, and for Day 13 of the single-dose MR part, the FDA-defined high-fat breakfast of 918 kcal consisted of:
- 2 fried eggs (in 15 g butter/margarine) (approximately 100 g)
- 1 portion of bacon (40 g) (or brie 60+ for vegetarians)
- 1 portion of fried potatoes (115 g)
- 2 slices of (toasted) (wheat) bread (approximately 70 g) with 15 g margarine
- 1 glass of whole milk (240 mL)

The total of 918 kcal (vegetarian version 915 kcal) could be broken down as follows:
- 39 g protein=156 kcal
- 59 g fat=527 kcal
- 59 g carbohydrates=235 kcal Blinding In each group of the SAD part, except for Group A5, 6 subjects received IMB-1018972 and 2 subjects received placebo according to the randomization code. In Group A5, all 8 subjects received trimetazidine. In each group of the MAD part, 9 subjects received IMB-1018972, and 3 subjects received placebo according to the randomization code. In both MR parts, all 12 subjects received IMB-1018972. The following controls were employed to maintain the double-blind status of the study:
- The oral capsules containing active drug or placebo were indistinguishable in
- appearance and taste.
- The randomization code was provided to the pharmacist at PRA for dispensing
- purposes and kept in the pharmacy, accessible to the pharmacist and the pharmacy
- assistant only.

Individual code break envelopes were provided for all subjects by PRA. Each sealed envelope containing the randomization code was kept in a medication storage room that was locked with restricted access. To manage the subject's condition in case of a medical emergency, the Investigator was allowed to break the code to know whether a subject received IMB-1018972 or placebo. If opened, the name of the person who opened it, the date and time of opening, and the reason for opening were to be written on the envelope. The Sponsor was to be informed in case of unblinding.

The Bioanalytical Laboratory of PRA where the PK samples were analyzed was provided a copy of the randomization code by the pharmacy since only samples of subjects who had received the active drug IMB-1018972 were to be analyzed.

Previous and Concomitant Therapy and Other Restrictions During the Study

The use of all prescribed medication was not allowed from (first) admission to the clinical research center until follow-up. An exception was made for hormonal contraceptives, which were allowed throughout the study. The use of all over-the-counter medication, vitamin preparations and other food supplements, or herbal medications (eg, St. John's Wort) was not allowed from (first) admission to the clinical research center until follow-up. An exception was made for paracetamol: from (first) admission onwards, the Investigator could permit a limited amount of paracetamol for the treatment of headache or any other pain. Other medication to treat AEs could only be prescribed if deemed necessary by the Investigator. If medication was used, the name of the drug, the dose, and dosage regimen were recorded in the eCRF.

The use of alcohol, methylxanthine-containing beverages or food (coffee, tea, cola, chocolate, energy drinks), grapefruit (juice), and tobacco products was not allowed during the stay in the clinical research center.

Strenuous exercise was not allowed within 96 hours (4 days) prior to (each) admission and during the stay(s) in the clinical research center.

Subjects were not allowed to consume any foods containing poppy seeds within 48 hours (2 days) prior to (each) admission to the clinical research center as this could cause a false positive drug screen result.

Female subjects of childbearing potential, with a fertile male sexual partner, were required to use adequate contraception (see description below) from screening until 90 days after the follow-up visit.

Male subjects, if not surgically sterilized, were required to use adequate contraception (see description below) and not donate sperm from (first) admission to the clinical research center until 90 days after the follow-up visit.

Adequate contraception was defined as using hormonal contraceptives or an intrauterine device combined with at least 1 of the following forms of contraception: a diaphragm, a cervical cap, or a condom. Total abstinence, in accordance with the lifestyle of the subject, was also acceptable.

Subjects were not allowed to donate blood during the study until the follow-up visit (other than the blood sampling planned for this study).

Treatment Compliance

Study drug was administered in the clinical research center. To ensure treatment compliance, administration of the study drug was supervised by the Investigator or authorized designee. Compliance was further confirmed by bioanalytical assessment of IMB-1018972, IMB-1028814, and trimetazidine in plasma and urine samples.

The exact times of study drug administration and the number of units administered were recorded in the eCRF. Drug accountability procedures as specified in the CSP were followed.

Safety and Pharmacokinetic Measurements and Variables

The present study was performed to assess safety, tolerability, and PK following single and multiple doses of single and multiple oral doses of IMB-1018972, single oral doses of trimetazidine, single oral doses of MR formulations of IMB-1018972, and multiple oral doses of the 200 mg 8-hour MR formulation of IMB-1018972. This study did not comprise efficacy or pharmacodynamic assessments.

Adverse Events

AEs were recorded from (first) admission until completion of the follow-up visit. Any clinically significant observations in results of clinical laboratory, 12-lead ECGs, vital signs, or physical examinations were recorded as AEs.

A treatment-emergent AE (TEAE) was defined as any event not present prior to (the first) administration of the study drug or any event already present that worsened in either severity or frequency following exposure to the study drug.

An AE that occurred prior to (the first) administration of the study drug was considered a pretreatment AE.

At several time points before and after drug administration, subjects were asked nonleading questions to determine the occurrence of AEs. Subjects were asked in general terms about any AEs at regular intervals during the study. In addition, all AEs reported spontaneously during the course of the study were recorded. Details included description of the event, date and time of onset, date and time of end, total duration, severity, relationship to study drug, intervention, seriousness, and outcome. All answers were interpreted by the Investigator and were recorded in the eCRF. All AEs were classified according to the Medical Dictionary for Regulatory Activities (MedDRA; Version 22.0) for AEs.

The severity of the AEs was rated as mild, moderate, or severe; the relationship between the AEs and the study drug was indicated as none, unlikely, possibly, likely, or definitely. Adverse events assessed as possibly, likely, or definitely were considered related to the study drug; AEs assessed as none or unlikely were considered not related to the study drug.

Concomitant medication or other therapy required in case of any AEs was recorded. Concomitant medications were classified according to the World Health Organization Drug Dictionary (Version 22.0).

All AEs were followed up until their resolution or stabilization.

Clinical Laboratory

Blood and urine samples for clinical laboratory assessments were collected according to PRA SOPs.

The following parameters were measured:
- Clinical chemistry (serum quantitatively): total bilirubin, alkaline phosphatase, gamma glutamyl transferase, aspartate aminotransferase (AST), alanine aminotransferase (ALT), lactate dehydrogenase, creatinine, urea, total protein, glucose, inorganic phosphate, sodium, potassium,
- calcium, and chloride
- Hematology (blood quantitatively): leukocytes, erythrocytes, hemoglobin, hematocrit, thrombocytes, partial automated differentiation (lymphocytes, monocytes, eosinophils, basophils, and neutrophils), mean corpuscular volume, mean corpuscular hemoglobin, and mean corpuscular hemoglobin concentration
- Coagulation (blood quantitatively): prothrombin time (reported in seconds and as international normalized ratio), activated partial thromboplastin time, and fibrinogen
- Urinalysis (urine qualitatively): hemoglobin, urobilinogen, ketones, glucose, and protein
- Serology: HBsAg, anti-HCV, and anti-HIV 1 and 2
- Drug and alcohol screen: opiates, methadone, cocaine, amphetamines (including ecstasy), cannabinoids, barbiturates, benzodiazepines, tricyclic antidepressants, and alcohol
- Pregnancy test (females only): (3-human chorionic gonadotropin in serum Urine for urinalysis was taken from the PK urine collection container at the end of a collection interval.

In case of unexplained or unexpected clinical laboratory test values, the tests were repeated as soon as possible and followed up until the results had returned to the normal range and/or an adequate explanation for the abnormality was found. The clinical laboratory clearly marked all laboratory test values that were outside the normal range, and the Investigator indicated which of these deviations were clinically significant. Clinically significant laboratory result deviations were recorded as AEs and the relationship to the treatment was indicated.

Vital Signs

Systolic and diastolic blood pressure and pulse were recorded after the subject had been resting for at least 5 minutes in the supine position. These assessments were made using an automated device. Body temperature and respiratory rate were measured subsequently.

Electrocardiogram

A standard 12-lead ECG was recorded after the subject had been resting for at least 5 minutes in the supine position. The ECG was recorded using an ECG machine equipped with computer-based interval measurements (with no/minimal disturbance by procedures). The following ECG parameters were recorded: heart rate, PR-interval, QRS-duration, QT-interval, QTcF-interval, and the interpretation of the ECG profile by the Investigator.

Continuous Cardiac Monitoring (Telemetry)

In the SAD part (not in the second period of the FE group A4, and not in Group A5), a 12-lead ECG was recorded continuously by telemetry from 2 hours before to 24 hours after drug administration on Day 1.

In the MAD part, a 12-lead ECG was recorded continuously by telemetry from 2 hours before to 12 hours after drug administration on Day 1, and from 2 hours before to 24 hours after drug administration on Day 14.

In the single-dose and multiple-dose MR parts, no telemetry was performed.

All relevant or significant arrhythmic events were recorded in rhythm strips (10 seconds). The ECG was evaluated by the Investigator for clinically significant events.

During days with telemetry, meals were standardized, and subjects remained quietly supine (with no/minimal disturbance by procedures) for 10 minutes followed by an up to 5-minute period for each ECG assessment that was planned just prior to PK sampling. Start and stop time of the (in total) 15-minute periods were recorded. The ECGs collected by continuous monitoring (telemetry) were stored for potential later use.

These ECGs may or may not be analyzed for the purpose of concentration-effect modeling, based on future development decisions for IMB-1018972. If analyzed, results of the modeling were not to be included in this CSR, but to be included in a separate report.

Physical Examination

Physical examination was performed according to PRA SOPs. In addition, body weight and height were measured according to PRA SOPs.

Pharmacokinetic Measurements

Blood Sampling

At the time points defined in the schedules of assessments, blood samples of 3 mL per time point were taken for the analysis of IMB-1018972, IMB-1028814, and trimetazidine in plasma samples. The blood samples were taken via an indwelling intravenous catheter or by direct venipuncture. The exact times of blood sampling were recorded in the eCRF.

During days with telemetry, subjects remained quietly supine (with no/minimal disturbance by procedures) for 10 minutes followed by an up to 5-minute period for each ECG assessment that was planned just prior to PK sampling. Start and stop time of the (in total) 15-minute periods were recorded.

Details on sample collection, sample aliquoting, sample handling, sample storage, and sample shipping can be found in the laboratory manual prepared by PRA.

Plasma samples may (in the future) also be used for research purposes such as evaluation of the activity of IMB-1018972 and trimetazidine, identification of exploratory biomarkers that are predictive of activity, cytochrome P450 profiling, or other exploratory evaluations that may help characterize the molecular mechanisms of IMB-1018972 and trimetazidine. The samples will be stored for a maximum of 15 years for this purpose.

Urine Collection

Urine collection for PK was only conducted in the SAD part, but not in the second period of the FE group A4.

During the intervals defined in the schedules of assessments, urine was collected for the analysis of IMB-1018972, IMB-1028814, and trimetazidine. The subjects were instructed to empty their bladders completely before study drug administration and at the end of each collection interval. A blank urine sample was collected within 12 hours prior to study drug administration. The exact times of urine collection and the urine weight of the entire interval (before and after addition of any urine stabilizers, if used) were recorded in the eCRF.

Details on sample collection, sample aliquoting, sample handling, sample storage, and sample shipping can be found in the laboratory manual prepared by PRA.

Urine samples could be kept for a maximum of 1 year for further analysis of metabolites in urine in case unknown metabolites were found in plasma.

Genotyping

At the time points defined in the schedules of assessments, a blood sample of a maximum of 7 mL was collected for genotyping to better understand the effects of genotype, such as CYP alleles, on PK data. This blood sample was optional for subjects that had already been screened prior to IEC approval of protocol Version 3.0 (25 Mar. 2019), whereas it was mandatory for subjects participating in this study that had been screened after IEC approval of protocol Version 3.0 (25 Mar. 2019).

The blood sample was double coded (1 code at PRA and 1 code at the Sponsor), and the sample was kept until 15 years after completion of the study.

The blood sample was taken via an indwelling intravenous catheter or by direct venipuncture. The exact time of blood sampling was recorded in the eCRF.

Details on sample collection, sample aliquoting, sample handling, sample storage, and sample shipping can be found in the laboratory manual prepared by PRA.

Safety and Pharmacokinetic Variables

The safety variables to be measured included:
  AEs
  Clinical laboratory
  Vital signs
  12-lead ECG
  Continuous cardiac monitoring (telemetry)
  Physical examination Pharmacokinetic Variables Pharmacokinetic variables were the plasma and urine concentrations of IMB-1018972, IMB-1028814, and trimetazidine, and their PK parameters. The PK parameters that were determined or calculated using noncompartmental analysis are given in Table

TABLE 2

Plasma IMB-1018972, IMB-1028814, and Trimetazidine Parameters

| Parameter | SAD/FE and SD-MR | MAD Day 1 and MD-MR Day 1 | MAD Day 14 and MD-MR Day 5 | Description |
|---|---|---|---|---|
| $C_{max}$ | X | X | X | Maximum plasma concentration. Observed peak analyte concentration obtained directly from the experimental data without interpolation, expressed in concentration units. |
| $C_{min}$ | | | X | Minimum plasma concentration (predose concentration excluded). |
| $t_{max}$ | X | X | X | Time to maximum plasma concentration. First observed time to reach peak analyte concentration obtained directly from the experimental data without interpolation, expressed in time units. |
| $AUC_{0-t}$ | X | | | Area under the plasma concentration-time curve (time 0 to time of last quantifiable concentration). |
| $AUC_{0-inf}$ | X | | | Area under the plasma concentration-time curve (time 0 to infinity). Percent extrapolation less than or equal to 20% is required to obtain a reliable $AUC_{0-inf}$. |
| % $AUC_{extra}$ | X | | | Percentage of estimated part of the calculation of $AUC_{0-inf}$. Calculated as: ([$AUC_{0-inf}$ − $AUC_{0-t}$]/$AUC_{0-inf}$)*100%. |
| $AUC_{0-T}$ | | X | X | Area under the plasma concentration-time curve over the dosing interval of 0-12 hours postmorning dose. |
| $k_{el}$ | X | | X | Terminal elimination rate constant calculated by linear regression of the terminal log-linear portion of the concentration vs time curve. Linear regression of at least 3 points and an adjusted $r^2$ greater than 0.80 were required to obtain a reliable $k_{el}$. |
| $t_{1/2}$ | X | | X | Terminal elimination half-life expressed in time units. Percent extrapolation less than or equal to 20% and adjusted $r^2$ greater than 0.80 was required to obtain a reliable $t_{1/2}$. |
| CL/F | X | | | Apparent oral clearance, calculated as dose/$AUC_{0-inf}$. IMB-1028814 only, assuming 100% IMB-1018972 was converted to IMB-1028814. |
| $CL_{ss}/F$ | | | X | Apparent oral clearance at steady state, calculated as dose/$AUC_{0-T}$. The $AUC_{0-T}$ after the morning dose was used in the calculation. IMB-1028814 only, assuming 100% IMB-1018972 was converted to IMB-1028814. |
| $V_z/F$ | X | | X | Apparent volume of distribution at terminal phase, calculated as (CL/F)/$k_{el}$ (SAD/FE/MR), or as ($CL_{SS}/F$)/$k_{el}$ (MAD). For IMB-1028814 only. |

TABLE 2-continued

Plasma IMB-1018972, IMB-1028814, and Trimetazidine Parameters

| Parameter | SAD/FE and SD-MR | MAD Day 1 and MD-MR Day 1 | MAD Day 14 and MD-MR Day 5 | Description |
|---|---|---|---|---|
| $R_{ac}$ | | | X | Accumulation ratio, based on $AUC_{0-T}$ of Day 14 vs Day 1 ($AUC_{0-T}$ after morning dose). |

FE = food effect;
MAD = multiple ascending dose;
SAD = single ascending dose;
MD = multiple dose;
MR = modified release;
SD = single dose The sum of IMB-1028814 and trimetazidine concentrations and PK parameters was calculated corrected for molecular weights of 310 kDa for IMB-1028814 and 266 kDa for trimetazidine.

Plasma trough levels of IMB-1018972, IMB-1028814, and trimetazidine were also determined (MAD part only).

The AUCs were calculated using the linear up/log down trapezoidal rule, expressed in units of concentration×time.

TABLE 3

Urine IMB-1018972, IMB-1028814, and Trimetazidine Parameters

| Parameter | SAD/FE (first period) | Description |
|---|---|---|
| $Ae_{urine}$ | X | Total amount of drug excreted unchanged into urine to time t (time of last measurable concentration), obtained by adding the amounts excreted over each collection interval. |
| $Fe_{urine}$ | X | Fraction (%) of the administered dose excreted unchanged into urine. Calculated as: $Fe_{urine}$ = ($Ae_{urine}$/Dose) * 100. |
| $CL_R$ | X | Renal clearance. Calculated as $Ae_{urine}/AUC_{0-t}$. |

Drug Concentration Measurements

The analysis of IMB1018972, IMB-1028814, and trimetazidine in plasma and urine samples was performed at the Bioanalytical Laboratory of PRA using validated liquid chromatography-mass spectrometry/mass spectrometry methods. The results from calibration samples and quality control samples demonstrated acceptable performance of the methods throughout the experimental period. Data on the performance of the method and stability indicate that the sample results as reported are reliable.

Statistical and Analytical Plan for Safety and Pharmacokinetic Evolution

Safety Set

All subjects who had received at least 1 dose of IMB1018972, trimetazidine, or placebo.

Pharmacokinetic Set

All subjects who had received at least 1 dose of IMB-1018972 or trimetazidine and provided sufficient bioanalytical assessment results to calculate reliable estimates of the PK parameters.

Statistical and Analytical Plan for Safety and Pharmacokinetic Evaluation

Details on the preparation of the listings and summary tables and figures can be found in the SAP and was generated by the Biostatistics Department of PRA. The SAP was finalized prior to database lock (and unblinding of study treatment codes).

All safety and PK data were listed. In addition, all data were summarized in tabular and/or graphical form and descriptive statistics were given, as appropriate.

Evolution of Safety and Tolerability

Safety and tolerability were assessed through AEs, clinical laboratory, vital signs, ECGs, continuous cardiac monitoring (telemetry), and physical examination findings, and any other parameter that was relevant for safety assessment.

All individual safety results were listed and descriptive statistics including change from baseline were calculated, where applicable.

Pharmacokinetic Evaluation

Descriptive statistics (number, arithmetic mean, SD, coefficient of variation, minimum, maximum, median, and geometric mean) were calculated for plasma and urine PK parameters of IMB-1028814, trimetazidine, and IMB-1028814+trimetazidine in the PK population, where applicable.

Dose proportionality of IMB-1018972, IMB-1028814 and trimetazidine was explored for SAD Groups A1 to A4 (fasted) using a regression (power) model relating log-transformed $C_{max}$, $AUC_{0-t}$, and $AUC_{0-inf}$. Subjects with R2 below 0.80 or % AUCextra>20% were not excluded from the dose-proportionality evaluation based on $AUC_{0-inf}$. A point estimate and 95% CI were produced for the slope. A slope of 1 (i.e., a 95% CI containing 1) means that no evidence of a deviation from dose proportionality was found. Since there were only 2 dose levels in the MAD part, no dose-proportionality analysis was performed for the MAD part.

The effect of food on the relative oral bioavailability of IMB-1018972 following a single oral administration was explored. This occurred in Group A4 of the SAD part and in the single-dose MR part where subjects received the same dose, first under fasted conditions and then under fed conditions. The evaluation was based on 90% CIs for the ratio of the geometric means, based on log-transformed data, for $C_{max}$, $AUC_{0-t}$, and $AUC_{0-inf}$.

Determination of Sample Size

For this FIH study, no prospective calculations of statistical power were made. The sample size was selected to provide information on safety, tolerability, and PK following single and multiple doses of IMB-1018972, single doses of trimetazidine, single doses of MR formulations of IMB-1018972, and multiple doses of the 200 mg 8-hour MR formulation of IMB-1018972, and is typical for a FIH study. Any p-values to be calculated according to the SAP were interpreted in the perspective of the explorative character of this study.

Study Subjects

Of the 220 subjects who were screened, 88 subjects were included in the study and received the study drug. Sixty-six subjects received a dose of IMB-1018972, 8 received trimetazidine, and 14 received placebo.

Eighty-five of 88 subjects completed the study. Subject 129 of the FE arm Group A4 withdrew consent on Day 1 of the second period after receiving the single oral dose of 150 mg IMB-1018972 under fed conditions. Subject 131 of the FE arm Group A4 was withdrawn from the study due to an SAE of influenza like illness (of moderate severity and unlikely related) in the first period and only received the single oral dose of 150 mg IMB-1018972 under fasted conditions and not the fed dose in the second treatment period. Subject 505 of the single-dose MR part was withdrawn from the study due to a moderate TEAE of ALT increased (possibly related; up to 149 IU/L on Day 11) and did not receive the last single oral dose of 200 mg 8-hour MR formulation of IMB-1018972 under fed conditions on Day 13. None of these discontinued subjects were replaced. All 88 subjects were included in the PK and safety sets.

FIG. 2 is a table of the disposition of subjects.

Protocol Deviations/Violations

Several protocol deviations that were not deemed significant are described in the listings given above; these are not further described in this section.

Two major deviations were recorded in the study:
There was 1 major deviation from the GCP and PRA procedures. Three volunteers were screened 1 day before the study initiation visit was conducted. This deviation was not considered to have had any implications for the safety of the involved volunteers.

The pharmacy at PRA had only received an original set of randomization lists for the SAD part with the treatments as described in Versions 2.0 and 3.0 of the CSP. They did not receive updated randomization lists based on Versions 4.0 and 5.0 of the CSP which changed the designs of Groups A4 and A5. Similarly, the Bioanalytical Laboratory of PRA also did not receive the updated randomization lists from the pharmacy. However, all subjects of Groups A4 and A5 received the correct dose and therefore, this deviation did not have any implications for the safety of the involved volunteers.

In addition, a memo to file, dated 22 Oct. 2019, was issued documenting the following protocol deviations:
For all subjects of Groups B1 and B2 of the MAD part, vital signs on Day 1 at 12 hours after the morning dose were recorded prior to instead of after the ECG and PK blood sampling because of the risk that the evening dose could not be administered in time.

For all subjects of Groups B1 and B2 of the MAD part, vital signs on Day 14 in the morning were scheduled 25 minutes earlier than planned because of the risk that the morning dose could not be administered in time.

Genotyping

Except for 1 subject in the SAD part, all subjects provided a blood sample for genotyping. The blood sample was used to genotype subjects with a particular interest on CYP2D6 to better understand differences in the PK data. Any results of the analysis of the relationship between genotype and PK data will presented separately from this CSR.

Measurements of Treatment Compliance

Study drug was administered in the clinical research center. To ensure treatment compliance, administration of the study drug was supervised by the Investigator or authorized designee. There was no indication of noncompliance based on observations during study drug administration. In addition, bioanalytical assessment of IMB-1018972, IMB-1028814, and trimetazidine in plasma and urine samples confirmed treatment compliance.

Clinical Laboratory Evaluation

Laboratory Values over Time

Although several individual changes from baseline were observed in the clinical laboratory values, no clinically important trends were seen.

Individual Subject Changes

The majority of the subjects had one or more out of range values for clinical laboratory tests at various times during the study. Most of these were minor and considered by the Investigator to have no clinical implication. A number of ALT levels measured for 1 subject were above the normal range and considered to be clinically significant abnormal.

Vital Signs, ECGs, Physical Findings, and Other Observations Related to Safety

Vital Signs

Although several individual changes from baseline were observed, blood pressure, pulse, body temperature, and respiratory rate showed no trends or clinically relevant changes during any of the study parts.

Electrocardiogram

No changes or trends of clinical significance were seen for the heart rate, PR-interval, QRS-duration, QT-interval, or QTcF-interval during any of the study parts. All 12-lead ECG evaluations were recorded as normal or, in case of abnormal recordings, these were not considered to be clinically significant.

Continuous Cardiac Monitoring (Telemetry)

All telemetric ECG evaluations obtained in the SAD and MAD parts were recorded as normal or, in case of abnormal recordings, these were not considered to be clinically significant.

Physical Examination

All abnormalities observed at screening and all changes observed after screening for physical examinations were considered to be of no clinical significance.

Tables for Immediate Release Formulations

FIG. 3 is a Schedule of Assessments for SAD part Group A5, with the following notations:
BMI=body mass index;
ECG=electrocardiogram;
HBsAg=hepatitis B surface antigen;
HCV=hepatitis C virus;
PK=pharmacokinetic(s)

a. Physical examination: at screening, on Day −1 (admission; this was a directed examination only done at the discretion of the Investigator), at discharge on Day 3 (this was a directed examination only done at the discretion of the Investigator), and at follow-up.

b. Clinical laboratory tests (including clinical chemistry, hematology, coagulation, and urinalysis): at screening, on Day −1 (admission) and at 24 hours postdose, and at follow-up.

c. 12-lead ECG at screening, on Day −1 (admission), at 48 hours postdose, and at follow-up.

d. Vital signs (supine systolic and diastolic blood pressure, pulse, body temperature, and respiratory rate): at screening, on Day −1 (admission), at 48 hours postdose, and at follow-up. e Study drug administration was conducted under fasted conditions FIG. 4 is a table of assessments given for the SAD part (and integrated FE arm) Groups A1 to A4, with the following notations:
BMI=body mass index
ECG=electrocardiogram;
FDA=Food and Drug Administration;
FE=food effect;
HBsAg=hepatitis B surface antigen;
HCV=hepatitis C virus;
PK=pharmacokinetic(s); SAD=single ascending dose a. Subjects were in the clinic for 1 period, except for subjects of Group A4 also participating in the FE arm who were in the clinic for 2 periods; a period was from Day −1 until 48 hours (Day 3) postdose.

b. The planned confinement period, day of discharge, and follow-up period could be adapted depending on emerging study results. Also, the timing, type, and number of safety and PK assessments could be changed during the study.

c. Physical examination: at screening, each period on Day −1 (admission; this was a directed examination only done at the discretion of the Investigator), at discharge on Day 3 (this was a directed examination only done at the discretion of the Investigator), and at follow-up.
d. Clinical laboratory tests (including clinical chemistry, hematology, coagulation, and urinalysis): at screening, each period on Day −1 (admission) and at 24 hours postdose, and at follow-up.
e. 12-lead ECG for Groups A1, A2, A3, and A4 (first period only): at screening, on Day −1 (admission), at 48 hours postdose, and at follow-up. Data for 12-lead ECGs at predose and 1, 2, 4, 6, 12, and 24 hours postdose were taken from the 12-lead ECG prints from telemetry. The predose baseline value was the average values of the 3 predose telemetry 12-lead ECGs at −1.25, −1.0, and −0.75 hours predose. 12-lead ECG for Group A4 (second period only): on Day −1 (admission), at predose and 1, 2, 4, 6, 12, 24, and 48 hours postdose, and at follow-up.
f. Only in the SAD part; not in the second period of Group A4 also participating in the FE arm: Continuous cardiac monitoring (12-lead telemetry): from at least 2 hours predose until at least 24 hours postdose. 12-lead ECG reads were printed at −1.25, −1.0, and −0.75 hours predose and just prior to the PK sampling time points of 0.25, 0.5, 1, 2, 4, 6, 12, and 24 (Day 2) hours postdose.
g. Vital signs (supine systolic and diastolic blood pressure, pulse, body temperature, and respiratory rate): at screening, each period on Day −1 (admission), each period at predose and 1, 2, 4, 6, 12, 24, and 48 hours postdose, and at follow-up.
h In Groups A1, A2, A3, and, A4, and in the first period of Group A4 also participating in the FE arm, study drug administration was conducted under fasted conditions. In the second period of Group A4, drug administration was conducted under fed conditions (FDA-defined high-fat breakfast).
i. Blood sampling for PK of IMB-1018972, IMB-1028814, and trimetazidine in plasma: each period at predose and 0.25, 0.5, 1, 2, 3, 4, 5, 6, 8, 10, 12, 16, 24, 36, and 48 hours postdose.
j. Only in the SAD part; not in the second period of Group A4 also participating in the FE arm: Urine collection for PK of IMB-1018972, IMB-1028814, and trimetazidine in urine: each period at predose (within 12 hours prior to dosing) and over 0-6, 6-12, 12-24, 24-36, and 36-48 hours postdose collection intervals.
k. AEs were recorded from (first) admission until completion of the follow-up visit. 1 Blood sampling for genotyping was optional for subjects that had already been screened prior to IEC approval of protocol Version 3.0 (25 Mar. 2019), whereas it was mandatory for subjects participating in this study that had been screened after IEC approval of protocol Version 3.0 (25 Mar. 2019). For the subjects for which this sample was mandatory, the sample was taken on Day 1 of the first period only. For the subjects for which this sample was optional and who consented to provide this sample, the sample could be taken on any day during the study; a separate visit could be planned after follow-up to take this sample, if needed.

FIG. 5 is a table of assessments given for the MAD part, with the following notations:
BMI=body mass index;
ECG=electrocardiogram;
FE=food effect;
HBsAg=hepatitis B surface antigen;
HCV=hepatitis C virus;
MAD=multiple ascending dose;
PK=pharmacokinetic(s);
q8h=every 8 hours; q12h=every 12 hours; qd=once daily; SAD=single ascending dose; tid=three times a day
a. The planned confinement period, day of discharge, and follow-up period could be adapted depending on emerging study results. Also, the timing, type, and number of safety and PK assessments could be changed during the study.
b. Physical examination: at screening, on Day −1 (admission; this was a directed examination only done at the discretion of the Investigator), and at follow-up. On other days, a physical examination could be done on indication only at the discretion of the Investigator.
c. Clinical laboratory tests (including clinical chemistry, hematology, coagulation, and urinalysis): at screening, on Day −1 (admission), before the morning dose on Day 8 and at the same time on Day 15, and at follow-up.
d. 12-lead ECG: at screening, on Day −1 (admission), on Day 1 at 24 hours after the morning dose, on Day 8 at predose and 1, 2, 4, 6, 12 (prior to the evening dose) and 24 hours after the morning dose, on Day 16 (day of discharge) at the same time as before the morning dose on dosing days, and at follow-up. Data for 12-lead ECGs on Day 1 at predose and 1, 2, 4, 6, and 12 hours postdose, and on Day 14 at predose and 1, 2, 4, 6, 12, and 24 hours postdose were taken from the 12-lead ECG prints from telemetry. The predose baseline value on Day 1 and Day 14 was the respective average values of the 3 predose telemetry 12-lead ECGs at −1.25, −1.0, and −0.75 hours predose.
e. Continuous cardiac monitoring (12-lead telemetry): from at least 2 hours before the morning dose until at least 12 hours after the morning dose on Day 1 and until at least 24 hours after the morning dose on Day 14. 12-lead ECG reads were printed at −1.25, −1.0, and −0.75 hours before the morning dose and just prior to the PK sampling time points of 0.25, 0.5, 1, 2, 4, 6, 12, and 24 (Day 14 only) hours after the morning dose.
f. Vital signs (supine systolic and diastolic blood pressure, pulse, body temperature, and respiratory rate): at screening, on Day −1 (admission), on Days 1, 8, and 14 at predose and 1, 2, 4, 6, 12 (prior to the evening dose on Days 1 and 8) and 24 hours after the morning dose, on Day 16 (day of discharge) at the same time as before the morning dose on dosing days, and at follow-up.
g. The study drug was administered twice daily for 14 days; on Day 14 only a single morning dose was administered. Study drug administration was conducted under fed conditions as determined based on the results of Group A4 in the FE arm. Note: The study drug was given for 14 consecutive days, but this could be revised based on the safety and tolerability results (and plasma PK results, if available) of the SAD part and of previous group(s) in the MAD part. Similarly, it could be decided to change q12h dosing to qd or tid (q8h) dosing.
h. Blood sampling for PK of IMB-1018972, IMB-1028814, and trimetazidine in plasma: on Days 1 and 14 before the morning dose and at 0.25, 0.5, 1, 2, 3, 4, 5, 6, 8, 10, 12 (prior to the evening dose on Day 1), 16, 24, 36, and 48 hours after the morning dose, and on Days 4, 6, 8, 10, and 12 before the morning dose.
i. AEs were recorded from admission until completion of the follow-up visit.
j. Blood sampling for genotyping was mandatory.

FIG. 6 is a table of analysis data sets for the SAD Part (and integrated FE Arm) per dose level and total for IMB-1018972.

FIG. 7 is a table of analysis data sets for the MAD Part per dose level and total for IMB-1018972.

Demographic and Other Baseline Characteristics

SAD Part (and Integrated FE Arm)

In the SAD part with integrated FE arm, a total of 40 subjects were included.

IMB-1018972 and Placebo

Thirty-two subjects were included of whom 23 were female and 9 were male Mean age ranged between 29 and 46 years and mean BMI ranged between 23.0 and 26.6 kg/m2 over all treatments, including placebo. Individual age ranged between 18 and 65 years and individual BMI ranged between 19.5 and 30.3 kg/m2. Twenty-nine subjects were of white race, 1 subject was Asian, 1 subject was Black or African American, and 1 subject was Native Hawaiian or Other Pacific Islander. Thirty-one subjects were not of Hispanic or Latino ethnicity whereas 1 subject was of Hispanic or Latino ethnicity. The summary of the PK set was identical to that of the safety set minus the pooled placebo group.

Trimetazidine Group

Eight subjects were included of whom 5 were female and 3 were male. Mean age was 32 years and mean BMI was 23.7 kg/m2. Individual age ranged between 20 and 65 years and individual BMI ranged between 19.4 and 26.7 kg/m2. Seven subjects were of white race and 1 subject was of multiple race. Seven subjects were not of Hispanic or Latino ethnicity whereas 1 subject was of Hispanic or Latino ethnicity. The summary of the PK set was identical to that of the safety set.

FIG. 8 is a table of a summary of demographic characteristics—SAD Part (and Integrated FE Arm) (Safety Set).

MAD Part

Twenty-four subjects were included of whom 12 were female and 12 were male. Mean age ranged between 38 and 44 years and mean BMI ranged between 25.2 and 26.7 kg/m2 over all treatments, including placebo. Individual age ranged between 18 and 64 years and individual BMI ranged between 19.1 and 30.9 kg/m2. Eighteen subjects were of white race, 2 subjects were of multiple race, 2 subjects were American Indian or Alaska Native, 1 subject was Asian, and 1 subject was Black or African American. Twenty-one subjects were not of Hispanic or Latino ethnicity whereas 3 subjects were of Hispanic or Latino ethnicity. The summary of the PK set was identical to that of the safety set minus the pooled placebo group.

FIG. 9 is a table of a summary of demographic characteristics—MAD Part (Safety Set).

Other Baseline Characteristics

All subjects complied with the inclusion and exclusion criteria. There were no clinically significant findings with regard to medical history or previous medication. Drug and alcohol screen results were negative for all subjects at screening and (each) admission. The results for the serology parameters were negative at screening for all subjects. The pregnancy test results were negative at screening, (each) admission, and follow-up for all females participating in this study.

Extent of Exposure

A total of 88 subjects were dosed in this study: 40 subjects in the SAD part with integrated FE arm, 24 subjects in the MAD part, 12 subjects in the single-dose MR part, and 12 subjects in the multiple-dose MR part.

In each of Groups A1, A2, A3 and A4 of the SAD part, 6 subjects received a single dose of IMB-1018972 and 2 subjects received a single dose of matching placebo under fasted conditions. IMB-1018972 doses ranged from 50 mg to 400 mg over these 4 groups. Subjects of SAD Groups A1, A2, and A3 participated in 1 single-dose treatment period, and subjects of SAD Group A4 (the FE group) participated in 2 singledose treatment periods with fasted dosing in the first period and fed dosing in the second period. Subject 131 of FE Group A4 only received the fasted IMB-1018972 dose in the first treatment period and not the fed dose in the second treatment period since the subject was withdrawn from the study in the first period due to a moderate SAE of influenza like illness (unlikely related).

In Group A5 of the SAD part, 8 subjects received a single oral dose of 35 mg trimetazidine under fasted conditions.

FIG. 10 is a table of the Extent of Exposure—SAD Part (and Integrated FE Arm) (Safety Set)

In both groups of the MAD part, 9 subjects received IMB-1018972 (150 mg for Group B1 and 50 mg for Group B2) and 3 subjects received matching placebo under fed conditions. In both groups, multiple oral doses of IMB-1018972 or matching placebo were administered q12h on Days 1 to 13 followed by a single morning dose on Day 14.

FIG. 11 is a table of the Extent of Exposure—MAD Part

Pharmacokinetic Evaluation

The lower limit of quantification (LLOQ) was 0.5 ng/mL for IMB-1018972, IMB-1028814 and trimetazidine plasma concentrations, 10 ng/mL for IMB-1028814 urine concentrations, and 50 ng/mL for trimetazidine urine concentrations.

When more than 50% of the plasma values at a particular time point were below LLOQ, geometric means were not determined.

All blood samples of subjects that received IMB-1018972 in this study were analyzed for IMB-1018972 in plasma, but IMB-1018972 could be measured in only few plasma samples. Therefore, the IMB-1018972 concentrations have only been listed and no descriptive statistics or concentration-time profiles have been presented in this CSR. In addition, no PK parameters have been calculated for plasma IMB-1018972. As a result, urine samples were not analyzed for IMB-1018972 concentrations. Since the pharmacodynamic effect of IMB-1028814 and trimetazidine is the same, data are presented for IMB-1028814 and trimetazidine individually, as well as for the sum of IMB-1028814 and trimetazidine concentrations. The sum of IMB-1028814 and trimetazidine concentrations and PK parameters was calculated corrected for molecular weights of 310 kDa for IMB-1028814 and 266 kDa for trimetazidine.

SAD Part (and Integrated FE Arm)

PK in Plasma Following Administration of IMB-1018972 under Fasted Conditions

All predose samples were below the LLOQ for IMB-1028814 and trimetazidine plasma concentrations.

The geometric mean concentration-time profiles for IMB-1028814, metabolite trimetazidine, and IMB-1028814+ trimetazidine showed a clear dose-dependent increase in plasma concentrations following administration of single doses of IMB-1018972 under fasted conditions in the dose range of 50 mg to 400 mg IMB-1018972.

The initial hydrolysis of IMB-1018972 to IMB-1028814 and subsequent systemic bioavailability of IMB-1028814 was relatively rapid with detectable concentrations generally seen between 15 and 30 minutes postdose. Detectable concentrations for trimetazidine also generally appeared between 15 and 30 minutes postdose. Median $t_{max}$ was around 1 hour postdose for IMB-1028814, and between 1.5 hours and 2 hours postdose for trimetazidine over the studied single-dose range of 50 mg to 400 mg IMB-1018972 under fasted conditions. Median $t_{max}$ did not increase with increasing IMB-1018972 dose.

The geometric mean $C_{max}$ increased with dose and ranged between 104 ng/mL and 870 ng/mL for IMB-1028814, between 36.9 ng/mL and 274 ng/mL for trimetazidine, and between 516 nmol/L and 3,839 nmol/L (molar units to account for differences in molecular weight) for IMB-1028814+trimetazidine over the studied single-dose range of 50 mg to 400 mg IMB-1018972 under fasted conditions. Similarly, the geometric mean AUC0-t increased with dose and ranged between 290 ng·h/mL and 2,795 ng·h/mL for IMB-1028814, between 424 ng·h/mL and 3,305 ng·h/mL for trimetazidine, and between 2,970 nmol·h/L and 22,365 nmol·h/L for IMB-1028814+trimetazidine over the studied single-dose range of 50 mg to 400 mg IMB-1018972 under fasted conditions. The predefined stopping criterion for IMB-1028814 plasma exposure of 417,733 and 652,849 ng·h/mL for males and females, respectively, was not reached by any of the subjects during the SAD part.

Elimination of IMB-1028814 took place in a biphasic fashion, whereas elimination of trimetazidine occurred in a monophasic fashion. The geometric mean $t_{1/2}$ of IMB-1028814 was relatively short, ranging between 2.6 hours and 3 hours over the IMB-1018972 single-dose range under fasted conditions. For metabolite trimetazidine, geometric mean $t_{1/2}$ was longer, ranging between 6.76 hours and 8 hours over the IMB-1018972 single-dose range under fasted conditions. Geometric mean $t_{1/2}$ of IMB-1028814 and trimetazidine did not increase with increasing IMB-1018972 dose indicating that the PK of the 2 moieties was linear.

Detectable individual IMB-1028814 concentrations were observed until 10, 12, 16, or 24 hours postdose after 50 mg, and until 16 or 24 hours postdose after 150 mg and 400 mg IMB-101897. Detectable individual trimetazidine concentrations were observed until 24, 36, or 48 hours postdose after 50 mg, until 36 or 48 hours postdose after 150 mg, and until 48 hours postdose after 400 mg IMB-1018972.

An aberrant IMB-1028814 and trimetazidine concentration-time profile was observed for Subject 108 who had received a single oral dose of 50 mg IMB-1018972 under fasted conditions. IMB-1028814 and trimetazidine $t_{max}$ was much later for this subject (5.00 hours for IMB-1028814 and 8.00 hours for trimetazidine) than for the other subjects who received the same dose (between 0.50 and 1.02 hours for IMB-1028814 and between 1.00 and 2.00 hours for trimetazidine). Therefore, absorption of IMB-1018972 by this subject is much slower than for the other subjects who received the same dose.

Dose proportionality for IMB-1028814 and trimetazidine was explored by plotting the dose-normalized exposure parameters $C_{max}$, $AUC_{0-t}$, and $AUC_{0-inf}$ on a linear scale. The 95% CIs of the slopes of all 3 exposure parameters included 1 for both IMB-1028814 and trimetazidine. This indicates that no evidence of a deviation from dose proportionality of IMB-1028814 and trimetazidine was found over the IMB-1018972 single-dose range of 50 to 400 mg.

PK in Plasma Following Administration of Trimetazidine

All predose samples were below the LLOQ for trimetazidine plasma concentrations. Following administration of a single oral dose of 35 mg trimetazidine, detectable trimetazidine concentrations were generally seen between 15 and 30 minutes postdose. Median trimetazidine $t_{max}$ was 5 hours, and geometric mean values were 68.6 ng/mL for $C_{max}$, 912 ng·h/mL for AUC0-t, and 929 ng·h/mL for $AUC_{0-inf}$.

Elimination of trimetazidine occurred in a monophasic fashion up to the last time point above LLOQ with a geometric mean $t_{1/2}$ of 7.49 hours. Detectable individual trimetazidine concentrations were observed until the last sampling time point of 48 hours postdose.

Figure 12:
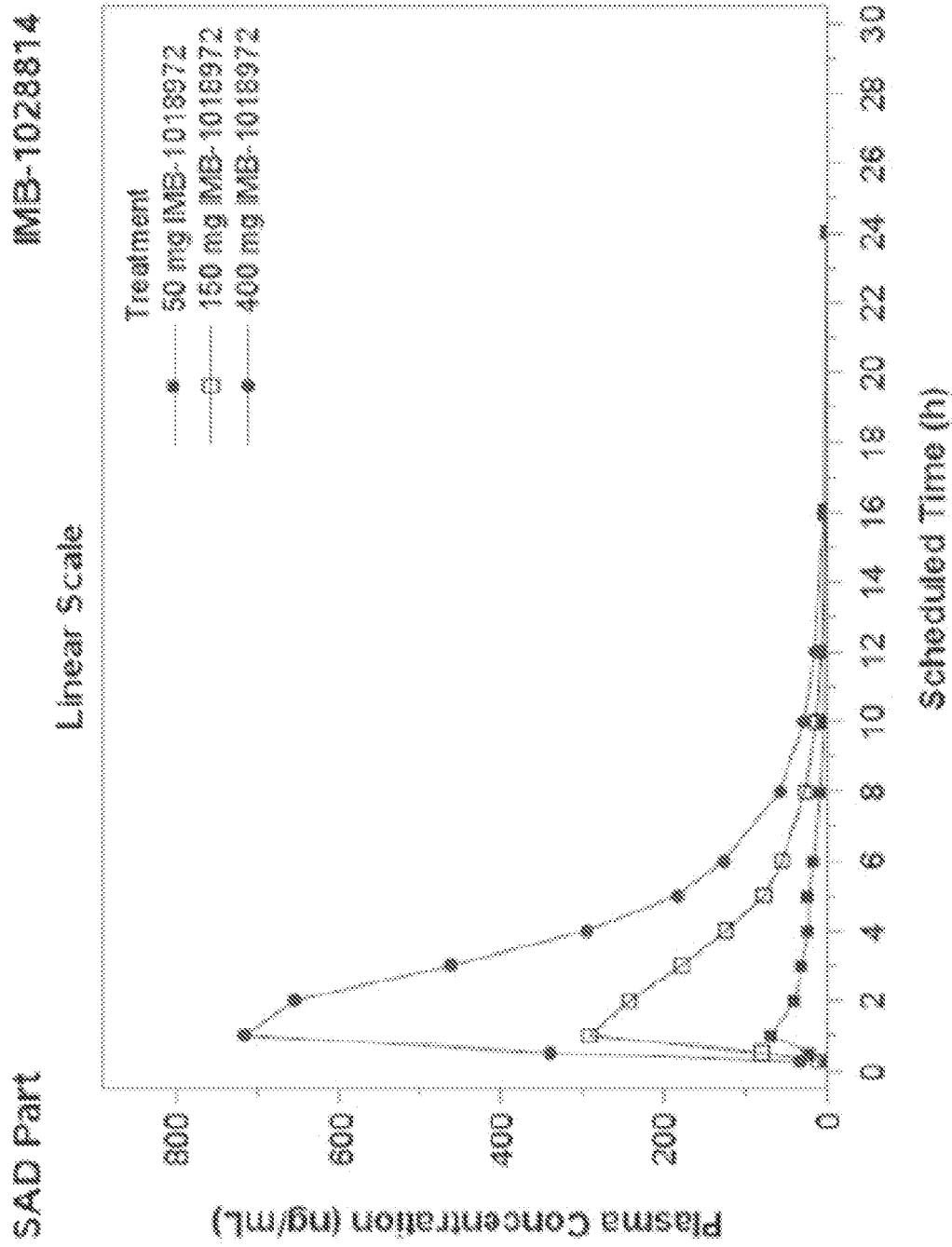
FIG. 12 is a graph of Geometric Mean IMB-1028814 Plasma Concentration-Time Profiles (Linear)—SAD Part (PK Set) of an FIH study of IMB-1018972.

FIG. 12 is a graph of Geometric Mean IMB-1028814 Plasma Concentration-Time Profiles (Linear)—SAD Part (PK Set)

Figure 13:
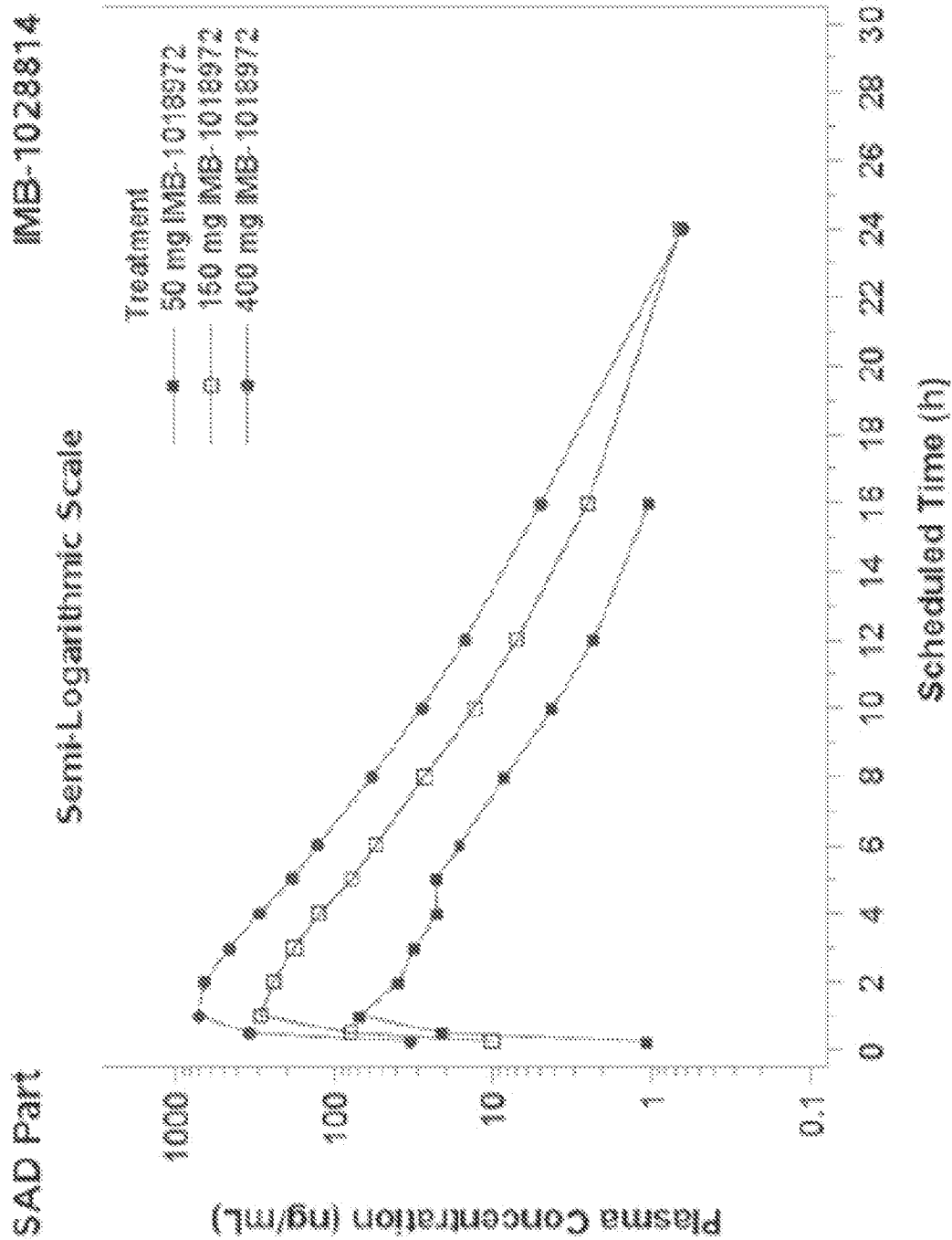
FIG. 13 is a graph of Geometric Mean IMB-1028814 Plasma Concentration-Time Profiles (Semi-Logarithmic)—SAD Part (PK Set) of an FIH study of IMB-1018972.

FIG. 13 is a graph of Geometric Mean IMB-1028814 Plasma Concentration-Time Profiles (Semi-Logarithmic)—SAD Part (PK Set)

Figure 14:
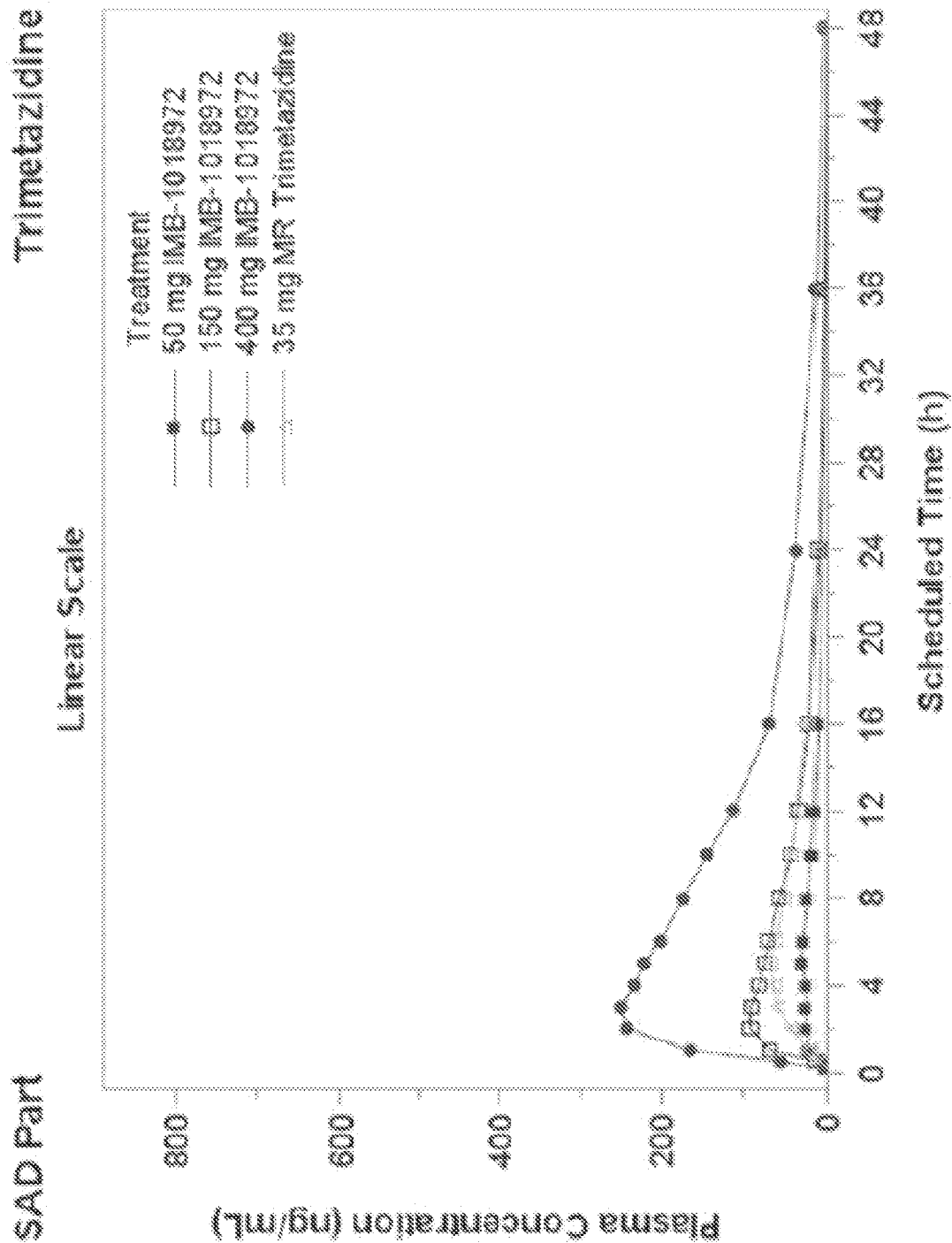
FIG. 14 is a graph of Geometric Mean Trimetazidine Plasma Concentration-Time Profiles (Linear)—SAD Part (PK Set) of an FIH study of IMB-1018972.

FIG. 14 is a graph of Geometric Mean Trimetazidine Plasma Concentration-Time Profiles (Linear)—SAD Part (PK Set)

Figure 15:
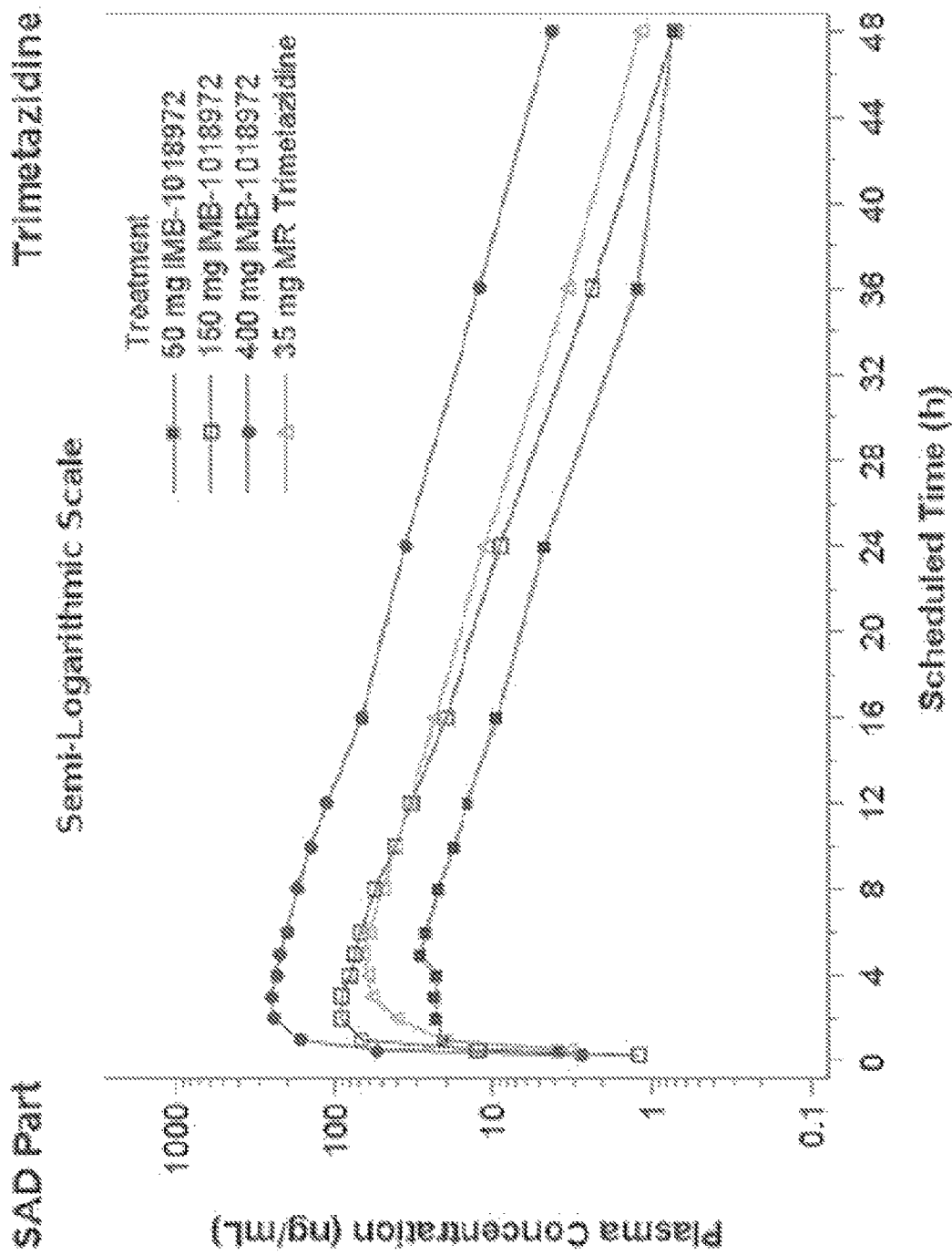
FIG. 15 is a graph of Geometric Mean Trimetazidine Plasma Concentration-Time Profiles (Semi-Logarithmic)—SAD Part (PK Set) of an FIH study of IMB-1018972.

FIG. 15 is a graph of Geometric Mean Trimetazidine Plasma Concentration-Time Profiles (Semi-Logarithmic)—SAD Part (PK Set)

Figure 16:
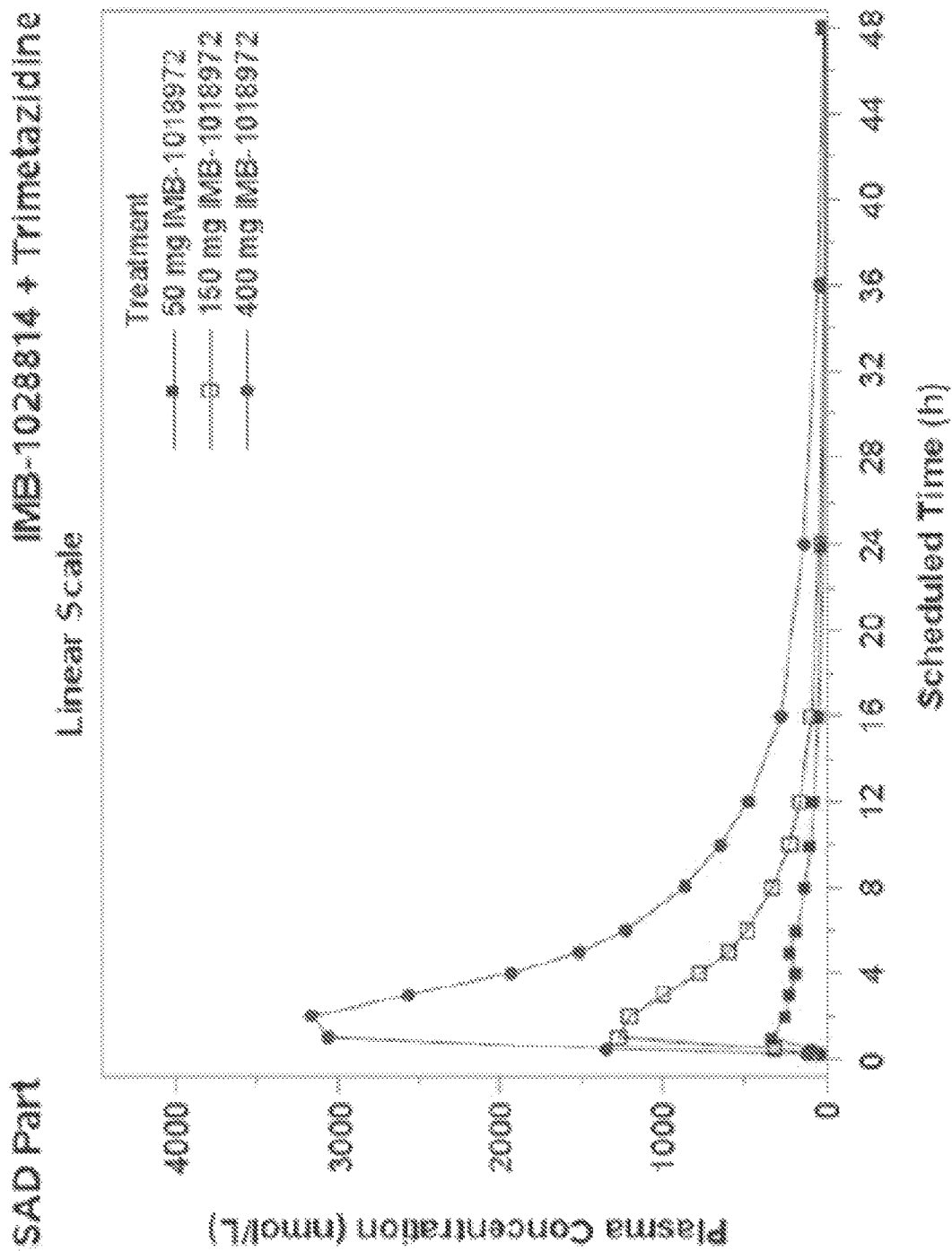
FIG. 16 is a graph of Geometric Mean IMB-1028814+Trimetazidine Plasma Concentration-Time Profiles (Semi-Logarithmic)—SAD Part (PK Set) of an FIH study of IMB-1018972.

FIG. 16 is a graph of Geometric Mean IMB-1028814+ Trimetazidine Plasma Concentration-Time Profiles (Semi-Logarithmic)—SAD Part (PK Set)

Figure 17:
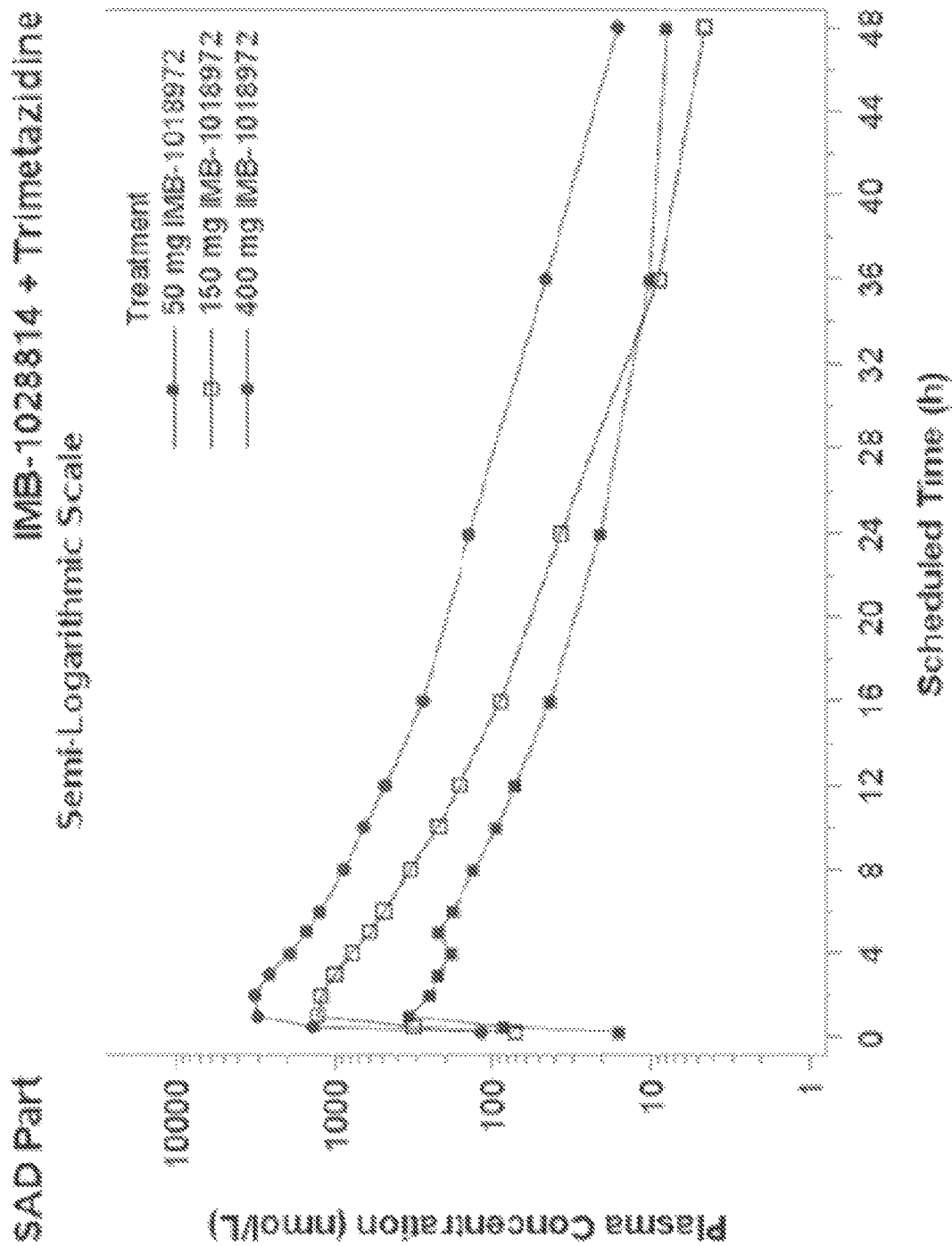
FIG. 17 is a graph of Geometric Mean IMB-1028814+Trimetazidine Plasma Concentration-Time Profiles (Semi-Logarithmic)—SAD Part (PK Set) of an FIH study of IMB-1018972.

FIG. 17 is a graph of Geometric Mean IMB-1028814+ Trimetazidine Plasma Concentration-Time Profiles (Semi-Logarithmic)—SAD Part (PK Set)

FIG. 18 is a table of Summary Statistics (Geometric Mean [Range]) of IMB-1028814, Trimetazidine, and IMB-1028814+Trimetazidine Plasma Pharmacokinetic Parameters—SAD Part (PK Set)

FIG. 19 is a table of Exploratory Analysis of Dose Proportionality for IMB-1028814 and Trimetazidine over the Dose Range of 50 mg to 400 mg IMB-1018972 under Faster Conditions—SAD Part (PK Set)

Figure 20:
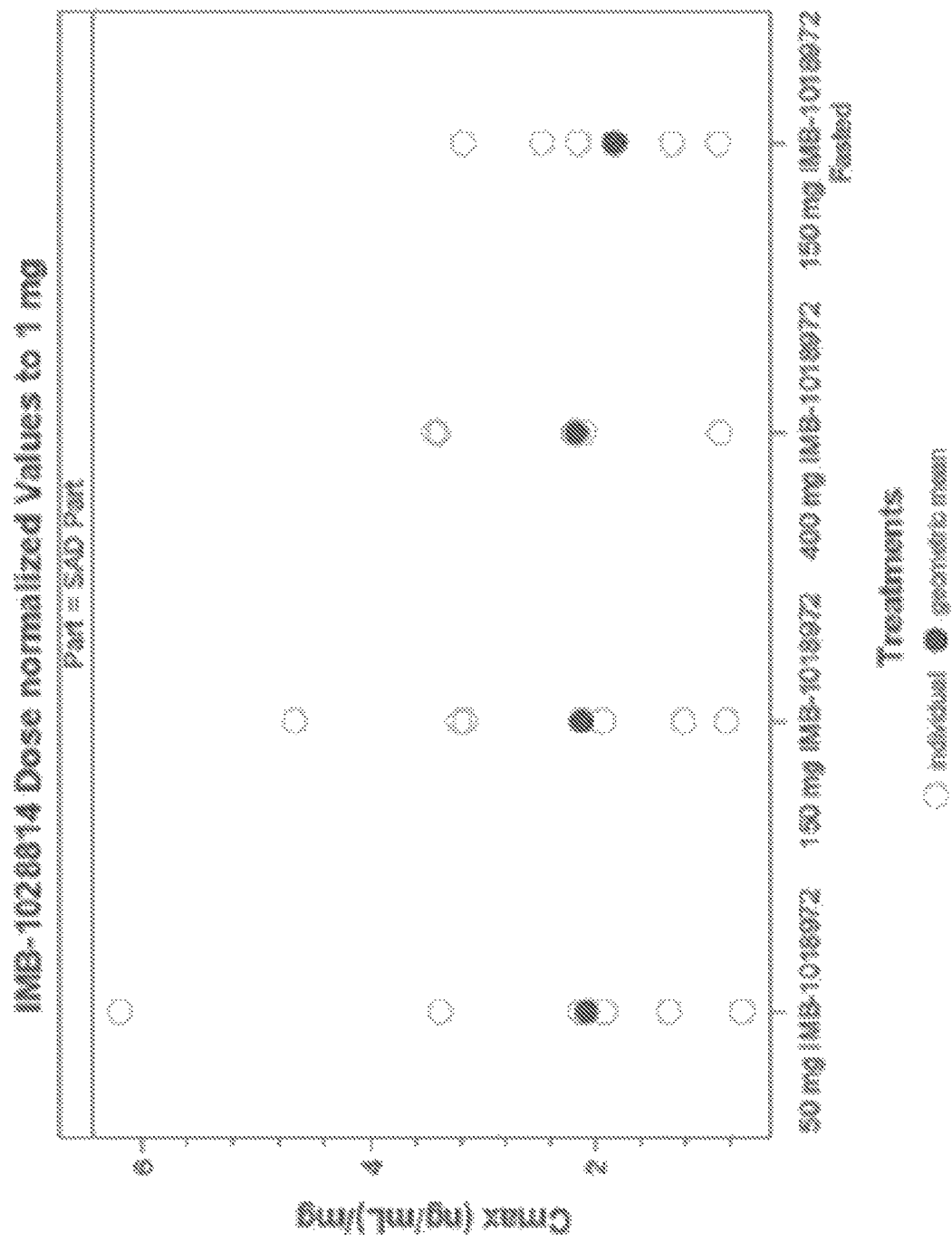
FIG. 20 is a graph of Plot of Combined Individual and Geometric Mean Dose-Normalized IMB-1028814 $C_{max}$ over the Dose Range of 50 mg to 400 mg IMB-1018972 under Fasted Conditions—SAD Part (PK Set) of an FIH study of IMB-1018972.

FIG. 20 is a graph of Plot of Combined Individual and Geometric Mean Dose-Normalized IMB-1028814 $C_{max}$ over the Dose Range of 50 mg to 400 mg IMB-1018972 under Fasted Conditions—SAD Part (PK Set)

Figure 21:
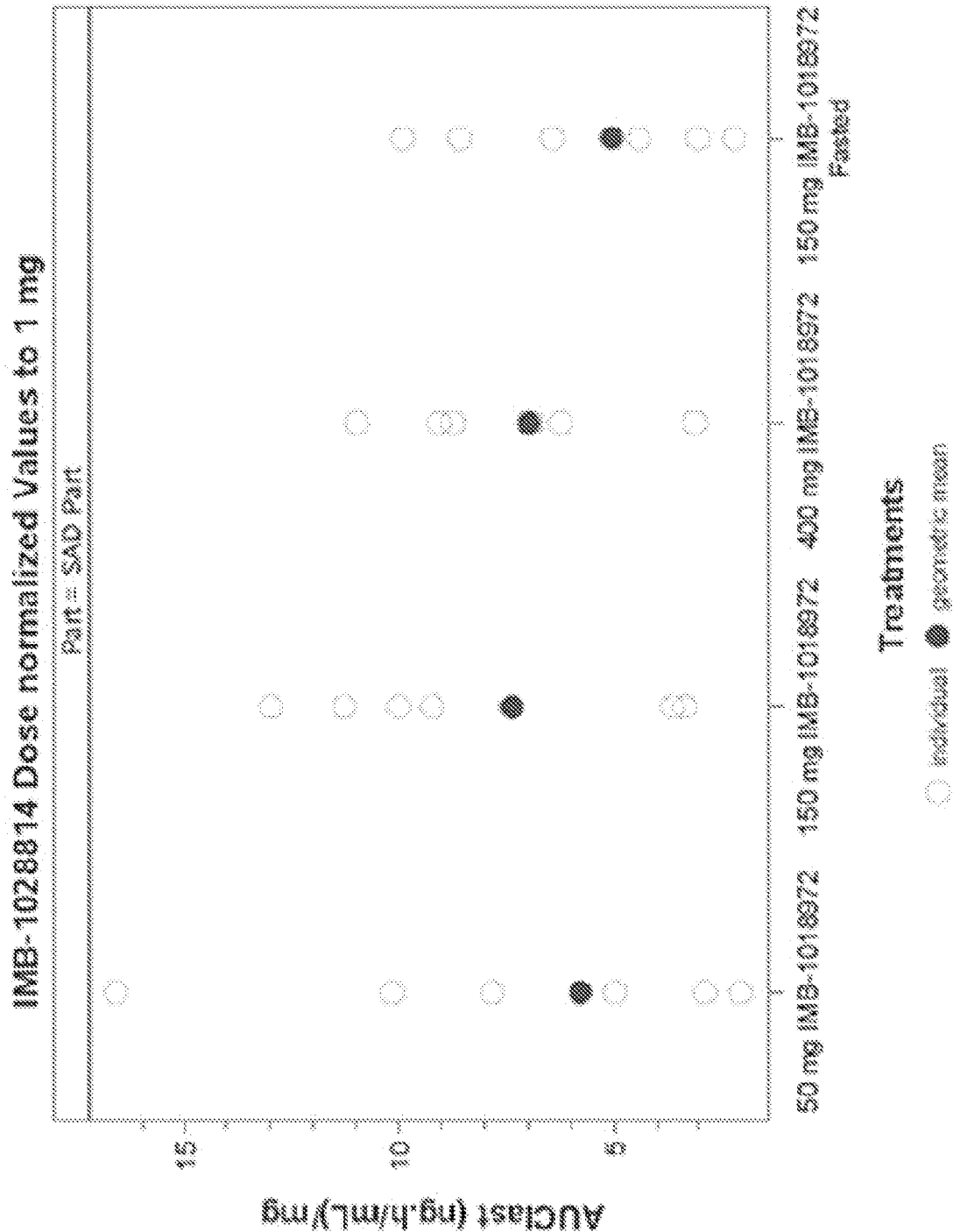
FIG. 21 is a graph of Plot of Combined Individual and Geometric Mean Dose-Normalized IMB-1028814 $AUC_{0-t}$ over the Dose Range of 50 mg to 400 mg IMB-1018972 under Fasted Conditions—SAD Part (PK Set) of an FIH study of IMB-1018972.

FIG. 21 is a graph of Plot of Combined Individual and Geometric Mean Dose-Normalized IMB-1028814 $AUC_{0-t}$ over the Dose Range of 50 mg to 400 mg IMB-1018972 under Fasted Conditions—SAD Part (PK Set)

Figure 22:
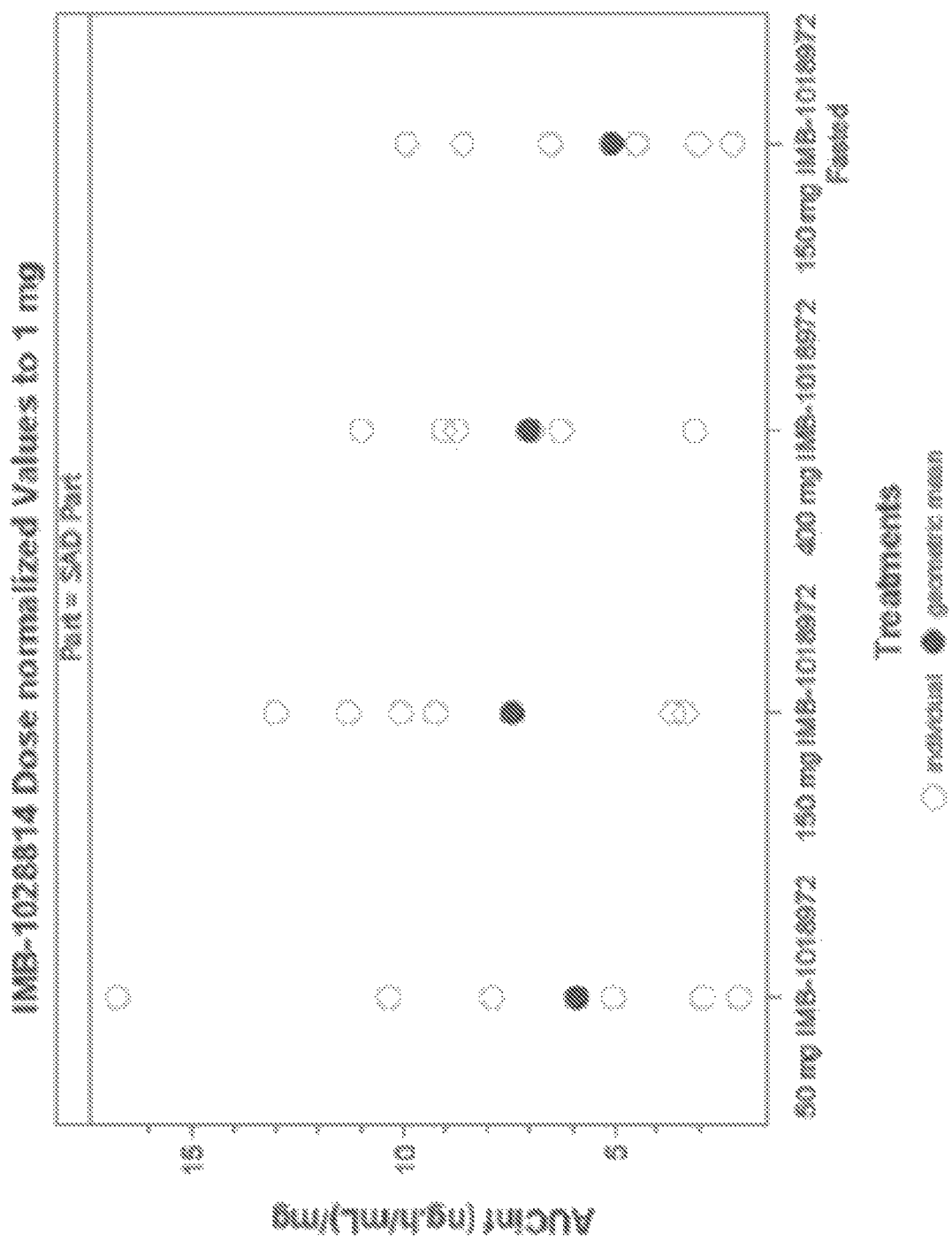
FIG. 22 is a graph of Plot of Combined Individual and Geometric Mean Dose-Normalized IMB-1028814 $AUC_{0-inf}$ over the Dose Range of 50 mg to 400 mg IMB-1018972 under Fasted Conditions—SAD Part (PK Set) of an FIH study of IMB-1018972.

FIG. 22 is a graph of Plot of Combined Individual and Geometric Mean Dose-Normalized IMB-1028814 $AUC_{0-inf}$ over the Dose Range of 50 mg to 400 mg IMB-1018972 under Fasted Conditions—SAD Part (PK Set)

Figure 23:
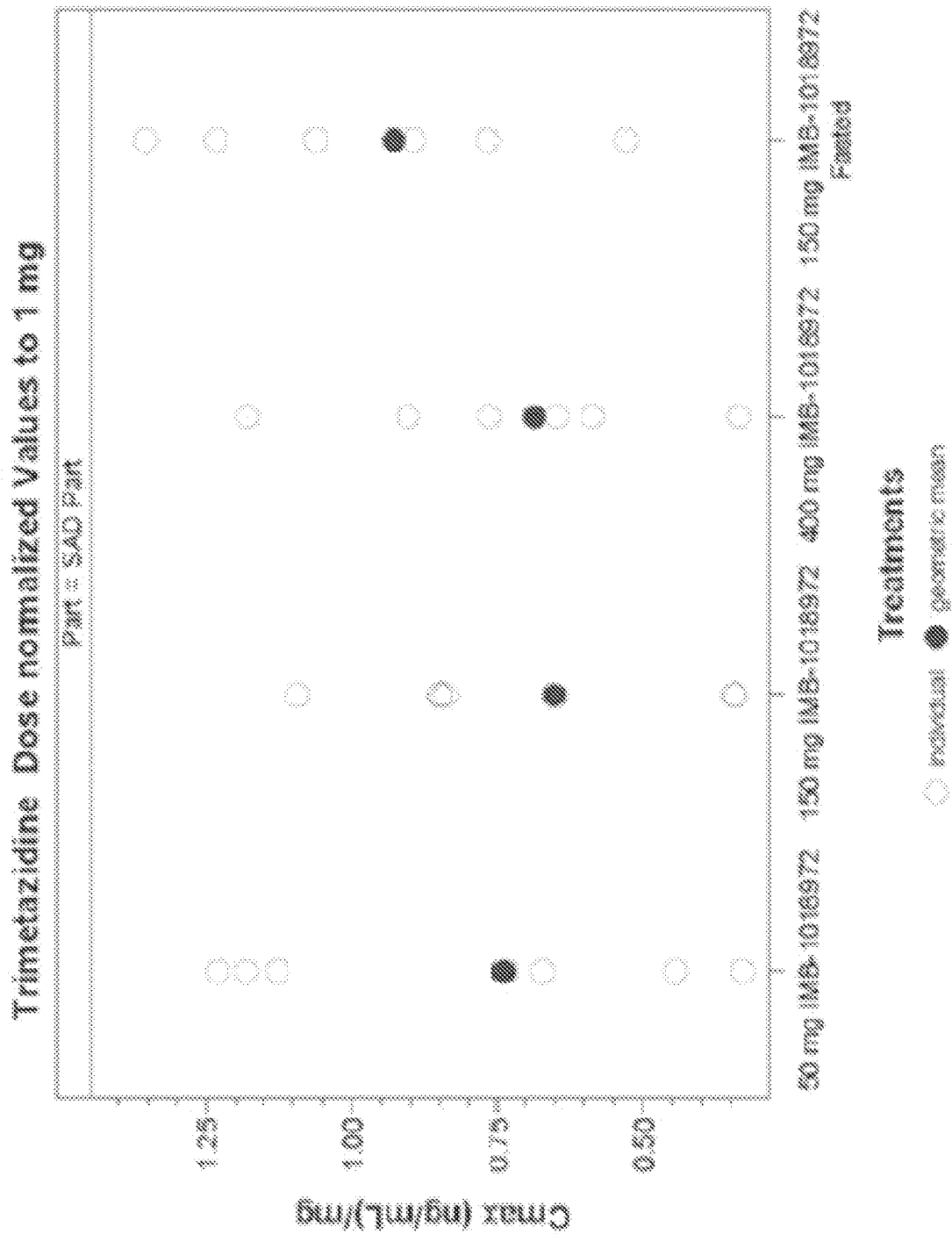
FIG. 23 is a graph of Plot of Combined Individual and Geometric Mean Dose-Normalized Trimetazidine $C_{max}$ over the Dose Range of 50 mg to 400 mg IMB-1018972 under Fasted Conditions—SAD Part (PK Set) of an FIH study of IMB-1018972.

FIG. 23 is a graph of Plot of Combined Individual and Geometric Mean Dose-Normalized Trimetazidine $C_{max}$ over the Dose Range of 50 mg to 400 mg IMB-1018972 under Fasted Conditions—SAD Part (PK Set)

Figure 24:
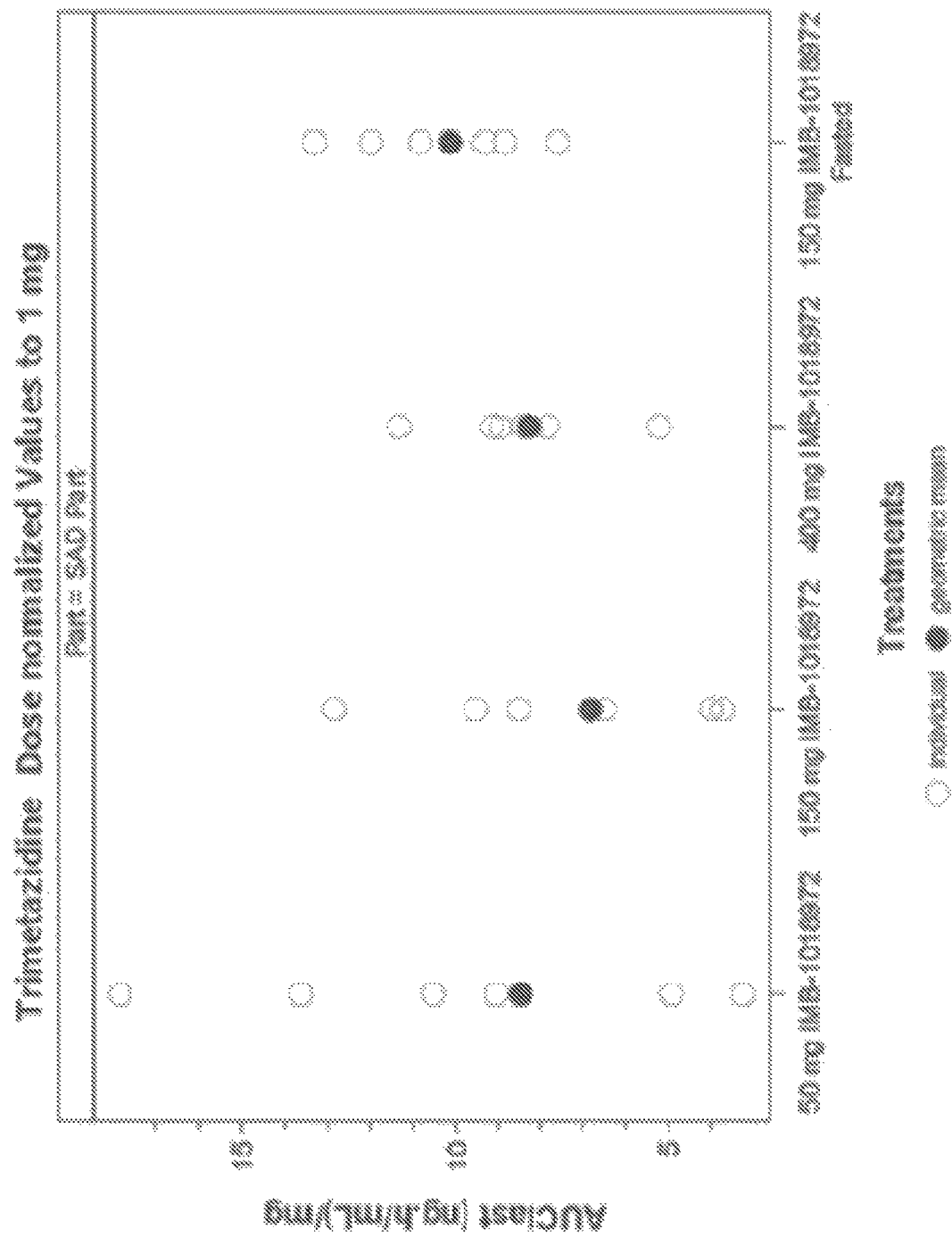
FIG. 24 is a graph of Plot of Combined Individual and Geometric Mean Dose-Normalized Trimetazidine $AUC_{0-t}$ over the Dose Range of 50 mg to 400 mg IMB-1018972 under Fasted Conditions—SAD Part (PK Set) of an FIH study of IMB-1018972.

FIG. 24 is a graph of Plot of Combined Individual and Geometric Mean Dose-Normalized Trimetazidine $AUC_{0-t}$ over the Dose Range of 50 mg to 400 mg IMB-1018972 under Fasted Conditions—SAD Part (PK Set)

Figure 25:
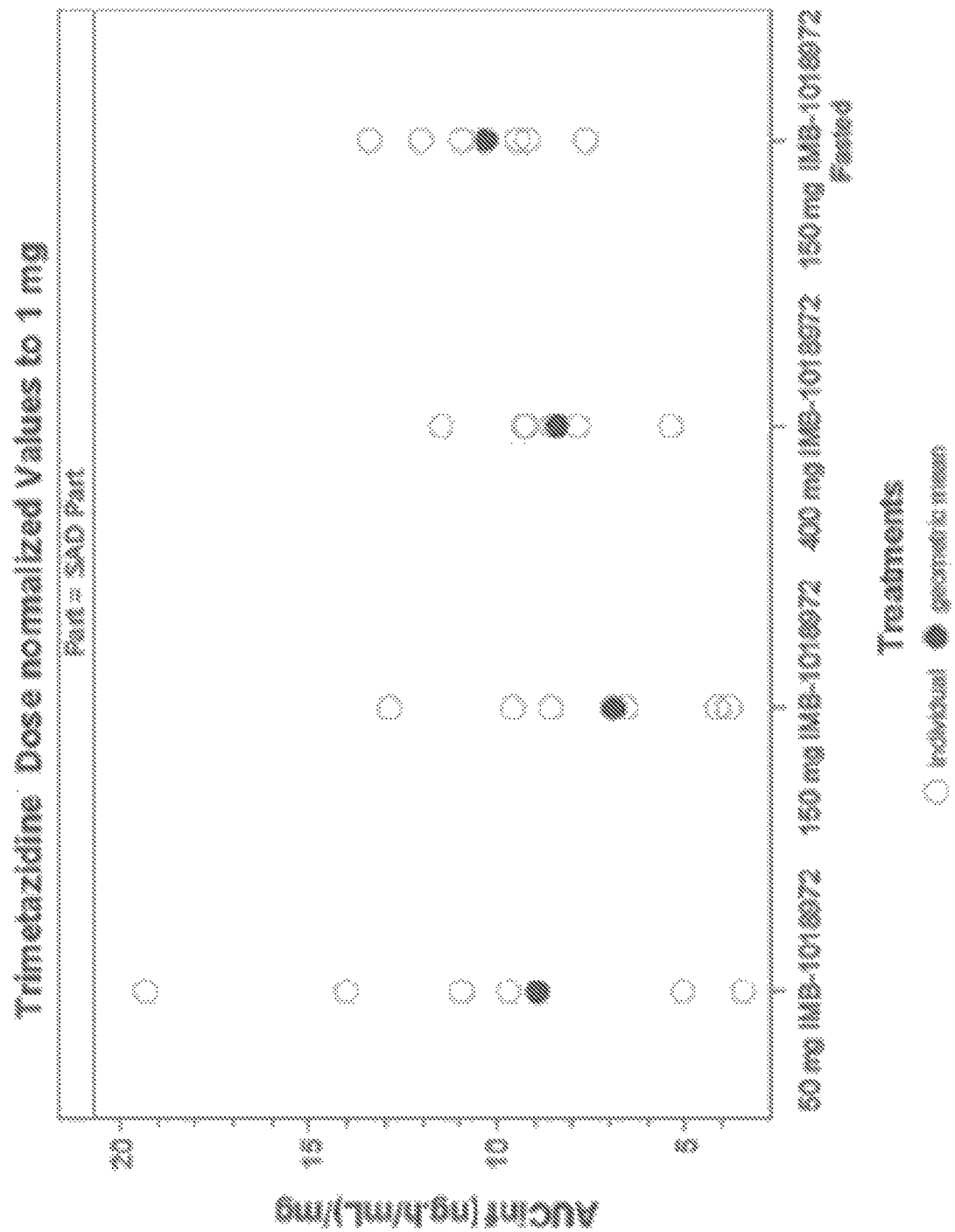
FIG. 25 is a graph of Plot of Combined Individual and Geometric Mean Dose-Normalized Trimetazidine $AUC_{0-inf}$ over the Dose Range of 50 mg to 400 mg IMB-1018972 under Fasted Conditions—SAD Part (PK Set) of an FIH study of IMB-1018972.

FIG. 25 is a graph of Plot of Combined Individual and Geometric Mean Dose-Normalized Trimetazidine $AUC_{0-inf}$ over the Dose Range of 50 mg to 400 mg IMB-1018972 under Fasted Conditions—SAD Part (PK Set)

Effect of Food

The possible effect of food on the PK of IMB-1028814 and trimetazidine was explored by comparing administration of single oral doses of 150 mg IMB-1018972 after an FDA-defined high-fat breakfast and under fasted conditions.

All predose samples were below the LLOQ for IMB-1028814 and trimetazidine plasma concentrations.

After study drug administration under fed conditions, the geometric mean IMB-1028814 plasma concentrations initially increased at the same speed as under fasted conditions but then a plateau was reached. When looking at individual profiles, no plateau was observed, but individual IMB- 1028814 tmax values ranged between 0.42 and 5 hours. Median tmax was reached at 2 hours postdose under fed conditions relative to 1 hour postdose under fasted conditions.

The trimetazidine plasma concentrations under fed conditions increased less rapidly than after study drug administration under fasted conditions and median tmax was reached at 4 hours postdose under fed conditions relative to 1.5 hours postdose under fasted conditions.

No evidence for an effect of food was observed on the IMB-1028814 exposure parameters $AUC_{0-t}$ and $AUC_{0-inf}$ (both with an estimate of 1.12 and 90% CI ranging from 1.02 to 1.23). However, Cmax was approximately 36% lower following administration of a single dose of 150 mg IMB-1018972 after an FDA-defined high-fat breakfast relative to administration under fasted conditions (estimate of 0.64; 90% CI ranging from 0.39 to 1.04).

No evidence for an effect of food was observed on the trimetazidine exposure parameters Cmax (estimate of 0.91; 90% CI ranging from 0.85 to 0.98), and $AUC_{0-t}$ and $AUC_{0-inf}$ (both with an estimate of 1.04 and 90% CI ranging from 0.98 to 1.10).

Figure 26:
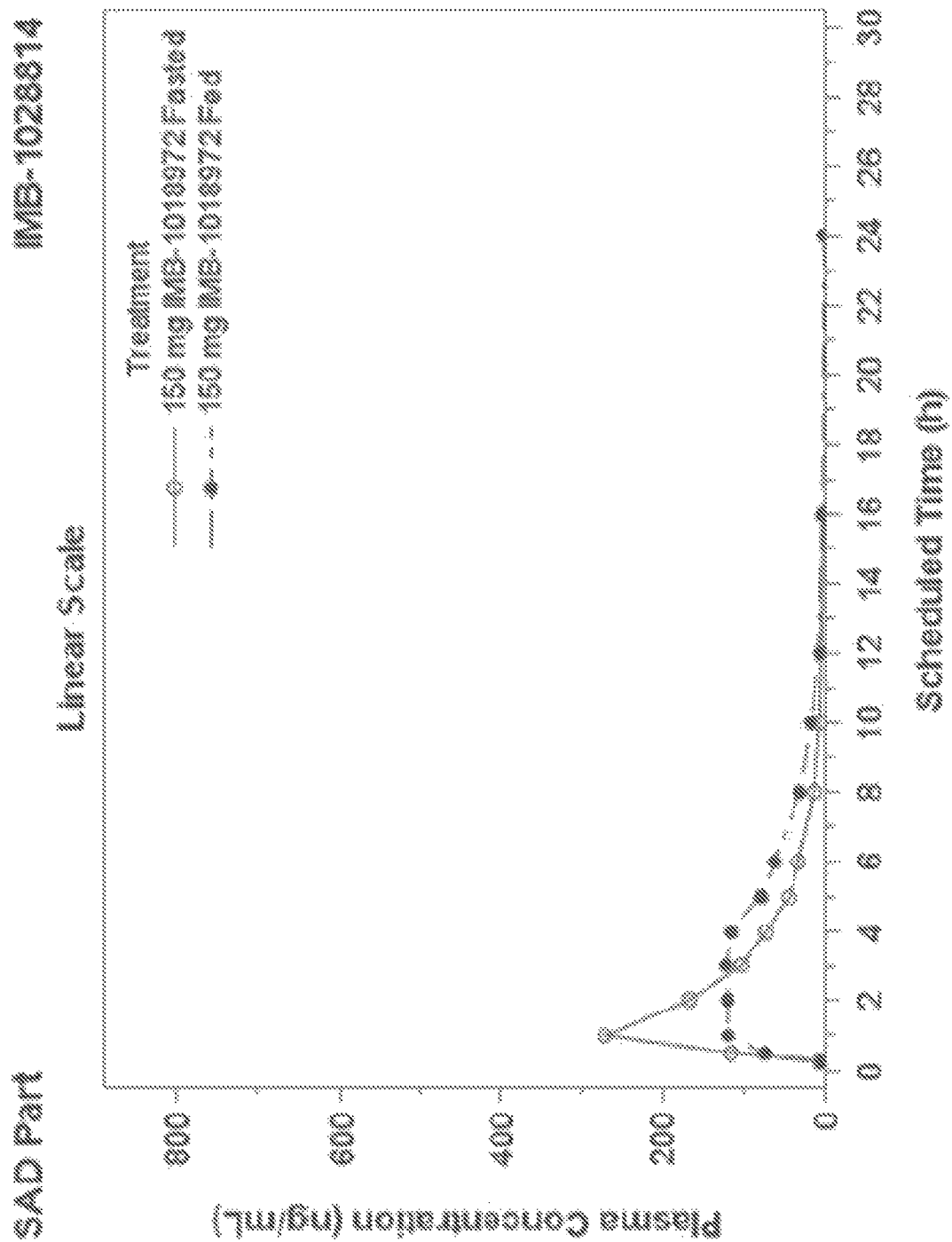
FIG. 26 is a graph of Geometric Mean IMB-1028814 Plasma Concentration-Time Profiles (Linear)—FE Arm of SAD Part (PK Set) of an FIH study of IMB-1018972.

FIG. 26 is a graph of Geometric Mean IMB-1028814 Plasma Concentration-Time Profiles (Linear)—FE Arm of SAD Part (PK Set)

Figure 27:
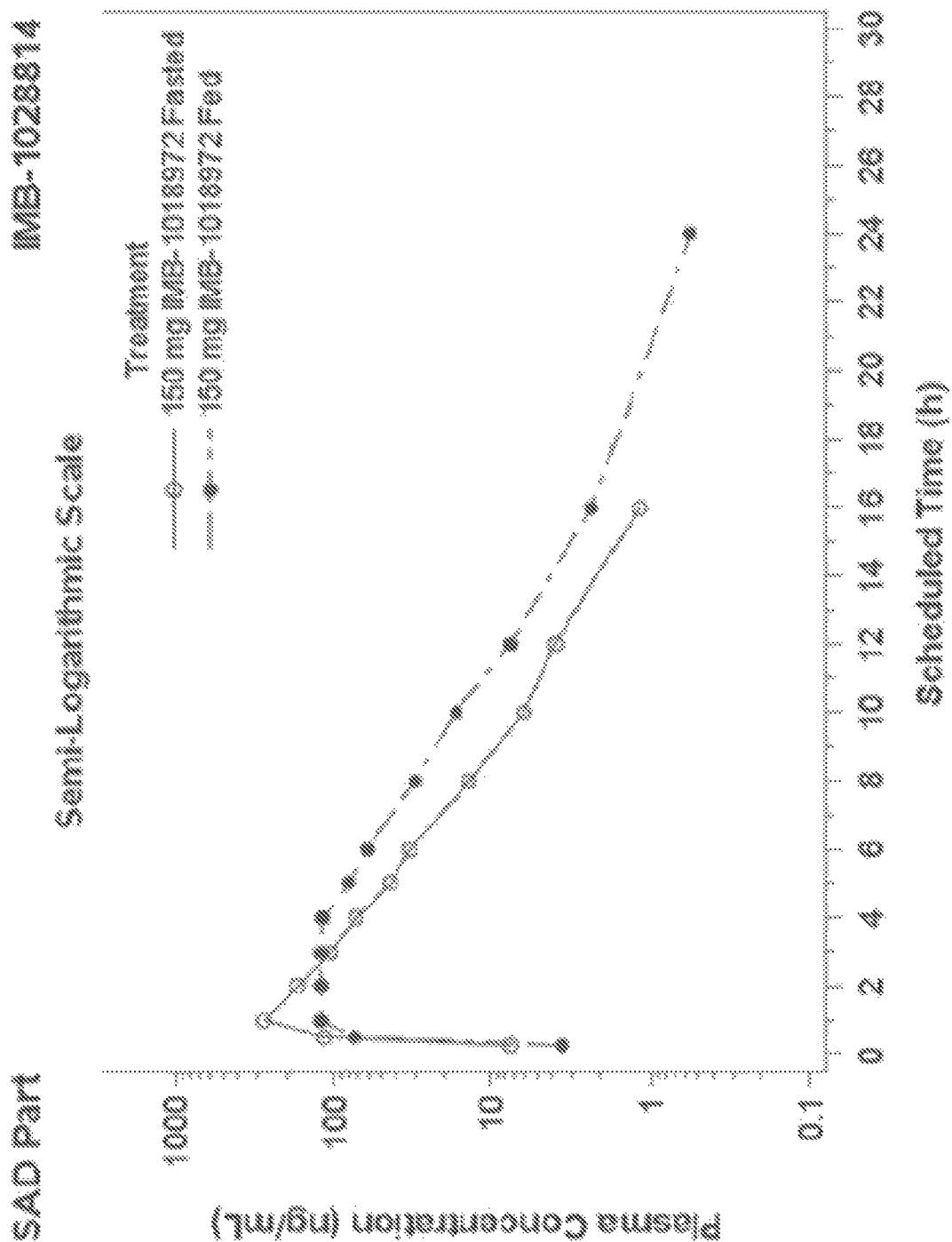
FIG. 27 is a graph of Geometric Mean IMB-1028814 Plasma Concentration-Time Profiles (Semi-Logarithmic Scale)—FE Arm of SAD Part (PK Set) of an FIH study of IMB-1018972.

FIG. 27 is a graph of Geometric Mean IMB-1028814 Plasma Concentration-Time Profiles (Semi-Logarithmic Scale)—FE Arm of SAD Part (PK Set)

Figure 28:
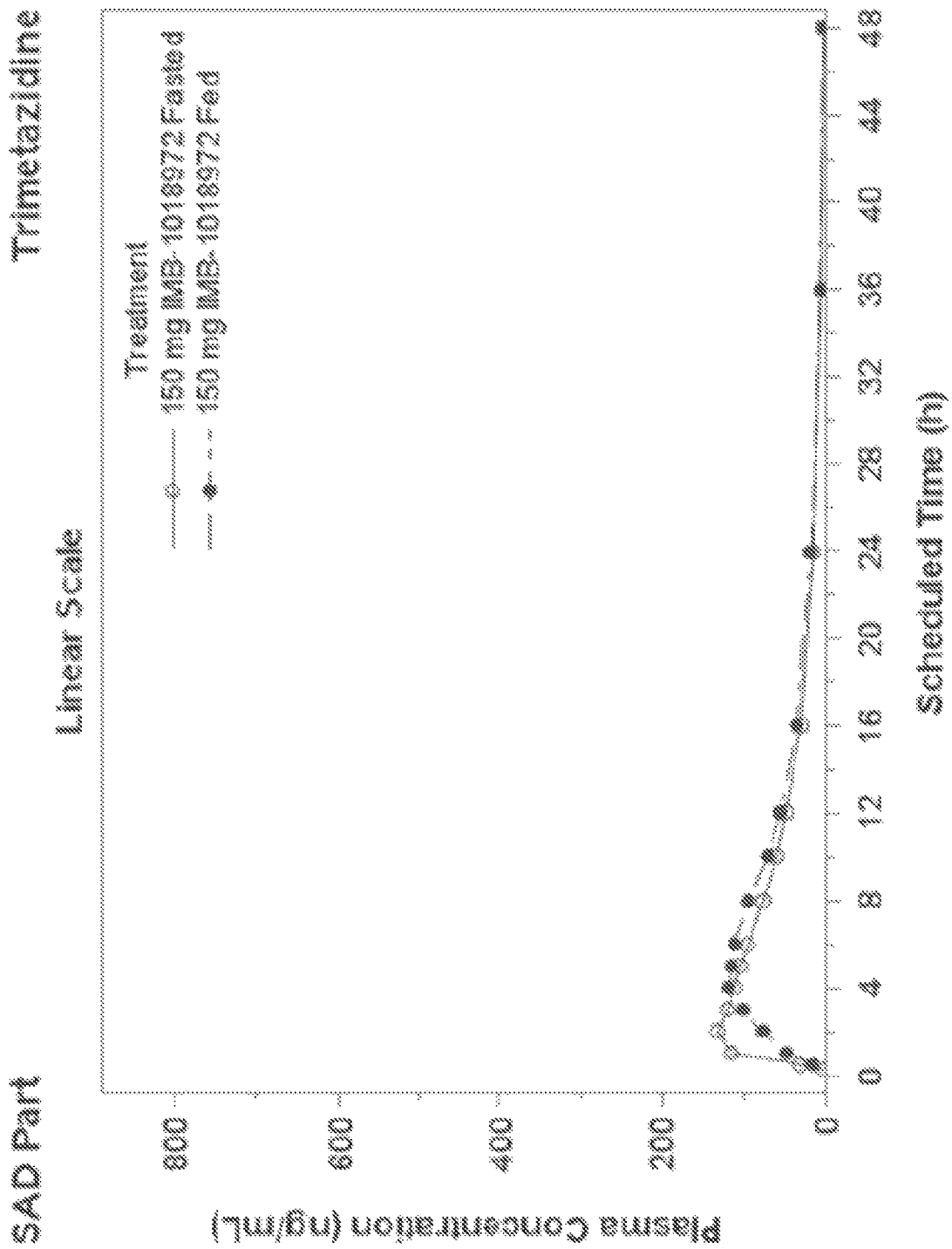
FIG. 28 is a graph of Geometric Mean Trimetazidine Plasma Concentration-Time Profiles (Linear)—FE Arm of SAD Part (PK Set) of an FIH study of IMB-1018972.

FIG. 28 is a graph of Geometric Mean Trimetazidine Plasma Concentration-Time Profiles (Linear)—FE Arm of SAD Part (PK Set)

Figure 29:
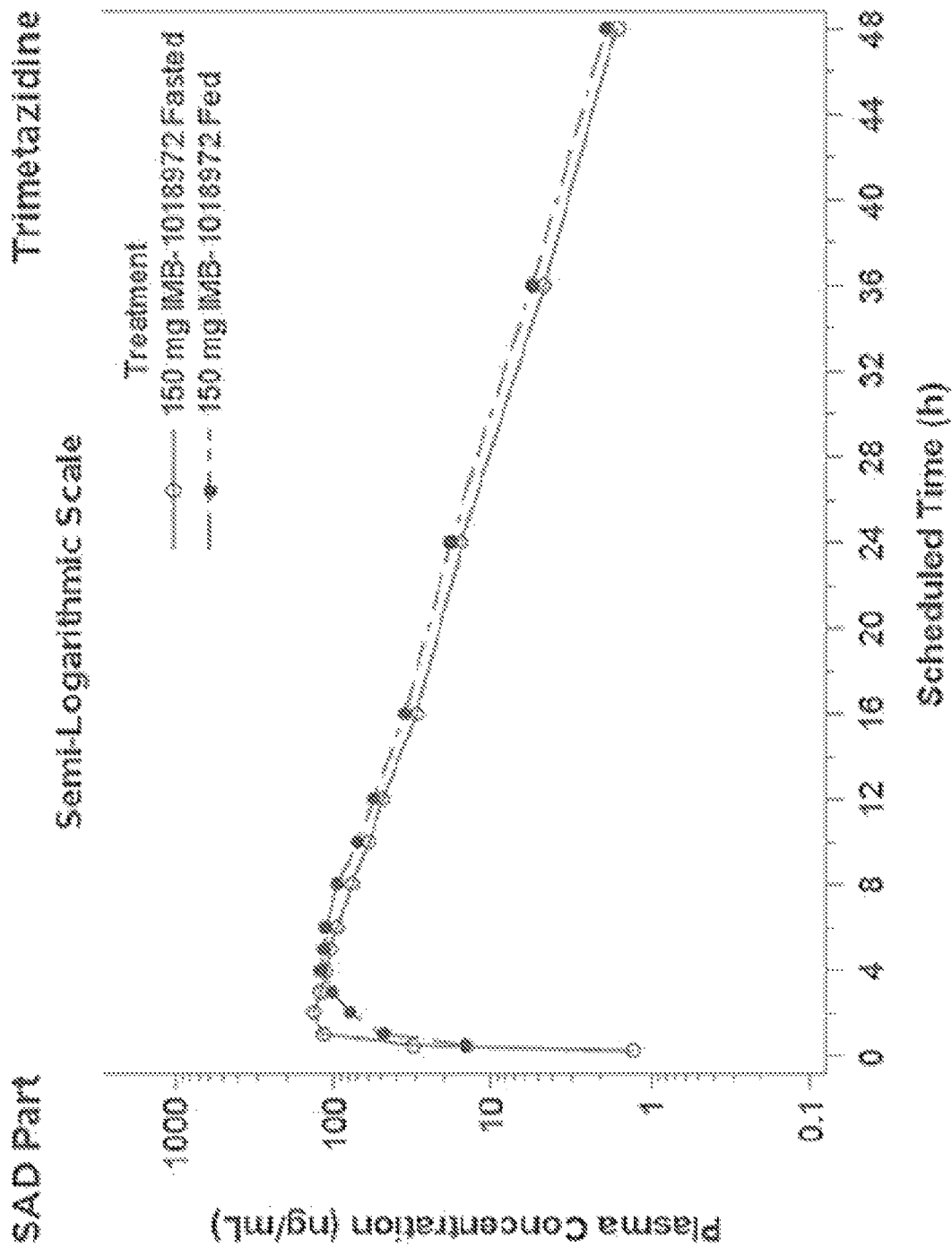
FIG. 29 is a graph of Geometric Mean Trimetazidine Plasma Concentration-Time Profiles (Semi-Logarithmic Scale)—FE Arm of SAD Part (PK Set) of an FIH study of IMB-1018972.

FIG. 29 is a graph of Geometric Mean Trimetazidine Plasma Concentration-Time Profiles (Semi-Logarithmic Scale)—FE Arm of SAD Part (PK Set)

Figure 30:
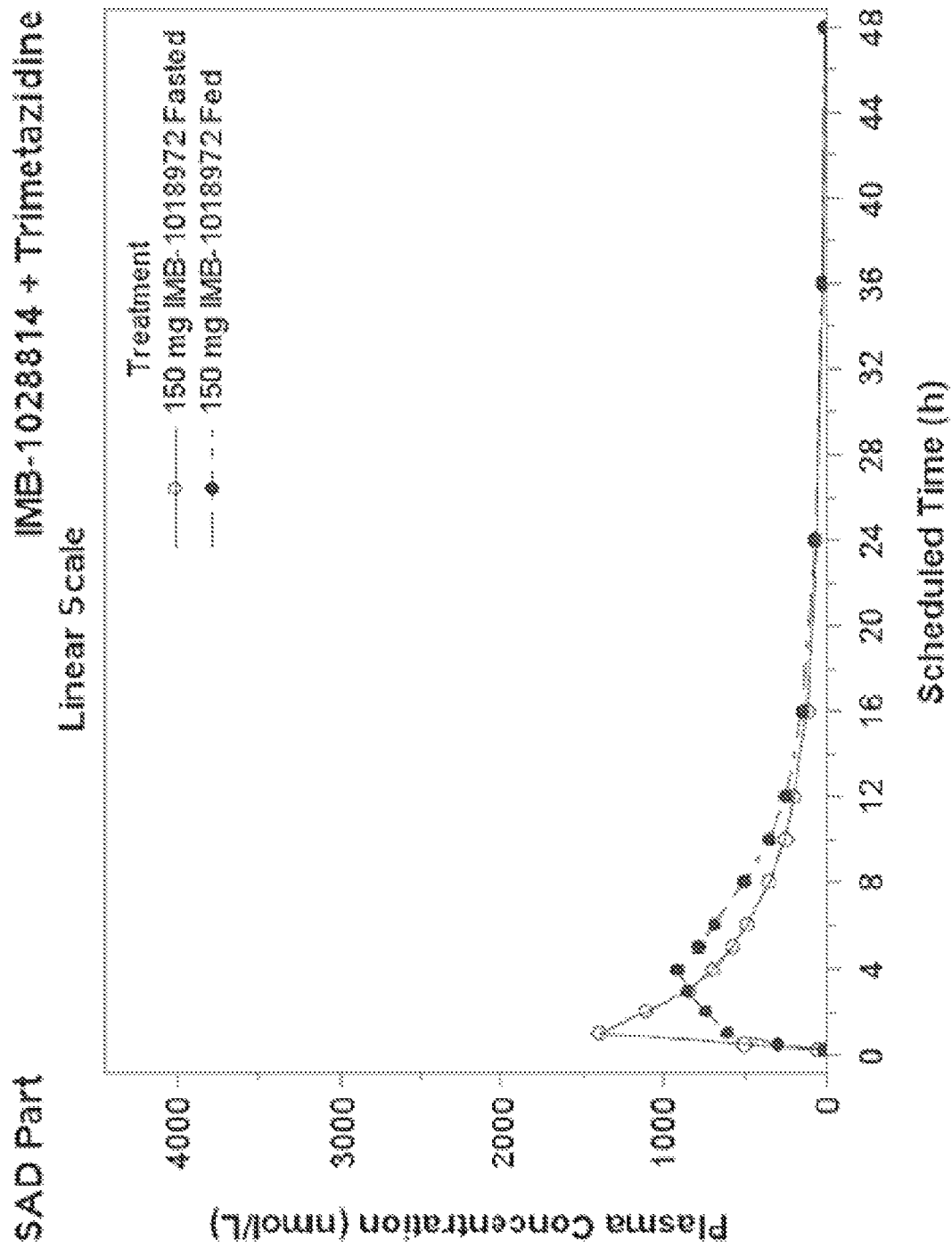
FIG. 30 is a graph of Geometric Mean IMB-1028814+ Trimetazidine Plasma Concentration-Time Profiles (Linear)—FE Arm of SAD Part (PK Set) of an FIH study of IMB-1018972.

FIG. 30 is a graph of Geometric Mean IMB-1028814+ Trimetazidine Plasma Concentration-Time Profiles (Linear)—FE Arm of SAD Part (PK Set)

Figure 31:
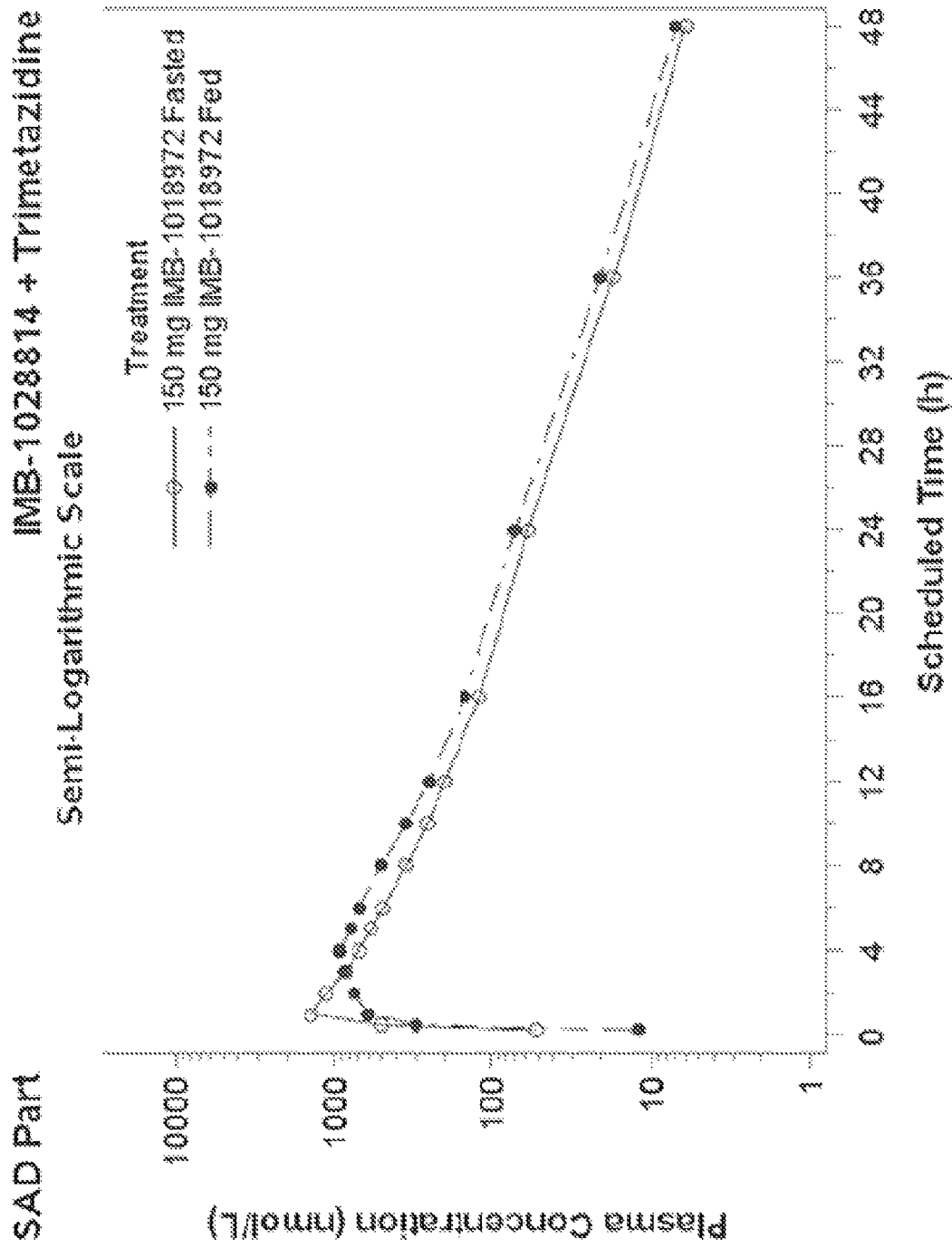
FIG. 31 is a graph of Geometric Mean IMB-1028814+ Trimetazidine Plasma Concentration-Time Profiles (Semi-Logarithmic Scale)—FE Arm of SAD Part (PK Set) of an FIE study of IMB-1018972.

FIG. 31 is a graph of Geometric Mean IMB-1028814+ Trimetazidine Plasma Concentration-Time Profiles (Semi-Logarithmic Scale)—FE Arm of SAD Part (PK Set)

FIG. 32 is a table of Summary Statistics (Geometric Mean [Range]) of IMB-1028814, Trimetazidine, and IMB-128814+Trimetazidine, and IMB-1028814+Trimetazidine Plasma Pharmacokinetic Parameters—FE Arm of SAD Part (PK Set)

FIG. 33 is a table of Exploratory Analysis of Food Effect for IMB-1028814 and Trimetazidine following Administration of 150 mg IMB-1018972—FE Arm of SAD Part (PK Set)

Pharmacokinetic Results of IMB-1028814 and Trimetazidine in Urine

Urinary excretion of IMB-1028814 and trimetazidine was determined in urine samples from subjects who received a single oral dose of IMB-1018972 in the range of 50 mg to 400 mg under fasted conditions. Further, urinary excretion of trimetazidine was determined in urine samples from subjects who received a single oral dose of 35 mg trimetazidine.

The arithmetic mean percent of the dose excreted in urine ranged between 3.99% and 5.74% for IMB-1028814, and between 23.11% and 32.55% for trimetazidine within 48 hours after a single oral IMB-1018972 dose over the studied dose range of 50 mg to 400 mg. Within 48 hours following administration of a single oral dose of 35 mg trimetazidine, an arithmetic mean of 54.47% was excreted in urine as trimetazidine. These results indicate that metabolism is the primary clearance mechanism for IMB-1028814 while renal excretion is the primary clearance mechanism for trimetazidine.

The geometric mean renal clearance (CLR) ranged between 3.76 L/h and 5.37 L/h for IMB-1028814, and between 18.1 L/h and 20.8 L/h for trimetazidine over the studied single-dose range of 50 mg to 400 mg IMB-1018972. Geometric mean CLR for trimetazidine was 20.4 L/h following administration of a single oral dose of 35 mg trimetazidine. The renal clearance of trimetazidine is greater than glomerular filtration rate (125 mL/min or 7.5 L/h), indicating that trimetazidine undergoes net tubular secretion.

FIG. 34 is a table of Summary Statistics (Arithmetic Mean [SD]) of Urine Pharmacokinetic Parameters for IMB-1028814, Trimetazidine, and IMB-1028814+Trimetazidine—SAD Part (PK Set)

Pharmacokinetic Results of IMB-1028814 and Trimetazidine in Urine

Urinary excretion of IMB-1028814 and trimetazidine was determined in urine samples from subjects who received a single oral dose of IMB-1018972 in the range of 50 mg to 400 mg under fasted conditions. Further, urinary excretion of trimetazidine was determined in urine samples from subjects who received a single oral dose of 35 mg trimetazidine.

The arithmetic mean percent of the dose excreted in urine ranged between 3.99% and 5.74% for IMB-1028814, and between 23.11% and 32.55% for trimetazidine within 48 hours after a single oral IMB-1018972 dose over the studied dose range of 50 mg to 400 mg. Within 48 hours following administration of a single oral dose of 35 mg trimetazidine, an arithmetic mean of 54.47% was excreted in urine as trimetazidine. These results indicate that metabolism is the primary clearance mechanism for IMB-1028814 while renal excretion is the primary clearance mechanism for trimetazidine.

The geometric mean renal clearance (CLR) ranged between 3.76 L/h and 5.37 L/h for IMB-1028814, and between 18.1 L/h and 20.8 L/h for trimetazidine over the studied single-dose range of 50 mg to 400 mg IMB-1018972. Geometric mean CLR for trimetazidine was 20.4 L/h following administration of a single oral dose of 35 mg trimetazidine. The renal clearance of trimetazidine is greater than glomerular filtration rate (125 mL/min or 7.5 L/h), indicating that trimetazidine undergoes net tubular secretion.

MAD Part

Pharmacokinetic Results of IMB-1028814, Trimetazidine and IMB-1028814+Trimetazidine in Plasma All predose samples on Day 1 were below the LLOQ for IMB-1028814 and trimetazidine plasma concentrations.

The geometric mean concentration-time profiles for IMB-1028814, metabolite trimetazidine, and IMB-1028814+ trimetazidine on Day 1 and Day 14 showed a dose dependent increase in plasma concentrations following administration of multiple doses of IMB-1018972 under fed conditions of 50 mg q12h and 150 mg q12h.

Similar to the SAD part, initial hydrolysis of IVB-1018972 to IMB-1028814 and subsequent systemic bioavailability of IMB-1028814 on Days 1 and 14 was relatively rapid. Over the 2 multiple-dose levels, median tmax ranged between 0.5 hours and 1 hours postdose for IVB-1028814 on Day 1, and was 3 hours postdose for trimetazidine on Day 1. On Day 14, median tmax was 0.5 hours postdose for IMB-1028814 and 2 hours postdose for trimetazidine.

Exposure Parameters on Day 1

No dose-proportionality analysis was done since there were only 2 IVB-1018972 dose levels in the MAD part: multiple oral doses of 50 mg or 150 mg q12h for 14 days under fed conditions.

The geometric mean $C_{max}$ and $AUC_0$-T were higher after 150 mg fed than after 50 mg fed for IMB-1028814 (297% and 336% higher for $C_{max}$ and $AUC_{0-T}$, respectively), trimetazidine (154% and 163% higher for $C_{max}$ and $AUC_{0-T}$, respectively), and IMB-1028814+trimetazidine (257% and 239% higher for Cmax and $AUC_{0-T}$, respectively).

When comparing the MAD and SAD parts, geometric mean Cmax was 97% higher on Day 1 after 150 mg fed in the MAD part than after a single dose of 150 mg fed in the SAD part for IMB-1028814. For trimetazidine however, geometric mean Cmax was 32% lower on Day 1 after 150 mg fed in the MAD part than after a single dose of 150 mg fed in the SAD part.

Exposure Parameters on Day 14 Following Repeated q12h Dosing

The geometric mean Cmax and $AUC_{0-T}$ were higher after 150 mg fed than after 50 mg fed for IMB-1028814 (377% and 367% higher for Cmax and $AUC_{0-T}$, respectively), trimetazidine (127% and 126% higher for Cmax and $AUC_{0-T}$, respectively), and IMB-1028814+trimetazidine (286% and 211% higher for Cmax and $AUC_{0-T}$, respectively).

The predefined stopping criterion for IMB-1028814 plasma exposure of 417,733 and 652,849 ng·h/mL for males and females, respectively, was not reached by any of the subjects during the MAD part.

Trough Concentrations Following Repeated q12h Dosing

Based upon visual inspection of the geometric mean plasma concentration-time profiles and the geometric mean trough concentrations, it can be concluded that for both 150 mg fed and 50 mg fed, the Day 14 IMB-1018972 dose was administered under steady-state conditions of IMB-1028814 and trimetazidine concentrations Accumulation Following Repeated q12h Dosing For both the 50 mg and 150 mg fed dose levels, geometric mean $AUC_0$-T values of IMB-1028814, trimetazidine, and IMB-1028814+trimetazidine were higher on Day 14 relative to Day 1.

Geometric mean $R_{ac}$ for IMB-1028814 was 1.18 and 1.10 after the 150 mg fed dose and 50 mg fed dose, respectively, indicating minimal accumulation of IMB-1028814 in plasma. Geometric mean $R_{ac}$ for trimetazidine was 1.63 and 1.89 after the 150 mg fed dose and 50 mg fed dose, respectively, indicating modest accumulation of trimetazidine in plasma. Geometric mean $R_{ac}$ for IMB-1028814+trimetazidine was 1.39 and 1.52 after the 150 mg fed dose and 50 mg fed dose, respectively, indicating modest accumulation of IMB-1028814+trimetazidine in plasma.

Terminal Elimination Half-Life Following Repeated q12h Dosing

For IMB-1028814, the geometric mean t½ of 4.48 hours after 150 mg fed was longer than that of 2.79 hours after 50 mg fed. For trimetazidine, the geometric mean t½ of 9.36 hours after 150 mg fed was similar to that of 9.32 hours after 50 mg fed. For IMB-1028814+trimetazidine, the geometric mean t½ of 8.90 hours for IMB-1028814 after 150 mg fed was similar to that of 9.08 hours after 50 mg fed.

Figure 35:
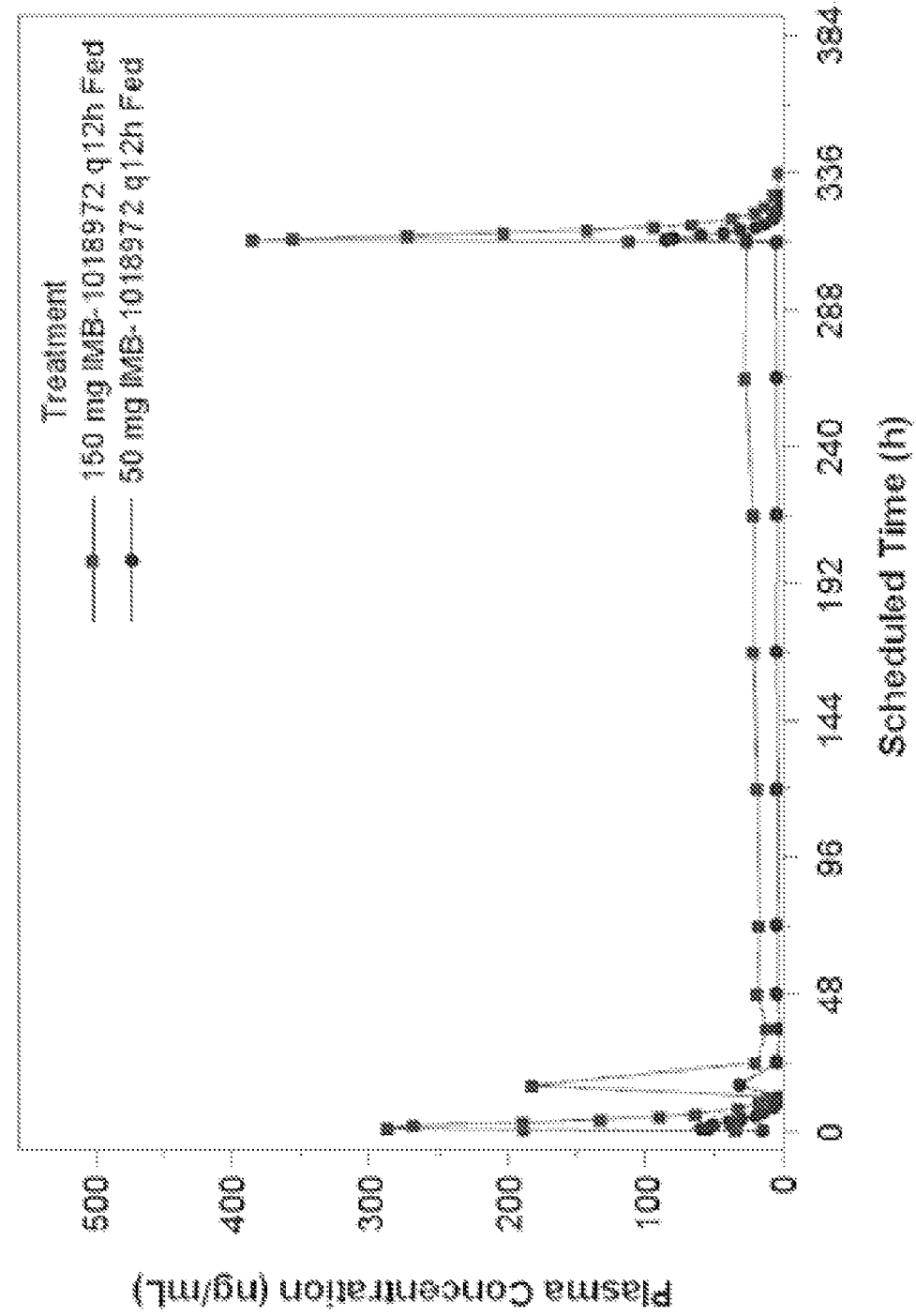
FIG. 35 is a graph of Geometric Mean IMB-1028814 Plasma Concentration-Time Profiles from Day 1 through Day 14 (Linear)—MAD Part (PK Set) of an FIE study of IMB-1018972.

FIG. 35 is a graph of Geometric Mean IMB-1028814 Plasma Concentration-Time Profiles from Day 1 through Day 14 (Linear)—MAD Part (PK Set)

Figure 36:
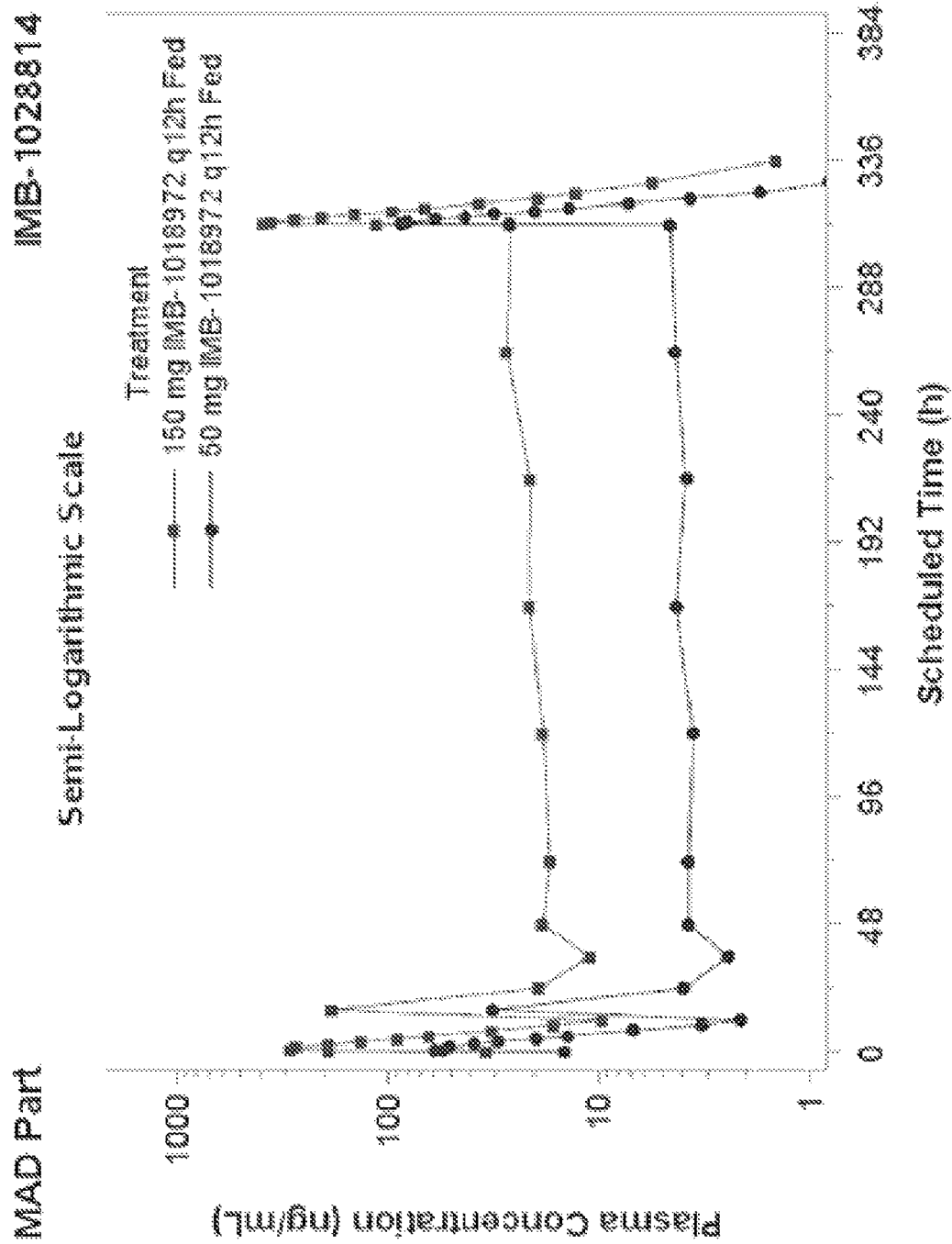
FIG. 36 is a graph of Geometric Mean IMB-1028814 Plasma Concentration-Time Profiles from Day 1 through Day 14 (Semi-Logarithmic Scale)—MAD Part (PK Set) of an FIE study of IMB-1018972.

FIG. 36 is a graph of Geometric Mean IMB-1028814 Plasma Concentration-Time Profiles from Day 1 through Day 14 (Semi-Logarithmic Scale)—MAD Part (PK Set)

Figure 37:
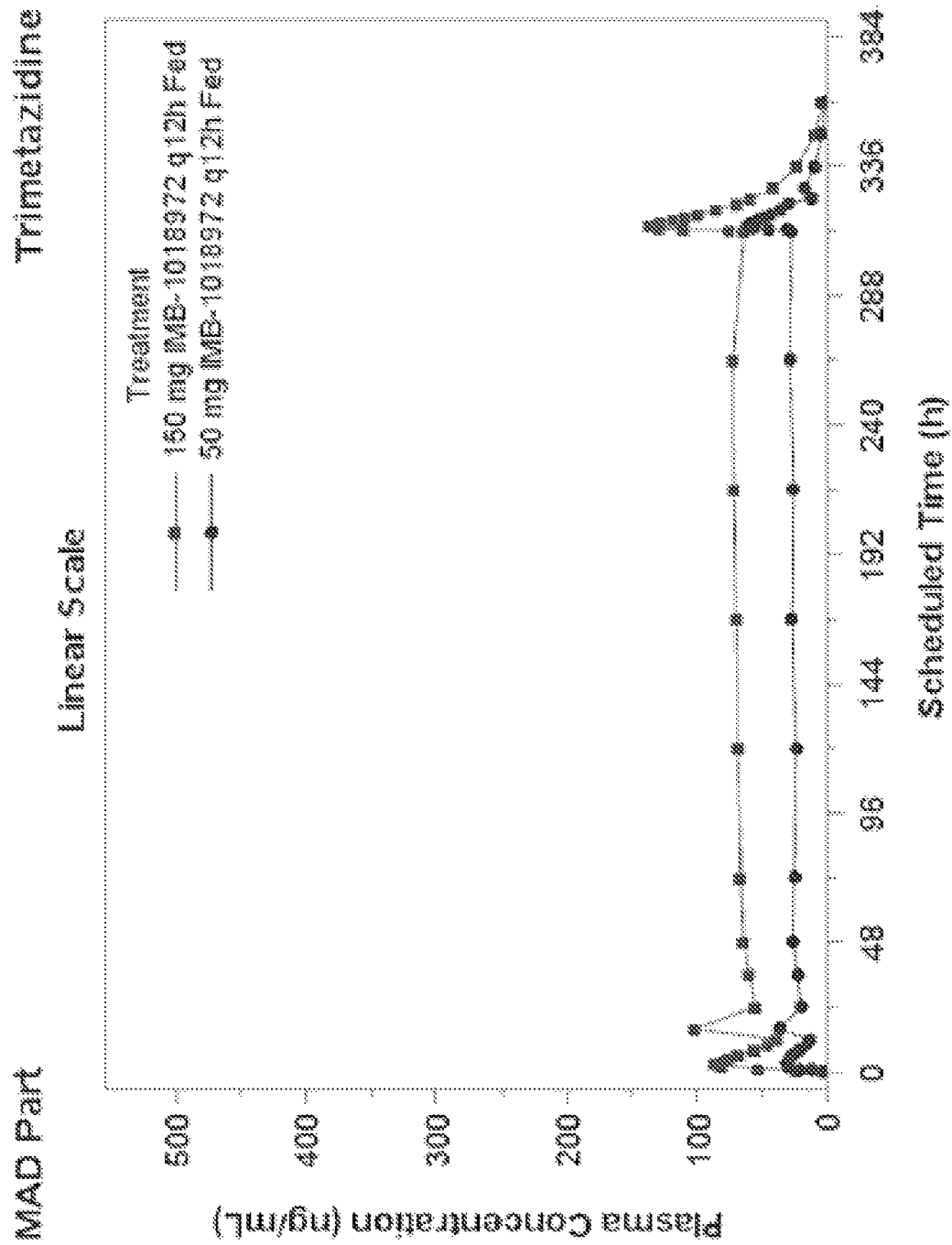
FIG. 37 is a graph of Geometric Mean Trimetazidine Plasma Concentration-Time Profiles from Day 1 through Day 14 (Linear)—MAD Part (PK Set) of an FIH study of IMB-1018972.

FIG. 37 is a graph of Geometric Mean Trimetazidine Plasma Concentration-Time Profiles from Day 1 through Day 14 (Linear)—MAD Part (PK Set)

Figure 38:
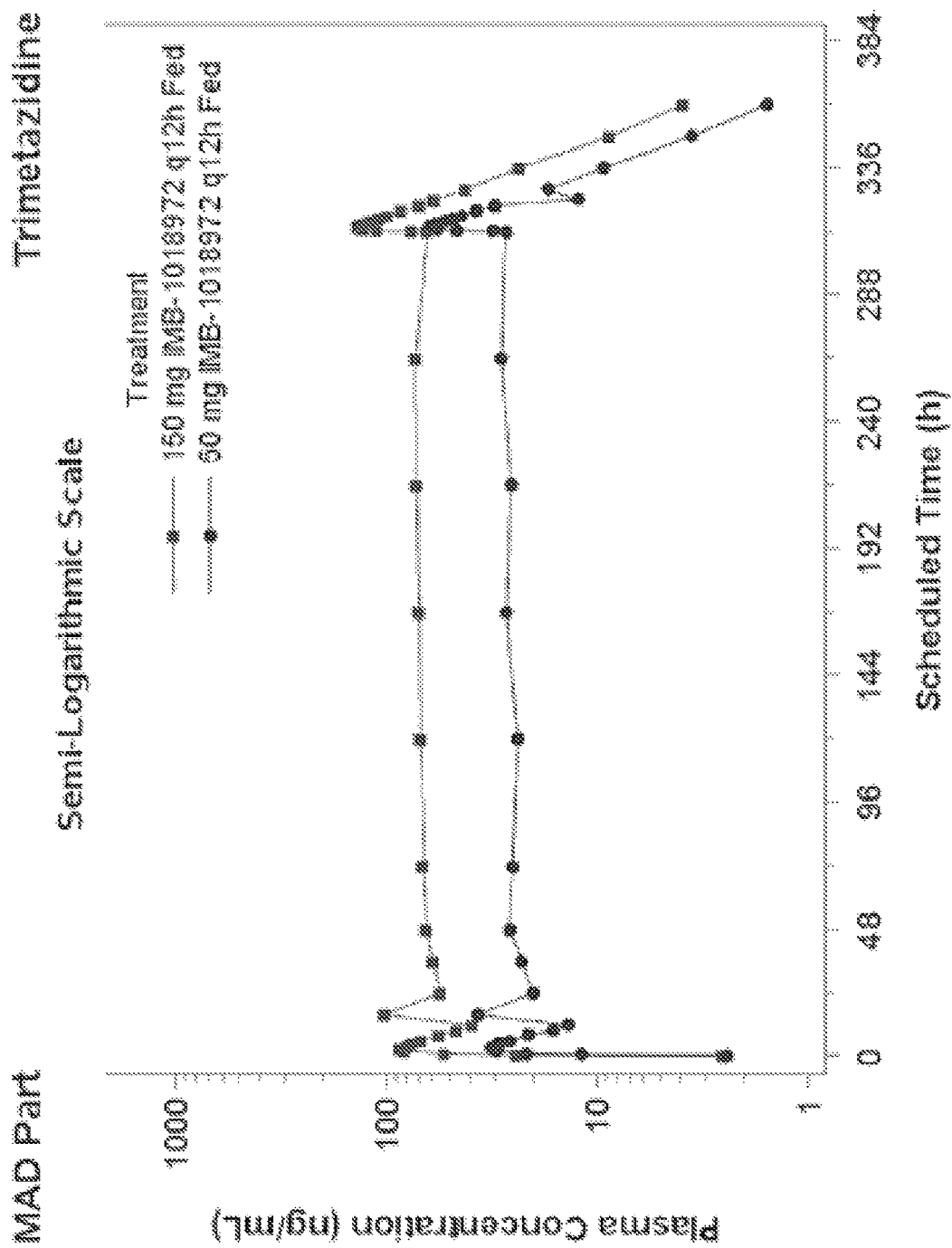
FIG. 38 is a graph of Geometric Mean Trimetazidine Plasma Concentration-Time Profiles from Day 1 through Day 14 (Semi-Logarithmic Scale)—MAD Part (PK Set) of an FIH study of IMB-1018972.

FIG. 38 is a graph of Geometric Mean Trimetazidine Plasma Concentration-Time Profiles from Day 1 through Day 14 (Semi-Logarithmic Scale)—MAD Part (PK Set)

Figure 39:
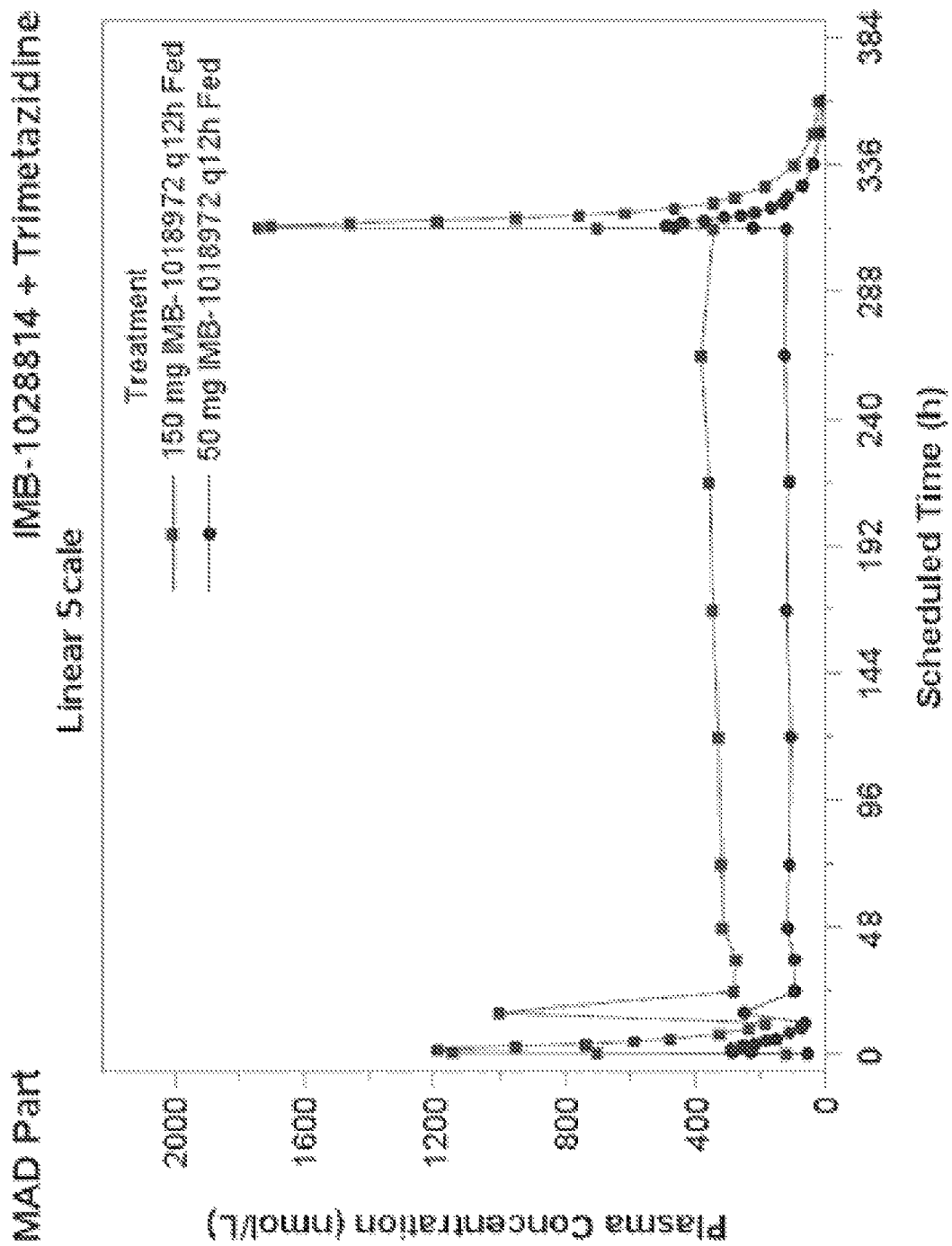
FIG. 39 is a graph of Geometric Mean IMB-1028814+ Trimetazidine Plasma Concentration-Time Profiles from Day 1 through Day 14 (Linear)—MAD Part (PK Set) of an FIH study of IMB-1018972.

FIG. 39 is a graph of Geometric Mean IMB-1028814+Trimetazidine Plasma Concentration-Time Profiles from Day 1 through Day 14 (Linear)—MAD Part (PK Set)

Figure 40:
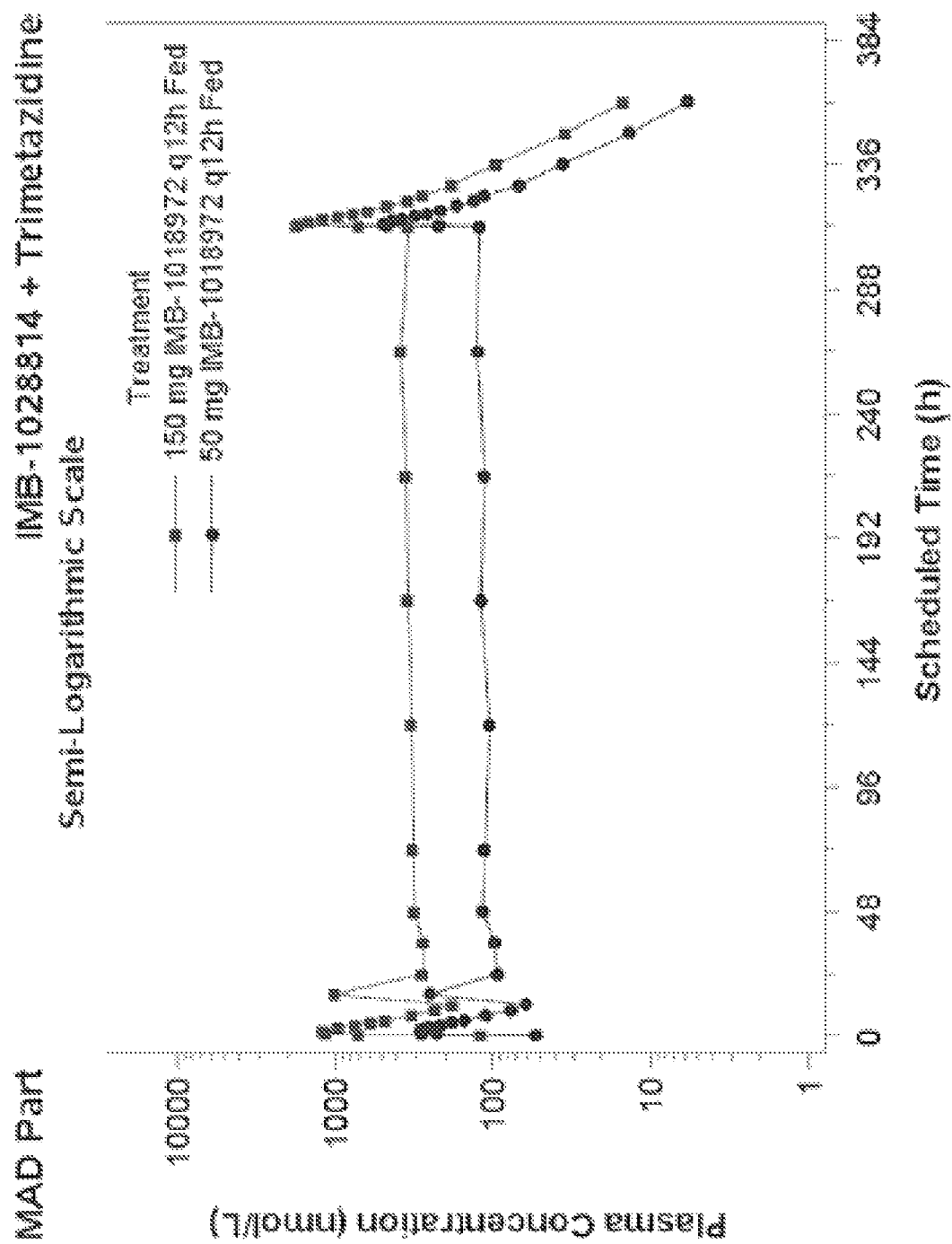
FIG. 40 is a graph of Geometric Mean IMB-1028814+ Trimetazidine Plasma Concentration-Time Profiles from Day 1 through Day 14 (Semi-Logarithmic Scale)—MAD Part (PK Set) of an FIH study of IMB-1018972.

FIG. 40 is a graph of Geometric Mean IMB-1028814+Trimetazidine Plasma Concentration-Time Profiles from Day 1 through Day 14 (Semi-Logarithmic Scale)—MAD Part (PK Set)

Figure 41:
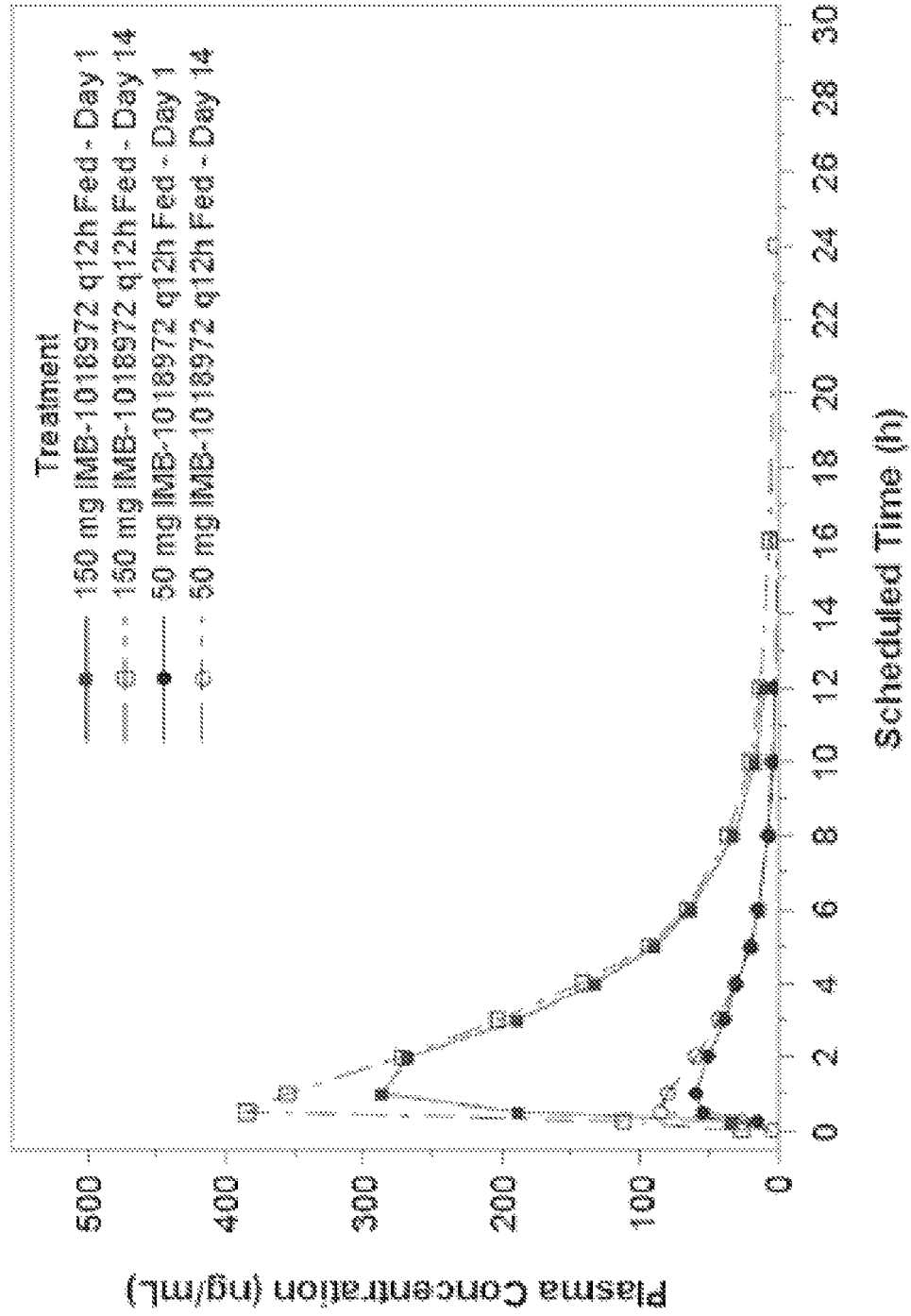
FIG. 41 is a graph of Geometric Mean IMB-1028814 Plasma Concentration-Time Profiles from Day 1 through Day 14 (Linear)—MAD Part (PK Set) of an FIH study of IMB-1018972.

FIG. 41 is a graph of Geometric Mean IMB-1028814 Plasma Concentration-Time Profiles from Day 1 through Day 14 (Linear)—MAD Part (PK Set)

Figure 42:
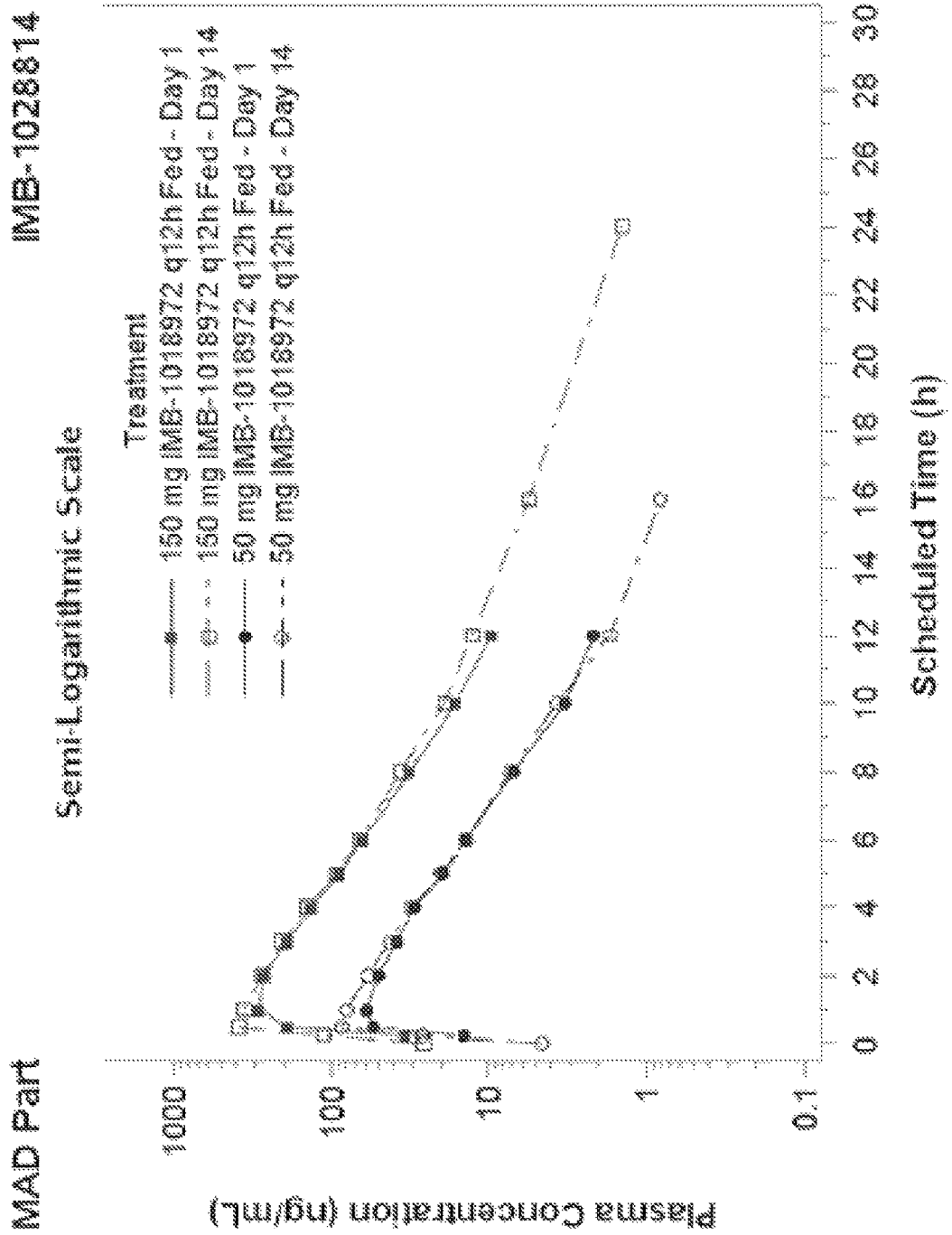
FIG. 42 is a graph of Geometric Mean IMB-1028814 Plasma Concentration-Time Profiles from Day 1 through Day 14 (Semi-Logarithmic Scale)—MAD Part (PK Set) of an FIH study of IMB-1018972.

FIG. 42 is a graph of Geometric Mean IMB-1028814 Plasma Concentration-Time Profiles from Day 1 through Day 14 (Semi-Logarithmic Scale)—MAD Part (PK Set)

Figure 43:
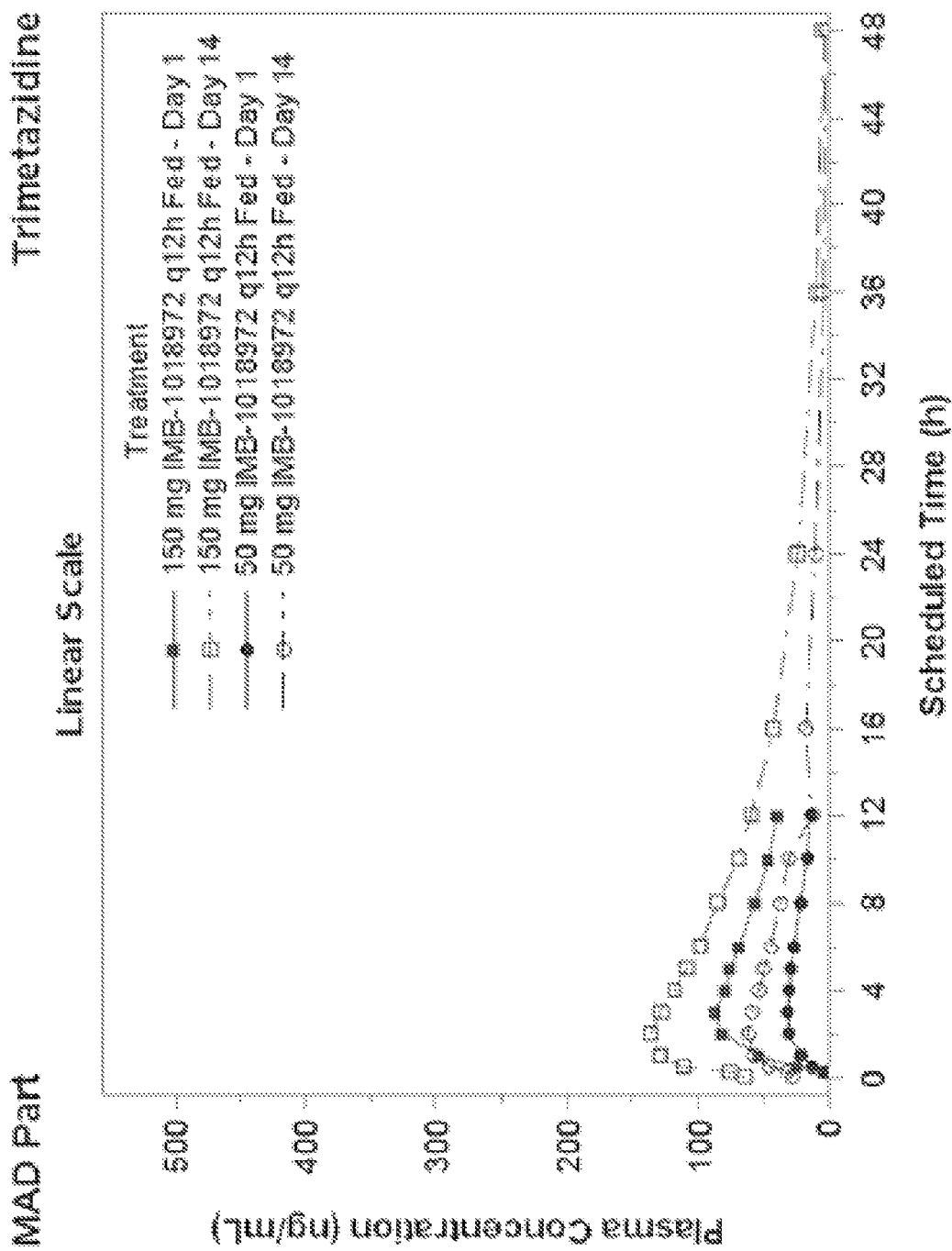
FIG. 43 is a graph of Geometric Mean Trimetazidine Plasma Concentration-Time Profiles after Dosing on Day 1 through Day 14 (Linear)—MAD Part (PK Set) of an FIH study of IMB-1018972.

FIG. 43 is a graph of Geometric Mean Trimetazidine Plasma Concentration-Time Profiles after Dosing on Day 1 through Day 14 (Linear)—MAD Part (PK Set)

Figure 44:
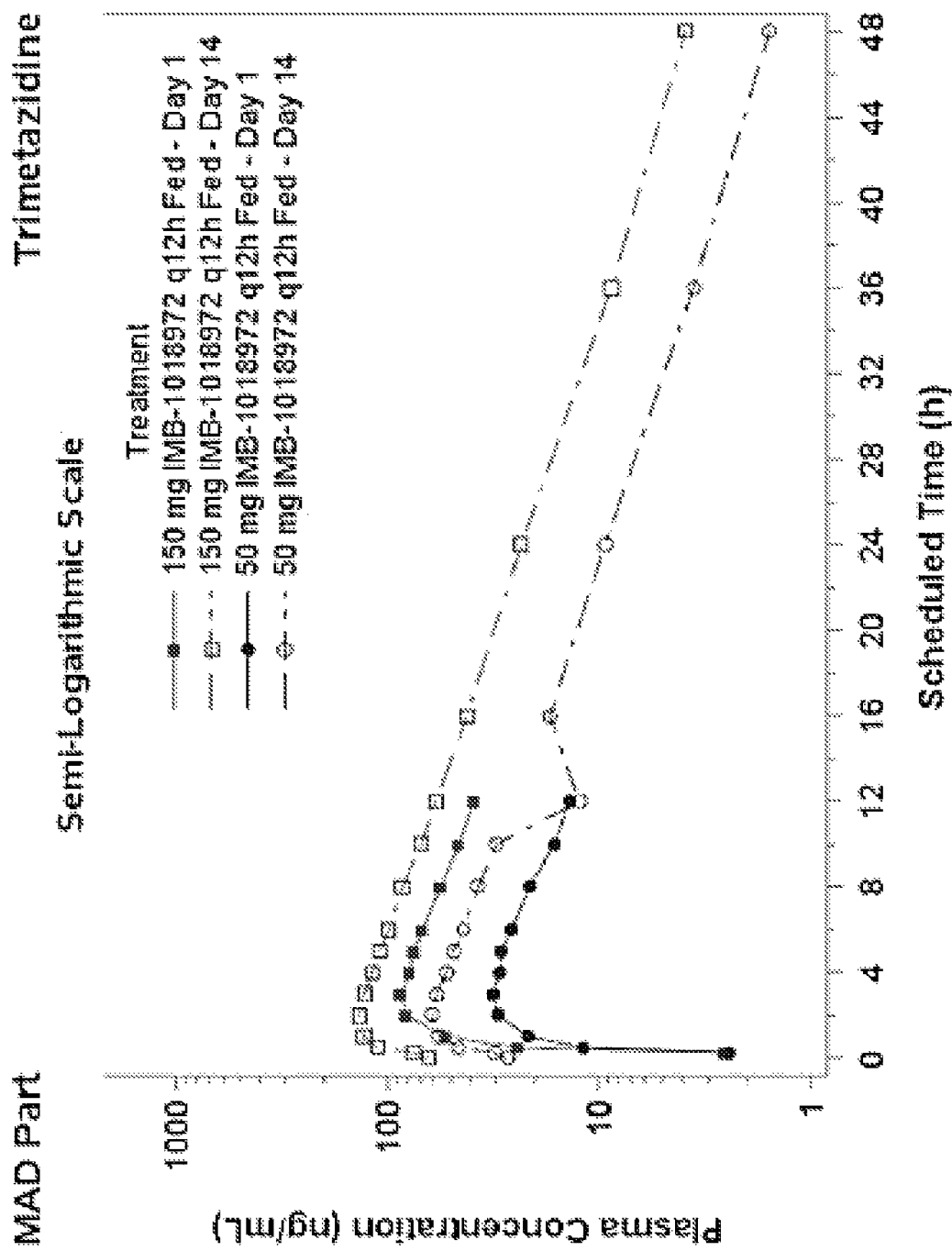
FIG. 44 is a graph of Geometric Mean Trimetazidine Plasma Concentration-Time Profiles after Dosing on Day 1 through Day 14 (Semi-Logarithmic Scale)—MAD Part (PK Set) of an FIH study of IMB-1018972.

FIG. 44 is a graph of Geometric Mean Trimetazidine Plasma Concentration-Time Profiles after Dosing on Day 1 through Day 14 (Semi-Logarithmic Scale)—MAD Part (PK Set)

Figure 45:
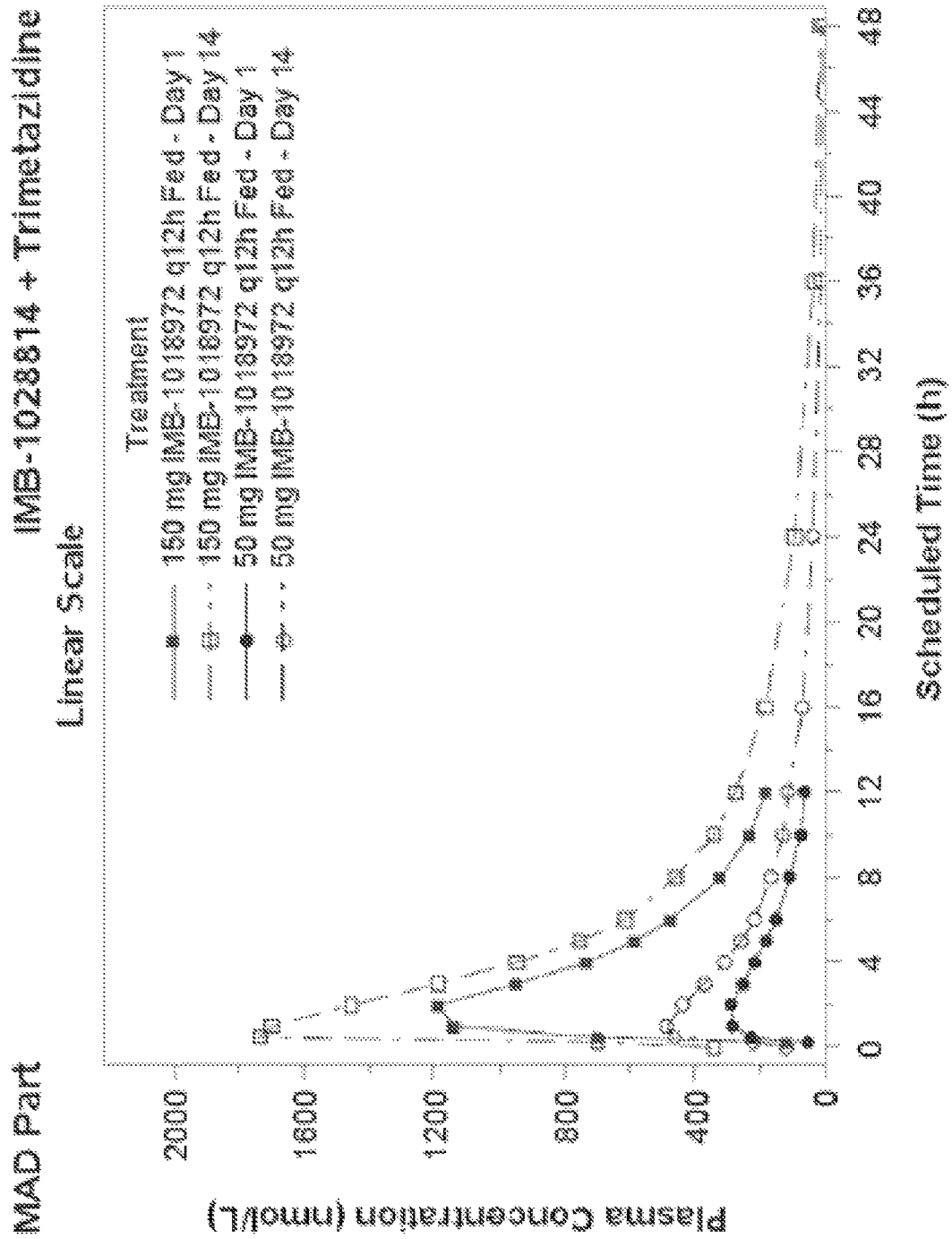
FIG. 45 is a graph of Geometric Mean IMB-1028814+ Trimetazidine Plasma Concentration-Time Profiles after Dosing on Day 1 through Day 14 (Linear)—MAD Part (PK Set) of an FIH study of IMB-1018972.

FIG. 45 is a graph of Geometric Mean IMB-1028814+Trimetazidine Plasma Concentration-Time Profiles after Dosing on Day 1 through Day 14 (Linear)—MAD Part (PK Set)

Figure 46:
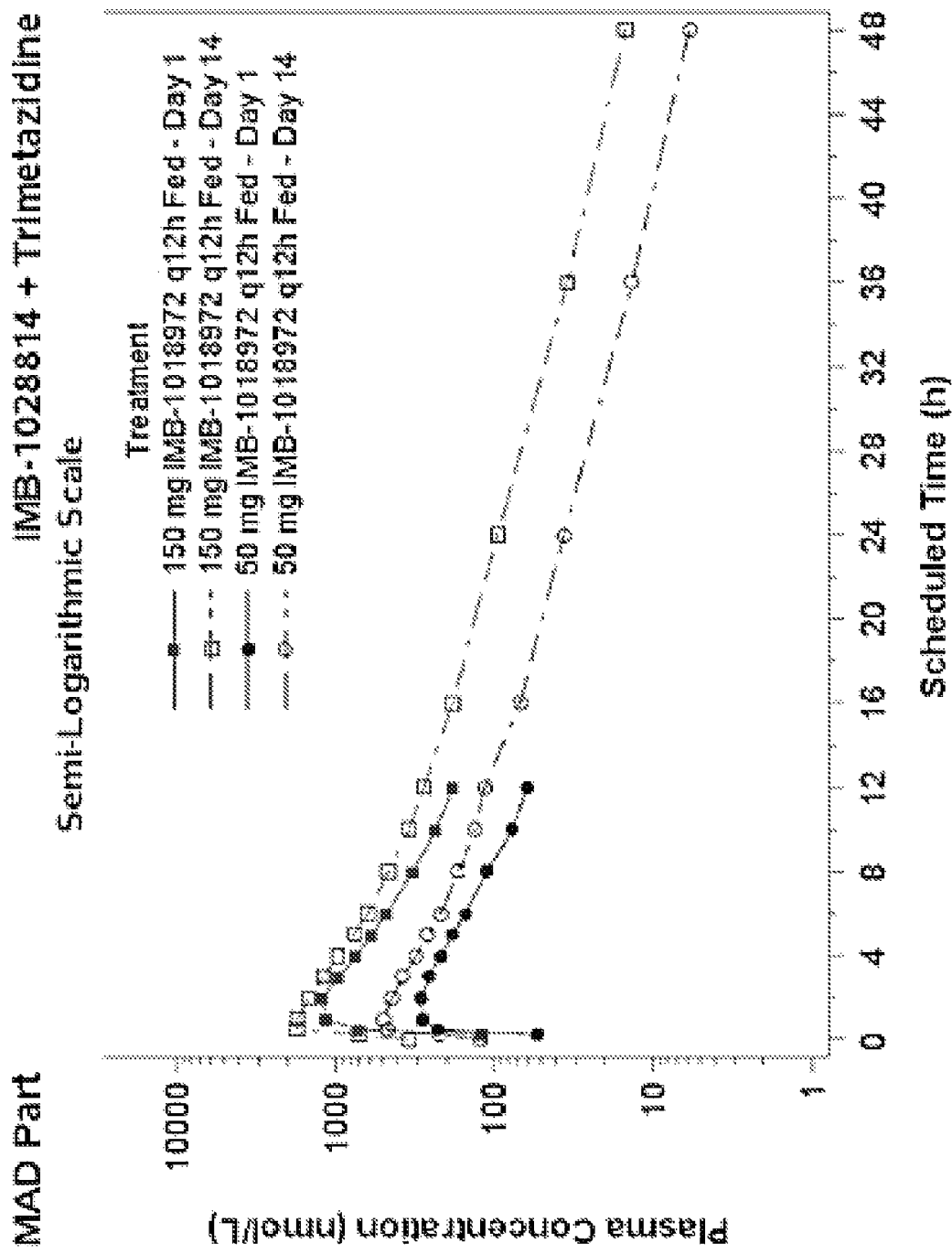
FIG. 46 is a graph of Geometric Mean IMB-1028814+ Trimetazidine Plasma Concentration-Time Profiles after Dosing on Day 1 through Day 14 (Semi-Logarithmic Scale)—MAD Part (PK Set) of an FIH study of IMB-1018972.

FIG. 46 is a graph of Geometric Mean IMB-1028814+Trimetazidine Plasma Concentration-Time Profiles after Dosing on Day 1 through Day 14 (Semi-Logarithmic Scale)—MAD Part (PK Set)

FIG. 47 is a table of Summary Statistics (Geometric Mean [Range]) of IMB-1028814, Trimetazidine, and IMB-1028814+Trimetazidine Plasma Pharmacokinetic Parameters—MAD Part (PK Set)

FIG. 48A and FIG. 48B is a table Summary of All TEAEs by System Organ Class, Preferred Term and Treatment—SAD Part (and integrated FE Arm) (Safety Set) with the following notifications:

%=number of subjects (n) as a percentage of number of subjects (N) per treatment; AE=adverse event; E=number of AEs; FE=food effect; MedDRA=Medical Dictionary for Regulatory Activities; N=number of subjects exposed; n=number of subjects that experienced the AE; SAD=single ascending dose; TEAE=treatment-emergent adverse event Adverse events were classified according to MedDRA 22.0

Subjects were counted once, per preferred term, for multiple occurrences of a specific MedDRA term FIG. 49A and FIG. 49B is a table Summary of All TEAEs by System Organ Class, Preferred Term and Treatment—MAD Part (Safety Set)

FIG. 50 is a table Summary of All TEAEs by Treatment, Relationship, and Severity-SAD Part (and Integrated FE Arm) (Safety Set)

FIG. 51 is a table Summary of All TEAEs by Treatment, Relationship, and Severity—MAD Part (Safety Set)

Summary of Adverse Events

SAD Part (and Integrated FE Arm)

TEAEs Reported with Administration of IMB-1018972 or Placebo

A total of 45 TEAEs was reported by 16 of 24 (66.7%) subjects who received IMB-1018972, and a total of 3 TEAEs was reported by 2 of 8 (25%) subjects who received placebo. There were no deaths reported and all TEAEs were transient and resolved without sequelae by follow-up. Subject 131 of the FE arm Group A4 was withdrawn from the study due to a moderate SAE of influenza like illness (unlikely related) in the first period after receiving the single oral dose of 150 mg IMB-1018972 under fasted conditions.

Thirty-seven of 48 TEAEs reported with IMB-1018972 or placebo were of mild severity and 11 TEAEs were of moderate severity. No severe TEAEs were reported. The 11 moderate TEAEs were as follows:

Five moderate TEAEs of flushing (reported term was 'niacin flush') were reported by 5 subjects (Subjects 117, 122, 123, 124, and 132). Subjects 117, 122, 123, and 124 reported flushing after a single dose of 400 mg IMB-1018972 under fasted conditions. Subject 132 of the FE arm reported flushing after a single dose of 150 mg IMB-1018972 under fasted conditions. These TEAEs were all considered by the Investigator to be definitely related to the study drug. The niacin flushing events observed in this study were typically short-lasting with generalized cutaneous vasodilation and to varying degrees associated with an intense burning and tingling sensation of the skin, a feeling of warmth, and/or generalized erythema, starting shortly after intake of the drug and lasting about 1 to 2.5 hours.

One moderate TEAE each of restlessness, back pain, and nausea was reported by 1 subject (Subject 122) who also reported a moderate TEAE of flushing. This subject had received a single dose of 400 mg IMB-1018972 under fasted conditions. The TEAEs of back pain and nausea were considered by the Investigator to be possibly related to the study drug, whereas the Investigator considered the TEAE of restlessness to be likely related.

One moderate TEAE each of tonsillitis and post procedural hemorrhage (reported term was 'post tonsillectomy hemorrhage') was reported by 1 subject (Subject 129). This subject had received a single dose of 150 mg IMB-1018972 under fed conditions. The TEAEs of tonsillitis and post procedural hemorrhage were considered by the Investigator not to be related to the study drug.

One TEAE of influenza like illness of moderate severity was reported by 1 subject (Subject 131) and was considered by the Investigator to be an SAE and unlikely related to the study drug. This subject had received a single dose of 150 mg IMB-1018972 under fasted conditions and did not receive the planned dose in the fed state.

Of 48 TEAEs, 3 were reported by 2 (25.0%) subjects receiving placebo, 3 were reported by 3 (50.0%) subjects receiving 50 mg IMB-1018972 under fasted conditions, 5 were reported by 3 (50.0%) subjects receiving 150 mg IMB-1018972 under fasted conditions, 16 were reported by 6 (100%) subjects receiving 400 mg IMB-1018972 under fasted conditions, 17 were reported by 4 (66.7%) subjects receiving 150 mg IMB-1018972 under fasted conditions (in the fasted-fed group), and 4 were reported by 1 (20%) subject receiving 150 mg IMB-1018972 under fed conditions (in the fasted-fed group). There was no clear dose dependency of the number and incidence of TEAEs. Neither was there any clear difference between fasted and fed IMB-1018972 administration for the number and incidence of TEAEs.

The most frequently reported TEAEs (ie, reported by >15% of the subjects) with IMB-1018972 by system organ class (SOC) were:

Nervous system disorders with 9 TEAEs reported by 7 (29.2%) subjects (4 TEAEs of dizziness, 3 TEAEs of headache, and 1 TEAE each of burning sensation and somnolence).

Vascular disorders with 7 TEAEs reported by 7 (29.2%) subjects (6 TEAEs of flushing and 1 TEAE of peripheral coldness).

General disorders and administration site conditions with 9 TEAEs reported by 5 (20.8%) subjects (3 TEAEs of medical device site pruritus, 2 TEAEs of influenza like illness, and 1 TEAE each of catheter site related reaction, fatigue, feeling hot, and pyrexia).

Gastrointestinal disorders with 9 TEAEs reported by 4 (16.7%) subjects (4 TEAEs of nausea and 1 TEAE each of diarrhea, dry mouth, dysphagia, gingival pain, and vomiting).

Skin and subcutaneous tissue disorders with 4 TEAEs reported by 4 (16.7%) subjects (3 TEAEs of dermatitis contact and 1 TEAE of erythema).

Of 45 TEAEs reported with IMB-1018972, 21 TEAEs reported by 7 of 24 (29.2%) subjects were considered by the Investigator to be related to the study drug. No drug-related TEAEs were reported following 50 mg and 150 mg (fasted only group) IMB-1018972. The most frequently reported drug-related TEAEs (ie, reported by >15% of the subjects) with IMB-1018972 by SOC were:

Vascular disorders with 6 TEAEs of flushing reported by 6 (25%) subjects.

Nervous system disorders with 5 TEAEs reported by 4 (16.7%) subjects (3 TEAEs of headache and 2 TEAEs of dizziness).

TEAEs Reported with Administration of Trimetazidine

A total of 4 TEAEs was reported by 3 of 8 (37.5%) subjects who received trimetazidine. There were no deaths reported and all TEAEs were transient and resolved without sequelae by follow-up. All 4 TEAEs (1 TEAE each of neck pain, abdominal pain, pollakiuria, and headache) reported were of mild severity and considered by the Investigator not to be related to the study drug.

Overall Tolerability

In the SAD part, treatment with single oral doses of 50 mg, 150 mg, and 400 mg IMB-1018972 under fasted conditions, treatment with single oral doses of 150 mg IMB-1018972 under fed conditions, and treatment with single oral doses of 35 mg trimetazidine were well tolerated by healthy male and female subjects. In the FE arm of the SAD part, dosing under fed conditions appeared to attenuate the number and incidence of TEAEs. In the single-dose MR part, there was no clear difference between fasted and fed IMB-1018972 administration for the number and incidence of TEAEs. During the SAD part, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions. These TEAEs were all considered by the Investigator to be related to the study drug. No subjects dropped out due to flushing and flushing was not considered a safety issue. There were no clinically important trends in the physical examinations, vital signs, clinical laboratory, or ECG results. Dose escalation beyond 400 mg IMB-1018972 IR did not proceed as planned based on the PK exposure levels of IMB-1028814 and trimetazidine exceeding the target exposure levels in the 400 mg group and the findings of flushing at that dose. The predefined target exposure level was approximately 3 to 4 'trimetazidine equivalents', ie, the ratio of the combined exposure of the active metabolites of IMB1018972 to the single oral doses of 35 mg MR trimetazidine as seen in published literature.

MAD Part

A total of 35 TEAEs was reported by 14 of 18 (77.8%) subjects who received IMB-1018972, and a total of 17 TEAEs was reported by 5 of 6 (83.3%) subjects who received placebo. All TEAEs were of mild severity and there were no deaths reported. The majority of the TEAEs were transient and resolved without sequelae by follow-up. Three TEAEs were still ongoing at follow-up: vessel puncture site hematoma, medical device site irritation, and paresthesia of the left hand.

Of 35 TEAEs reported by subjects receiving IMB-1018972, 14 were reported by 7 (77.8%) subjects receiving 150 mg IMB-1018972 q12h under fed conditions, and 21 were reported by 7 (77.8%) subjects receiving 50 mg IMB-1018972 q12h under fed conditions. There was no clear dose dependency of the number and incidence of TEAEs.

The most frequently reported TEAEs (ie, reported by >25% of the subjects) with IMB-1018972 by SOC were:
  Vascular disorders with 7 TEAEs of flushing reported by 6 (33.3%) subjects.
  General disorders and administration site conditions with 7 TEAEs reported by 5 (27.8%) subjects (1 TEAE each of catheter site hematoma, chest discomfort, fatigue, feeling hot, medical device site erythema, medical device site irritation, and vessel puncture site hematoma).
  Musculoskeletal and connective tissue disorders with 7 TEAEs reported by 5 (27.8%) subjects (2 TEAEs of myalgia and 1 TEAE each of muscle twitching, muscular weakness, musculoskeletal pain, neck pain, and pain in extremity).

Of 35 TEAEs reported with IMB-1018972, 7 TEAEs reported by 6 of 18 (33.3%) subjects were considered by the Investigator to be related to the study drug and 28 TEAEs reported by 11 of 18 (61.1%) subjects were considered by the Investigator not to be related to the study drug. All 7 reported drug-related TEAEs were events of flushing and all of these were reported following the highest multiple dose of 150 mg IMB-1018972 q12h under fed conditions.

Overall Tolerability

Fourteen-day treatment with oral q12h doses of 50 mg and 150 mg IMB-1018972 under fed conditions was well tolerated by healthy male and female subjects. Incidental mild TEAEs of flushing occurred in 6 subjects who had received 150 mg IMB-1018972 q12h. Five of these 6 subjects reported only a single TEAE of flushing during the 14 days dosing period. One subject reported flushing twice, on Day 2 and on Day 14. The severity of flushing was less in the 150 mg IR MAD group relative to that in the 400 mg IR SAD group. No TEAEs of flushing were reported following administration of 50 mg IMB-1018972 q12h. No subjects dropped out and no modification of the dose was needed due to the TEAEs of flushing.

Deaths, other Serious Adverse Events, and Other Significant Adverse Events

One subject was withdrawn during the study.

Subject 131 was a 25-year old white male with a BMI of 21.9 kg/m2. The subject participated in the FE arm Group A4 and was planned to receive 150 mg IMB-1018972 under fasted conditions in the first treatment period and 150 mg IMB-1018972 under fed conditions in the second treatment period. Initially, he reported no relevant medical history and received no concomitant medication at baseline. The subject received a single dose of 150 mg IMB-1018972 under fasted conditions on Day 1 of the first period. Within half an hour after dosing, the subject reported mild short-lasting TEAEs of dizziness, feeling hot, flushing, nausea, and dysphagia, which were all considered by the Investigator to be likely related. He recovered swiftly and completely, and safety assessments including clinical laboratory results showed no abnormalities throughout the in-house period. The subject left the clinic on Day 3 as planned. On Day 5, the subject was assessed by a healthcare provider for the event of flu like symptoms and spontaneous generalized myalgia. On Day 6, the subject was also assessed for the event of anuria despite ample fluid intake. On Day 7, the subject was referred to a hospital where he was immediately hydrated intravenously. Diuresis did not resume immediately and consequently he was admitted to the hospital. The subject's body temperature on admission was 38° C. Hydration was continued and during the evening and night diuresis resumed. The subject's clinical condition improved rapidly, and the subject was discharged on Day 8. Further medical history elucidated dengue fever (December 2018) and viral infection of unknown origin (January 2019) in the months prior to the clinical study and were added to the subject's medical history (this medical history has not been added to the database). A nonspecific diagnosis was established in the hospital. The hospital summarized the event as anuria with normal renal functions, no abnormalities in urinalysis, and resumption of diuresis during admission. The Investigator reported normal renal function and no rhabdomyolysis. The events of flu like symptoms, myalgia, and anuria together were recorded as an SAE of 'influenza like illness' starting on Day 5 and ending approximately 8 days later, on Day 13. This SAE was of moderate severity and considered by the Investigator to be unlikely related to the study drug. The subject did not receive the planned dose of 150 mg IMB-1018972 under fed conditions in the second treatment period. The subject returned on Day for a follow-up with safety assessments conducted as planned. The subject received 37.5 mg tramadol twice daily on Days 6 and 7 and 1000 mg paracetamol twice daily on Days 7 and 8 because of the flu like symptoms. The subject also reported mild TEAEs of back pain from Day 1 to Day 2 (not related), medical device site pruritus on Day 2 (not related), erythema on Day 2 (unlikely related), and burning sensation from Day 2 to Day 5 (unlikely related).

The SAE of 'influenza like illness' that led to the withdrawal of Subject 131 from the study was considered by the Investigator to be unlikely related to the study drug due to its weak time-relationship with study drug administration. The Investigator considers this SAE may have been caused by an infection.

Concomitant Treatment

SAD Part (and Integrated FE Arm)

Eighteen subjects in the SAD part (with integrated FE arm) received or took concomitant medication. Fifteen female subjects used contraception during the study. In addition, 4 subjects received concomitant medication as follows:
  One subject (Subject 103; 50 mg IMB-1018972 under fasted conditions) received triamcinolone once daily for 2 days because of contact dermatitis on the chest (preferred term: contact dermatitis).
  One subject (Subject 116 150 mg IMB-1018972 under fasted conditions) received 500 mg paracetamol once because of dizziness.

One subject (Subject 129; 150 mg IMB-1018972 under fasted conditions [fasted-fed group]) received 1000 mg paracetamol once or twice per day twice because of headache, and once because of muscular cramps of the upper legs (preferred term: muscle spasms). The same subject also received 5 mg oxycodone 4 times a day for 12 days, 1000 mg paracetamol 4 times a day for 5 days, 80 mg macrogol 4 times a day for 12 days, and 200 mg celecoxib once daily for 5 days because of tonsillitis.

One subject (Subject 131; 150 mg IMB-1018972 under fasted conditions [fasted-fed group]) received 37.5 mg tramadol twice daily for 2 days and 1000 mg paracetamol twice daily for 2 days because of flu like disease (preferred term: influenza like illness).

These medications were not considered to have influenced the outcome of the study MAD Part Seven subjects in the MAD part received or took concomitant medication. Six female subjects used contraception during the study. In addition, 1 subject (Subject 221; placebo q12h under fed conditions) received concomitant 500 mg paracetamol once because of a sore throat (preferred term: oropharyngeal pain).

These medications were not considered to have influenced the outcome of the study.

Safety Conclusions

Overall, single oral IMB-1018972 doses and multiple oral IMB-1018972 doses of an IR formulation, and single and multiple doses of MR formulations, were generally well tolerated by healthy male and female subjects. There were no findings of clinical relevance with respect to clinical laboratory, vital signs, 12-lead ECG, continuous cardiac monitoring (telemetry), or physical examination. Of note, there were no findings of hemodynamic changes, nor changes in the QTc-interval, after administration of IMB-1018972 either as the IR or MR formulations.

During the SAD part, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions. These TEAEs were all considered by the Investigator to be related to the study drug. No subjects dropped out due to flushing and flushing was not considered a safety issue. Dose escalation beyond 400 mg IMB-1018972 IR did not proceed as planned based on the PK exposure levels of IMB-1028814 and trimetazidine exceeding the target exposure levels in the 400 mg group and the findings of flushing at that dose. The predefined target exposure level was approximately 3 to 4 'trimetazidine equivalents', ie, the ratio of the combined exposure of the active metabolites of IMB-1018972 to the single oral doses of 35 mg MR trimetazidine as seen in published literature.

There were no deaths reported during the study. Most TEAEs were of mild severity and no severe TEAEs were reported during the study. Overall, 12 of a total of 181 TEAEs were of moderate severity.

Two subjects were withdrawn from the study: 1 subject due to a moderate SAE of influenza like illness (unlikely related) and 1 due to a moderate TEAE of ALT increased (possibly related).

Overall, there was no clear dose dependency of the number and incidence of TEAEs.

Dosing under fed conditions appeared to attenuate the number and incidence of TEAEs in the FE arm of the SAD part, whereas no clear difference between fasted and fed IMB-1018972 administration for the number and incidence of TEAEs was observed in the single-dose MR part.

Tables for Modified Release Formulations

FIG. 52 is a table of assessments given for the Single-Dose MR Part, with the following notations:

a. Physical examination: at screening, on Day −1 (admission; this was a directed examination only done at the discretion of the Investigator), and at follow-up. On other days, a physical examination could be done on indication only at the discretion of the Investigator.

b. Clinical laboratory tests (including clinical chemistry, hematology, coagulation, and urinalysis): at screening, on Day −1 (admission), at 24 hours after each dose, and at follow-up.

c. 12-lead ECG: at screening, on Day −1 (admission), prior to each dose and just prior to the PK sampling time points of 1, 4, 6, 12, 24, and 48 hours after each dose, and at follow-up.

d. Vital signs (supine systolic and diastolic blood pressure, pulse, body temperature, and respiratory rate): at screening, on Day −1 (admission), prior to each dose and at 1, 4, 6, 12, 24, and 48 hours after each dose, and at follow-up.

e. The subjects received a single oral dose of 1 of 4 MR formulations of IMB-1018972 under fasted conditions (an overnight fast of at least 10 hours) on Days 1, 4, 7, and 10 in a fixed order which was the same for all subjects. The MR formulation of IMB-1018972 to be administered on Day 13 under fed conditions was 1 of the 4 MR formulations administered on Days 1, 4, 7, and 10 under fasted conditions.

f. Blood sampling for PK of IMB-1018972, IMB-1028814, and trimetazidine in plasma: prior to each dose and 0.25, 0.5, 1, 2, 3, 4, 5, 6, 8, 10, 12, 16, 24, 36, and 48 hours after each dose (and 72 hours after dosing on Day 13).

g. AEs were recorded from admission until completion of the follow-up visit.

h. Blood sampling for genotyping was mandatory.

FIG. 53 is a table of assessments given for the Multiple-Dose MR part, with the following notations:

a. Physical examination: at screening, on Day −1 (admission; this was a directed examination only done at the discretion of the Investigator), and at follow-up. On other days, a physical examination could be done on indication only at the discretion of the Investigator.

b. Clinical laboratory tests (including clinical chemistry, hematology, coagulation, and urinalysis): at screening, on Day −1 (admission), at 24 hours after the last dose, and at follow-up.

c. 12-lead ECG: at screening, on Day −1 (admission), just before the time points of 1, 4, 6, 12, 24, and 48 hours after the first dose on Day 1 and after the last dose on Day 5, and at follow-up.

d. Vital signs (supine systolic and diastolic blood pressure, pulse, body temperature, and respiratory rate): at screening, on Day −1 (admission), before the last dose, at 1, 4, 6, 12, 24, and 48 hours after the last dose, and at follow-up.

e. Study drug (200 mg 8-hour MR formulation) was administered twice daily for 5 days; on Day 5 only a single morning dose was administered. Study drug administration was conducted under fed conditions.

f. On Day 1, blood sampling for PK of IMB-1028814 and trimetazidine was predose and 0.5, 1, 2, 4, 5, 6, 8, 10, and 12 hours postdose. The 12-hour sample was collected prior to the evening dose. On Day 5, blood sampling for PK of IMB-1028814 and trimetazidine was predose and 0.5, 1, 2, 4, 5, 6, 8, 10, 12, 16, 24, 36, and 48 hours postdose. Morning predose samples were also collected on Days 2, 3, and 4.

g. AEs were recorded from admission until completion of the follow-up visit.

h. Blood sampling for genotyping was mandatory.

FIG. 54 is a table of analysis data sets for the Single-Dose MR Part

FIG. 55 a table of analysis data sets for the Multiple-Dose MR Part

Demographic and Other Baseline Characteristics

Single-Dose MR Part

Twelve subjects were included of whom 6 were female and 6 were male. Mean age was 32 years and mean BMI was 25.8 kg/m2. Individual age ranged between 19 and 62 years and individual BMI ranged between 21.5 and 31.0 kg/m2. Eleven subjects were of white race and 1 subject was Black or African American. Eleven subjects were not of Hispanic or Latino ethnicity whereas 1 subject was of Hispanic or Latino ethnicity. The summary of the PK set was identical to that of the safety set.

FIG. 56 is a table of a summary of demographic characteristics—Single-Dose MR Part (Safety Set).

Multiple-Dose MR Part

Twelve subjects were included of whom 6 were female and 6 were male. Mean age was 45 years and mean BMI was 25.1 kg/m2. Individual age ranged between 24 and 64 years and individual BMI ranged between 20.0 and 29.2 kg/m2. Eleven subjects were of white race and 1 subject was Asian. None of the 12 subjects were of Hispanic or Latino ethnicity. The summary of the PK set was identical to that of the safety set.

FIG. 57 is a table of a summary of demographic characteristics—Multiple-Dose MR Part (Safety Set).

Other Baseline Characteristics

All subjects complied with the inclusion and exclusion criteria. There were no clinically significant findings with regard to medical history or previous medication. Drug and alcohol screen results were negative for all subjects at screening and (each) admission. The results for the serology parameters were negative at screening for all subjects. The pregnancy test results were negative at screening, (each) admission, and follow-up for all females participating in this study.

Extent of Exposure

A total of 88 subjects were dosed in this study: 12 subjects in the single-dose MR part, and 12 subjects in the multiple-dose MR part.

In the single-dose MR part, all 12 subjects received 4 single doses of an MR formulation of IMB-1018972 under fasted conditions: 50 mg 8-hour MR formulation on Day 1, 50 mg 4-hour MR formulation on Day 4, 200 mg 8-hour MR formulation on Day 7, and 200 mg 4-hour MR formulation on Day 10. On Day 13, all 11 of 12 subjects received the 200 mg 8-hour MR formulation of IMB-1018972 under fed conditions. Subject 505 was withdrawn from the study due to a moderate TEAE of ALT increased (possibly related; up to 149 IU/L on Day 11) and did not receive the last single oral dose of 200 mg 8-hour MR formulation of IMB-1018972 under fed conditions on Day 13.

FIG. 58 is a table of the Extent of Exposure—Single-Dose MR Part (Safety Set)

In the multiple-dose MR part, all 12 subjects received multiple oral doses of the 200 mg 8-hour MR formulation of IMB-1018972 q12h under fed conditions from Day 1 to Day 4 followed by a single morning dose on Day 5.

FIG. 59 is a table of the Extent of Exposure—Multiple-Dose MR Part (Safety Set)

Single-Dose MR Part

Following administration of both the 50-mg and 200-mg single oral fasted doses of IMB-1018972, $t_{max}$ for IMB-1028814 was earlier with the 8-hour MR formulation (2 hours for 50 mg and 200 mg IMB-1018972) than with the 4-hour MR formulation (5 hours for 50 mg IMB-1018972 and 3 hours for 200 mg IMB-1018972). Following administration of both the 50-mg and 200-mg single oral fasted doses of IMB-1018972, tmax for trimetazidine was later with the 8-hour MR formulation (8 hours for 50 mg IMB-1018972 and 5 hours for 200 mg IMB-1018972) than with the 4-hour MR formulation (6 hours for 50 mg IMB-1018972 and 3 hours for 200 mg IMB-1018972). Following administration of both the 50-mg and 200-mg single oral fasted doses of IMB-1018972, tmax for IMB-1028814+trimetazidine was similar for the 8-hour MR formulation (5 hours for 50 mg IMB-1018972 and 2.5 hours for 200 mg IMB-1018972) and the 4-hour MR formulation (5 hours for 50 mg IMB-1018972 and 3 hours for 200 mg IMB-1018972).

Following administration of the 50-mg and 200-mg single oral fasted doses of IMB-1018972, Cmax for IMB-1028814 was 35% and 32% lower, respectively, Cmax for trimetazidine was 20% and 24% lower, respectively, and Cmax for IMB-1028814+trimetazidine was 21% and 34% lower, respectively, for the 8-hour MR formulation relative to the 4-hour MR formulation (Table 28).

Following administration of the 50-mg single oral fasted dose of IMB-1018972, $AUC_{0-t}$ for IMB-1028814 was 26% lower, $C_{max}$ for trimetazidine was 12% lower, and $C_{max}$ for IMB-1028814+trimetazidine was 18% lower after the 8-hour MR formulation than after the 4-hour MR formulation. Following the 200-mg single oral fasted dose of IMB-1018972, AUC0-t for IMB-1028814 was 6% higher, $C_{max}$ for trimetazidine was 4% higher, and $C_{max}$ for IMB-1028814+trimetazidine was 5% higher after the 8-hour MR formulation than after the 4-hour MR formulation.

Following administration of the 50-mg MR formulation and 200 mg MR formulation with 4-hour and 8-hour dissolution profile under fasted conditions, geometric mean $t_{1/2}$ ranged between 3.35 hours and 4.27 hours for IMB-1028814, between 8.11 hours and 9.35 hours for trimetazidine, and between 6.95 hours and 7.96 hours for IMB-1028814+trimetazidine. Thus, for each of the analytes, no difference was observed in t½ was between the 4 fasted treatments.

Effect of Food

The possible effect of food on the PK of IMB-1028814 and trimetazidine was explored by comparing administration of single oral doses of 200 mg MR formulation of IMB-1018972 with 8-hour dissolution profile after an FDA-defined high-fat breakfast and under fasted conditions.

After study drug administration under fed conditions, the geometric mean IMB-1028814 plasma concentrations initially increased less rapidly than after study drug administration under fasted conditions. However, median $t_{max}$ was reached at 3 hours postdose under both conditions.

The trimetazidine plasma concentrations under fed conditions increased less rapidly than after study drug administration under fasted conditions. Median $t_{max}$ was reached at 5 hours postdose relative to 3 hours postdose under fasted conditions.

The effect of food of IMB-1028814 and trimetazidine was explored for $C_{max}$, $AUC_{0-t}$, and $AUC_0$-mom. No evidence for an effect of food was observed on the IMB-1028814 exposure parameters $AUC_{0-t}$ and $AUC_{0-inf}$ (both with an estimate of 1.16 and 90% CI ranging from 1.05 to 1.28). However, $C_{max}$ was approximately 42% higher following administration of a single dose of 200 mg 8-hour MR IMB-1018972 after an FDA-defined high-fat breakfast relative to administration under fasted conditions (estimate of 1.42; 90% CI ranging from 1.24 to 1.63).

No evidence for an effect of food was observed on the trimetazidine exposure parameters $C_{max}$ (estimate of 1.10; 90% CI ranging from 0.99 to 1.21), $AUC_{0-t}$ (estimate of 0.99; 90% CI ranging from 0.91 to 1.09), and $AUC_{0-inf}$ (estimate of 0.97; 90% CI ranging from 0.88 to 1.07) following administration of a single dose of 200 mg 8-hour MR IMB-1018972.

Figure 60:
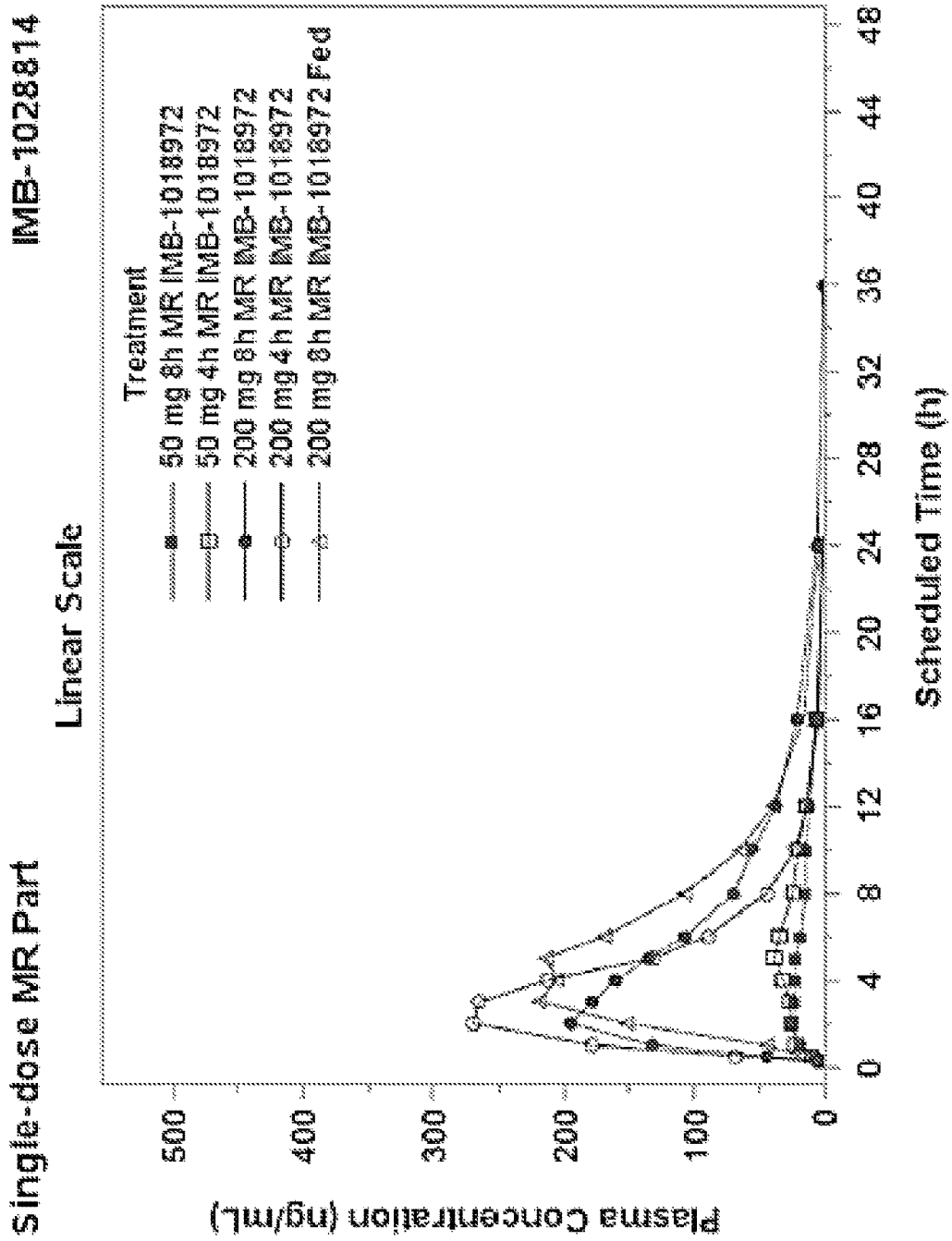
FIG. 60 is a graph of Geometric Mean IMB-1028814 Plasma Concentration-Time Profiles (Linear)—Single-Dose MR Part (PK Set) of an FIH study of IMB-1018972.

FIG. 60 is a graph of Geometric Mean IMB-1028814 Plasma Concentration-Time Profiles (Linear)—Single-Dose MR Part (PK Set)

Figure 61:
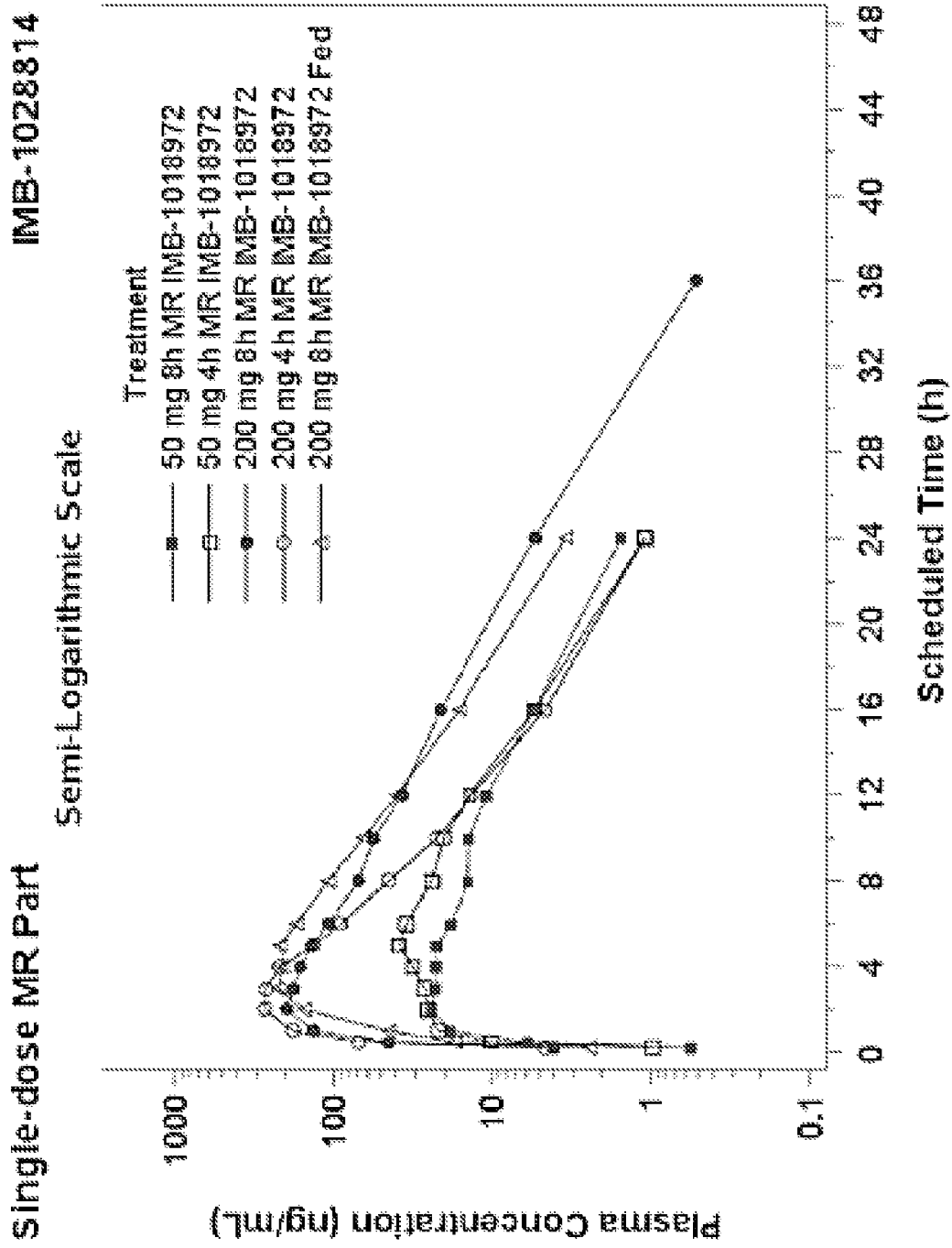
FIG. 61 is a graph of Geometric Mean IMB-1028814 Plasma Concentration-Time Profiles (Semi-Logarithmic Scale)—Single-Dose MR Part (PK Set) of an FIH study of IMB-1018972.

FIG. 61 is a graph of Geometric Mean IMB-1028814 Plasma Concentration-Time Profiles (Semi-Logarithmic Scale)—Single-Dose MR Part (PK Set)

Figure 62:
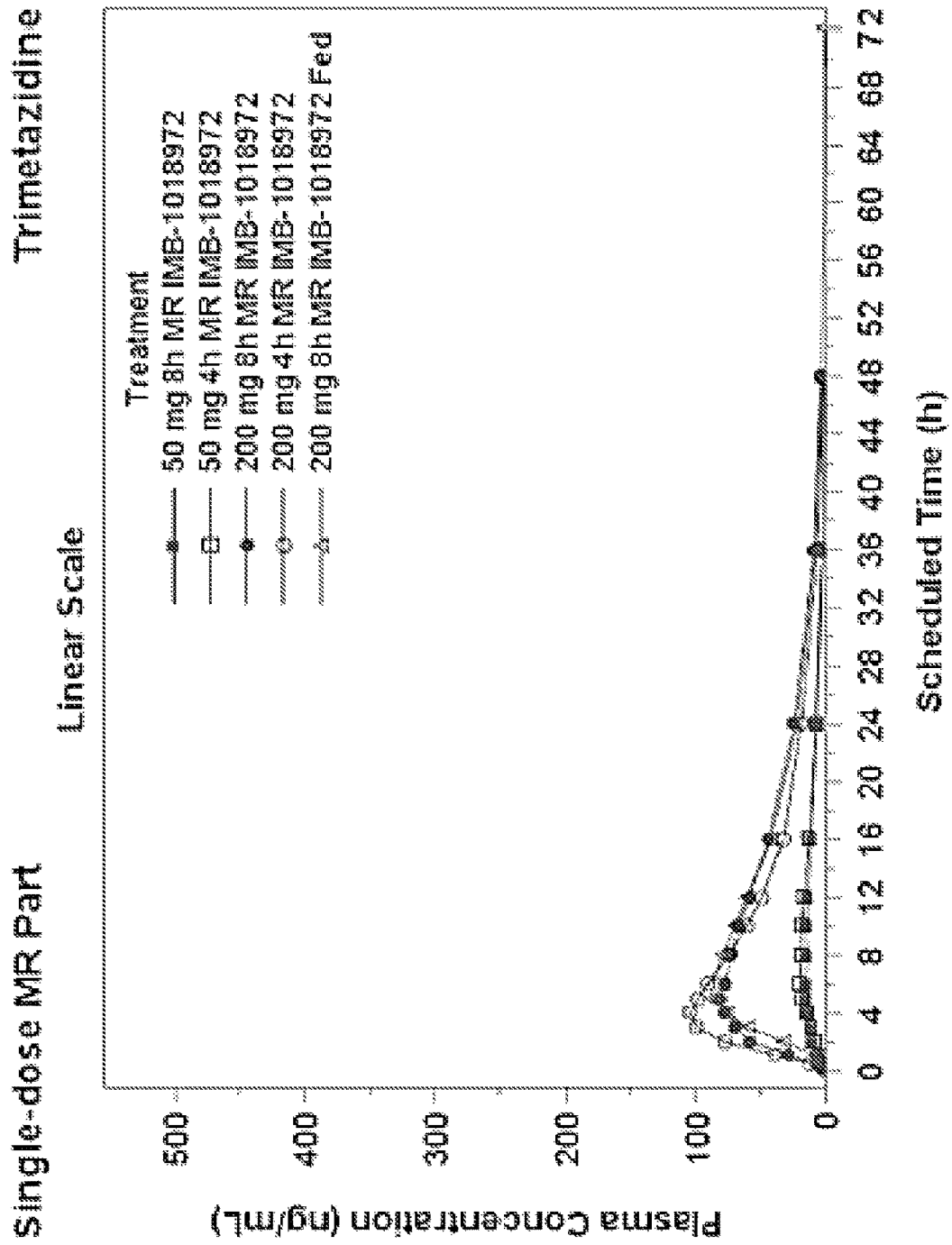
FIG. 62 is a graph of Geometric Mean Trimetazidine Plasma Concentration-Time Profiles (Linear)—Single-Dose MR Part (PK Set) of an FIH study of IMB-1018972.

FIG. 62 is a graph of Geometric Mean Trimetazidine Plasma Concentration-Time Profiles (Linear)—Single-Dose MR Part (PK Set)

Figure 63:
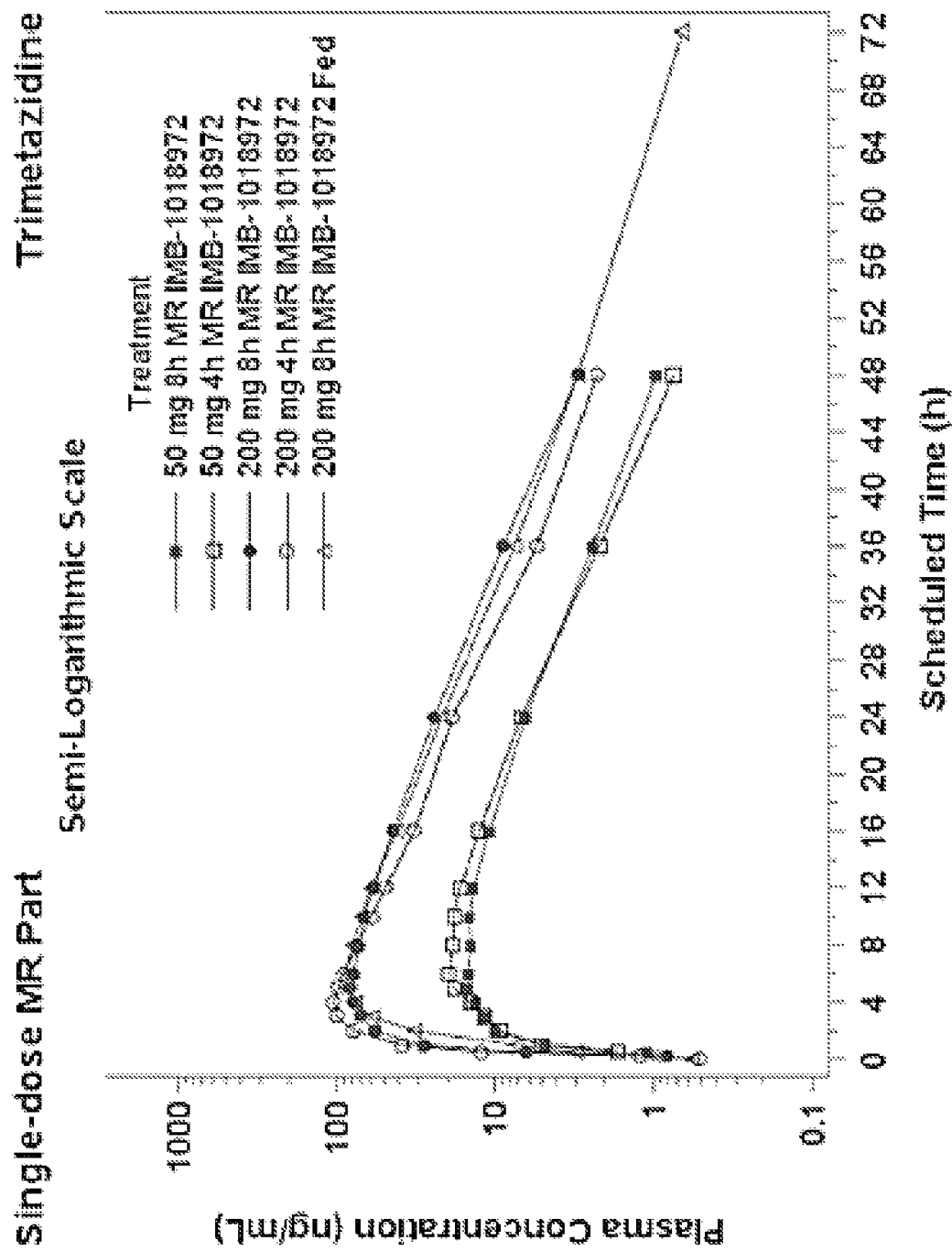
FIG. 63 is a graph of Geometric Mean Trimetazidine Plasma Concentration-Time Profiles (Semi-Logarithmic Scale)—Single-Dose MR Part (PK Set) of an FIH study of IMB-1018972.

FIG. 63 is a graph of Geometric Mean Trimetazidine Plasma Concentration-Time Profiles (Semi-Logarithmic Scale)—Single-Dose MR Part (PK Set)

Figure 64:
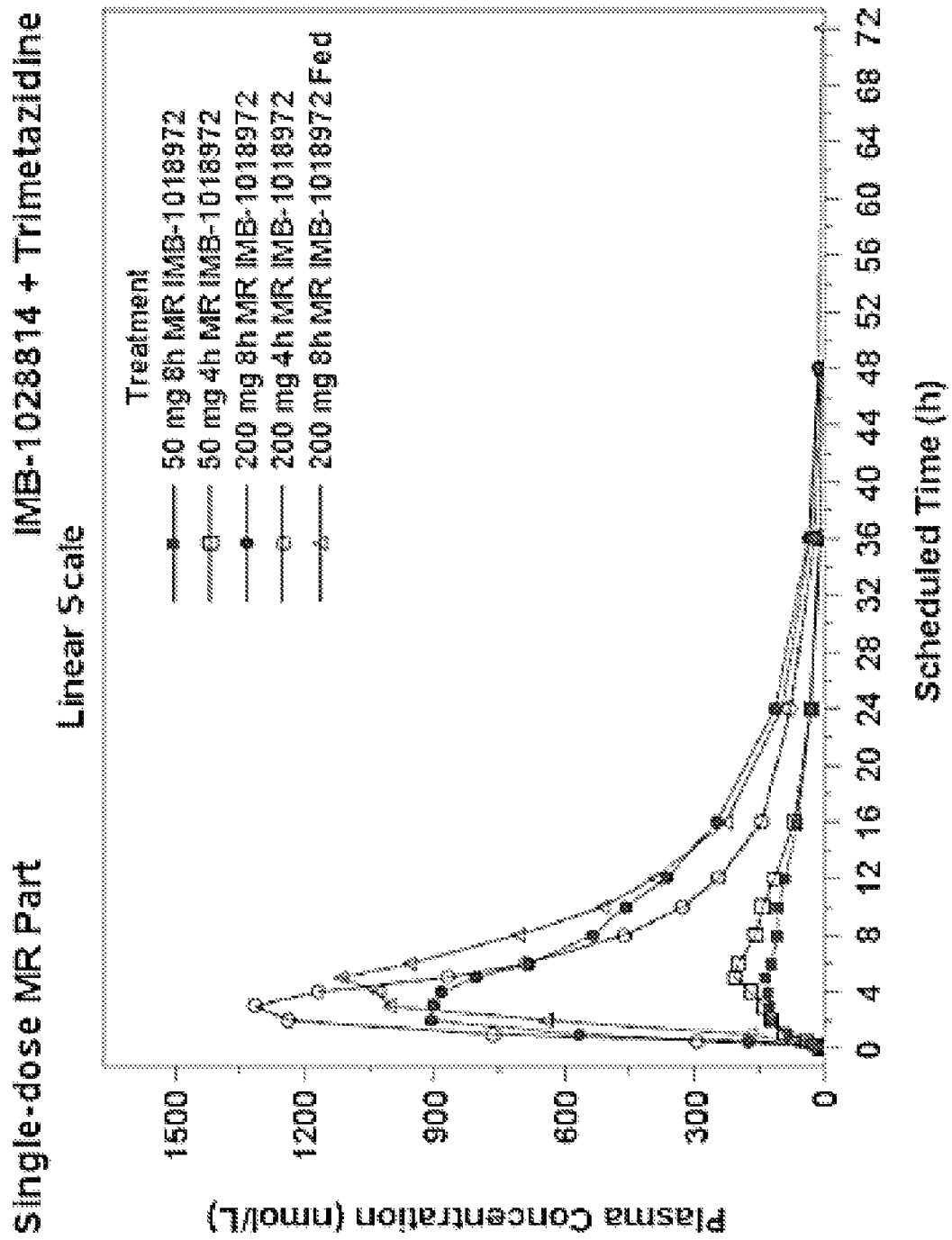
FIG. 64 is a graph of Geometric Mean IMB-1028814+Trimetazidine Plasma Concentration-Time Profiles (Linear)—Single-Dose MR Part (PK Set) of an FIH study of IMB-1018972.

FIG. 64 is a graph of Geometric Mean IMB-1028814+ Trimetazidine Plasma Concentration-Time Profiles (Linear)—Single-Dose MR Part (PK Set)

Figure 65:
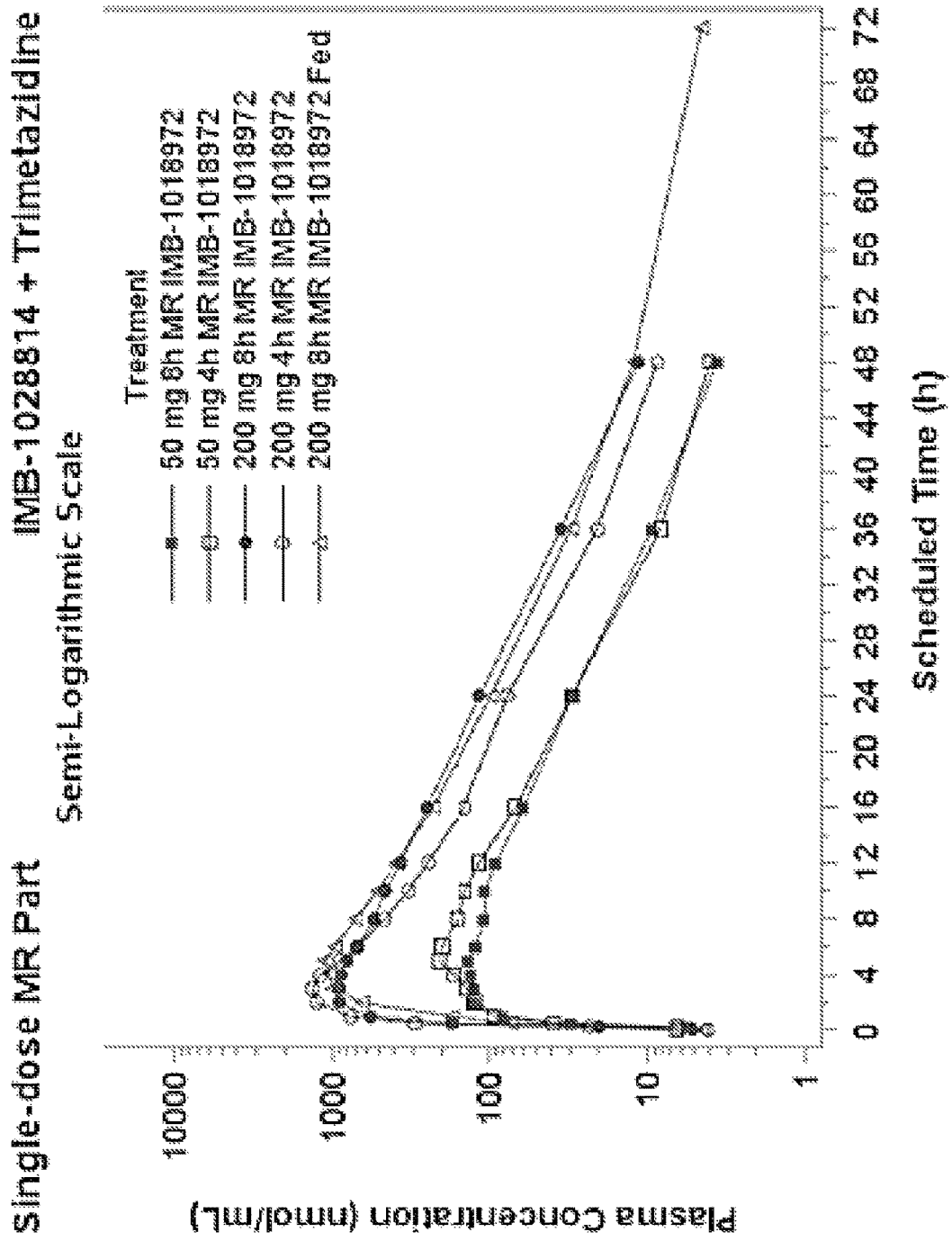
FIG. 65 is a graph of Geometric Mean IMB-1028814+Trimetazidine Plasma Concentration-Time Profiles (Semi-Logarithmic Scale)—Single-Dose MR Part (PK Set) of an FIE study of IMB-1018972.

FIG. 65 is a graph of Geometric Mean IMB-1028814+ Trimetazidine Plasma Concentration-Time Profiles (Semi-Logarithmic Scale)—Single-Dose MR Part (PK Set)

FIG. 66 is a table of Summary Statistics Geometric Mean [Range]) of IMB-1028814, Trimetazidine, and IMB-1028814+Trimetazidine Plasma Pharmacokinetic Parameters—Single-Dose MR Part (PK Set)

FIG. 67 is a table of Exploratory Analysis of Food Effect for IMB-1028814 and Trimetazidine following Administration of 200 mg 8-hour MR IMB-1018972—Single-Dose MR Part (PK Set)

Multiple-Dose MR Part

All predose samples on Day 1 were below the LLOQ for IMB-1028814 and trimetazidine plasma concentrations.

Similar to the SAD and MAD parts, initial hydrolysis of IMB-1018972 to IMB-1028814 and subsequent systemic bioavailability of IMB-1028814 of the 200 mg 8-hour MR IMB-1018972 dose on Days 1 and 5 was relatively rapid. Median IMB-1028814 tmax was 2 hours on Day 1 and Day 5, and median tmax was 5.5 hours and 5 hours for trimetazidine on Day 1 and Day 5, respectively.

Based upon visual inspection of the geometric mean plasma concentration-time profiles and the geometric mean trough concentrations, it can be concluded that steady state for both IMB-1028814 and trimetazidine concentrations was reached by Day 5 following multiple dose administration of 200 mg 8-hour MR IMB-1018972.

Geometric mean Rac for IMB-1028814, trimetazidine, and IMB-1028814+trimetazidine were 1.22, 2.28, and 1.66 on Day 5 relative to Day 1. This indicates minimal accumulation of IMB-1028814 in plasma, moderate accumulation of trimetazidine in plasma, and moderate accumulation of IMB-1028814+trimetazidine in plasma.

The geometric mean half-life of the 200 mg 8-hour MR IMB-1018972 dose was 3.85 hours, 9.52 hours, and 8.64 hours for IMB-1028814, trimetazidine, and IMB-1028814+ trimetazidine, respectively.

Figure 68:
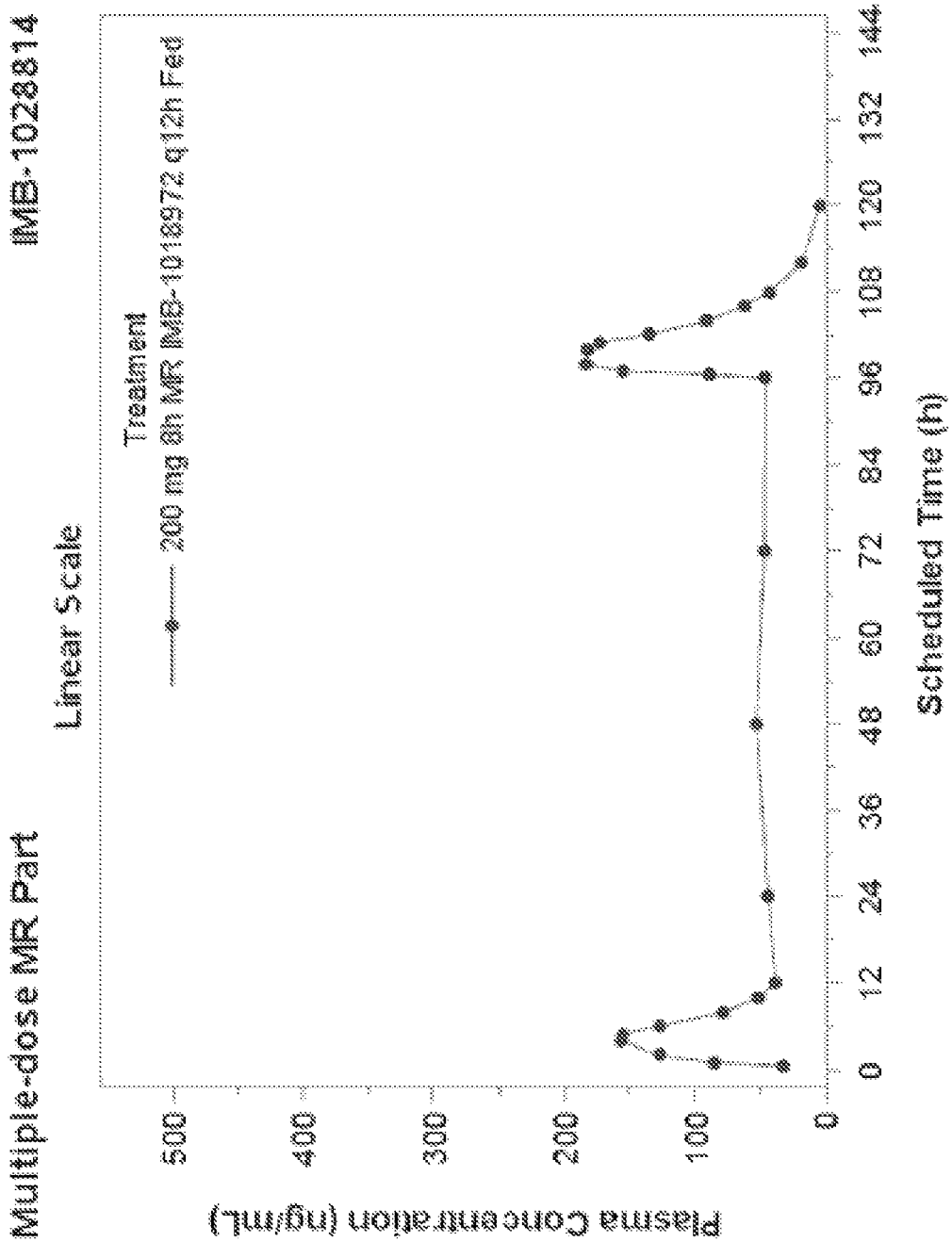
FIG. 68 is a graph of Geometric Mean IMB-1028814 Plasma Concentration-Time Profiles from Day 1 through Day 5 (Linear)—Multiple-Dose MR Part (PK Set) of an FIH study of IMB-1018972.

FIG. 68 is a graph of Geometric Mean IMB-1028814 Plasma Concentration-Time Profiles from Day 1 through Day 5 (Linear)—Multiple-Dose MR Part (PK Set)

Figure 69:
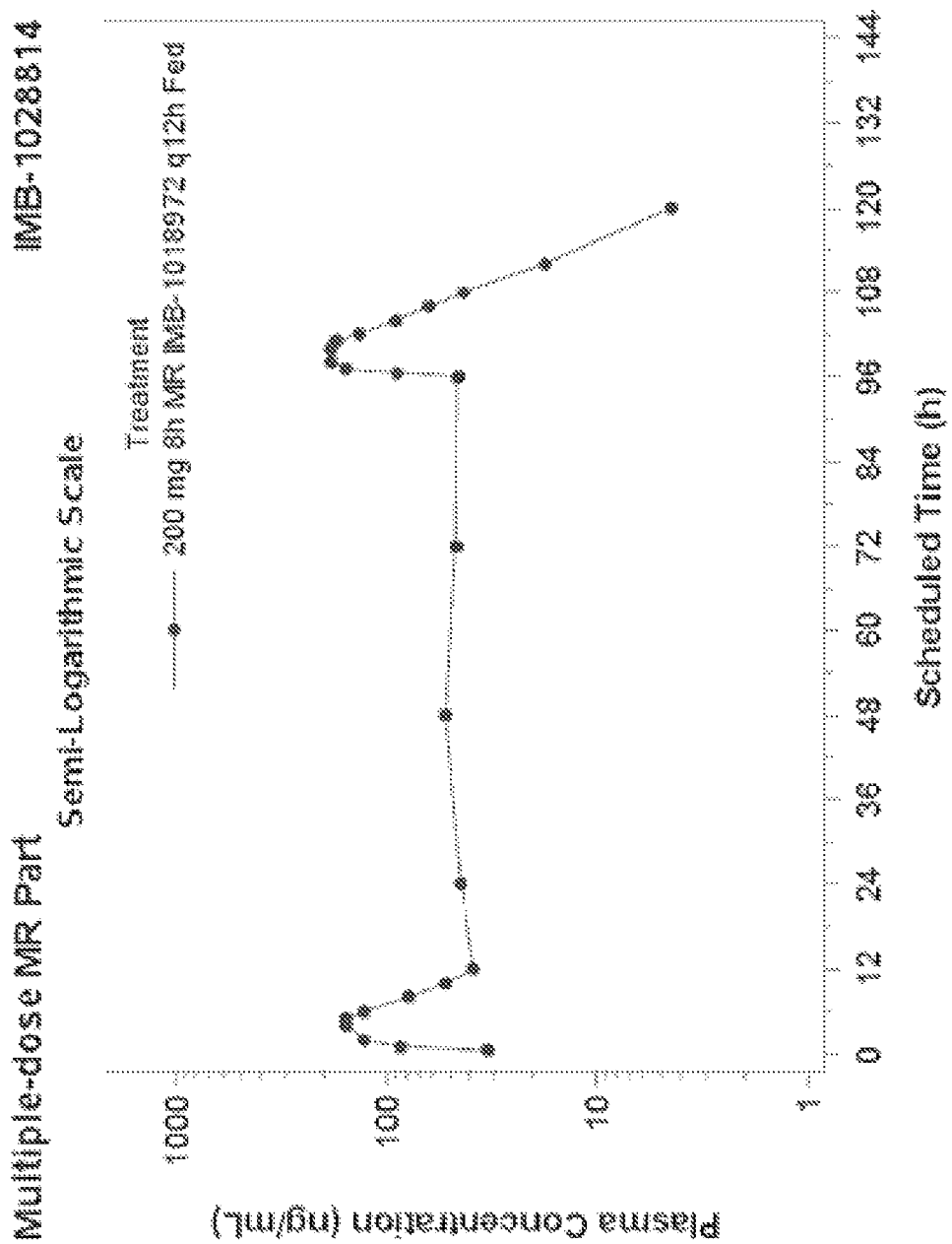
FIG. 69 is a graph of Geometric Mean IMB-1028814 Plasma Concentration-Time Profiles from Day 1 through Day 5 (Semi-Logarithmic Scale)—Multiple-Dose MR Part (PK Set) of an FIE study of IMB-1018972.

FIG. 69 is a graph of Geometric Mean IMB-1028814 Plasma Concentration-Time Profiles from Day 1 through Day 5 (Semi-Logarithmic Scale)—Multiple-Dose MR Part (PK Set)

Figure 70:
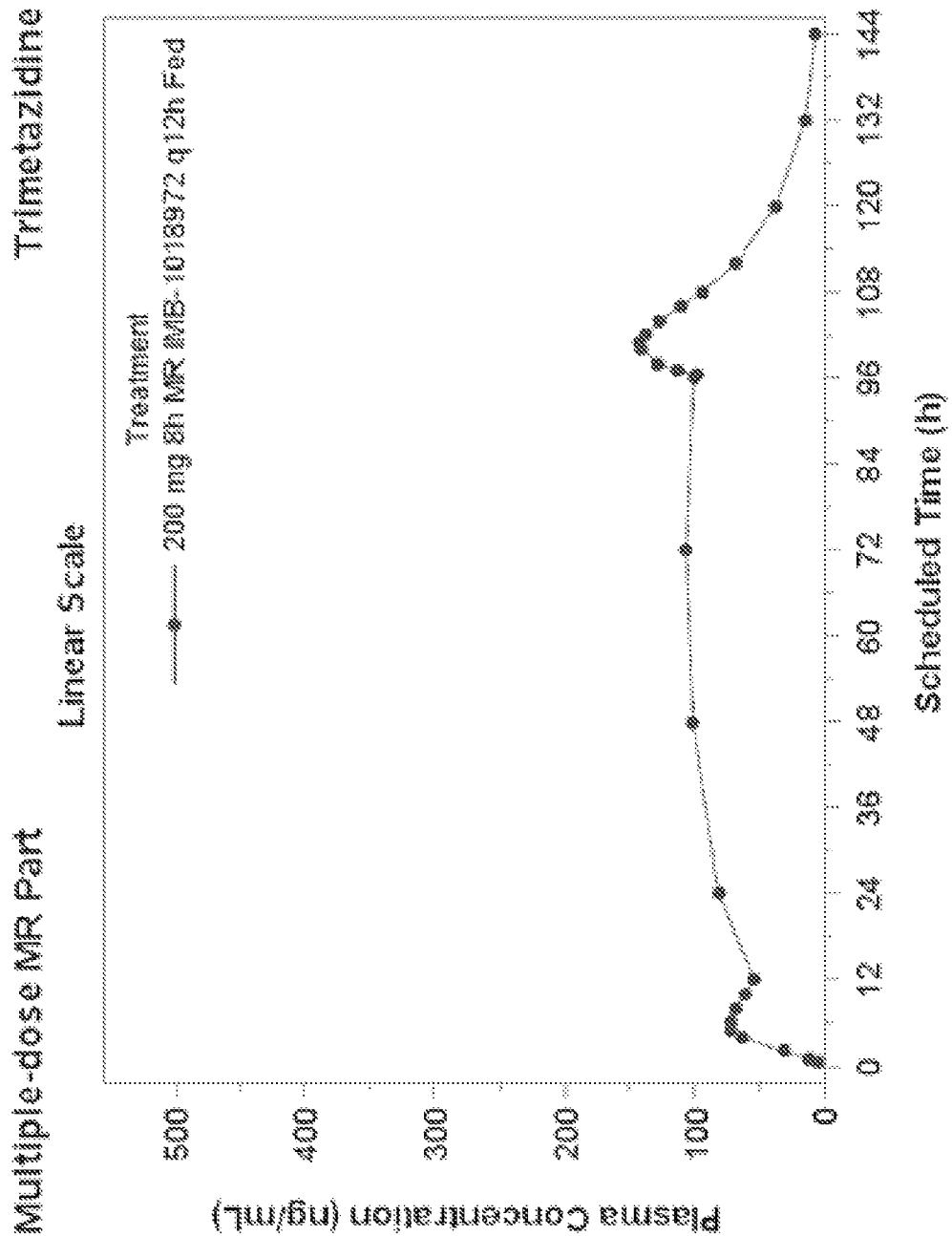
FIG. 70 is a graph of Geometric Mean Trimetazidine Plasma Concentration-Time Profiles from Day 1 through Day 5 (Linear)—Multiple-Dose MR Part (PK Set) of an FIH study of IMB-1018972.

FIG. 70 is a graph of Geometric Mean Trimetazidine Plasma Concentration-Time Profiles from Day 1 through Day 5 (Linear)—Multiple-Dose MR Part (PK Set)

Figure 71:
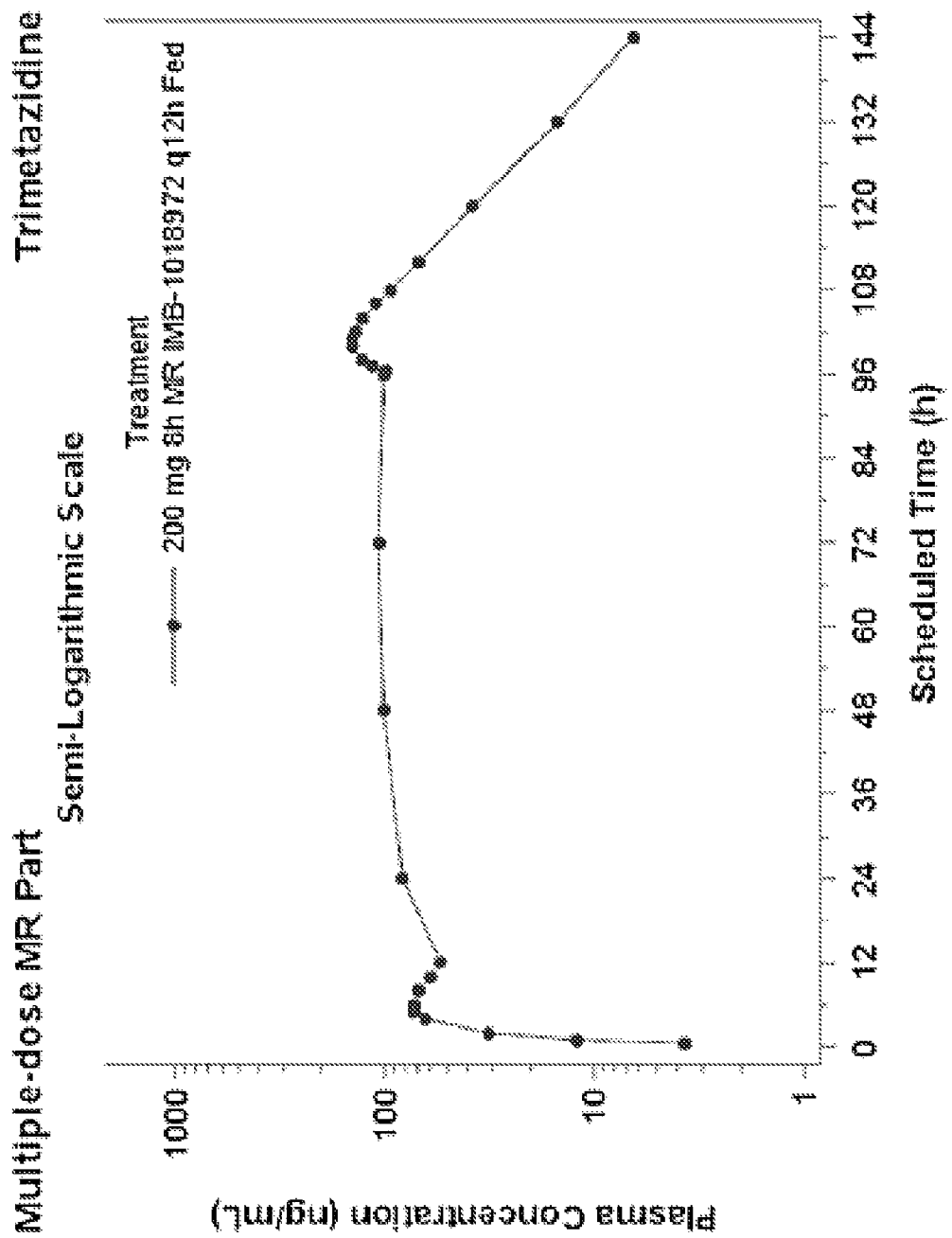
FIG. 71 is a graph of Geometric Mean Trimetazidine Plasma Concentration-Time Profiles from Day 1 through Day 5 (Semi-Logarithmic Scale)—Multiple-Dose MR Part (PK Set) of an FIE study of IMB-1018972.

FIG. 71 is a graph of Geometric Mean Trimetazidine Plasma Concentration-Time Profiles from Day 1 through Day 5 (Semi-Logarithmic Scale)—Multiple-Dose MR Part (PK Set)

Figure 72:
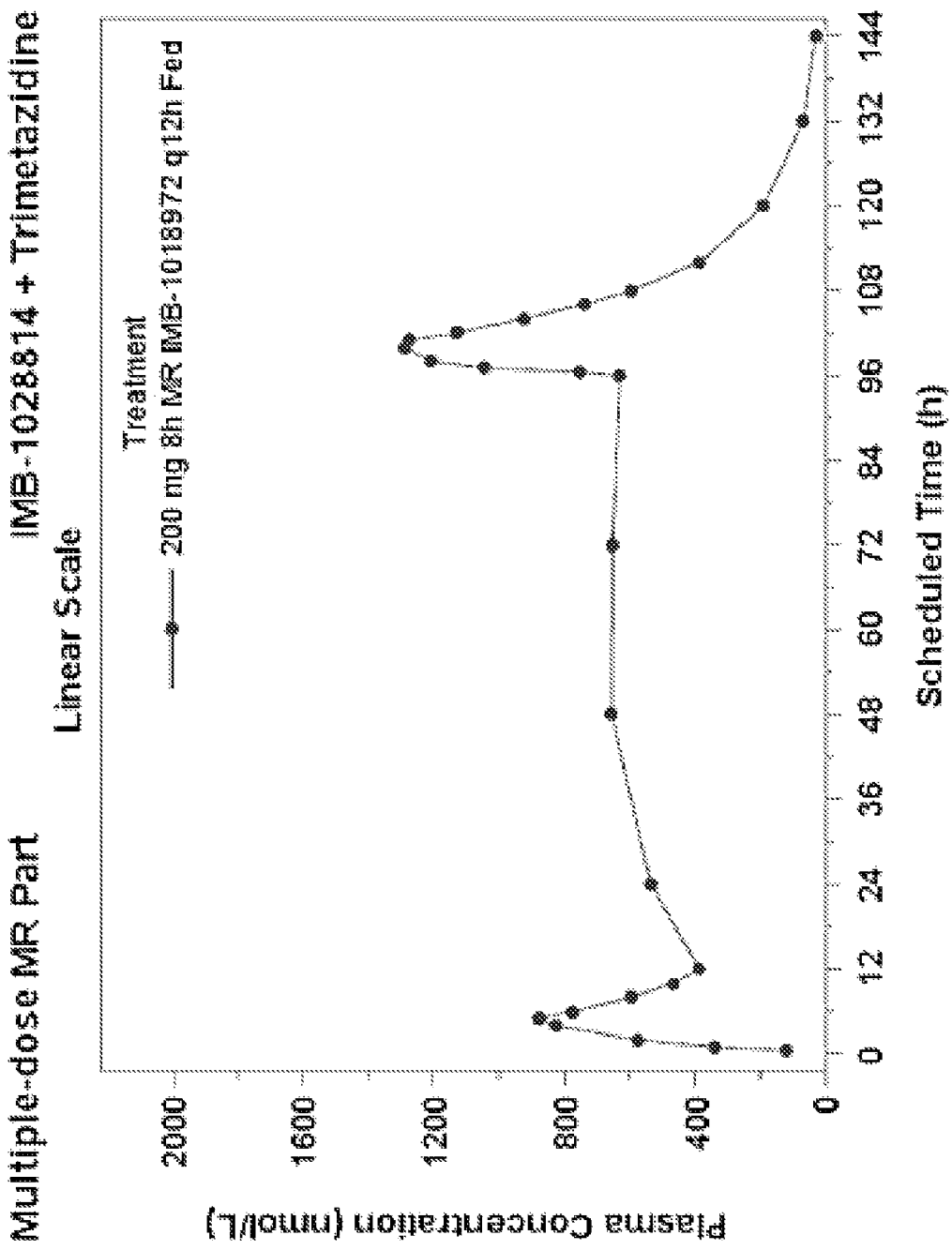
FIG. 72 is a graph of Geometric Mean IMB-1028814+Trimetazidine Plasma Concentration-Time Profiles from Day 1 through Day 5 (Linear)—Multiple-Dose MR Part (PK Set) of an FIH study of IMB-1018972.

FIG. 72 is a graph of Geometric Mean IMB-1028814+ Trimetazidine Plasma Concentration-Time Profiles from Day 1 through Day 5 (Linear)—Multiple-Dose MR Part (PK Set)

Figure 73:
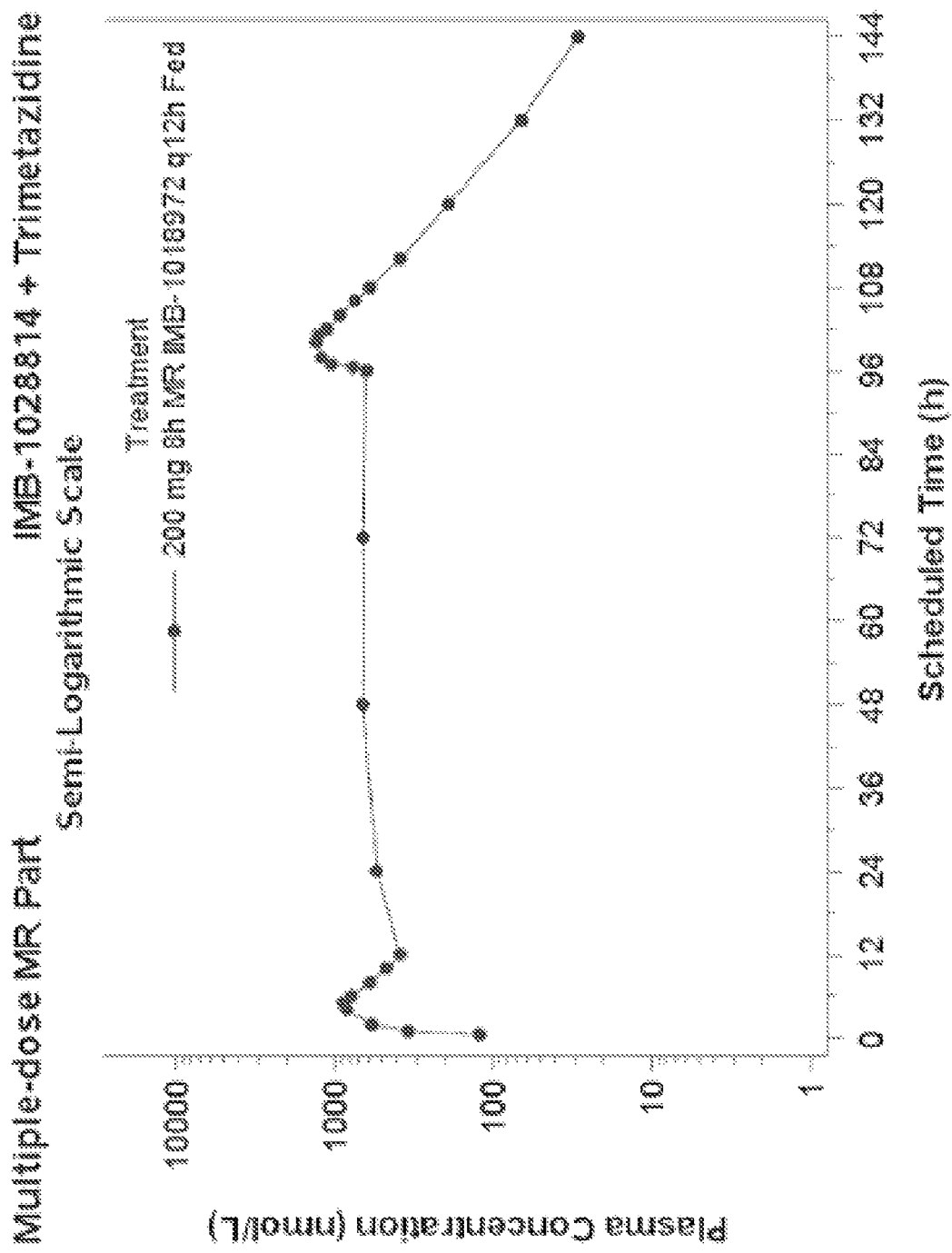
FIG. 73 is a graph of Geometric Mean IMB-1028814+Trimetazidine Plasma Concentration-Time Profiles from Day 1 through Day 5 (Semi-Logarithmic Scale)—Multiple-Dose MR Part (PK Set) of an FIH study of IMB-1018972.

FIG. 73 is a graph of Geometric Mean IMB-1028814+ Trimetazidine Plasma Concentration-Time Profiles from Day 1 through Day 5 (Semi-Logarithmic Scale)—Multiple-Dose MR Part (PK Set)

Figure 74:
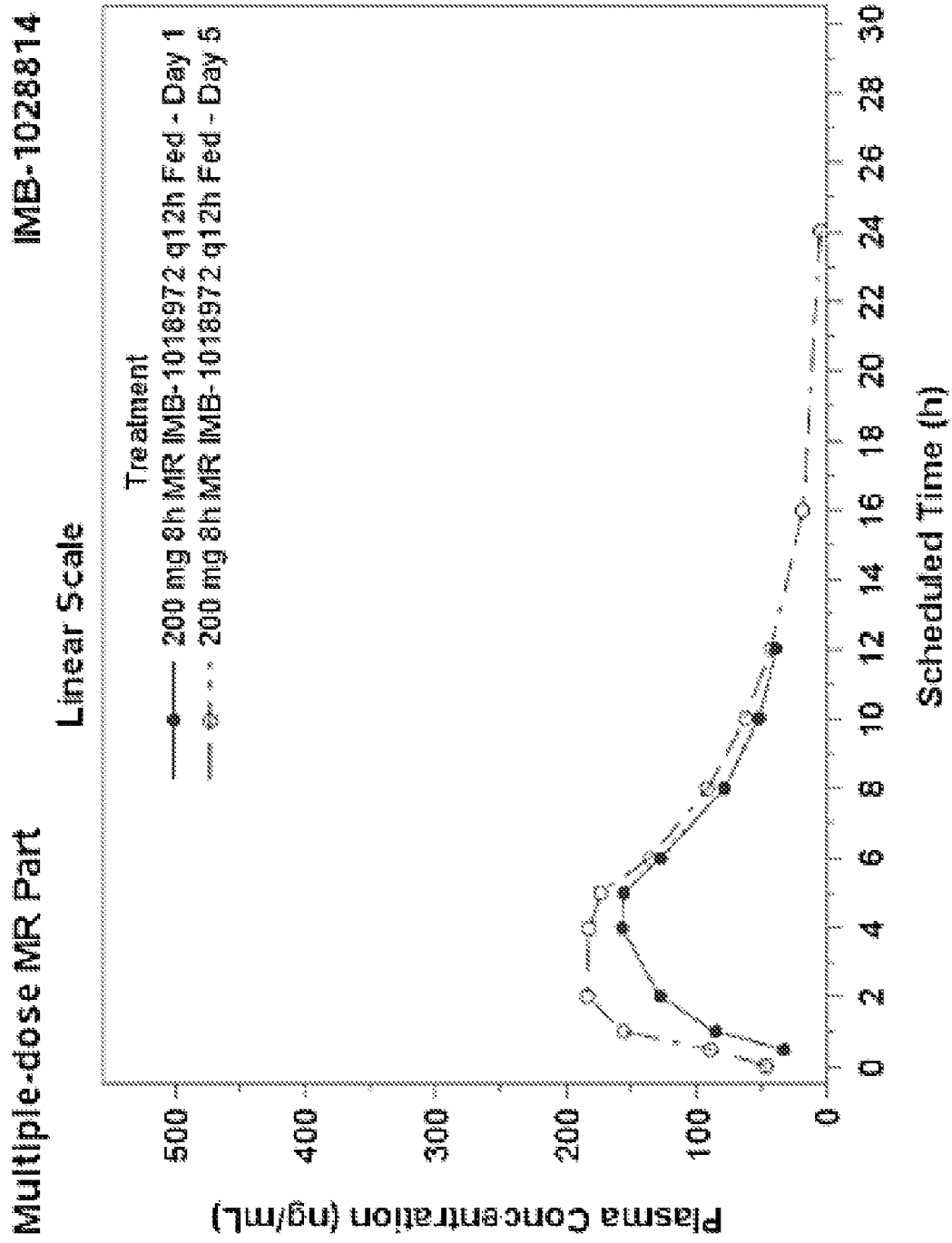
FIG. 74 is a graph of Geometric Mean IMB-1028814 Plasma Concentration-Time Profiles after Day 1 through Day 5 (Linear)—Multiple-Dose MR Part (PK Set) of an FIH study of IMB-1018972.

FIG. 74 is a graph of Geometric Mean IMB-1028814 Plasma Concentration-Time Profiles after Day 1 through Day 5 (Linear)—Multiple-Dose MR Part (PK Set)

Figure 75:
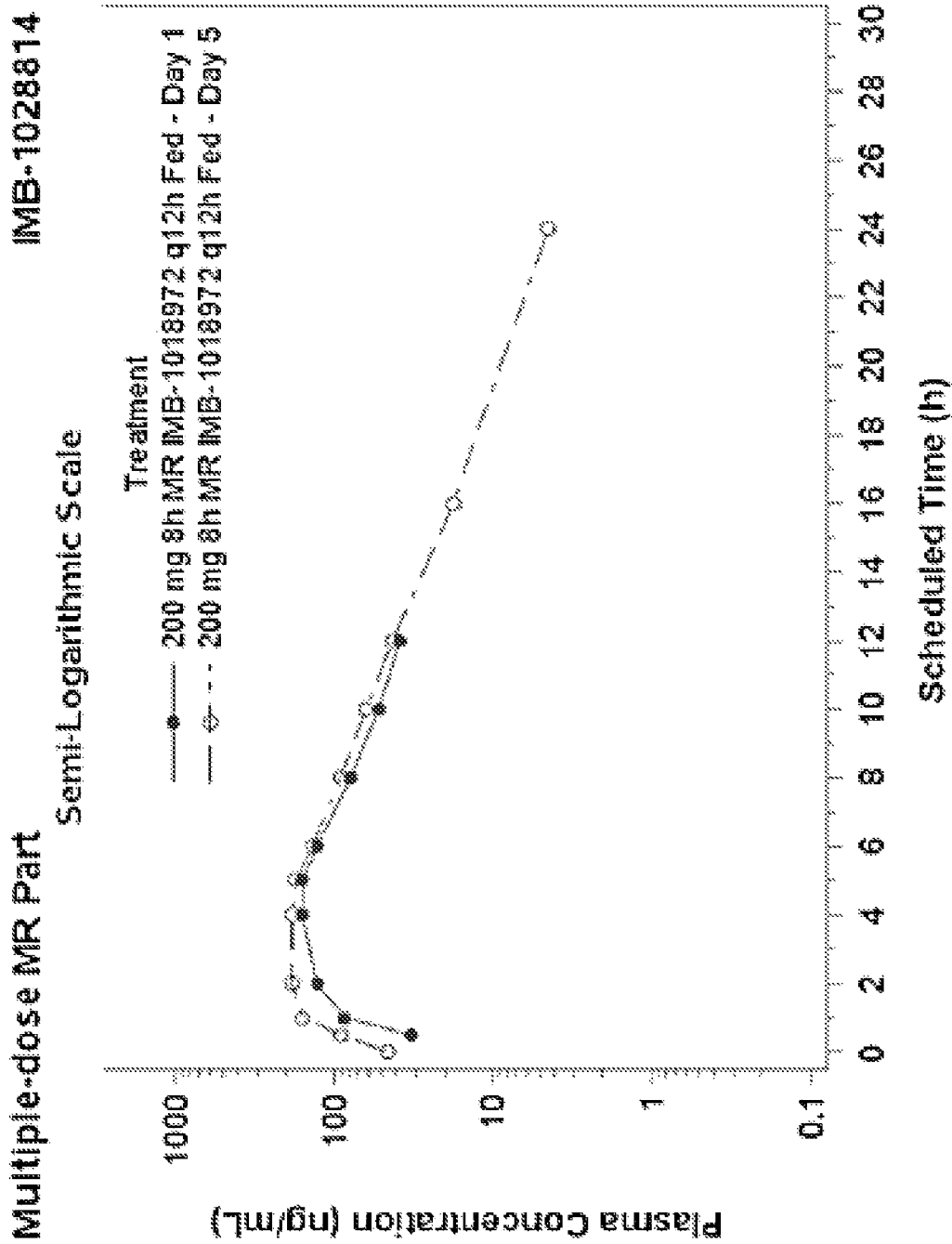
FIG. 75 is a graph of Geometric Mean IMB-1028814 Plasma Concentration-Time Profiles after Day 1 through Day 5 (Semi-Logarithmic Scale)—Multiple-Dose MR Part (PK Set) of an FIE study of IMB-1018972.

FIG. 75 is a graph of Geometric Mean IMB-1028814 Plasma Concentration-Time Profiles after Day 1 through Day 5 (Semi-Logarithmic Scale)—Multiple-Dose MR Part (PK Set)

Figure 76:
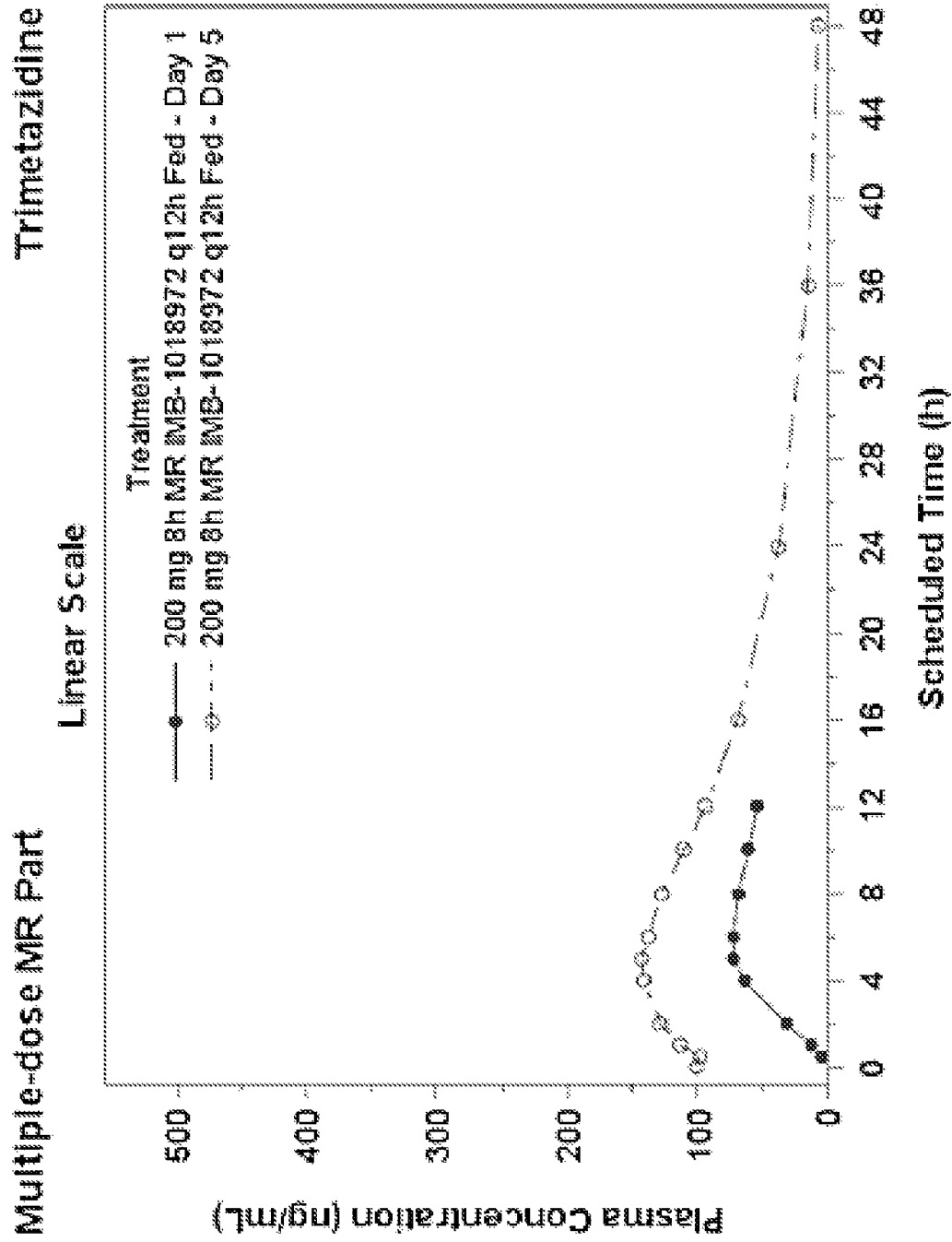
FIG. 76 is a graph of Geometric Mean Trimetazidine Plasma Concentration-Time Profiles after Day 1 through Day 5 (Linear)—Multiple-Dose MR Part (PK Set) of an FIH study of IMB-1018972.

FIG. 76 is a graph of Geometric Mean Trimetazidine Plasma Concentration-Time Profiles after Day 1 through Day 5 (Linear)—Multiple-Dose MR Part (PK Set)

Figure 77:
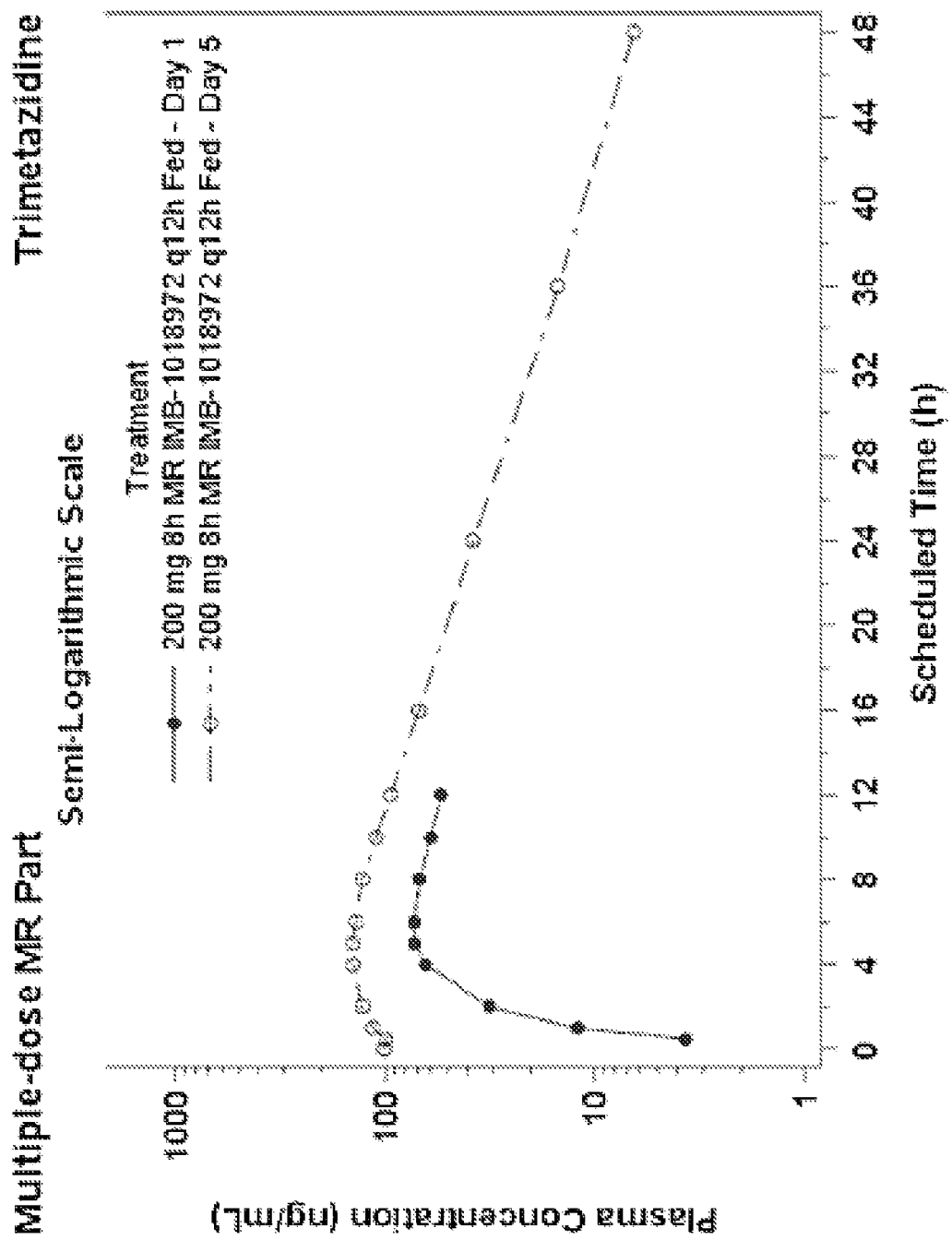
FIG. 77 is a graph of Geometric Mean Trimetazidine Plasma Concentration-Time Profiles after Day 1 through Day 5 (Semi-Logarithmic Scale)—Multiple-Dose MR Part (PK Set) of an FIE study of IMB-1018972.

FIG. 77 is a graph of Geometric Mean Trimetazidine Plasma Concentration-Time Profiles after Day 1 through Day 5 (Semi-Logarithmic Scale)—Multiple-Dose MR Part (PK Set)

Figure 78:
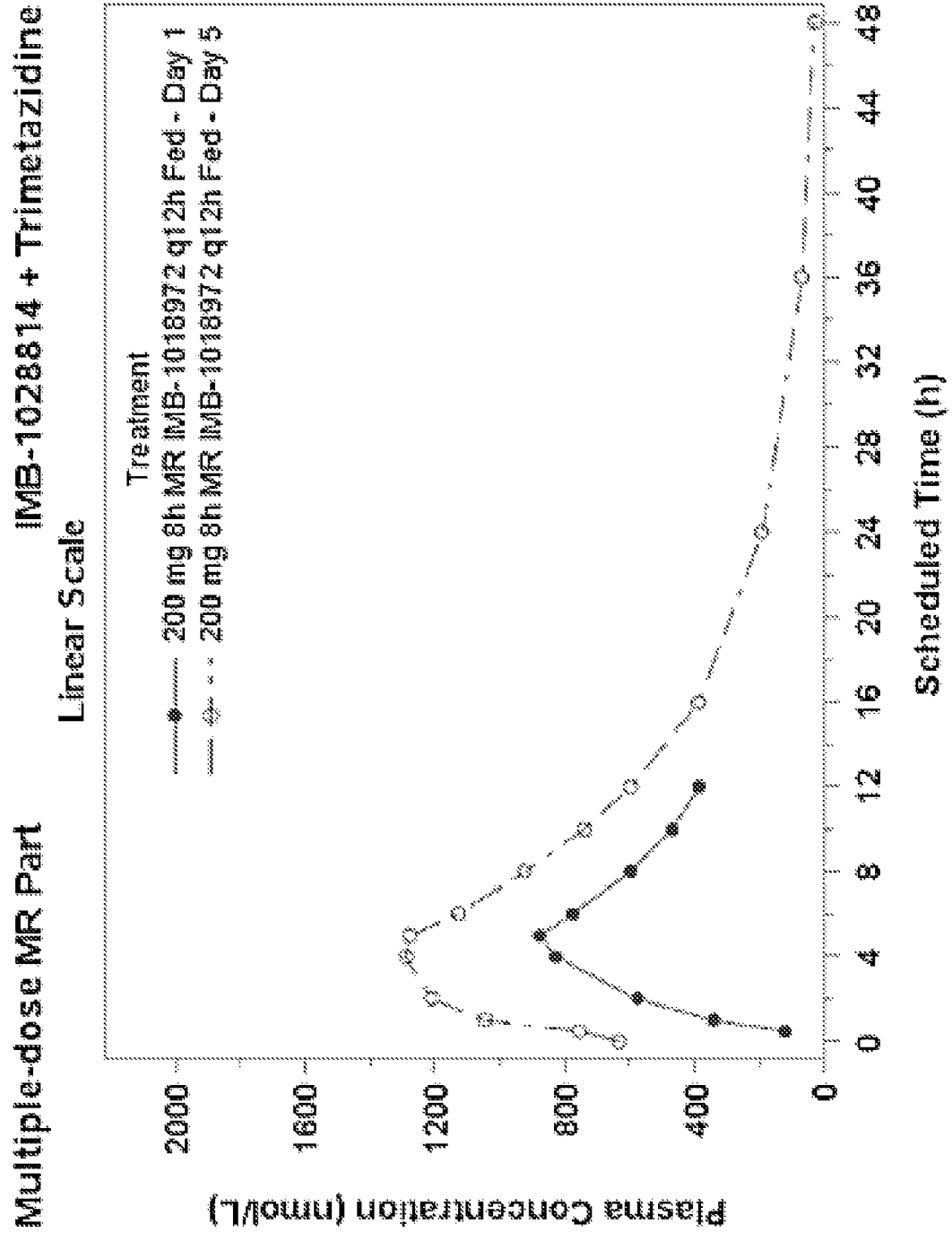
FIG. 78 is a graph of Geometric Mean IMB-1028814+Trimetazidine Plasma Concentration-Time Profiles after Day 1 through Day 5 (Linear)—Multiple-Dose MR Part (PK Set) of an FIH study of IMB-1018972.

FIG. 78 is a graph of Geometric Mean IMB-1028814+ Trimetazidine Plasma Concentration-Time Profiles after Day 1 through Day 5 (Linear)—Multiple-Dose MR Part (PK Set)

Figure 79:
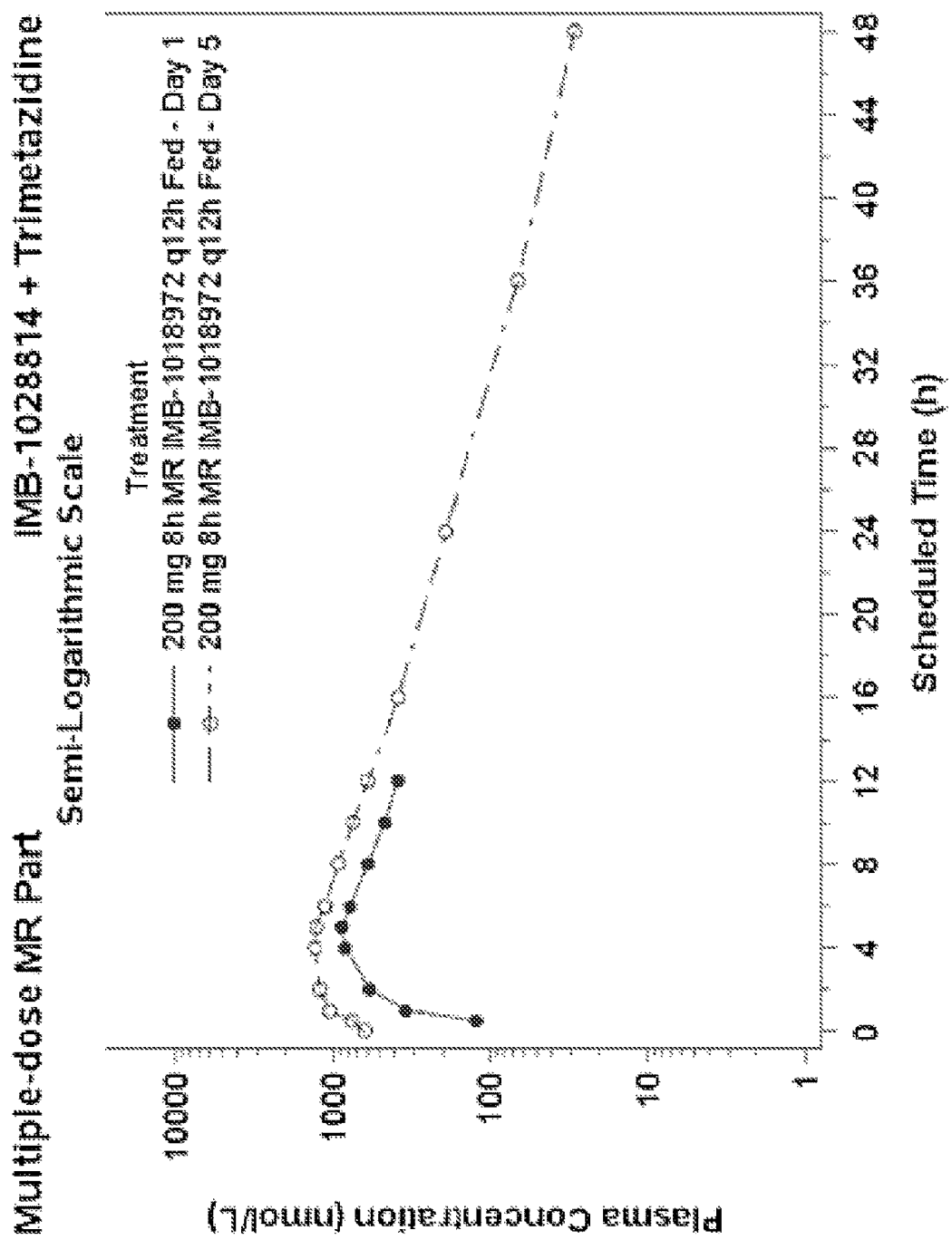
FIG. 79 is a graph of Geometric Mean IMB-1028814+Trimetazidine Plasma Concentration-Time Profiles after Day 1 through Day 5 (Semi-Logarithmic Scale)—Multiple-Dose MR Part (PK Set) of an FIH study of IMB-1018972.

FIG. 79 is a graph of Geometric Mean IMB-1028814+ Trimetazidine Plasma Concentration-Time Profiles after Day 1 through Day 5 (Semi-Logarithmic Scale)—Multiple-Dose MR Part (PK Set)

FIG. 80 is a table of Summary Statistics Geometric Mean [Range]) of IMB-1028814, Trimetazidine, and IMB-1028814+Trimetazidine Plasma Pharmacokinetic Parameters-Multiple-Dose MR Part (PK Set)

Conclusion on Pharmacokinetics

IMB-1018972 could be measured in only few plasma samples taken during this study.

When combining the single and multiple IMB-1018972 dose results under fasted and fed conditions, including those of the MR formulations, the initial hydrolysis of IMB-1018972 to IMB-1028814 and subsequent systemic bioavailability of IMB-1028814 was relatively rapid with median $t_{max}$ ranging between 0.5 hours and 5 hours postdose for IMB-1028814, and between 1.5 hours and 8 hours postdose for trimetazidine. Median $t_{max}$ did not increase with increasing IMB-1018972 dose.

The predefined stopping criterion for IMB-1028814 plasma exposure of 417,733 and 652,849 ng·h/mL for males and females, respectively, was not reached by any of the subjects during the SAD part or MAD part.

Following single oral IMB-1018972 doses in the range of 50 to 400 mg under fasted conditions, systemic exposure to IMB-1028814 and trimetazidine was dose proportional for $C_{max}$, $AUC_{0-t}$, and $AUC_{0-inf}$.

No evidence for an effect of food was observed on the IMB-1028814 exposure parameters $AUC_{0-t}$ and $AUC_{0-inf}$ following administration of a single dose of 150 mg IMB-1018972. However, $C_{max}$ was approximately 36% lower following administration of a single dose of 150 mg IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 150 mg IMB-1018972.

No evidence for an effect of food was observed on the IMB-1028814 exposure parameters $AUC_{0-t}$ and $AUC_{0-inf}$ following administration of a single dose of 200 mg 8-hour MR IMB-1018972. However, $C_{max}$ was approximately 42% higher following administration of a single dose of 200 mg 8-hour MR IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 200 mg 8-hour MR IMB-1018972.

When combining the single and multiple IMB-1018972 dose results under fasted and fed conditions, including those of the MR formulations, the geometric mean $t_{1/2}$ ranged between 2.5 hours and 4.5 hours for IMB-1028814, and between 6.5 hours and 9.5 hours for trimetazidine. Geometric mean t½ did not increase with increasing IMB-1018972 dose.

Within 48 hours following administration of a single oral dose of IMB-1018972 over the range of 50 mg to 400 mg, on average between 3.99% and 5.74% of the dose was excreted in urine as IMB-1028814, and on average between 23.11% and 32.55% of the dose was excreted in urine as trimetazidine.

Within 48 hours following administration of a single oral dose of 35 mg trimetazidine, on average 54.47% of the dose was excreted in urine as trimetazidine. ☐ Following 14 days of twice daily dosing with 150 mg and 50 mg IMB-1018972 under fed conditions, no relevant accumulation was observed of IMB-1028814 (Rac of 1.18 and 1.10 for 150 mg and 50 mg, respectively) and accumulation of trimetazidine was modest (Rac of 1.63 and 1.89 for 150 mg and 50 mg, respectively) was observed. Following 5 days of twice daily dosing with 200 mg 8-hour MR IMB-1018972 under fed conditions, no relevant accumulation of IMB-1028814 ($R_{ac}$ of 1.22) was observed, whereas accumulation of trimetazidine was moderate ($R_{ac}$ of 2.28).

Summary of Adverse Events
Single-Dose MR Part

A total of 37 TEAEs was reported by 10 of 12 (83.3%) subjects who received IMB-1018972. There were no deaths reported. Subject 505 of the single-dose MR part was withdrawn from the study due to a moderate TEAE of ALT increased. This TEAE is described below and more extensively in Section 12.2.2. The majority of the TEAEs were transient and resolved without sequelae by follow-up. Three TEAEs were still ongoing at follow-up: aphthous ulcer, catheter site hematoma, and catheter site related reaction. Thirty-six of 37 TEAEs were of mild severity and 1 TEAE was of moderate severity. No severe TEAEs were reported. The moderate TEAE was an event of ALT increased (up to 149 IU/L on Day 11) that was considered by the Investigator not to be related to the study drug. The subject (Subject 505) was withdrawn from the study due to this TEAE and did not receive the last single oral dose of 200 mg 8-hour MR formulation of IMB-1018972 under fed conditions on Day 13.

Of 37 TEAEs, 6 were reported by 4 (33.3%) subjects receiving the 50 mg 8-hour MR formulation of IMB-1018972 under fasted conditions, 9 were reported by 6 (50%) subjects receiving the 50 mg 4-hour MR formulation of IMB-1018972 under fasted conditions, 6 were reported by 5 (41.7%) subjects receiving the 200 mg 8-hour MR formulation of IMB-1018972 under fasted conditions, 11 were reported by 8 (66.7%) subjects receiving the 200 mg 4-hour MR formulation of IMB-1018972 under fasted conditions, and 5 were reported by 2 (18.2%) subjects receiving the 200 mg 8-hour MR formulation of IMB-1018972 under fed conditions.

There was no apparent dose or dissolution time dependency of the number and incidence of TEAEs. Neither was there any clear difference between fasted and fed IMB-1018972 administration of the 200 mg 8-hour MR formulation of IMB-1018972 for the number and incidence of TEAEs.

The most frequently reported TEAEs (ie, reported by >20% of the subjects) by SOC were:

General disorders and administration site conditions with 11 TEAEs reported by 7 (58.3%) subjects (5 TEAEs of catheter site related reaction, 2 TEAEs of catheter site hematoma, and 1 TEAE each of catheter site pain, malaise, medical device site dryness, and medical device site irritation.

Nervous system disorders with 8 TEAEs reported by 7 (58.3%) subjects (6 TEAEs of headache and 2 TEAEs of dizziness).

Gastrointestinal disorders with 5 TEAEs reported by 4 (33.3%) subjects (2 TEAEs of abdominal pain and 1 TEAE each of abdominal pain upper, aphthous ulcer, and diarrhea).

Of 37 TEAEs reported, 7 TEAEs reported by 4 of 12 (33.3%) subjects were considered by the Investigator to be related to the study drug and 30 TEAEs reported by 10 of 12 (83.3%) subjects were considered by the Investigator not to be related to the study drug. No drug-related TEAEs were reported following the 200 mg 8-hour MR formulation of IMB-1018972 under fed conditions. The reported drug-related TEAEs were:

Renal and urinary disorders with 5 TEAEs of pollakiuria in 2 (16.7%) subjects.

Investigations with 1 TEAE of ALT increased.

Nervous system disorders with 1 TEAE of headache.

Overall Tolerability

Treatment with the 50 mg MR formulation and 200 mg MR formulation with 4-hour and 8-hour dissolution profile under fasted conditions, and subsequently, the 200 mg 8-hour MR formulation of IMB-1018972 under fed conditions were well tolerated by healthy male and female subjects, except for 1 subject in which ALT was elevated (up to 149 IU/L) after 2 single doses of 50 mg MR formulation and 2 doses of 200 mg MR formulation.

Multiple-Dose MR Part

A total of 40 TEAEs was reported by 12 of 12 (100%) subjects who received IMB-1018972. All TEAEs were of mild severity and there were no deaths reported. The majority of the TEAEs were transient and resolved without sequelae by follow-up. Four TEAEs were still ongoing at follow-up: dermatitis contact, erythema, influenza like illness, oropharyngeal pain, and medical device site irritation.

The most frequently reported TEAEs (ie, reported by >30% of the subjects) by SOC were:

Nervous system disorders with 9 TEAEs reported by 7 (58.3%) subjects (6 TEAEs of headache, 2 TEAEs of dizziness, and 1 TEAE of dizziness postural).

Gastrointestinal disorders with 9 TEAEs reported by 5 (41.7%) subjects (2 TEAEs of abdominal pain and 1 TEAE each of diarrhea, dyspepsia, feces pale, flatulence, gingival pain, oral discomfort, and toothache).

General disorders and administration site conditions with 4 TEAEs reported by 4 (33.3%) subjects (1 TEAE each of catheter site pain, influenza like illness, medical device site irritation, and thirst.

Musculoskeletal and connective tissue disorders with 4 TEAEs reported by 4 (33.3%) subjects (2 TEAEs of myalgia, and 1 TEAE each of neck pain and pain in extremity.

Renal and urinary disorders with 4 TEAEs of pollakiuria in 4 (33.3%) subjects.

Of 40 TEAEs reported, 10 TEAEs reported by 7 of 12 (58.3%) subjects were considered by the Investigator to be related to the study drug and 30 TEAEs reported by 9 of 12 (75%) subjects were considered by the Investigator not to be related to the study drug. The most frequently reported drug-related TEAEs (ie, reported by >15% of the subjects) by SOC were:

Renal and urinary disorders with 4 TEAEs of pollakiuria in 4 (33.3%) subjects.

Nervous system disorders with 2 TEAEs reported by 2 (16.7%) subjects (1 TEAE each of dizziness and headache).

Vascular disorders with 2 TEAEs of flushing reported by 2 (16.7%) subjects.

Overall Tolerability

Five-day treatment with multiple oral doses of the 200 mg 8-hour MR formulation of IMB-1018972 q12h under fed conditions was well tolerated by healthy male and female subjects. Of note, 2 instances of flushing of mild severity were reported by 2 subjects, Subjects 513 and 517, who were post-menopausal females and 1 of whom had reported ongoing "hot flushes" as part of medical history. No subjects dropped out and no modification of the dose was needed due to the TEAEs of flushing.

FIG. 81A and FIG. 81B is a table Summary of All TEAEs by System Organ Class, Preferred Term and Treatment—Single-Dose MR Part (Safety Set)

FIG. 82 is a table Summary of All TEAEs by System Organ Class, Preferred Term and Treatment—Single-Dose MR Part (Safety Set)

FIG. 83 is a table Summary of All TEAEs by Treatment, Relationship, and Severity-Single-Dose MR Part (Safety Set)

FIG. 84 is a table Summary of All TEAEs by Treatment, Relationship, and Severity—Multiple-Dose MR Part (Safety Set)

Deaths, other Serious Adverse Events, and Other Significant Adverse Events

One subject was withdrawn during the study.

Subject 505 was a 21-year old white male with a BMI of 21.5 kg/m2. The subject participated in the single-dose MR part and was planned to receive 50 mg of the 8-hour MR formulation on Day 1 under fasted conditions, 50 mg of the 4-hour MR formulation on Day 4 under fasted conditions, 200 mg of the 8-hour MR formulation on Day 7 under fasted conditions, 200 mg of the 4-hour MR formulation on Day 10 under fasted conditions, and 200 mg 8-hour MR formulation of IMB-1018972 on Day 13 under fed conditions. He reported no relevant medical history and received no concomitant medication at baseline. A TEAE of ALT increased was reported for this subject starting on Day 5, 1 day after dosing with 50 mg of the 4-hour MR formulation on Day 4. This TEAE was of moderate severity and considered by the Investigator to be possibly related to the study drug. The subject also received the doses of 200 mg of the 8-hour MR formulation on Day 7 under fasted conditions and 200 mg of the 4-hour MR formulation on Day 10 under fasted conditions. ALT values for this subject were within normal range (0-68 IU/L) at screening (29 IU/L), on Day −1 (34 IU/L), and on Day 2 (31 IU/L). ALT levels increased to values above the upper limit of normal (68 IU/L) of 72 IU/L on Day 5, 97 IU/L on Day 8, and 149 IU/L on Day 11, and then decreased again to 102 IU/L on Day 14, and 84 IU/L on Day 16. By follow-up on Day 24, ALT levels had returned to 42 IU/L, which was within the normal range. This was also the day that this TEAE was recorded to have recovered. The high ALT level of 149 IU/L on Day 11 was considered by the Investigator to be clinically significant abnormal, based on which the Investigator decided to withdraw the subject from the study (receive no further doses). Throughout this entire period, AST levels were within normal range. As a result of withdrawal, the subject did not receive the planned last single oral dose of 200 mg 8-hour MR formulation of IMB-1018972 under fed conditions on Day 13. After withdrawal on Day 11, the subject returned on Day 24 for a follow-up with safety assessments conducted as planned. The subject also reported mild TEAEs of dermatitis contact on Day 1 (not related), skin exfoliation from Day 3 to Day 6 (not related), and abdominal pain from Day 13 to Day 14 (not related).

The TEAE of ALT increased that led to the withdrawal of Subject 505 from the study was considered by the Investigator to be possibly related to the study drug due to its time-relationship with study drug administration.

Subject 505 of the single-dose MR part was withdrawn from the study due to a moderate TEAE of ALT increased. The TEAE started on Day 5, 1 day after dosing with 50 mg of the 4-hour MR formulation on Day 4. ALT values for this subject were within normal range (0-68 IU/L) at screening (29 IU/L), on Day −1 (34 IU/L), and on Day 2 (31 IU/L). ALT levels increased to values above the upper limit of normal (68 IU/L) of 72 IU/L on Day 5, 97 IU/L on Day 8, and 149 IU/L on Day 11, and then decreased again to 102 IU/L on Day 14, and 84 IU/L on Day 16. By follow-up on Day 24, ALT levels had returned to 42 IU/L, which was within the normal range. This was also the day that this TEAE was recorded to have recovered. The high ALT level of 149 IU/L on Day 11 was considered by the Investigator to be clinically significant abnormal, based on which the Investigator decided to withdraw the subject from the study. Throughout this entire period, AST levels for Subject 505 were within normal range. No other cases of clinically significant abnormal laboratory parameters were recorded at any time during this study.

Concomitant Treatment

Single-Dose MR Part

Seven subjects in the single-dose MR part received or took concomitant medication. Five female subjects used contraception during the study. In addition, 4 subjects received concomitant medication as follows:

One subject (Subject 501) received 1000 mg paracetamol once because of headache.

One subject (Subject 509) received 1000 mg paracetamol once because of headache intermittent (preferred term: headache).

One subject (Subject 510) received 500 mg paracetamol twice and 1000 mg paracetamol once because of headache.

One subject (Subject 511) received 1000 mg paracetamol once because of common cold (preferred term: nasopharyngitis).

These medications were not considered to have influenced the outcome of the study.

Multiple-Dose MR Part

Five subjects in the multiple-dose MR part received or took concomitant medication. Three female subjects used contraception during the study. In addition, 3 subjects received concomitant medication as follows:

One subject (Subject 514) received 1000 mg paracetamol twice because of headache.

One subject (Subject 519) received gelomyrtol 3 times a day for 2 days and 500 mg paracetamol 3 times a day for 2 days because of flu like symptoms (preferred term: influenza like illness).

One subject (Subject 524) received 500 mg paracetamol once because of headache. These medications were not considered to have influenced the outcome of the study.

Discussion and Overall Conclusions

This was a double-blind, randomized, placebo-controlled study, consisting of a SAD part with integrated FE arm, a MAD part, and single-dose and multiple-dose MR parts to assess the safety, tolerability, and PK of ascending single and multiple oral doses of IMB-1018972 (IR formulation in the SAD and MAD parts), single oral doses of a MR formulation of trimetazidine, single oral doses of MR formulations of IMB-1018972, and multiple oral doses of the 200 mg 8-hour MR formulation of IMB-1018972. The study started with the SAD part Safety Discussion Overall, single oral IMB-1018972 doses and multiple oral IMB-1018972 doses of an IR formulation, and single and multiple doses of MR formulations, were generally well tolerated by healthy male and female subjects. There were no findings of clinical relevance with respect to clinical laboratory, vital signs, 12-lead ECG, continuous cardiac monitoring (telemetry), or physical examination. Of note, there were no findings of hemodynamic changes, nor changes in the QTc-interval, after administration of IMB-1018972 either as the IR or MR formulations.

Nicotinic acid (niacin) is an immediate hydrolysis product of IMB-1018972 and constitutes approximately 30% of the molecular mass of IMB-1018972. In this study, TEAEs of flushing, of which the characteristics were consistent with the flushing seen with the administration of niacin, were reported. All events were transient and resolved without intervention. No subjects dropped out and no modification of the dose was needed due to the TEAEs of flushing.

In the SAD (IR) part of the study, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions.

In the 14-day multiple dose part of the study, subjects received 150 or 50 mg IR 1 MB-1018972 q12h in the fed state. Six subjects in the 150 mg q12h group reported ingle instances of flushing that were mild in severity. No TEAEs of flushing were reported following administration of 50 mg IR IMB-1018972 q12h.

In the multiple-dose MR part, 2 instances of flushing of mild severity were reported by 2 subjects who were postmenopausal females and 1 of whom had reported ongoing "hot flushes" as part of medical history. No subjects dropped out and no modification of the dose was needed due to the TEAEs. The nature of these TEAEs being sporadic, transient, self-limiting, and of mild severity in the MR formulation indicate an acceptable tolerability profile of IMB-1018972 in the 200 mg 8-hour MR formulation.

Two subjects were withdrawn from the study. One subject of the FE arm Group A4 was withdrawn from the study due to a moderate SAE of 'influenza like illness' following administration of a single oral dose of 150 mg IMB-1018972 under fasted conditions. The SAE of influenza like illness was considered by the Investigator unlikely to be related to the study drug.

One subject of the single-dose MR part was withdrawn from the study due to a moderate TEAE of ALT increased. The TEAE of ALT increased (up to 149 IU/L on Day 11) was considered by the Investigator to be possibly related to the study drug and resolved without intervention. The most frequently reported TEAEs during the study were of the SOC vascular disorders (mainly TEAEs of flushing), general disorders and administration site conditions, nervous system disorders, gastrointestinal disorders, and musculoskeletal and connective tissue disorders. The majority of the TEAEs reported during the study were considered by the Investigator not to be related to the study drug.

Pharmacokinetics

Based on the single-dose and multiple-dose PK results obtained for IMB-1028814 and trimetazidine in this study, the 200 mg 8-hour MR IMB-1018972 formulation has been chosen to be most suitable to be used in Phase 2 proof-of-concept studies.

Safety-Conclusion

Overall, single oral IMB-1018972 doses and multiple oral IMB-1018972 doses of an IR formulation, and single and multiple doses of MR formulations, were generally well tolerated by healthy male and female subjects. There were no findings of clinical relevance with respect to clinical laboratory, vital signs, 12-lead ECG, continuous cardiac monitoring (telemetry), or physical examination. Of note, there were no findings of hemodynamic changes, nor changes in the QTc-interval, after administration of IMB-1018972 either as the IR or MR formulations.

During the SAD part, the most common AEs were 6 TEAEs of flushing (reported terms were 'niacin flush' and 'flushing neck'), of which 5 TEAEs were of moderate severity and 1 TEAE was of mild severity. Four subjects reported flushing after a single dose of 400 mg IMB-1018972 under fasted conditions, and 2 subjects of the FE arm reported flushing after a single dose of 150 mg IMB-1018972 under fasted conditions. These TEAEs were all considered by the Investigator to be related to the study drug. No subjects dropped out due to flushing and flushing was not considered a safety issue. Dose escalation beyond 400 mg IMB-1018972 IR did not proceed as planned based on the PK exposure levels of IMB-1028814 and trimetazidine exceeding the target exposure levels in the 400 mg group and the findings of flushing at that dose. The predefined target exposure level was approximately 3 to 4 'trimetazidine equivalents', ie, the ratio of the combined exposure of the active metabolites of IMB-1018972 to the single oral doses of 35 mg MR trimetazidine as seen in published literature.

There were no deaths reported during the study. Most TEAEs were of mild severity and no severe TEAEs were reported during the study. Overall, 12 of a total of 181 TEAEs were of moderate severity.

Two subjects were withdrawn from the study: 1 subject due to a moderate SAE of influenza like illness (unlikely related) and 1 due to a moderate TEAE of ALT increased (possibly related).

Overall, there was no clear dose dependency of the number and incidence of TEAEs.

Dosing under fed conditions appeared to attenuate the number and incidence of TEAEs in the FE arm of the SAD part, whereas no clear difference between fasted and fed IMB-1018972 administration for the number and incidence of TEAEs was observed in the single-dose MR part.

Pharmacokinetics—Conclusions

IMB-1018972 could be measured in only few plasma samples taken during this study.

When combining the single and multiple IMB-1018972 dose results under fasted and fed conditions, including those of the MR formulations, the initial hydrolysis of IMB-1018972 to IMB-1028814 and subsequent systemic bioavailability of IMB-1028814 was relatively rapid with median tmax ranging between 0.5 hours and 5 hours postdose for IMB-1028814, and between 1.5 hours and 8 hours postdose for trimetazidine. Median tmax did not increase with increasing IMB-1018972 dose.

The predefined stopping criterion for IMB-1028814 plasma exposure of 417,733 and 652,849 ng·h/mL for males and females, respectively, was not reached by any of the subjects during the SAD part or MAD part.

Following single oral IMB-1018972 doses in the range of 50 to 400 mg under fasted conditions, systemic exposure to IMB-1028814 and trimetazidine was dose proportional for Cmax, $AUC_{0-t}$, and $AUC_{0-inf}$.

No evidence for an effect of food was observed on the IMB-1028814 exposure parameters $AUC_{0-t}$ and $AUC_{0-inf}$ following administration of a single dose of 150 mg IMB-1018972. However, $C_{max}$ was approximately 36% lower following administration of a single dose of 150 mg IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 150 mg IMB-1018972.

No evidence for an effect of food was observed on the IMB-1028814 exposure parameters $AUC_{0-t}$ and $AUC_{0-inf}$ following administration of a single dose of 200 mg 8-hour MR IMB-1018972. However, $C_{max}$ was approximately 42% higher following administration of a single dose of 200 mg 8-hour MR IMB-1018972 under fed conditions relative to administration under fasted conditions.

No evidence for an effect of food was observed on the trimetazidine exposure parameters $C_{max}$, $AUC_{0-t}$, and $AUC_{0-inf}$ following administration of a single dose of 200 mg 8-hour MR IMB-1018972.

When combining the single and multiple IMB-1018972 dose results under fasted and fed conditions, including those of the MR formulations, the geometric mean $t_{1/2}$ ranged between 2.5 hours and 4.5 hours for IMB-1028814, and between 6.5 hours and 9.5 hours for trimetazidine. Geometric mean $t_{1/2}$ did not increase with increasing IMB-1018972 dose.

Within 48 hours following administration of a single oral dose of IMB-1018972 over the range of 50 mg to 400 mg, on average between 3.99% and 5.74% of the dose was excreted in urine as IMB-1028814, and on average between 23.11% and 32.55% of the dose was excreted in urine as trimetazidine.

Within 48 hours following administration of a single oral dose of 35 mg trimetazidine, on average 54.47% of the dose was excreted in urine as trimetazidine.

Following 14 days of twice daily dosing with 150 mg and 50 mg IMB-10818972 under fed conditions, no relevant accumulation was observed of IMB-1028814 ($R_{ac}$ of 1.18 and 1.10 for 150 mg and 50 mg, respectively), and accumulation of trimetazidine was modest ($R_{ac}$ of 1.63 and 1.89 for 150 mg and 50 mg, respectively).

Following 5 days of twice daily dosing with 200 mg 8-hour MR IMB-1018972 under fed conditions, no relevant accumulation of IMB-1028814 (Rac of 1.22) was observed, whereas accumulation of trimetazidine was moderate (Rac of 2.28).

Preliminary Renal and Urinary Data from Phase 1 and Current Phase 2 Studies

In the early Phase 1 study in healthy volunteers and early Phase 2 studies in patients, there were instances of increased urine volume and increased urinary frequency spontaneously reported.

In the first-in-man study, CIMB8972-101, healthy volunteers were dosed with single doses of IMB-1018972 at 50 mg or 200 mg of the modified release (MR) formulation. Two of 12 subjects [2/12] (16.7%) reported 5 events of pollakiuria at both doses.

In an open label Phase 2 study (IMB101-005 DICE) treating patients with Type 2 Diabetes mellitus and obesity for 8 weeks with 200 mg MR BID, two of 22 patients [2/22] (9.1%) spontaneously reported renal and urinary findings. One patient reported pollakiuria and one patient reported increased nocturnal urinary frequency.

In a blinded, randomized, controlled, Phase 2 study (IMB101-006 ISCHEMIA) treating patients with stable angina for 8 weeks with 200 mg MR BID, one of 22 patients [1/22] (4.5%) spontaneously reported renal and urinary findings. One patient reported polyuria.

We know that the kidney is an ATP rich organ. The reports of increased urine volume and increased urinary frequency lead us to believe that IMB-1018972 metabolite IMB-1028814 may have a beneficial impact on the kidney.

Overall

In view of the positive risk/benefit profile and the observed PK characteristics of the IMB-1018972 metabolites IMB-1028814 and trimetazidine in this single-dose and multiple-dose FIH study, further clinical development of IMB-1018972 is warranted.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method of increasing ATP production in a kidney of a subject, the method comprising providing to a subject having a kidney condition a composition comprising a compound of formula (IX):

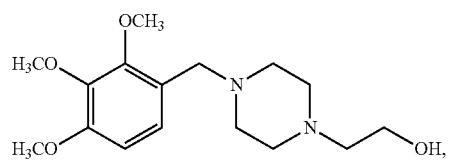

or a pharmaceutically acceptable salt thereof.

2. The method of claim 1, wherein the kidney condition is selected from the group consisting of accumulation of mesangial matrix, acute interstitial nephritis, acute kidney disease, acute tubular necrosis (ATN), Alport syndrome, atherosclerosis, atherosclerotic renal artery stenosis, systemic lupus erythematosus, autosomal dominant polycystic kidney disease (ADPKD), benign prostatic hyperplasia, bladder stones, cancer of the bladder, ureters, or prostate, cell apoptosis, chronic kidney disease, chronic kidney insufficiency, chronic tubulointerstitial nephritis, delayed graft function (DGF) renal, diabetic kidney, diabetic nephropathy, type 1 diabetic nephropathy (TID nephropathy), end-stage renal disease, Focal segmental glomerulosclerosis (FSGS), glomerular basement membrane thickening, glomerular hyperfiltration, glomerular and tubular epithelial hypertrophy, glomerulonephritis, glomerulosclerosis, hemolytic-uremic syndrome, IgA nephropathy (also called Berger's disease), ischemic nephropathy, kidney hypoxia, kidney stones, kidney transplantation, liver cirrhosis, methyl melonic acidosis (MMA), microalbuminuria, obstructed urinary catheter, proteinuria, reduced creatinine clearance, reduced glomerular filtration rate, reflux nephropathy, renal vein thrombosis, and rhabdomyolysis.

3. The method of claim 2, wherein the kidney condition is acute kidney disease, chronic kidney disease, chronic kidney insufficiency, diabetic kidney, or diabetic nephropathy.

4. The method of claim 1, wherein the composition is provided orally.

5. The method of claim 1, wherein the composition is provided is in one dose per day.

6. The method of claim 1, wherein the composition is provided is in multiple doses per day.

7. The method of claim 1, wherein the composition is provided in a daily dose comprising from about 25 mg to about 1000 mg of the compound of formula (X).

8. The method of claim 7, wherein the composition is provided in a daily dose comprising from about 100 mg to about 400 mg of the compound of formula (X).

9. The method of claim 1, wherein the composition comprises an immediate-release formulation.

10. The method of claim 1, wherein the composition comprises a modified-release formulation.

11. A method of treating a kidney condition in a subject, the method comprising providing to a subject having a kidney condition a composition comprising a compound of formula (IX):

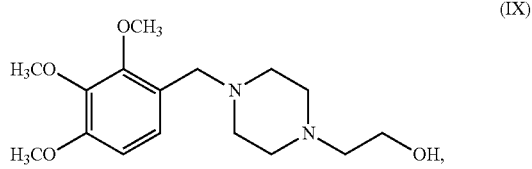 [SMILES: COc1ccc(CN2CCN(CCO)CC2)c(OC)c1OC]

or a pharmaceutically acceptable salt thereof.

12. The method of claim 11, wherein the kidney condition is selected from the group consisting of accumulation of mesangial matrix, acute interstitial nephritis, acute kidney disease, acute tubular necrosis (ATN), Alport syndrome, atherosclerosis, atherosclerotic renal artery stenosis, systemic lupus erythematosus, autosomal dominant polycystic kidney disease (ADPKD), benign prostatic hyperplasia, bladder stones, cancer of the bladder, ureters, or prostate, cell apoptosis, chronic kidney disease, chronic kidney insufficiency, chronic tubulointerstitial nephritis, delayed graft function (DGF) renal, diabetic kidney, diabetic nephropathy, type 1 diabetic nephropathy (TID nephropathy), end-stage renal disease, Focal segmental glomerulosclerosis (FSGS), glomerular basement membrane thickening, glomerular hyperfiltration, glomerular and tubular epithelial hypertrophy, glomerulonephritis, glomerulosclerosis, hemolytic-uremic syndrome, IgA nephropathy (also called Berger's disease), ischemic nephropathy, kidney hypoxia, kidney stones, kidney transplantation, liver cirrhosis, methyl melonic acidosis (MMA), microalbuminuria, obstructed urinary catheter, proteinuria, reduced creatinine clearance, reduced glomerular filtration rate, reflux nephropathy, renal vein thrombosis, and rhabdomyolysis.

13. The method of claim 12, wherein the kidney condition is acute kidney disease, chronic kidney disease, chronic kidney insufficiency, diabetic kidney, or diabetic nephropathy.

14. The method of claim 11, wherein the composition is provided orally.

15. The method of claim 11, wherein the composition is provided is in one dose per day.

16. The method of claim 11, wherein the composition is provided is in multiple doses per day.

17. The method of claim 11, wherein the composition is provided in a daily dose comprising from about 25 mg to about 1000 mg of the compound of formula (X).

18. The method of claim 17, wherein the composition is provided in a daily dose comprising from about 100 mg to about 400 mg of the compound of formula (X).

19. The method of claim 11, wherein the composition comprises an immediate-release formulation.

20. The method of claim 11, wherein the composition comprises a modified-release formulation.

* * * * *